United States Patent
Deadman et al.

(10) Patent No.: US 8,431,581 B2
(45) Date of Patent: Apr. 30, 2013

(54) IMIDAZOPYRIMIDINES AND USES THEREOF

(75) Inventors: John Joseph Deadman, Carlton (AU); Eric Dale Jones, Bentleigh East (AU); Giang Thanh Le, Lower Templestowe (AU); David Ian Rhodes, Heidelberg Heights (AU); Neeranat Thienthong, Malvern (AU); Nicholas Andrew Van de Graff, Prahran (AU); Lisa Jane Winfield, St Kilda (AU)

(73) Assignee: Avexa Limited, Richmond (Victoria) (AU)

( * ) Notice: Subject to any disclaimer, the term of this patent is extended or adjusted under 35 U.S.C. 154(b) by 70 days.

(21) Appl. No.: 12/734,042

(22) PCT Filed: Jul. 2, 2009

(86) PCT No.: PCT/AU2009/000857
§ 371 (c)(1), (2), (4) Date: Oct. 15, 2010

(87) PCT Pub. No.: WO2010/000031
PCT Pub. Date: Jan. 7, 2010

(65) Prior Publication Data
US 2011/0028487 A1    Feb. 3, 2011

Related U.S. Application Data

(60) Provisional application No. 61/161,931, filed on Mar. 20, 2009.

(30) Foreign Application Priority Data

Jul. 2, 2008 (AU) ................ 2008903406

(51) Int. Cl.
*A01N 43/90* (2006.01)
*A61K 31/519* (2006.01)
*C07D 487/00* (2006.01)

(52) U.S. Cl.
USPC ...................... 514/259.5; 544/281

(58) Field of Classification Search .......... None
See application file for complete search history.

(56) References Cited

U.S. PATENT DOCUMENTS

2004/0229909 A1   11/2004   Kiyama et al.
2005/0256109 A1   11/2005   Naidu

FOREIGN PATENT DOCUMENTS

| AU | WO2008/077188 | * | 7/2008 |
| WO | WO 2006/103399 | | 10/2006 |
| WO | 2008/077188 | | 7/2008 |

OTHER PUBLICATIONS

Wolff et. al., "Burger's Medicinal Chemistry and Drug Discovery," 5th Ed. Part 1, pp. 975-977 (1995).*
Banker, et. al., (1996) Modern Pharmaceuticals, p. 596.*

* cited by examiner

*Primary Examiner* — Jeffrey Murray
(74) *Attorney, Agent, or Firm* — Fish & Richardson P.C.

(57) ABSTRACT

The present invention provides a compound of formula (I) or a pharmaceutically acceptable derivative, salt or prodrug thereof. The present invention further provides a method of treatment or prophylaxis of a viral infection in a subject comprising administering to said subject an effective amount of a compound of formula (I) or a pharmaceutically acceptable derivative, salt or prodrug thereof. Pharmaceutical compositions comprising a compound of formula (I) are also provided.

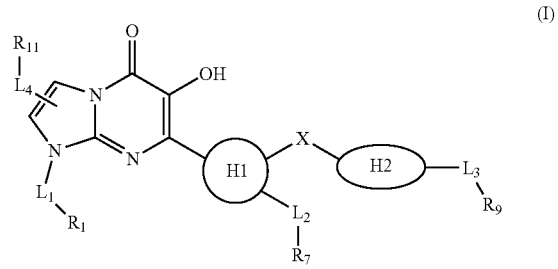

16 Claims, No Drawings

IMIDAZOPYRIMIDINES AND USES THEREOF

CROSS REFERENCE TO PRIOR APPLICATIONS

This is a U.S. National Phase application under 35 U.S.C. §371 of International Patent Application No. PCT/AU2009/000857, filed Jul. 2, 2009, and claims the priority of Australian Patent Application No. 2008903406, filed Jul. 2, 2008 and U.S. Provisional Application Ser. No. 61/161,931, filed Mar. 20, 2009 all of which are incorporated by reference herein. The International Application published in English on Jan. 7, 2010 as WO 2010/000031 under PCT Article 21(2).

FIELD OF THE INVENTION

The present invention relates to a class of compounds useful in the treatment of viral infections, particularly HIV infections which show resistance to known HIV inhibitors.

BACKGROUND OF THE INVENTION

The retrovirus designated "human immunodeficiency virus" or "HIV" is the etiological agent of a complex disease that progressively destroys the immune system. This disease is known as acquired immune deficiency syndrome or AIDS. As at December 2005 an estimated 40 million people are living with HIV world wide and over 3 million deaths are occurring annually.

A feature of retrovirus replication includes the reverse transcription of the viral genome into proviral DNA and its integration into the host cell genome. These steps are required for HIV replication and are mediated by the virus encoded enzymes, reverse transcriptase and integrase respectively.

HIV infection follows a path of the virus particle binding to cell surface receptors and co-receptors resulting in fusion of the virus particle with the cell. The contents of the virus are released into the cytoplasm where reverse transcription of the HIV genome occurs. Through a series of steps a double stranded proviral DNA copy is produced. The proviral DNA is transported to the nucleus in a complex known as the pre integration complex (PIC) which contains integrase and other viral and possibly cellular proteins. Once inside the nucleus the proviral DNA is integrated into the host cell genome via the action of integrase. Once integrated, transcription and translation of the viral genome can occur resulting in the production of viral proteins and a new viral RNA genome. These proteins and genome assemble at the cell surface and, depending on cell type, possibly other intracellular membranous compartments. Assembled particles then bud out from the cell and during, or soon after, this process mature into infectious HIV particles through the action of the viral protease.

The integration of the proviral genome into the host cell genome requires the action of an integrase which carries out this process in at least three steps, possibly four. The first step involves the assembly of the viral genome into a stable nucleoprotein complex, secondly, processing of two nucleotides from the 3' termini of the genome to give staggered ends with free 3' OH residues and thirdly the transfer of these ends into the host cell genome. The final step involves the gap filling and repair of the insertion site in the host genome. There is still some conjecture over whether the integrase performs this final step or whether it is carried out by cellular repair enzymes.

Currently HIV infection can be treated with a number of inhibitors on the market which target reverse transcriptase, protease or entry into the cell. Treatment of HIV infection with these, or a combination of these, drugs is known to be an effective treatment for AIDS and similar diseases. Shortcomings with the current inhibitors include the rapid emergence and increase incidence of resistance and numerous side effects.

Certain mutations within the wild-type viral integrase enzyme are known to confer resistance to a number of known integration inhibitors published in the literature. In particular, the viral variants containing Q148H/G140S double mutation in integrase and the N155H/E92Q double mutation in integrase represent the two of the more common viruses identified that are failing treatment with Isentress (Raltegravir, MK-0518). The triple mutant Q148K/G140A/E138A is also resistant to Raltegravir. See: Kobayashi et al, Antiviral Research, received 17 Apr. 2008, accepted 17 Jun. 2008; and Vacca et al; Discovery of MK-2048—subtle changes confer unique resistance properties to a series of tricyclic hydroxypyrrole integrase strand transfer inhibitors; Abstract from the 4$^{th}$ IAS Conference on HIV Pathogenesis Treatment and Prevention; 22-25 Jul. 2007, Sydney, Australia.

The specifications of Australian Provisional Patent Application Nos. 2006907283, 2007902479, 2007903401 and 2007904114 and International Patent Application No PCT/AU2007/001980 which derives priority from these applications describe a broad class of compounds that inhibit HIV integrase activity. The present inventors have now determined that a sub-class of these compounds are surprisingly effective (when compared to other members of the class) against viral variants containing the Q148H/G140S double mutation in integrase and the N155H/E92Q double mutation in integrase.

SUMMARY OF THE INVENTION

In a first aspect, the present invention provides a compound of Formula I or a pharmaceutically acceptable derivative, salt or prodrug thereof wherein:

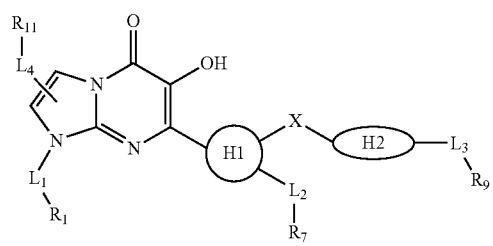

$L_1$-$R_1$ is hydrogen or is a substituent wherein
  $L_1$ is selected from the group consisting of Z, $C_{1-3}$alkylene, >C=Z, —$CZ_2$—, —C(=Z)$C_{1-3}$ alkylene, —$CZ_2$—$C_{1-3}$ alkylene, —$C_{1-3}$ alkylene-C(=Z)—, —$C_{1-3}$alkylene-$CZ_2$— wherein each Z is independently selected from O, S, and NH;
  each $R_1$ is independently selected from the group consisting of hydrogen, $C_{1-10}$alkyl wherein one or more of the carbon atoms of the alkyl chain may optionally be replaced with oxygen atoms, $C_{1-10}$alkylN$R_3R_4$, halo, N$R_3R_4$, alkylaryl, alkylheteroaryl, a 4-7 membered lactam, S(O)N$R_3R_4$, SO$_2$N$R_3R_4$, SO$_2C_{1-10}$alkyl, $C_{5-10}$cycloalkyl wherein one or more of the carbon atoms of the cycloalkyl ring are replaced with one or more oxygen atoms;
  $R_3$ and $R_4$ are each independently selected from the group consisting of hydrogen, $C_{1-10}$alkyl, $C_{3-6}$cycloalkyl, $C_{1-10}NR_5R_6$, —(CO)(CO)$NR_5R_6$; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, $C_{1-4}$alkyl, $CO_2C_{1-4}$alkyl, $NR_5R_6$; $C_{1-4}$alkyl$NR_5R_6$ and further wherein two carbons of said 5-7 membered heterocyclic ring may optionally be bridged by a $C_{1-3}$ alkylene bridging group;

$R_5$ and $R_6$ are each independently selected from the group consisting of H and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and $C_{1-4}$alkyl and further wherein two carbons of said 5-7 membered heterocyclic ring may optionally be bridged by a $C_{1-3}$ alkylene bridging group;

$L_4$-$R_{11}$ is 0-2 substituents wherein:
  each $L_4$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_{11}$ is independently selected from the group consisting of hydrogen, $C_{1-10}$alkyl wherein one or more of the carbon atoms of the alkyl chain may optionally be replaced with oxygen atoms, $C_{1-10}$alkyl where one of the carbon atoms is replaced by S in the S, S(O), or S(O)$_2$ oxidation state, $C_{1-10}$alkyl$NR_3R_4$, halo, $NR_3R_4$, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms;
  when $R_{11}$ is alkylaryl, the aryl group of said alkylaryl substituent is optionally substituted with a substituent selected from $C_{1-10}$alkyl, —O—$C_{1-10}$alkyl, $C_{1-10}$alkyl$NR_3R_4$, —O—$C_{1-10}$alkyl$NR_3R_4$, halo, $NR_3R_4$, alkylaryl, —O-alkylaryl, $SO_2NR_3R_4$ $H_1$ is a selected from the group consisting of —C(=O)NH— and a 5- or 6-membered saturated, partially saturated or aromatic ring containing between 1 and 4 heteroatoms wherein each heteroatom is independently selected from the group consisting of N, O and S;

$L_2$-$R_7$ is 0-2 substituents wherein:
  each $L_2$ is independently absent or is group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_7$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms;

X is $CR_8R_{8'}$
  each of $R_8$ and $R_{8'}$ is independently selected from the group consisting of H and $CH_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:
  each $L_3$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_9$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, heterocyclyl, heteroaryl, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

In a fourth aspect, the present invention provides pharmaceutical composition comprising a compound according to the first aspect and a pharmaceutically acceptable carrier, diluent or excipient.

DETAILED DESCRIPTION OF THE INVENTION

In a first aspect, the present invention provides a compound of Formula I or a pharmaceutically acceptable derivative, salt or prodrug thereof wherein:

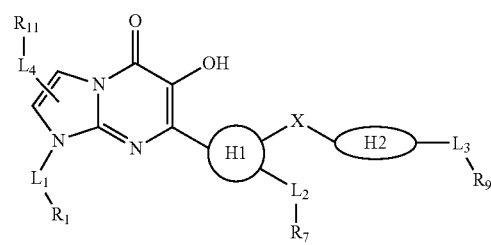

I $L_1$-$R_1$ is hydrogen or is a substituent wherein
  $L_1$ is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
  each $R_1$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, alkylheteroaryl, a 4-7 membered lactam, S(O)$NR_3R_4$, $SO_2NR_3R_4$, $SO_2C_{1-10}$alkyl, $C_{5-10}$cycloalkyl wherein one or more of the carbon atoms of the cycloalkyl ring are replaced with one or more oxygen atoms;
  $R_3$ and $R_4$ are each independently selected from the group consisting of hydrogen, $C_{1-10}$alkyl, $C_{3-6}$cycloalkyl, $C_{1-10}NR_5R_6$, —(CO)(CO)$NR_5R_6$; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, $C_{1-4}$alkyl, $CO_2C_{1-4}$alkyl, $NR_5R_6$; $C_{1-4}$alkyl$NR_5R_6$ and further wherein two carbons of said 5-7 membered heterocyclic ring may optionally be bridged by a $C_{1-3}$ alkylene bridging group;

$R_5$ and $R_6$ are each independently selected from the group consisting of H and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and $C_{1-4}$alkyl and further wherein two carbons of said 5-7 membered heterocyclic ring may optionally be bridged by a $C_{1-3}$ alkylene bridging group;

$L_4$-$R_{11}$ is 0-2 substituents wherein:
each $L_4$ is independently absent or is selected from the group consisting of Z, $C_{1-3}$alkylene, >C=Z, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_{11}$ is independently selected from the group consisting of hydrogen, $C_{1-10}$alkyl wherein one or more of the carbon atoms of the alkyl chain may optionally be replaced with oxygen atoms, $C_{1-10}$alkyl where one of the carbon atoms is replaced by S in the S, S(O), or S(O)$_2$ oxidation state, $C_{1-10}$alkyl$NR_3R_4$, halo, $NR_3R_4$, alkylaryl, S(O)$NR_3R_4$, SO$_2NR_3R_4$, SO$_2C_{1-10}$alkyl, and $C_{5-10}$cycloalkyl wherein one or more of the carbon atoms of the cycloalkyl ring are replaced with one or more oxygen atoms;
when $R_{11}$ is alkylaryl, the aryl group of said alkylaryl substituent is optionally substituted with a substituent selected from $C_{1-10}$alkyl, —O—$C_{1-10}$alkyl, $C_{1-10}$alkyl$NR_3R_4$, —O—$C_{1-10}$alkyl$NR_3R_4$, halo, $NR_3R_4$, alkylaryl, —O-alkylaryl, SO$_2NR_3R_4$ $H_1$ is a selected from the group consisting of —C(=O)NH— and a 5- or 6-membered saturated, partially saturated or aromatic ring containing between 1 and 4 heteroatoms wherein each heteroatom is independently selected from the group consisting of N, O and S;

$L_2$-$R_7$ is 0-2 substituents wherein:
each $L_2$ is independently absent or is group consisting of Z, $C_{1-3}$alkylene, >C=Z, —CZ$_2$—, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_7$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$NR_3R_4$, SO$_2NR_3R_4$, SO$_2C_{1-10}$alkyl, and $C_{5-10}$cycloalkyl wherein one or more of the carbon atoms of the cycloalkyl ring are replaced with one or more oxygen atoms;

X is $CR_8R_{8'}$
each of $R_8$ and $R_{8'}$ is independently selected from the group consisting of H and $CH_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:
each $L_3$ is independently absent or is selected from the group consisting of Z, $C_{1-3}$alkylene, >C=Z, —CZ$_2$—, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_9$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, heterocyclyl, heteroaryl, alkylaryl, S(O)$NR_3R_4$, SO$_2NR_3R_4$, SO$_2C_{1-10}$alkyl, and $C_{5-10}$cycloalkyl wherein one or more of the carbon atoms of the cycloalkyl ring are replaced with one or more oxygen atoms.

Preferably, $L_1$ is $CH_2$(C=O)— and $R_1$ is selected from the group consisting of N-piperidine, N-piperazine, N,N'-methyl-piperazine, and morpholino wherein each $R_1$ is optionally substituted at the carbon or nitrogen atoms with one or two methyl groups.

In one embodiment, $H_1$ is a five membered aromatic heterocycle selected from the group consisting of thiazole, oxazole, oxadiazole, thiadiazole, imidazole, triazole, and tetrazole.

More preferably, $H_1$ is thiazole.

Preferably, $H_2$ is phenyl.

In one form, $L_4$-$R_{11}$ is one substituent wherein $L_4$ is absent or is —CH$_2$— and $R_{11}$ is $NR_3R_4$.

In one embodiment, $L_3$-$R_9$ is at least 2 substituents wherein the first $L_3$-$R_9$ is halo and in the second $L_3$-$R_9$, $L_3$ is absent or is selected from >C=O and $R_9$ is selected from the group consisting of halo, $NR_3R_4$ and SO$_2NR_3R_4$.

In another embodiment, $L_3$-$R_9$ is one or two substituents wherein each $L_3$-$R_9$ is halo.

Preferably, at least one $NR_3R_4$ is independently selected from the group consisting of morpholino, a five-membered cyclic sulphonamide (such as isothiazolidine) and a six membered cyclic sulphonamide.

In a preferred form, the group "$C_{1-10}$alkyl where one of the carbon atoms is replaced by S in the S, S(O), or S(O)$_2$ oxidation state" is methylsulfanylmethyl or methylsulfonylmethyl.

In one embodiment, when $H_1$ is —C(=O)NH—, $L_1R_1$ is not hydrogen and $L_4$-$R_{11}$ is at least one substituent.

Preferably, when $H_1$ is —C(=O)NH— then $L_4$-$R_{11}$ is a cyclic sulphonamide.

Preferably, the compound is selected from the group consisting of:

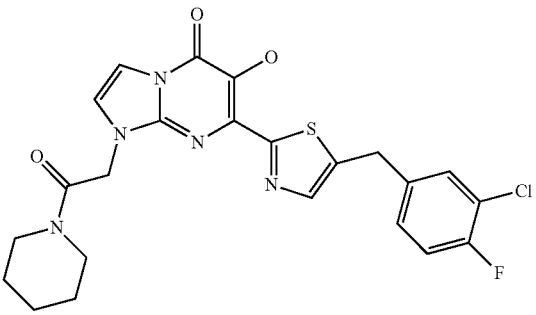

7-[5-(3-Chloro-4-fluoro-benzyl)-thiazol-2-yl]-6-hydroxy-1-(2-oxo-2-piperidin-1-yl-ethyl)-1H-imidazo[1,2-a]pyrimidin-5-one

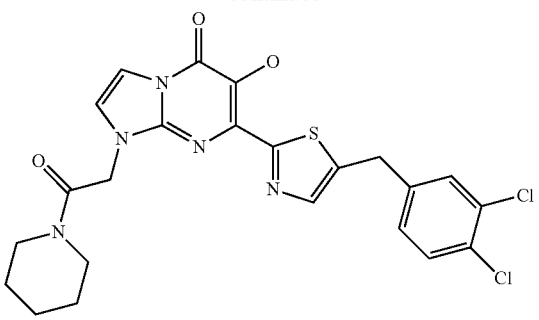

7-[5-(3,4-Dichloro-benzyl)-thiazol-2-yl]-6-hydroxy-1-(2-oxo-2-piperidin-1-yl-ethyl)-1H-imidazo[1,2-a]pyrimidin-5-one

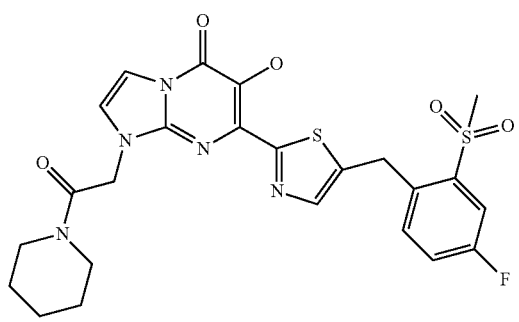

7-[5-(4-Fluoro-2-methanesulfonyl-benzyl)-thiazol-2-yl]-6-hydroxy-1-(2-oxo-2-piperidin-1-yl-ethyl)-1H-imidazo[1,2-a]pyrimidin-5-one

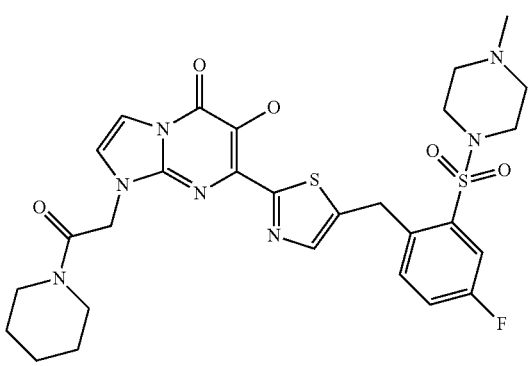

7-{5-[4-Fluoro-2-(4-methyl-piperazine-1-sulfonyl)-benzyl]-thiazol-2-yl}-6-hydroxy-1-(2-oxo-2-piperidin-1-yl-ethyl)-1H-imidazo[1,2-a]pyrimidin-5-one

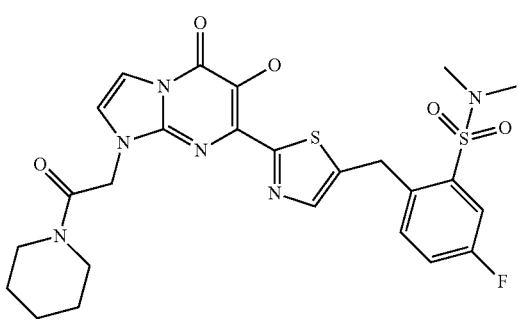

5-Fluoro-2-{2-[6-hydroxy-5-oxo-1-(2-oxo-2-piperidin-1-yl-ethyl)-1,5-dihydro-imidazo[1,2-a]pyrimidin-7-yl]-thiazol-5-ylmethyl}-N,N-dimethyl-benzenesulfonamide

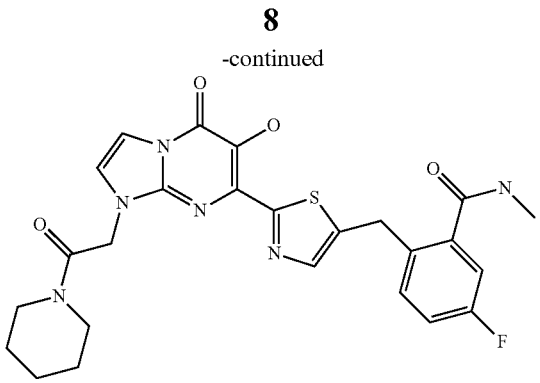

5-Fluoro-2-{2-[6-hydroxy-5-oxo-1-(2-oxo-2-piperidin-1-yl-ethyl)-1,5-dihydro-imidazo[1,2-a]pyrimidin-7-yl]-thiazol-5-ylmethyl}-N-methyl-benzamide

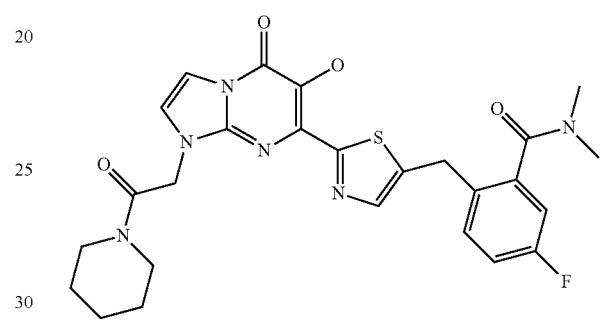

5-Fluoro-2-{2-[6-hydroxy-5-oxo-1-(2-oxo-2-piperidin-1-yl-ethyl)-1,5-dihydro-imidazo[1,2-a]pyrimidin-7-yl]-thiazol-5-ylmethyl}-N,N-dimethyl-benzamide

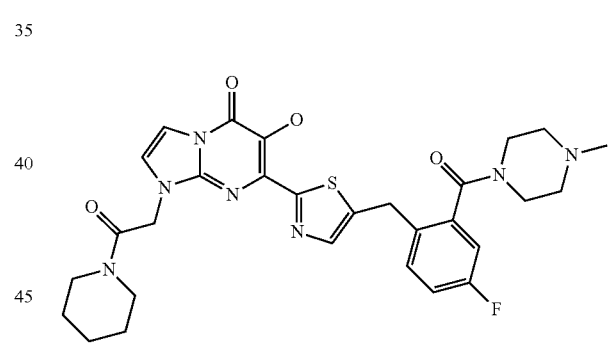

7-{5-[4-Fluoro-2-(4-methyl-piperazine-1-carbonyl)-benzyl]-thiazol-2-yl}-6-hydroxy-1-(2-oxo-2-piperidin-1-yl-ethyl)-1H-imidazo[1,2-a]pyrimidin-5-one

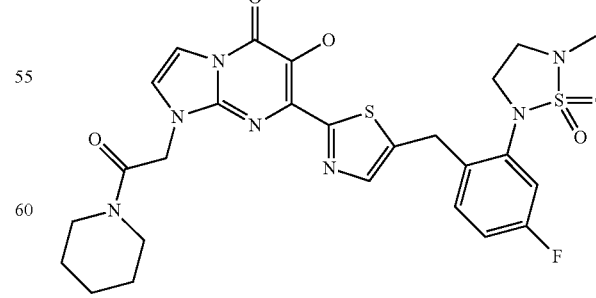

7-{5-[4-Fluoro-2-(5-methyl-1,1-dioxo-1lambda*6*-[1,2,5]thiadiazolidin-2-yl)-benzyl]-thiazol-2-yl}-6-hydroxyl-1-(2-oxo-2-piperidin-1-yl-ethyl)-1H-imidazo[1,2-a]pyrimidin-5-one

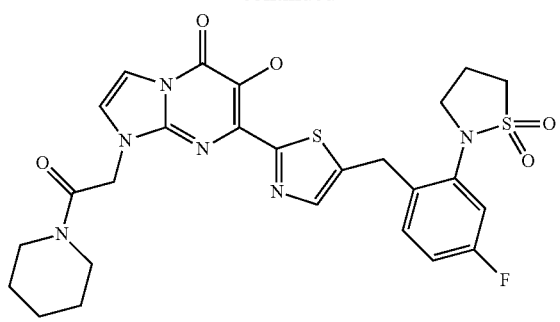

7-{5-[2-(1,1-Dioxo-1lambda*6*-isothiadiazolidin-2-yl)-4-fluoro-benzyl]-thiazol-2-yl}-6-hydroxyl-1-(2-oxo-2-piperidin-1-yl-ethyl)-1H-imidazo[1,2-a]pyrimidin-5-one

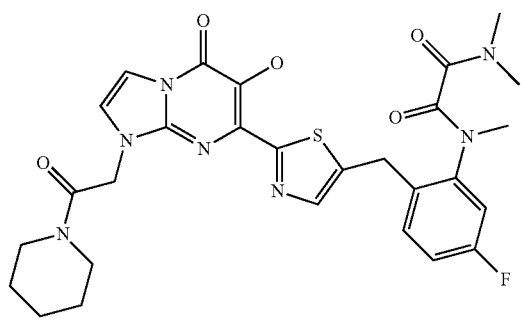

N-(5-Fluoro-2-{2-[6-hydroxy-5-oxo-1-(2-oxo-2-piperidin-1-yl-ethyl)-1,5-dihydro-imidazo[1,2-a]pyrimidin-7-yl]-thiazol-5-ylmethyl}-phenyl)-N,N',N'-trimethyl-oxalamide

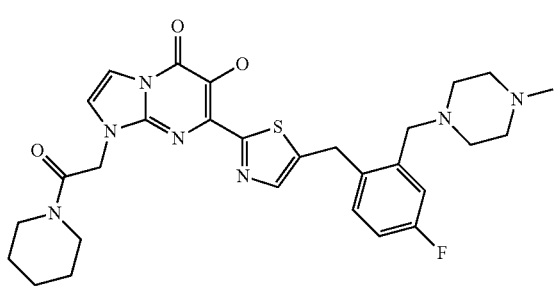

7-{5-[4-Fluoro-2-(4-methyl-piperazin-1-ylmethyl)-benzyl]-thiazol-2-yl}-6-hydroxyl-1-(2-oxo-2-piperidin-1-yl-ethyl)-1H-imidazo[1,2-a]pyrimidin-5-one

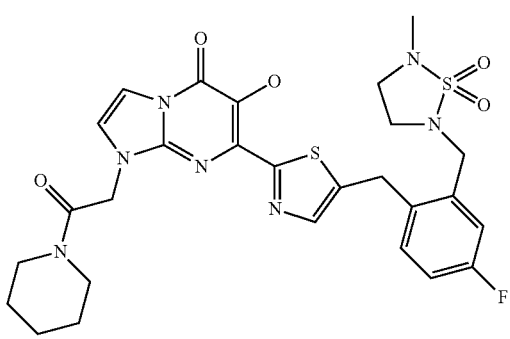

7-{5-[4-Fluoro-2-(5-methyl-1,1-dioxo-1lambda*6*-[1,2,5]thiadiazolidin-2-ylmethyl)-benzyl]-thiazol-2-yl}-6-hydroxy-1-(2-oxo-2-piperidin-1-yl-ethyl)-1H-imidazo[1,2-a]pyrimidin-5-one

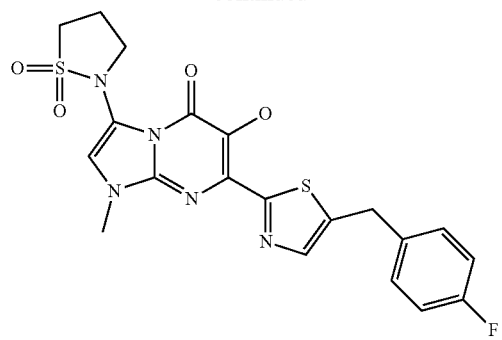

3-(1,1-Dioxo-1lambda*6*-isothiazolidin-2-yl)-7-[5-(4-fluoro-benzyl)-thiazol-2-yl]-6-hydroxy-1-methyl-1H-imidazo[1,2-a]pyrimidin-5-one

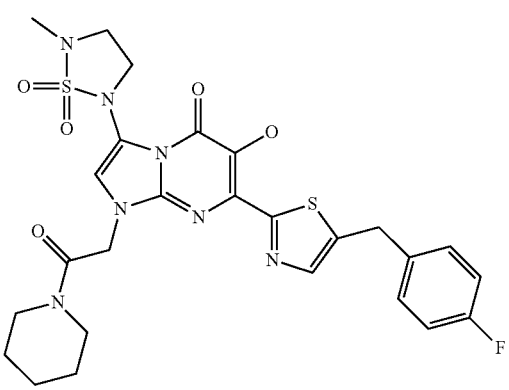

3-(1,1-Dioxo-1lambda*6*-isothiazolidin-2-yl)-7-[5-(4-fluoro-benzyl)-thiazol-2-yl]-6-hydroxy-1-(2-oxo-2-piperidin-1-yl-ethyl)-1H-imidazo[1,2-a]pyrimidin-5-one 7-[5-(4-Fluoro-benzyl)-thiazol-2-yl]-6-hydroxy-3-(5-methyl-1,1-dioxo-1lambda*6*-[1,2,5]thiadiazolidin-2-yl)-1-(2-oxo-2-piperidin-1-yl-ethyl)-1H-imidazo[1,2-a]pyrimidin-5-one -continued

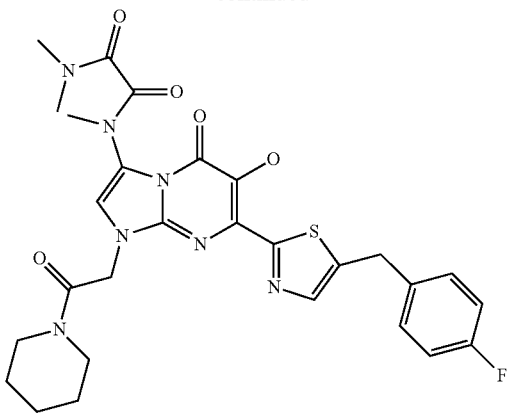

N-[7-[5-(4-Fluoro-benzyl)-thiazol-2-yl]-6-hydroxy-5-oxo-1-
(2-oxo-2-piperidin-1-yl-ethyl)-1,5-dihydro-imidazo[1,2-a]
pyrimidin-3-yl]-N,N′,N′-trimethyl-oxalamide

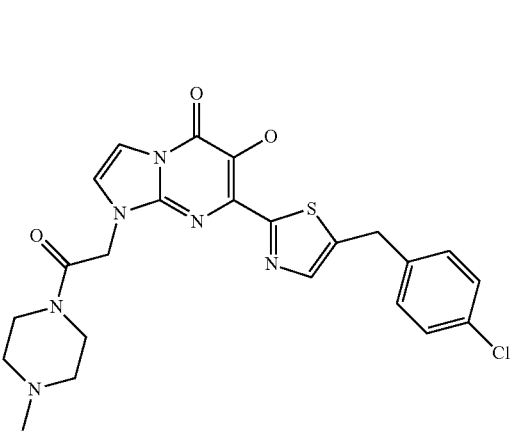

7-[5-(4-Chloro-benzyl)-thiazol-2-yl]-6-hydroxy-1-[2-(4-methyl-
piperazin-1-yl)-2-oxo-ethyl]-1H-imidazo[1,2-a]
pyrimidin-5-one

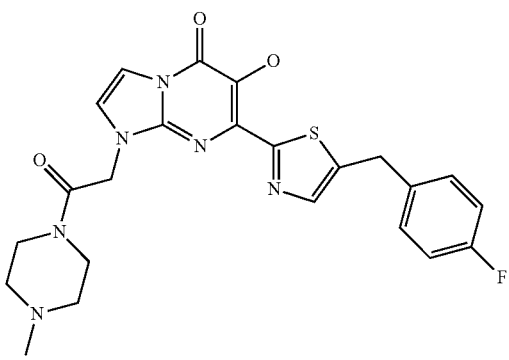

7-[5-(4-Fluoro-benzyl)-thiazol-2-yl]-6-hydroxy-1-[2-(4-methyl-
piperazin-1-yl)-2-oxo-ethyl]-1H-imidazo[1,2-a]
pyrimidin-5-one -continued

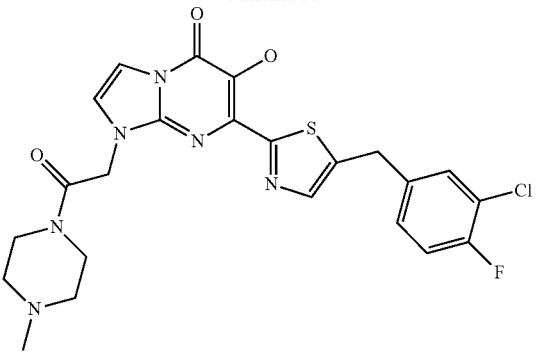

7-[5-(3-Chloro-4-fluoro-benzyl)-thiazol-2-yl]-6-hydroxy-1-
[2-(4-methyl-piperazin-1-yl)-2-oxo-ethyl]-1H-imidazo[1,2-a]
pyrimidin-5-one

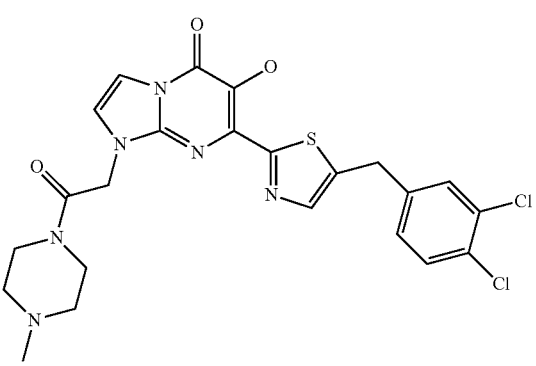

7-[5-(3,4-Dichloro-benzyl)-thiazol-2-yl]-6-hydroxy-1-[2-(4-methyl-
piperazin-1-yl)-2-oxo-ethyl]-1H-imidazo[1,2-a]
pyrimidin-5-one

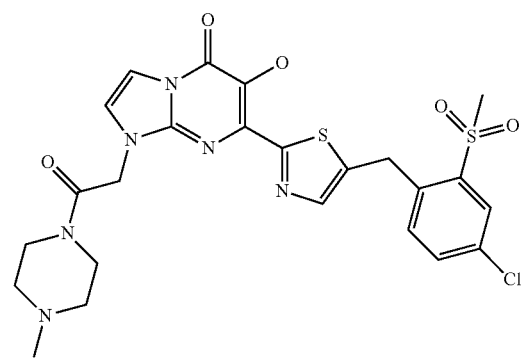

7-[5-(4-Fluoro-2-methanesulfonyl-benzyl)-thiazol-2-yl]-6-
hydroxy-1-[2-(4-methyl-piperazin-1-yl)-2-oxo-ethyl]-
1H-imidazo[1,2-a]pyrimidin-5-one 13
-continued

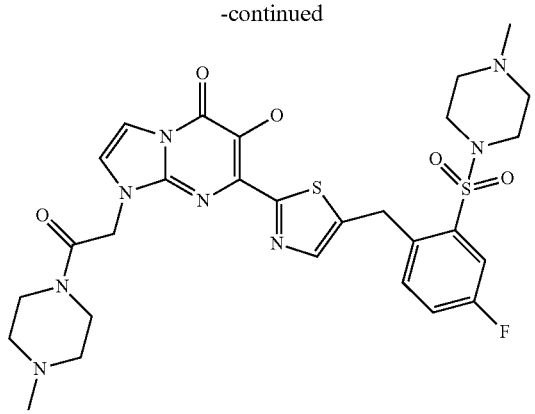

7-{5-[4-Fluoro-2-(4-methyl-piperazine-1-sulfonyl)-benzyl]-thiazol-
2-yl}-6-hydroxy-1-[2-(4-methyl-piperazin-1-yl)-2-oxo-ethyl]-
1H-imidazo[1,2-a]pyrimidin-5-one 5-Fluoro-2-(2-{6-hydroxy-1-[2-(4-methyl-piperazin-1-yl)-2-
oxo-ethyl]-5-oxo-1,5-dihydro-imidazo[1,2-a]pyrimidin-7-yl}-
thiazol-5-ylmethyl)-N,N-dimethyl-benzenesulfonamide

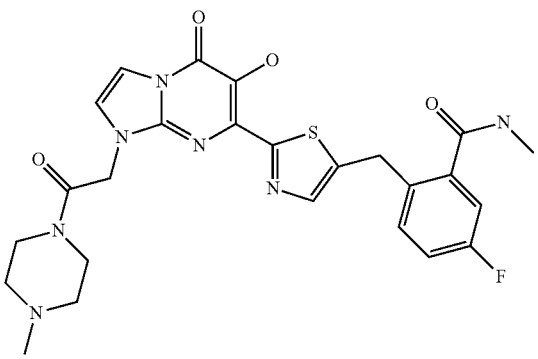

5-Fluoro-2-(2-{6-hydroxy-1-[2-(4-methyl-piperazin-1-yl)-2-
oxo-ethyl]-5-oxo-1,5-dihydro-imidazo[1,2-a]pyrimidin-7-yl}-
thiazol-5-ylmethyl)-N-methyl-benzamide 14
-continued

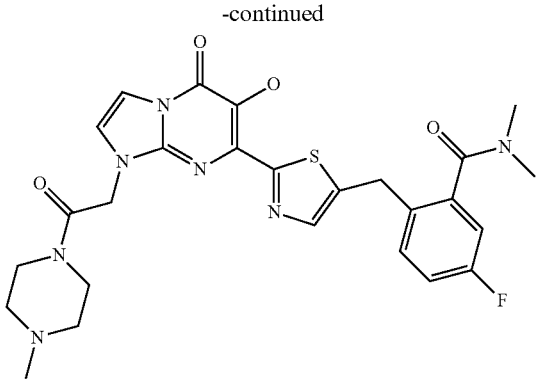

5-Fluoro-2-(2-{6-hydroxy-1-[2-(4-methyl-piperazin-1-yl)-2-
oxo-ethyl]-5-oxo-1,5-dihydro-imidazo[1,2-a]pyrimidin-7-yl}-
thiazol-5-ylmethyl)-N,N-dimethyl-benzamide 7-{5-[4-Fluoro-2-(4-methyl-piperazin-1-carbonyl)-benzyl]-thiazol-2-
yl}-6-hydroxy-1-[2-(4-methyl-piperazin-1-yl)-2-oxo-ethyl]-1H-
imidazo[1,2-a]pyrimidin-5-one 7-{5-[4-Fluoro-2-(5-methyl-1,1-dioxo-1lambda*6*-
[1,2,5]thiadiazolidin-2-yl)-benzyl]-thiazol-2-yl}-6-hydroxy-1-
[2-(4-methyl-piperazin-1-yl)-2-oxo-ethyl]-1H-imidazo
[1,2-a]pyrimidin-5-one

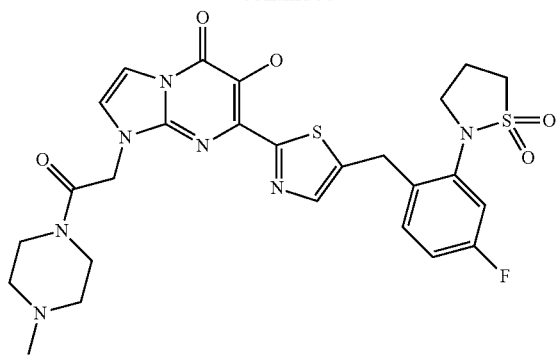

7-{5-[2-(1,1-Dioxo-1lambda*6*-isothiadiazolidin-2-yl)-
4-fluoro-benzyl]-thiazol-2-yl}-6-hydroxy-1-
[2-(4-methyl-piperazin-1-yl)-2-oxo-ethyl]-
1H-imidazo[1,2-a]pyrimidin-5-one

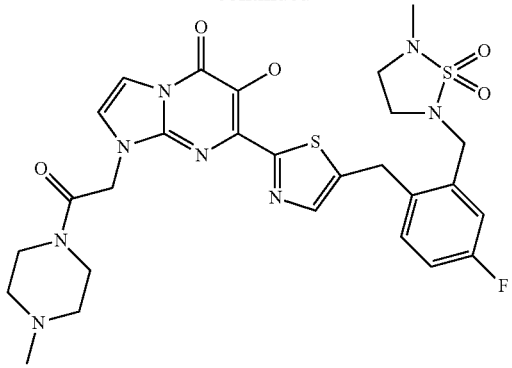

7-{5-[4-Fluoro-2-(5-methyl-1,1-dioxo-1lambda*6*-
[1,2,5]thiadiazolidin-2-ylmethyl)-benzyl)-thiazol-2-yl}-
6-hydroxy-1-[2-(4-methyl-piperazin-1-yl)-2-oxo-ethyl]-
1H-imidazo[1,2-a]pyrimidin-5-one

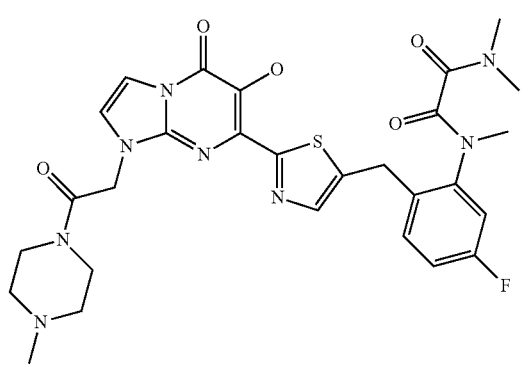

N-[5-Fluoro-2-(2-{6-hydroxy-1-[2-(4-methyl-piperazin-1-yl)-
2-oxo-ethyl]-5-oxo-1,5-dihydro-imidazo[1,2-a]pyrimidin-
7-yl}-thiazol-5-ylmethyl)-phenyl]-N,N',N'-trimethyl-oxalamide

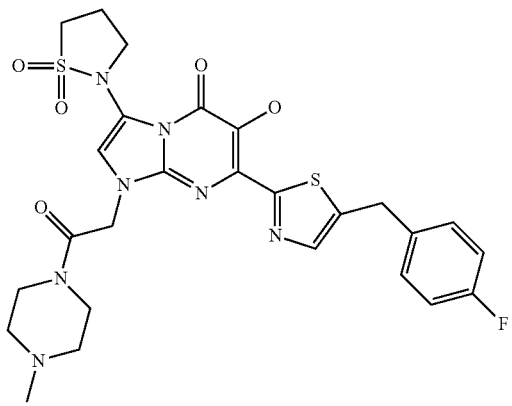

3-(1,1-Dioxo-1lambda*6*-isothiazolidin-2-yl)-7-
[5[(4-fluoro-benzyl)-thiazol-2-yl]-6-hydroxy-1-
[2-(4-methyl-piperazin-1-yl)-2-oxo-ethyl]-
1H-imidazo[1,2-a]pyrimidin-5-one

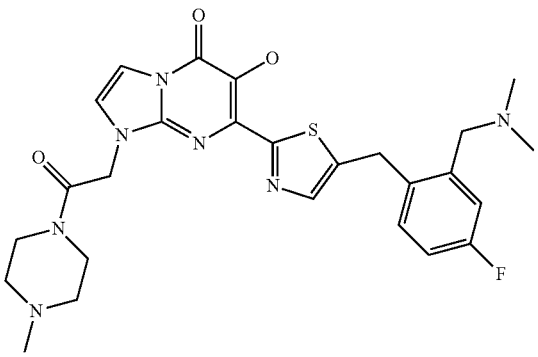

7-[5-(2-Dimethylaminomethyl-4-fluoro-benzyl)-thiazol-2-yl]-
6-hydroxy-1-[2-(4-methyl-piperazin-1-yl)-2-oxo-ethyl]-
1H-imidazo[1,2-a]pyrimidin-5-one

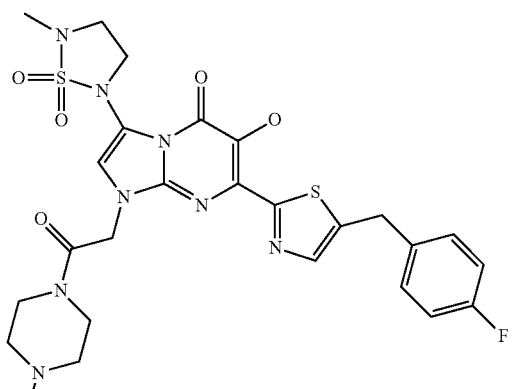

7-(5-(4-Fluoro-benzyl)-thiazol-2-yl]-6-hydroxy-3-(5-
methyl-1,1-dioxo-1lambda*6*-[1,2,5]thiadiazolidin-2-yl)-
1-[2-(4-methyl-piperazin-1-yl)-2-oxo-ethyl]-1H-
imidazo[1,2-a]pyrimidin-5-one -continued

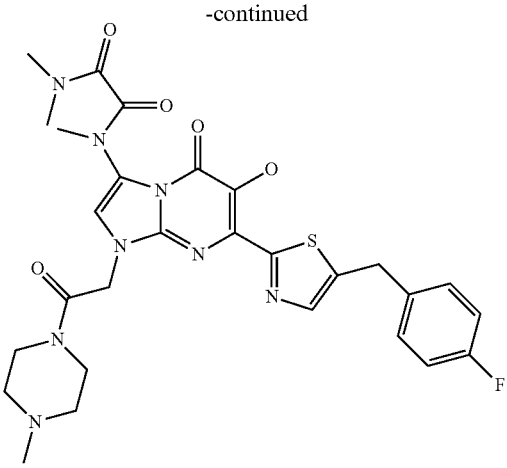

N-{7-(5-(4-Fluoro-benzyl)-thiazol-2-yl]-6-hydroxy-1-
[2-(4-methyl-piperazin-1-yl)-2-oxo-ethyl]-5-oxo-
1,5-dihydro-imidazo[1,2-a]pyrimidin-3-yl}-
N,N',N'-trimethyl-oxalamide Further preferred are compounds of Formula (I) as set out in the examples.

As used herein, the term "halo" or "halogen" refers to fluorine (fluoro), chlorine (chloro), bromine (bromo) or iodine (iodo).

As used herein, the terms "alkyl" and "alkylene" either used alone or in compound terms such as NH(alkyl) or N(alkyl)$_2$, refer respectively to monovalent and divalent straight chain or branched hydrocarbon groups, having 1 to 3, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

As used herein, the term "alkenyl" refers to a straight chain or branched hydrocarbon groups having one or more double bonds between carbon atoms. Suitable alkenyl groups include, but are not limited to, ethenyl, allyl, propenyl, isopropenyl, butenyl, pentenyl and hexenyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include, O, N and S. Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, 2,2'-dimethyl[1,3]-dioxolanyl, tetrahydrofuranyl, tetrahydropyranyl, tetrahydropyrrolyl etc.

The term "heteroaryl" includes a 5- or 6-membered heteroaromatic ring containing one or more heteroatoms selected from O, N and S. Suitable examples of heteroaryl groups include furanyl, thiophenyl, tetrazolyl, 1,2,3-triazolyl, 1,2,4-triazolyl, imidazolyl, pyrazolyl, pyridinyl, pyrimidinyl, oxazolyl, oxadiazolyl, thioazolyl, thiodiazolyl etc. The heteroaromatic ring may be fused to a 5- or 6-membered aromatic or heteroaromatic ring to form a bicyclic aromatic ring system eg benzofuran.

Unless otherwise stated, each alkyl, alkylene, cycloalkyl, alkylaryl, aryl, heterocyclyl, or heteroaryl group may be optionally substituted with one or more of $C_1$-$C_3$alkyl, $C_3$-$C_6$cycloalkyl, $C_6$aryl, heterocyclyl, heteroaryl, $C_1$-$C_3$alkylOH, alkylaryl, OH, O$C_1$-$C_3$alkyl, halo, CN, NO$_2$, CO$_2$H, CO$_2$$C_1$-$C_3$alkyl, CONH$_2$, CONH($C_1$-$C_3$alkyl), CON($C_1$-$C_3$alkyl)$_2$, trifluoromethyl, NH$_2$, NH($C_1$-$C_3$alkyl) or N($C_1$-$C_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

Examples of optional substituents also include suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an antibacterially active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1$^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid This invention also encompasses pharmaceutical compositions containing prodrugs of compounds of formula I. This invention also encompasses methods of treating or preventing a viral infection in a subject by administering prodrugs of compounds of the formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

Preferably, the viral infection of the second and third aspects is a HIV or SIV infection.

More preferably, the HIV or SIV infection comprises a viral strain resistant to other integrase inhibitors such as Isentrass (raltregavir, MK-0158) or elvitegravir. Even more preferably, the viral strain comprises HIV integrase enzyme containing the Q148H/G140S double mutation, N155H/E92Q double mutation, the F121Y/T124K double mutation or the Q148K/G140A/E138A triple mutation.

In a preferred form of the second and third aspects of the present invention, the compound of formula (I) is co-administered with Raltegravir. The compound of formula (I) can be administered simultaneously with Raltegravir, or the compound of formula (I) can be administered before or after the administration of Raltegravir provided they are in the same course of treatment as would be understood by the person skilled in the art.

In a fourth aspect, the present invention provides pharmaceutical composition comprising a compound according to the first aspect and a pharmaceutically acceptable carrier, diluent or excipient.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated.

However, the method can also be practiced in other species, such as avian species (e.g., chickens).

The term "effective amount" means the amount of the subject composition that will elicit the biological or medical response of a tissue, system, animal or human that is being sought by the researcher, veterinarian, medical doctor or other clinician.

As would be understood by those skilled in the art of treating viral infections, and particularly HIV infections, the term "treatment" does not necessarily mean that the viral infection is completely cured. The term "treatment" encompasses any reduction in the viral load and/or inhibition of replication in the subject being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require HIV inhibition or HIV integrase enzyme inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood preferred forms thereof will now be described by reference to the following non-limiting Examples.

1. ROUTES OF SYNTHESIS

1.1 For Core Formation

Scheme 1: Preparation of the pyrimidinone bicyclic system

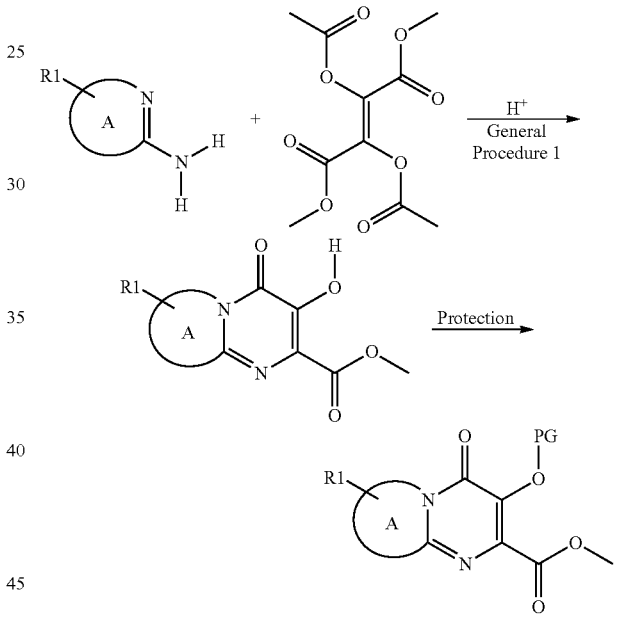

General Procedure 1: Adaption of Organic Preparations and Procedures International, 22(4), 1990, 532-534

International Patent Application No. PCT/AU2007/001980 in the name of Avexa.

The amino compound can be reacted as in scheme 1 with the fumarate derivative or suitable analogues of fumarate where for example the acetyl groups can be replaced by other suitable leaving groups such as tosyl or mesyl. The reaction can be carried out in a suitable solvent such as methanol, DME, DMA, DMSO, chloroform, THF or dioxane. The reaction can be heated or subject to microwave irradiation (see for example B. R. Roberts & C. R. Strauss, Acc. Chem. Res. 2005, 38, 653-661, "Toward Rapid, 'Green' Predictable Microwave-assisted Synthesis"). The reaction can be performed in the absence or presence of catalytic amounts of acid or base.

1.2 Generic Schemes: Azole Formation 1.2.1 For H1=1,3-oxazole and 1,3-thiazole, and imidazole:

Scheme 2: Preparation of the 1,3-oxazole and 1,3-thiazole via Gabriel or Robinson-Gabriel method

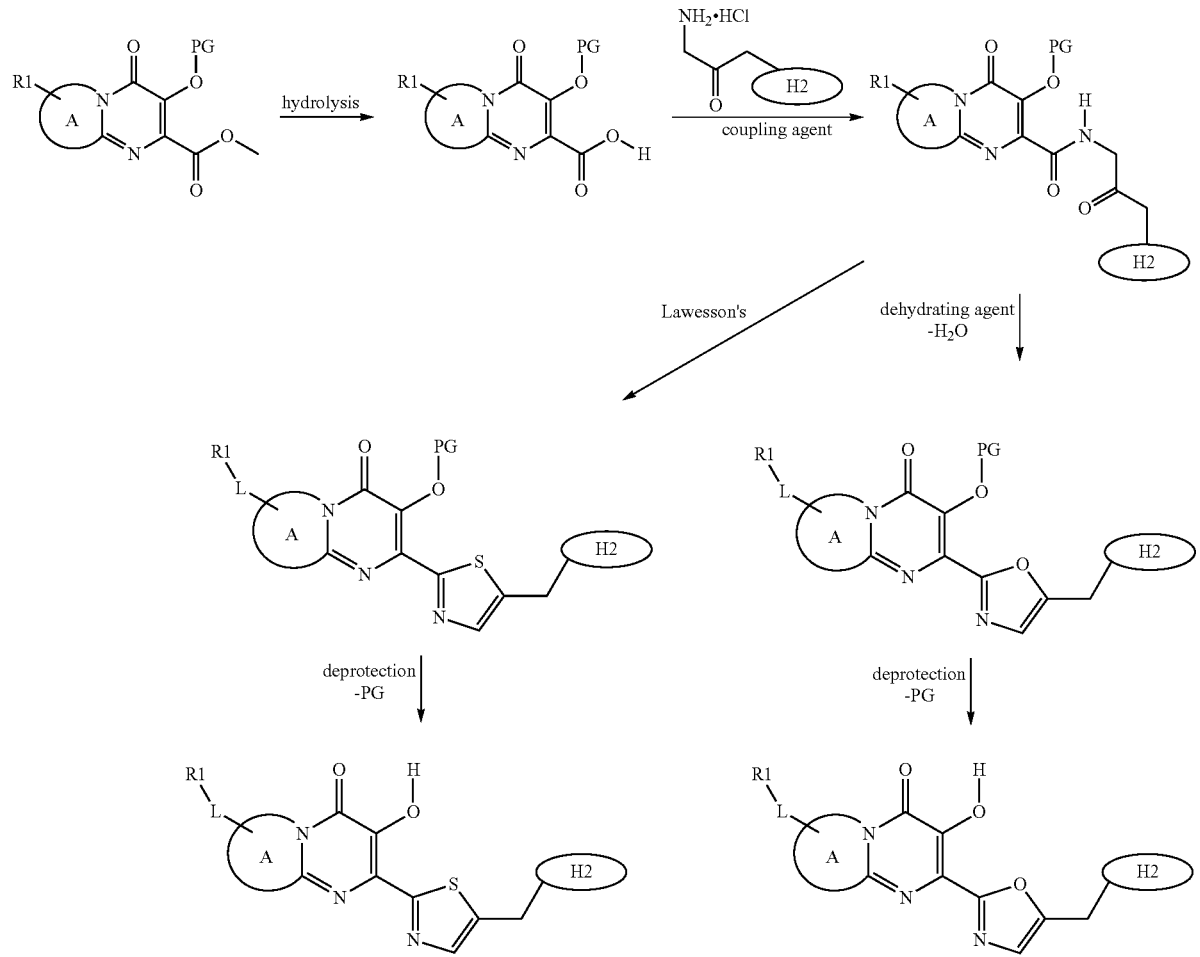

1. International Patent Application No. PCT/AU2007/001980 in the name of Avexa.
2. Editor R. R. Gupta, Microwave-Assisted Synthesis of Heterocycles, Springer Berlin/Heidelberg. ISSN: 1861-9282 (Print) 1861-9290 (Online), 2006

Scheme 3: Preparation of the imidazole

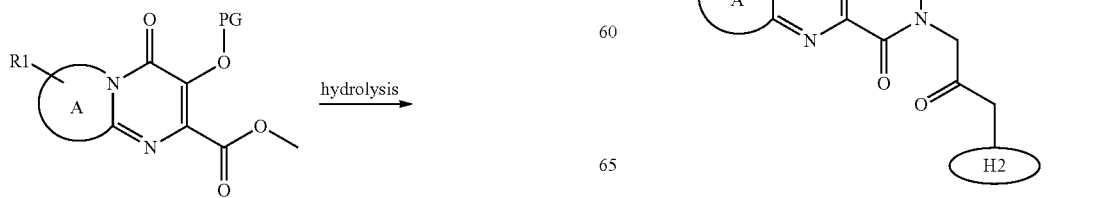

-continued

-continued

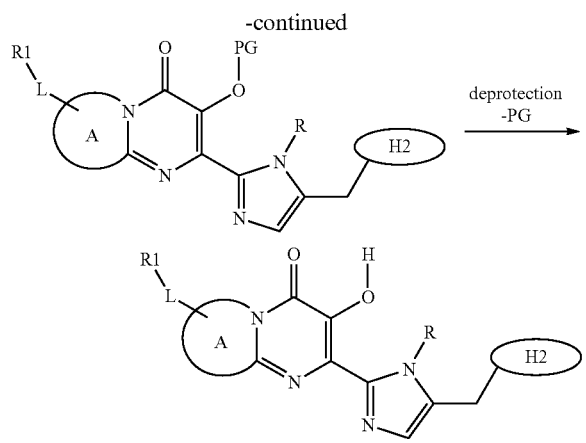

Editor R. R. Gupta, Microwave-Assisted Synthesis of Heterocycles, Springer Berlin/Heidelberg. ISSN: 1861-9282 (Print) 1861-9290 (Online), 2006

Scheme 4: Preparation of the 1,3-thiazole via Hantzsch method

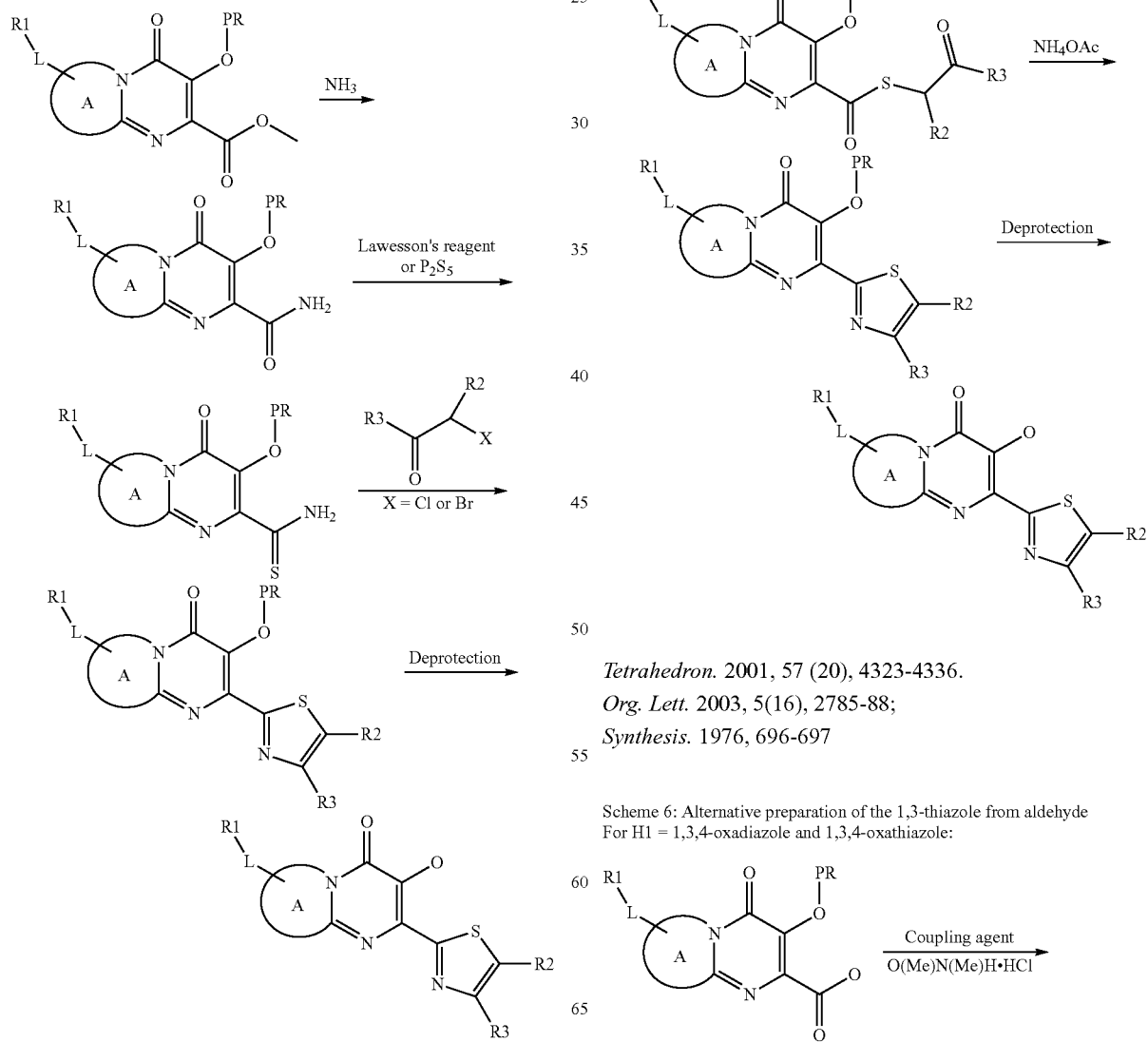

1. Wawzonek, O., In; Heterocyclic Compounds, John Wiley and Sons, New York, 1975.
2. Tetrahedron Letters, 1994, 35(16), 2473-2476
3. *Bioorg. Med. Chem. Chem. Lett.* 2003, 13(24), 4467-72.

Scheme 5: Alternative preparation of the 1,3-thiazole

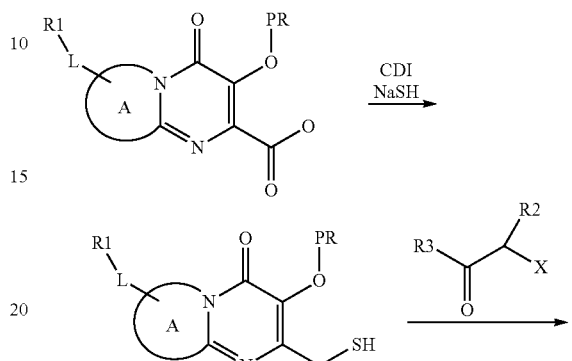

*Tetrahedron.* 2001, 57 (20), 4323-4336.
*Org. Lett.* 2003, 5(16), 2785-88;
*Synthesis.* 1976, 696-697

Scheme 6: Alternative preparation of the 1,3-thiazole from aldehyde
For H1 = 1,3,4-oxadiazole and 1,3,4-oxathiazole:

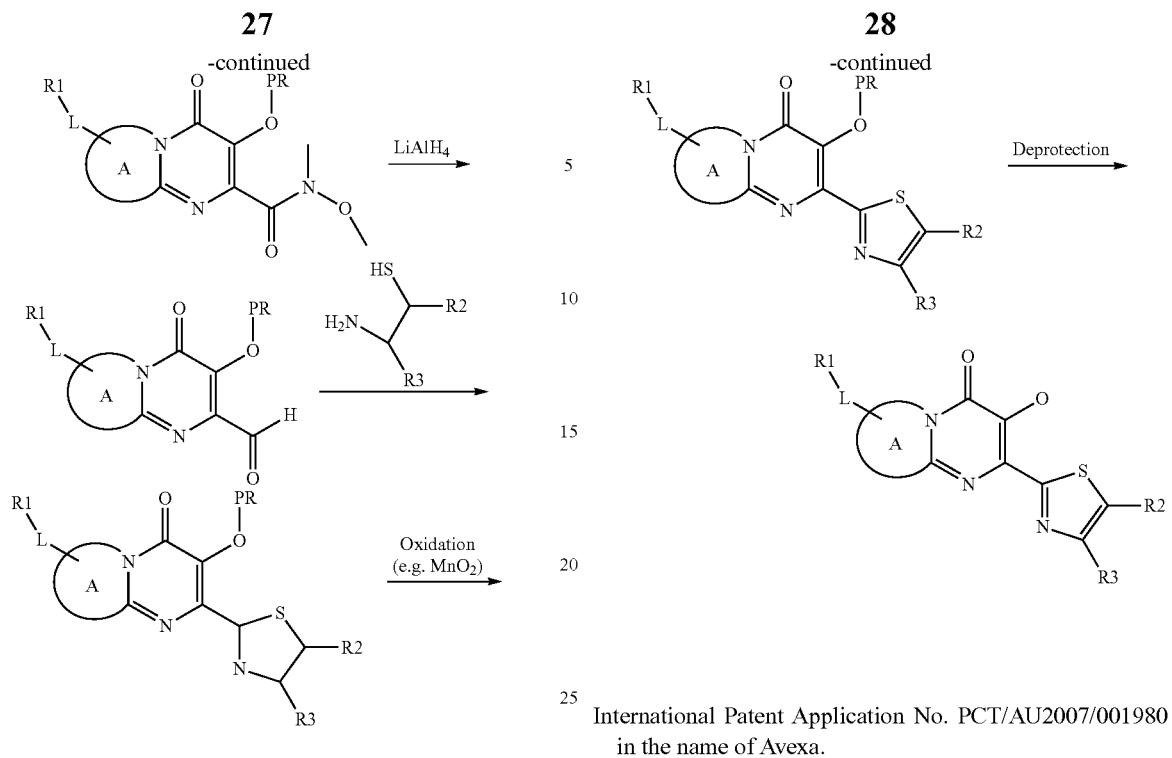
International Patent Application No. PCT/AU2007/001980 in the name of Avexa.
Scheme 7: Preparation of the 1,3,4-oxadiazole and 1,3,4-thiadiazole
For H1 = 1,2,4-oxadiazole
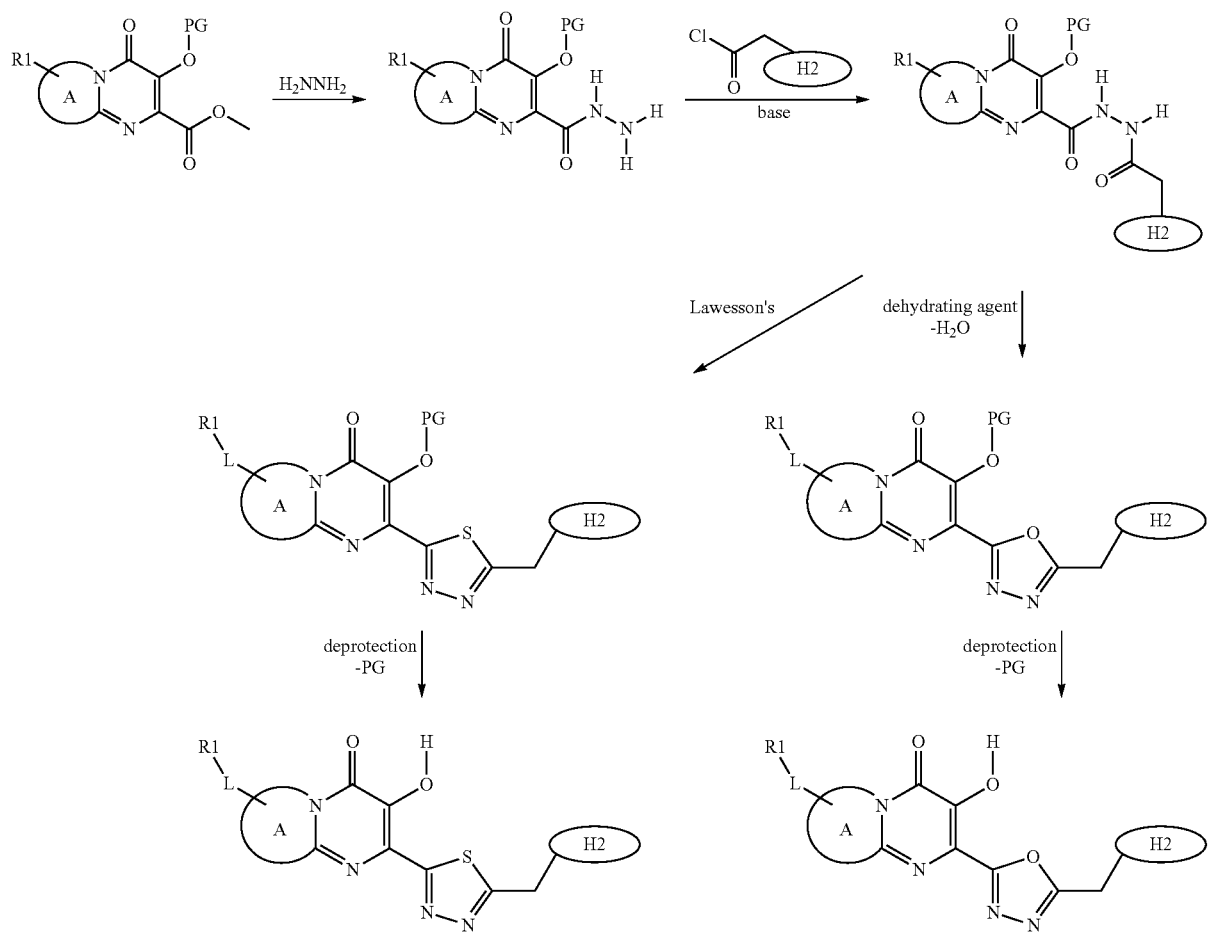

Scheme 8: Preparation of the 1,2,4-oxadiazole
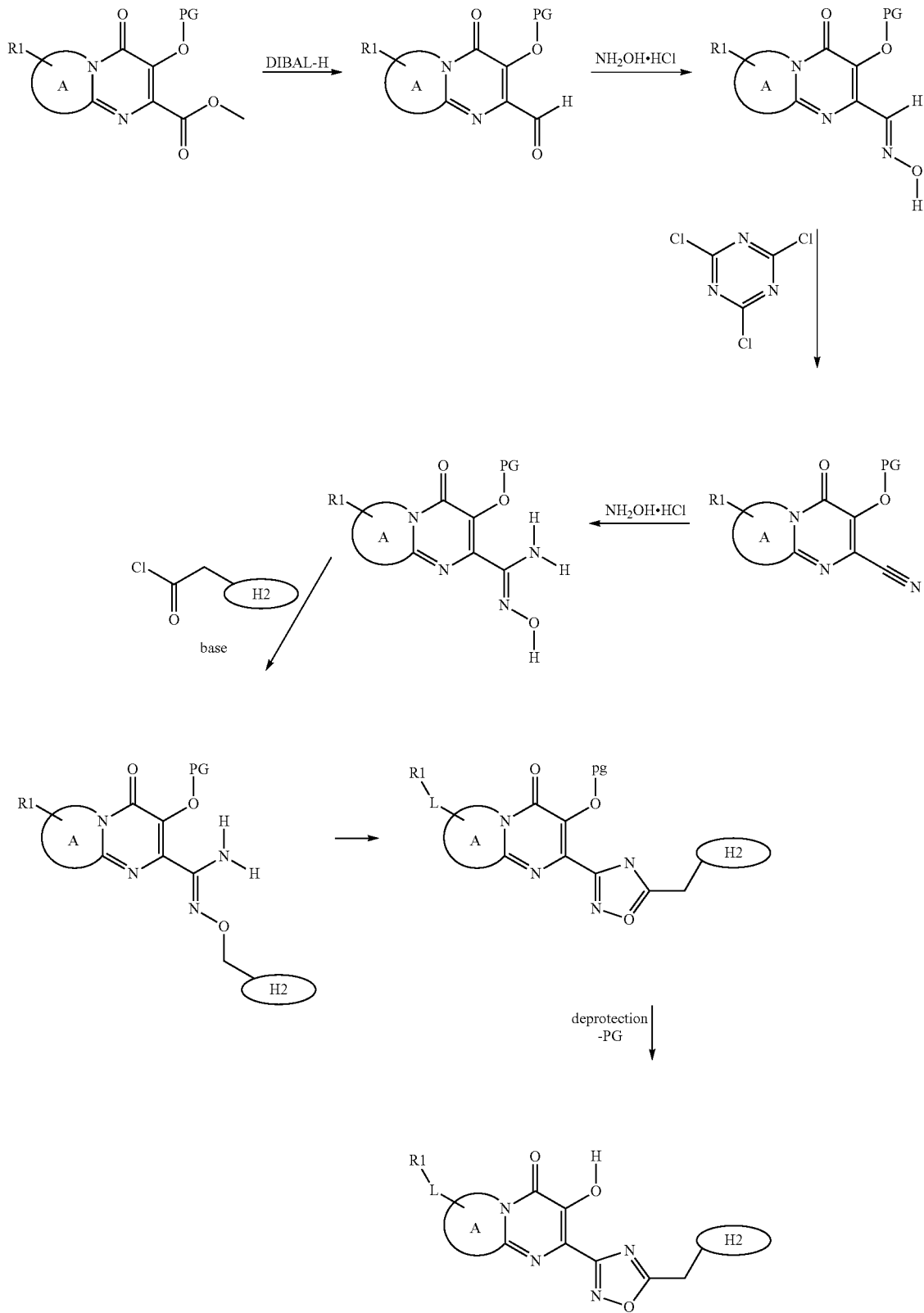

International Patent Application No. PCT/AU2007/001980 in the name of Avexa.

Scheme 9: Preparation of the 1,2,4-oxadiazole (reversed roles)

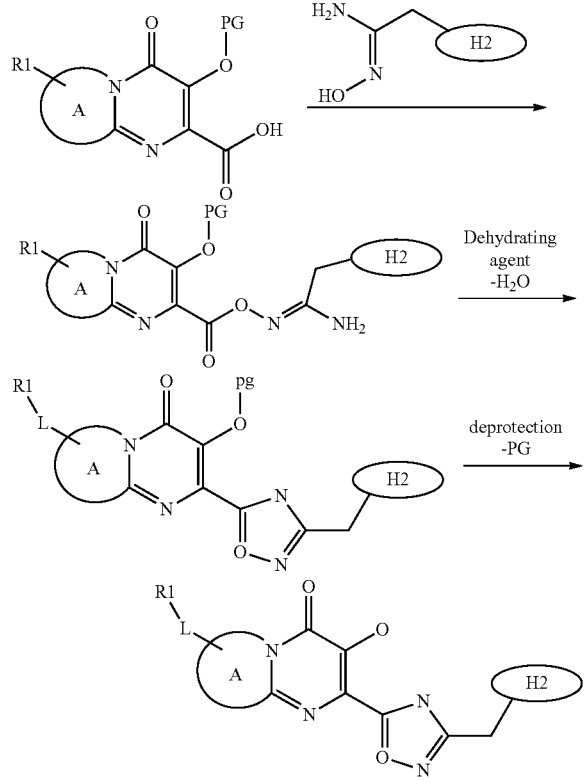

International Patent Application No. PCT/AU2007/001980 in the name of Avexa.

1.3 Generic Schemes: Preparation of Ketoamines

Scheme 10: Preparation of 1-Amino-3-aryl-propan-2-one hydrochloride

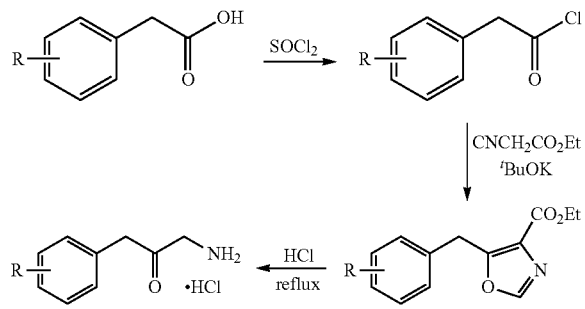

*Tetrahedron*, 1994, 50 (21), 6287-6298 and *Chem. Pharm. Bull.* 1984, 32 (7), 2536-2543

Examples

R=3-F,4-Cl; 3-Cl,4-F
R=4-F; 2,4-Cl$_2$ Avexa's patent
R=4-Cl: known. *Chem. Pharm. Bull.* 1984, 32 (7), 2536-2543
R=2-NO2 known: Tetrahedron 1994, 50(21) 6287-6298

Scheme 11: Alternative preparation of 1-Amino-3-aryl-propan-2-one hydrochloride

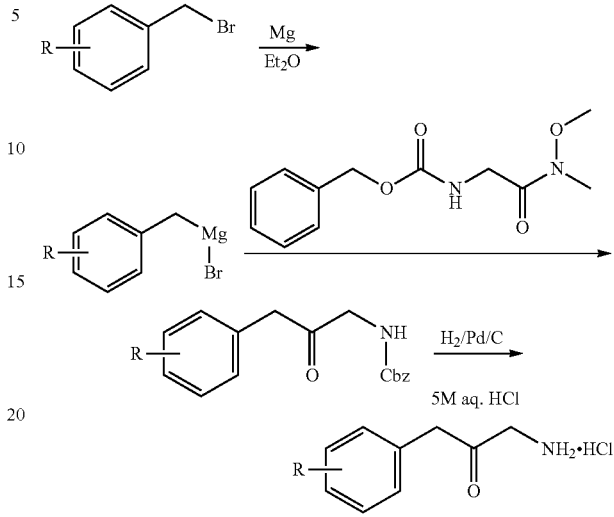

US20040229909; 'Antiviral agent", Shionog

Scheme 12: Alternative preparation of 1-Amino-3-aryl-propan-2-one hydrochloride

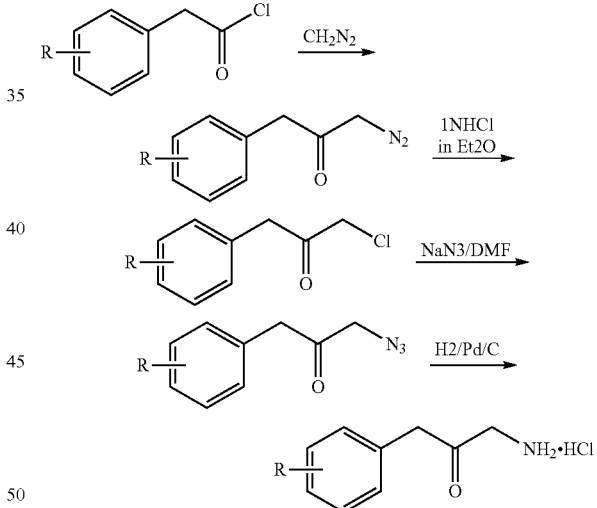

Journal of Organic Chemistry (2003), 68(7), 2798-2802. (for ketoazide from chloroketone)

Scheme 13: Alternative preparation of 1-Amino-3-aryl-propan-2-one hydrochloride

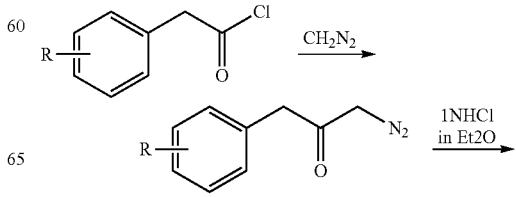

-continued
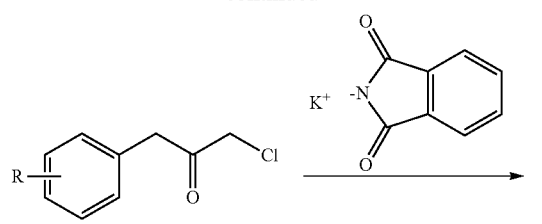
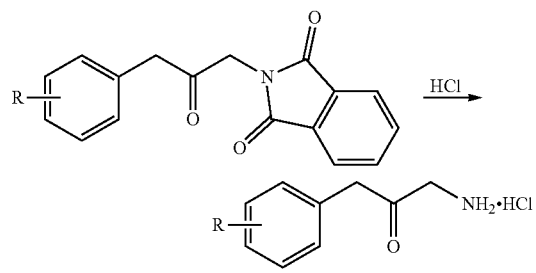
Scheme 14: Preparation of o-ester ketoamine
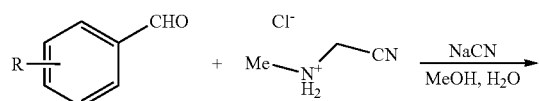
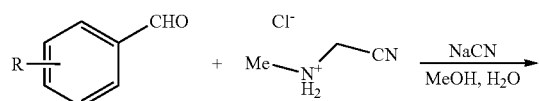
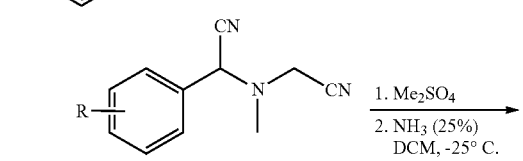
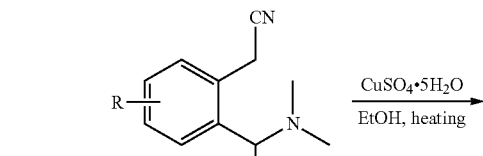
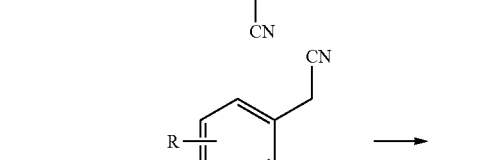
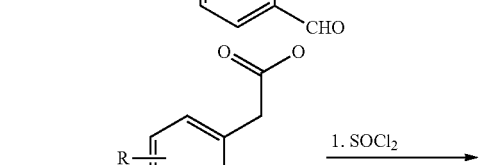
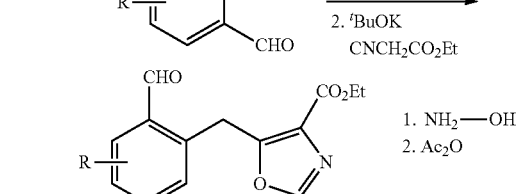
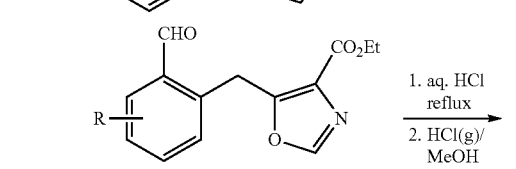
-continued
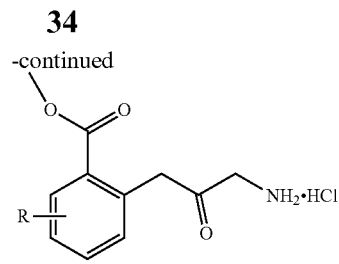
*J. Org. Chem.* 1991, 56(24), 6933-6937
Scheme 15: Preparation of o-aminomethyl ketoamine
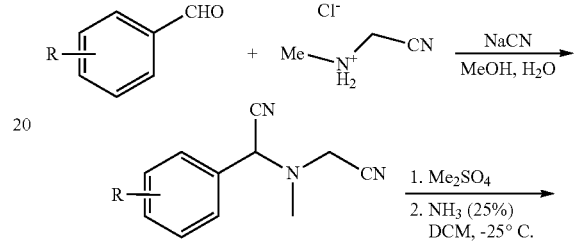
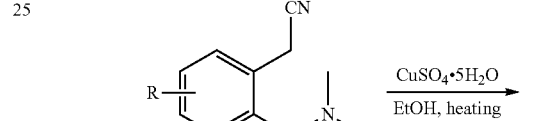
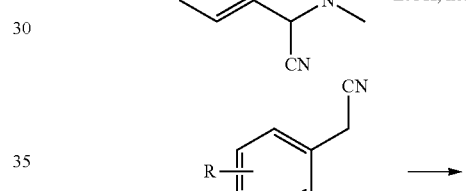
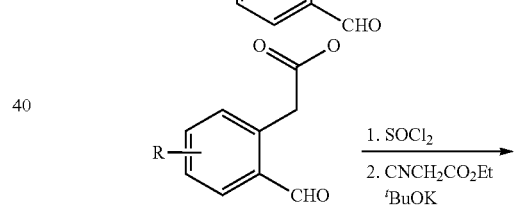
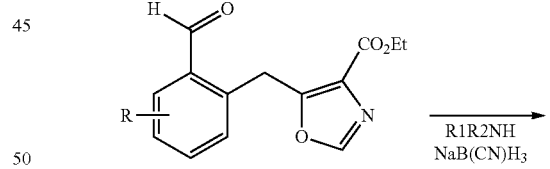
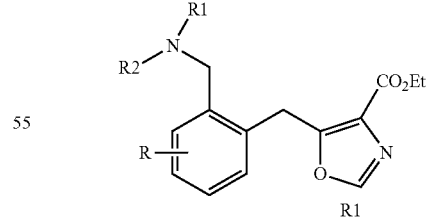
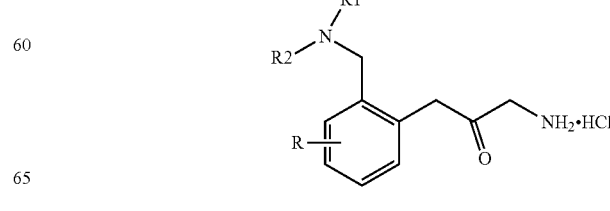

*J. Org. Chem.* 1991, 56(24), 6933-6937
1.4 Generic Schemes: Derivatization
Scheme 16: Derivatization of thiazole-imidazole examples: Variation at position 3 (Metal mediated coupling)
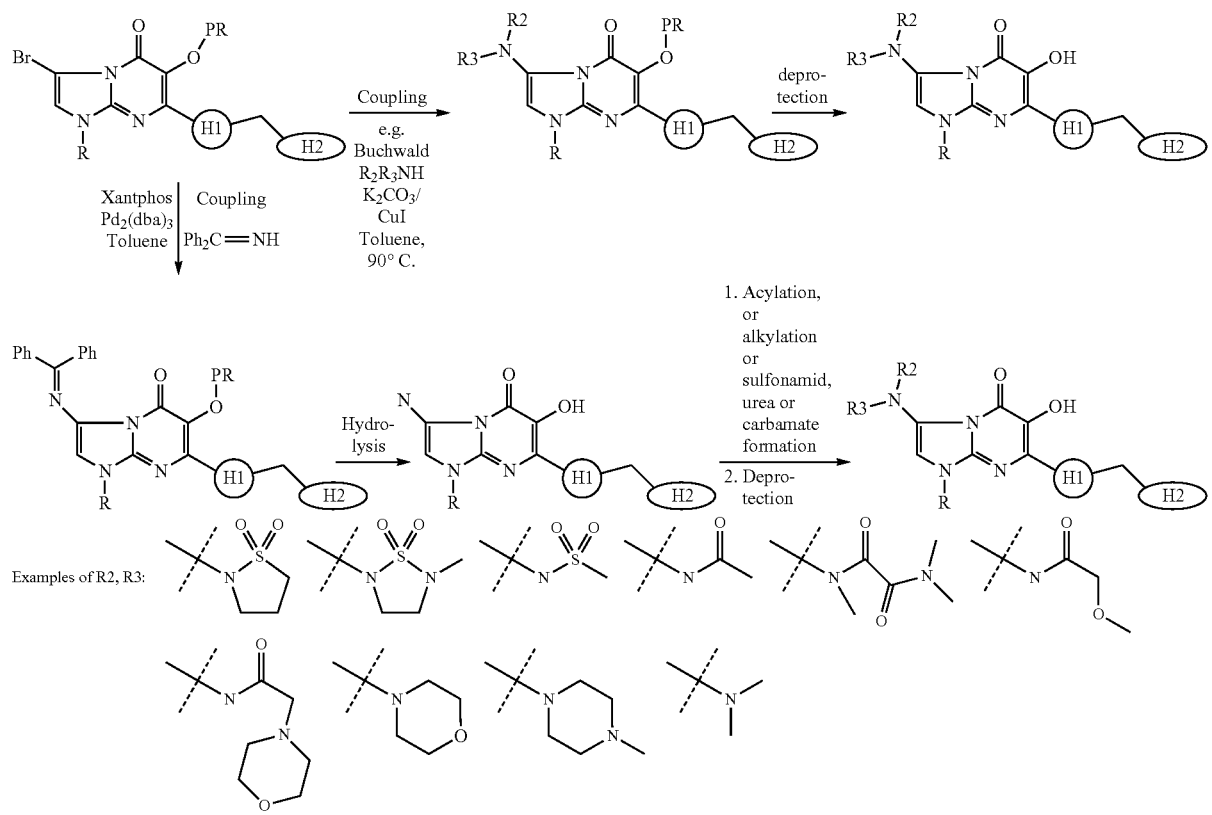
International Patent Application No. PCT/AU2007/001980 in the name of Avexa.
Scheme 17: Derivatization of N-substituents of imidazole
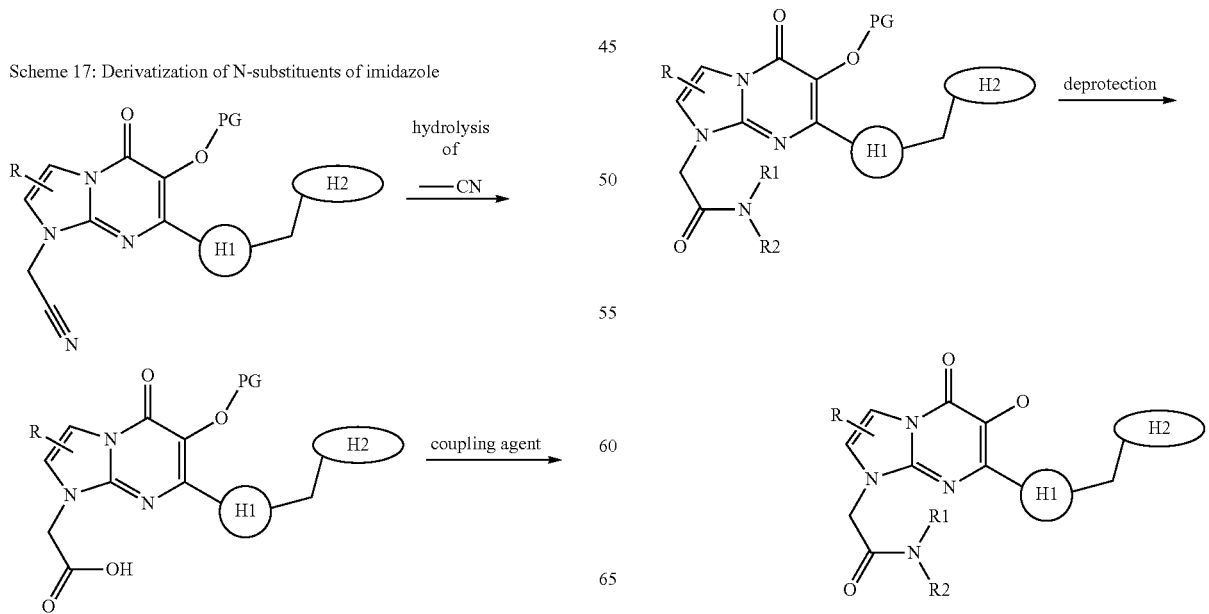

Scheme 18: Derivatization of N-substituents of imidazole
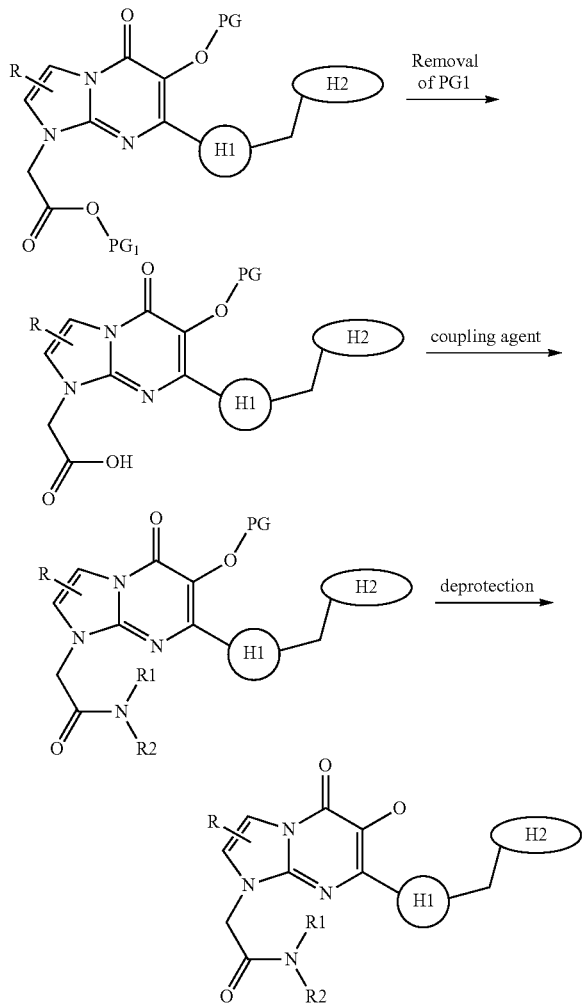
Scheme 19: Derivatization of N-substituents of imidazole
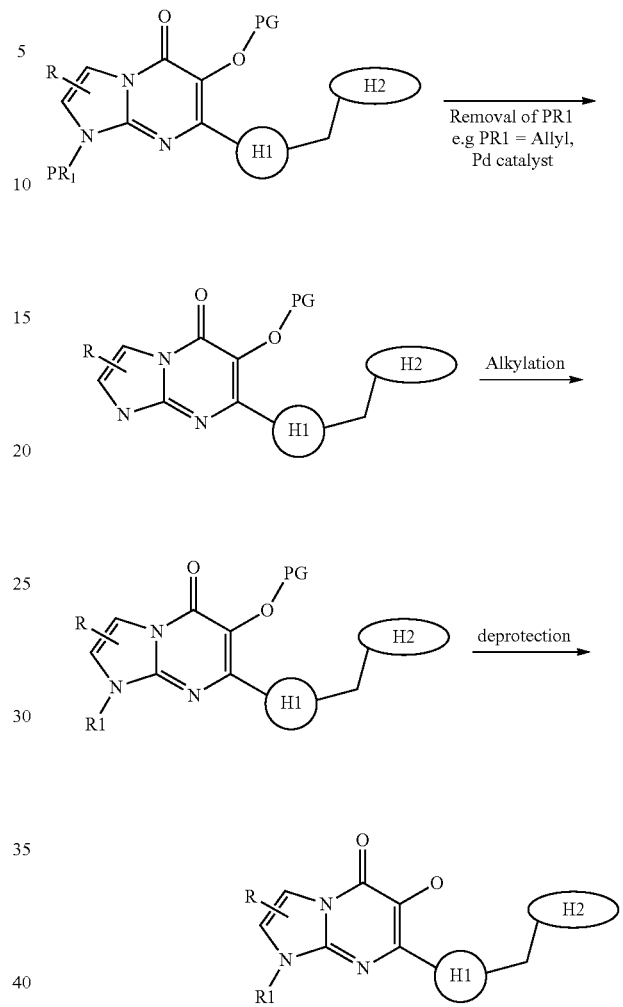
Scheme 20: Derivatization of thiazole-imidazole examples: Variation at position 3 (Vilsmeier reaction)
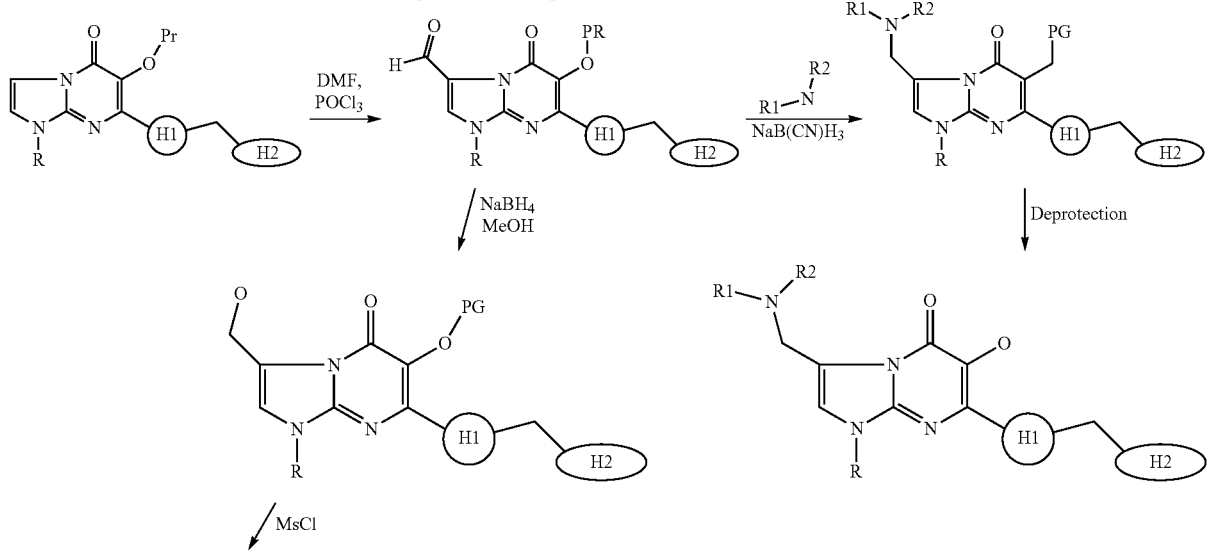

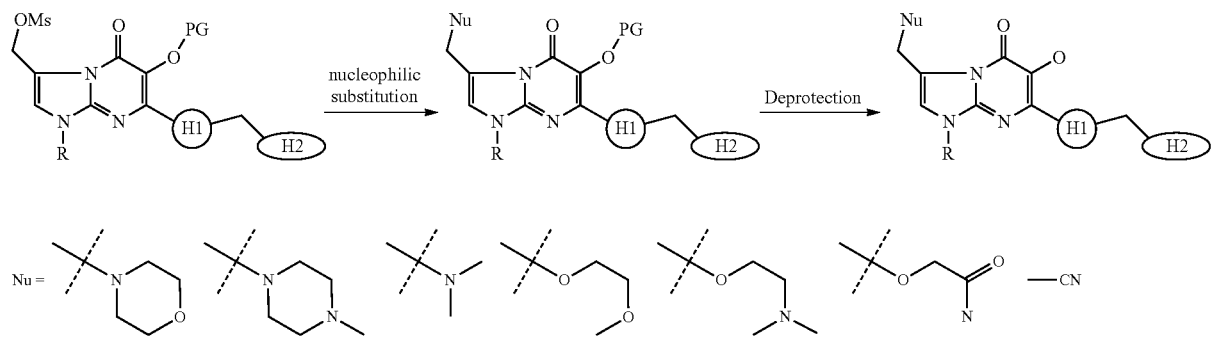
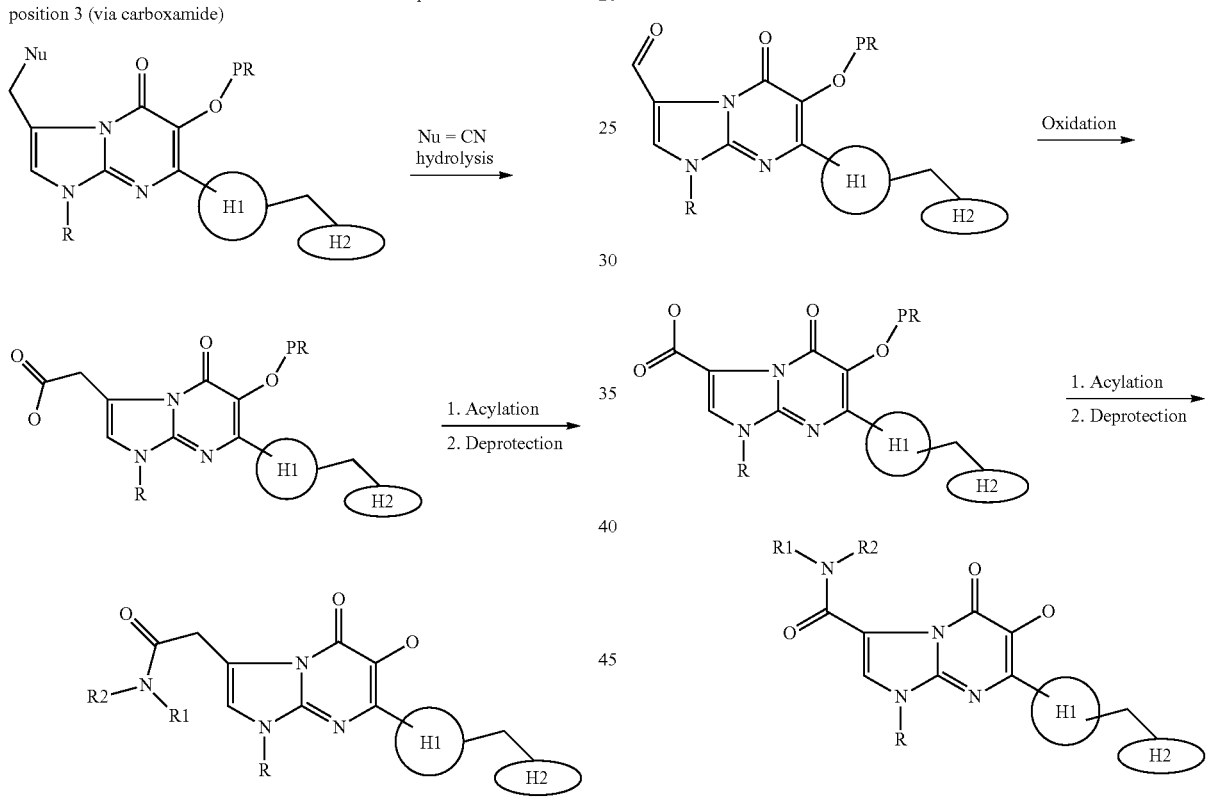
Scheme 21: Derivatization of thiazole-imidazole examples: Variation at position 3 (via carboxamide)
Scheme 22: Derivatization of the aromatic ring: metal mediated couplings with R2R3NH
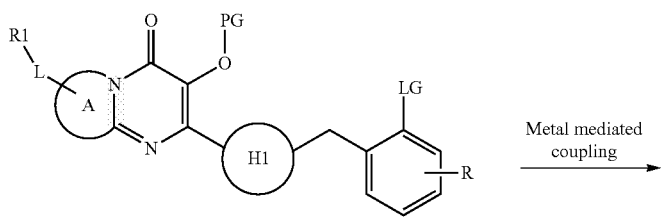
LG (leaving groups) = I, Br, Cl, F, OTf, OMs
R = 0-2 substituents -continued
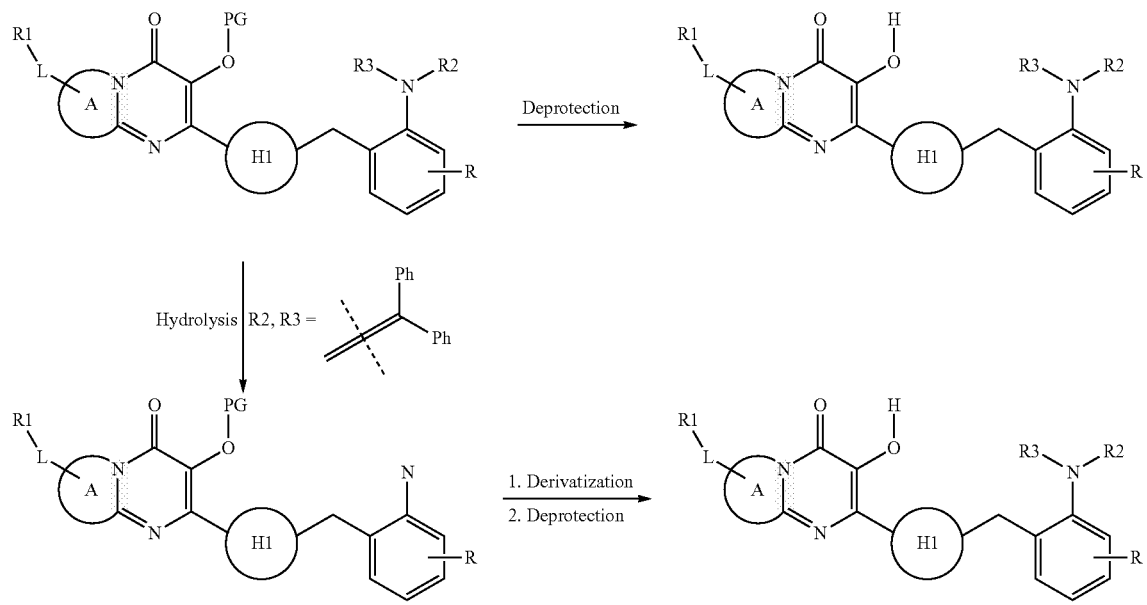
Scheme 23: Derivatization of the aromatic ring: metal mediated couplings with R2XH
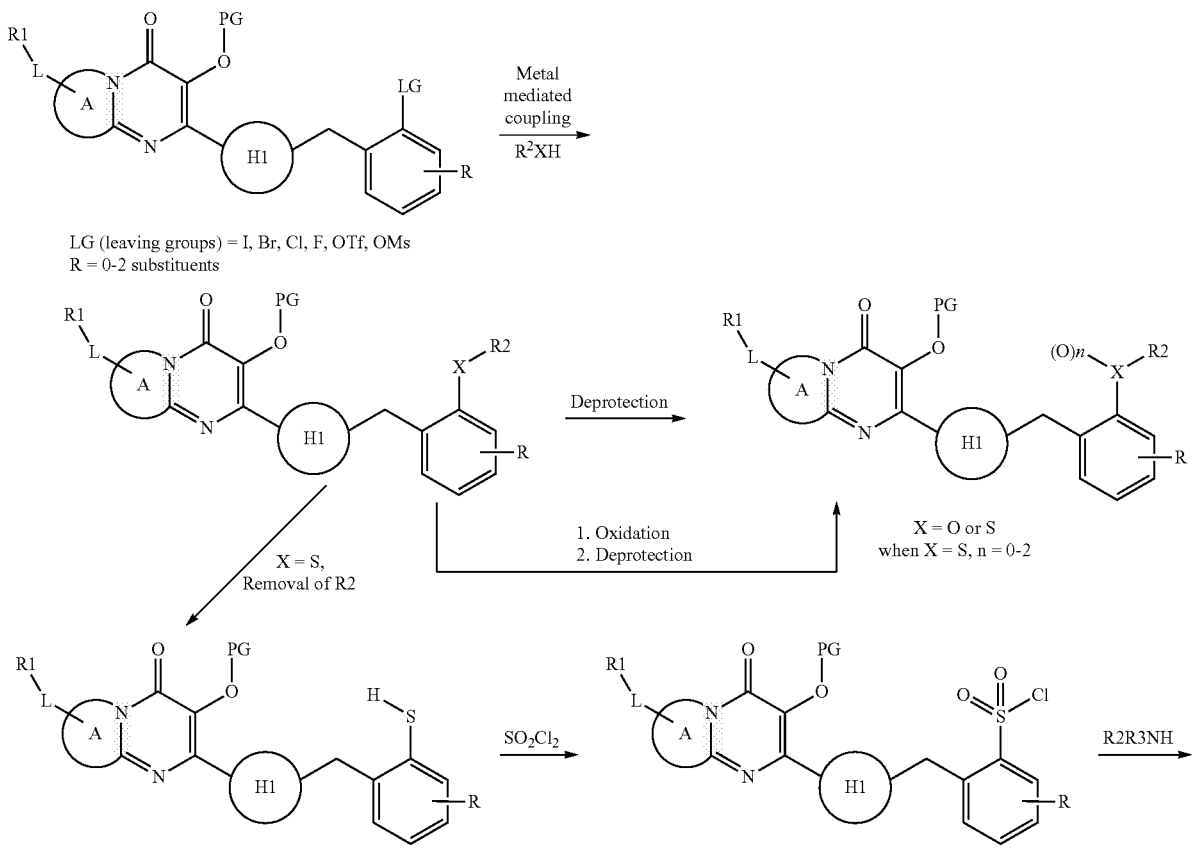
LG (leaving groups) = I, Br, Cl, F, OTf, OMs
R = 0-2 substituents -continued
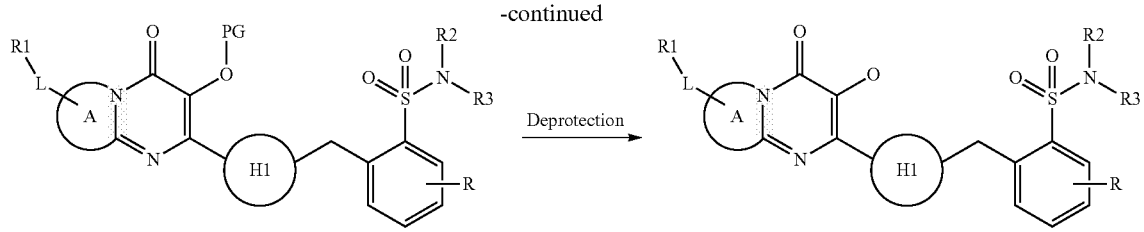
Scheme 24: Derivatization of the aromatic ring: metal mediated couplings with $CO_2$
Scheme 25: Derivatization of the aromatic ring: metal mediated couplings with DMF
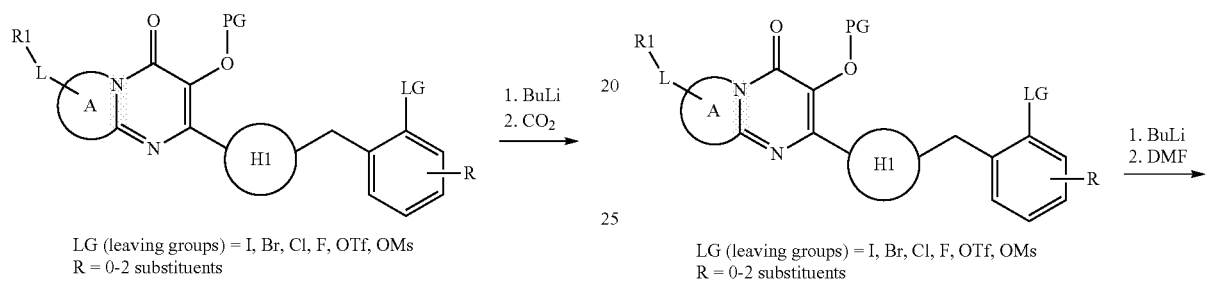
LG (leaving groups) = I, Br, Cl, F, OTf, OMs
R = 0-2 substituents
LG (leaving groups) = I, Br, Cl, F, OTf, OMs
R = 0-2 substituents
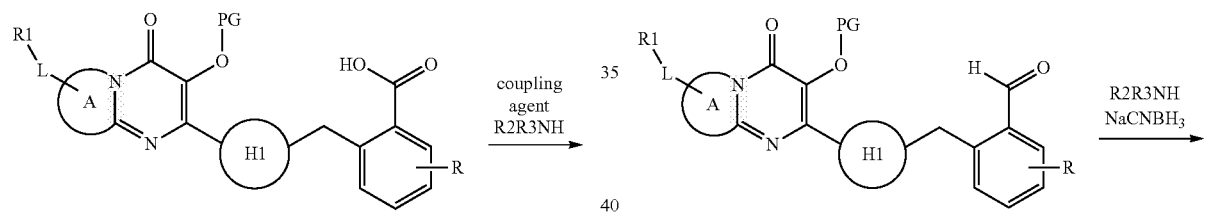
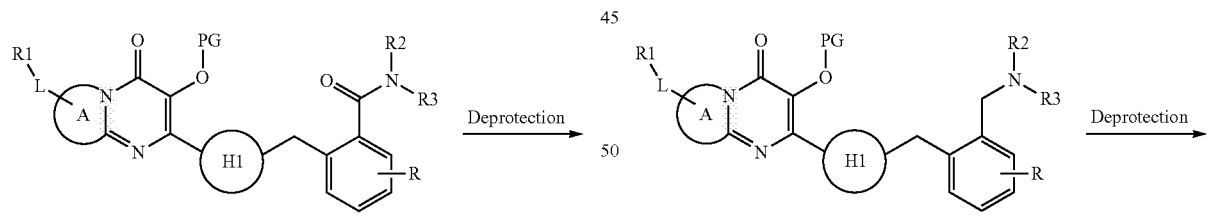
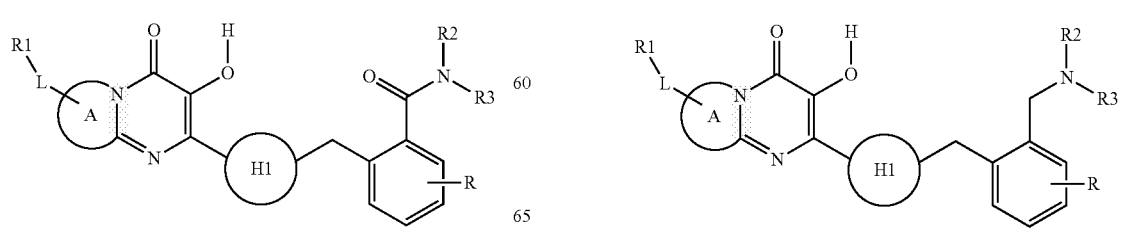

Scheme 26: Derivatization of the aromatic ring: amide formation in ortho position
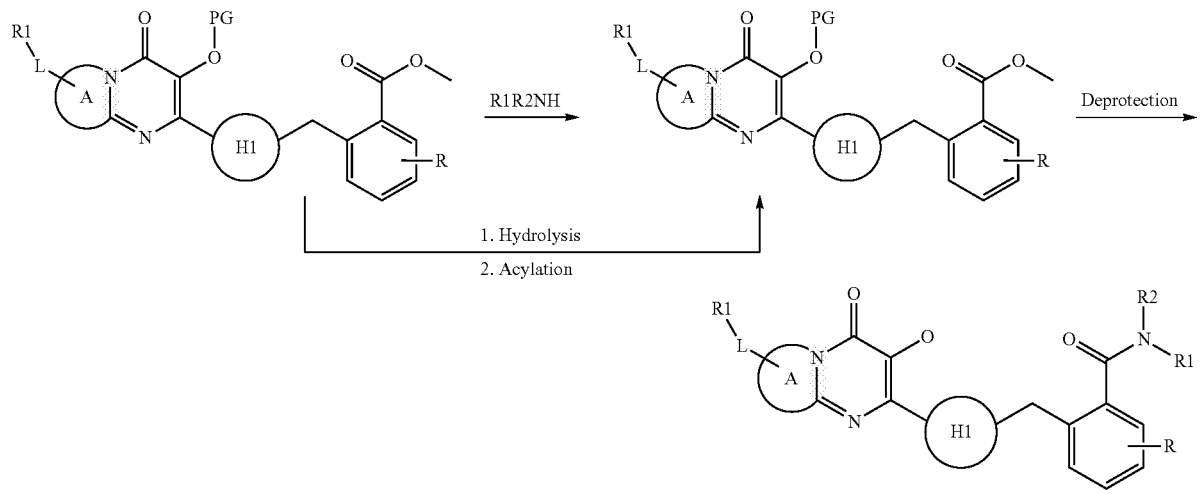
Scheme 27: Derivatization of the aromatic ring: amine in ortho position
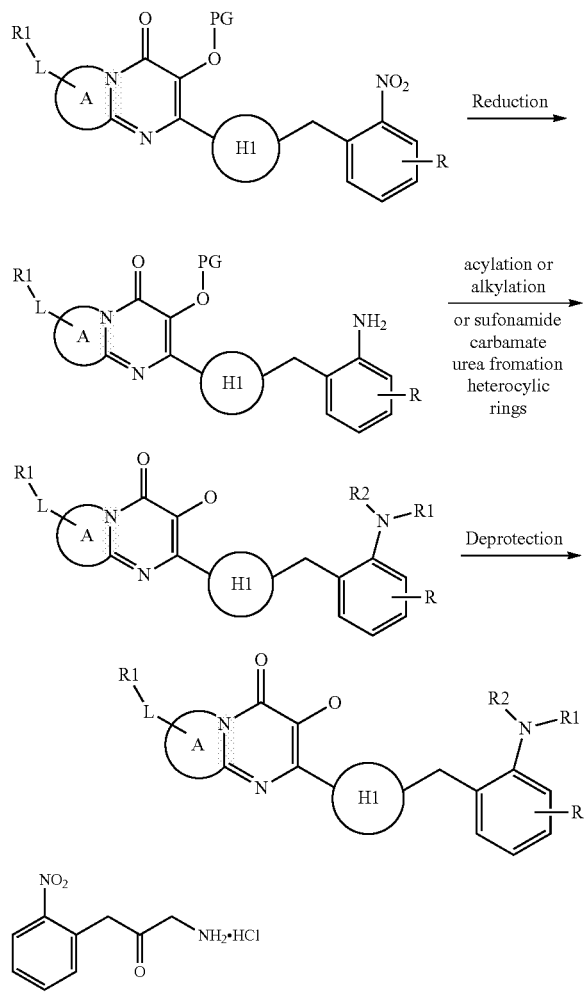
Tetrahedron (1994), 50(21), 6287-98.
Scheme 28: Derivatization of thiazole by coupling
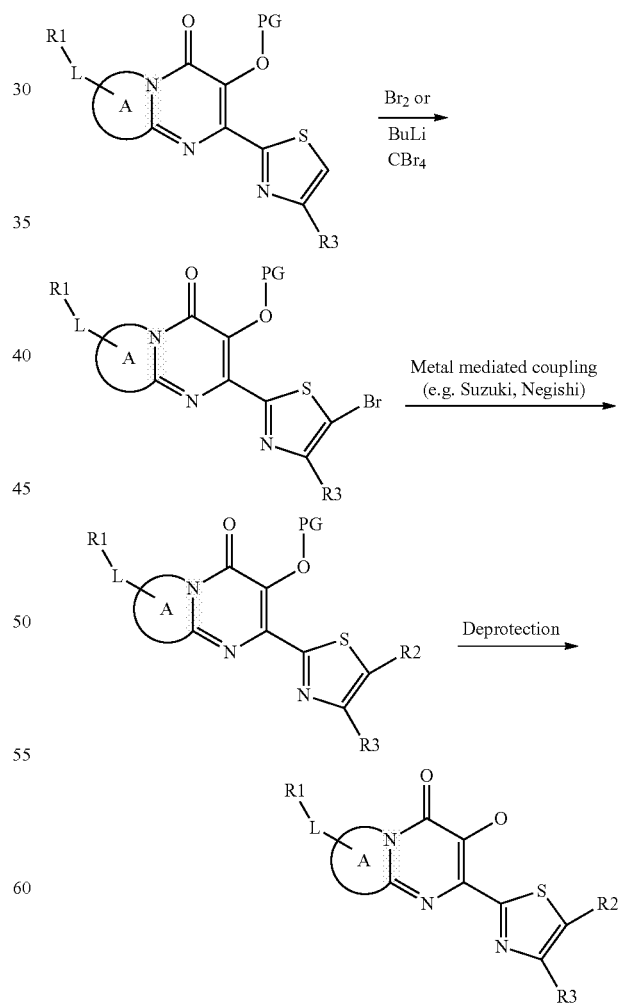

2 SYNTHETIC EXAMPLES

HPLC Conditions

All HPLC measurements were performed on a Varian ProStar System.

Column:

Waters Symmetry® C18 Column (Part No WAT045905) at 25° C., flow rate 1 mL/min, spectra measured at 254 nM Buffers:

Buffer A: 100% acetonitrile, Buffer B: 0.1% aqueous TFA

Gradient: (linear gradient curve 6)

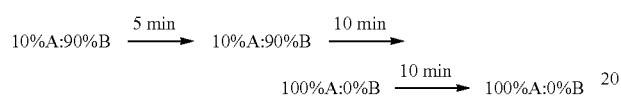

Example 1

Preparation of 6-acetoxy-5-oxo-1-(2-oxo-2-piperidin-1-yl-ethyl)-1,5-dihydro-imidazo[1,2-a]pyrimidine-7-carboxylic acid methyl ester

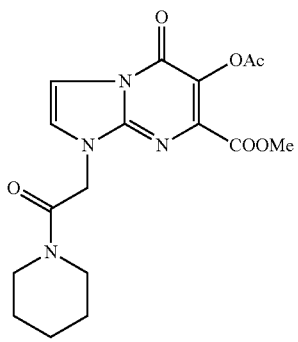 [SMILES: COC(=O)c1nc2n(CC(=O)N3CCCCC3)ccn2c(=O)c1OC(C)=O]

To a solution of compound 6-acetoxy-5-oxo-1,5-dihydro-imidazo[1,2-a]pyrimidine-7-carboxylic acid methyl ester (PCT/AU2007/001980) (2.0 g, 7.96 mmol) in anhydrous acetonitrile (20 ml) was added compound 2-chloro-1-piperidin-1-yl-ethanone (2.0 g, 12.42 mmol), $K_2CO_3$ (1.7 g, 12.32 mmol), KI (133 mg, 0.8 mmol) successively. The mixture was heated at refluxed for 3 hours. After cooling to the room temperature, the mixture was filtered and the filtrate was concentrated under reduced pressure. The resulting residue was recrystallized from ethyl acetate to give titled compound (2.0 g, yield 66.7%).

$^1$H NMR (300 MHz, DMSO-d$^6$) 1.40-1.52 (m, 2H), 1.56-1.70 (m, 4H), 2.27 (s, 3H), 3.38-3.46 (m, 2H), 3.46-3.53 (m, 2H), 3.84 (s, 3H), 5.13 (s, 2H), 7.70 (d, J=2.6 Hz, 1H), 7.81 (d, J=2.7 Hz, 1H)

Example 2

Preparation of 6-hydroxy-5-oxo-1-(2-oxo-2-piperidin-1-yl-ethyl)-1,5-dihydro-imidazo[1,2-a]pyrimidine-7-carboxylic acid methyl ester

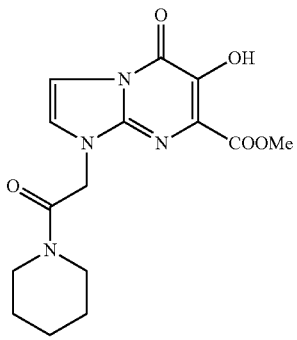 [SMILES: COC(=O)c1nc2n(CC(=O)N3CCCCC3)ccn2c(=O)c1O]

To a solution of the product of example 1 (3.6 g, 9.57 mmol) in MeOH (40 ml) was added $K_2CO_3$ (2.7 g, 19.5 mol). The mixture was stirred at room temperature for about 1 hour and then filtered. The filtrate was concentrated into dryness to give the titled product (crude yield 100%) as yellow solid, which was used directly in next step.

Example 3

Preparation of 6-benzyloxy-5-oxo-1-(2-oxo-2-piperidin-1-yl-ethyl)-1,5-dihydro-imidazo[1,2-a]pyrimidine-7-carboxylic acid methyl ester

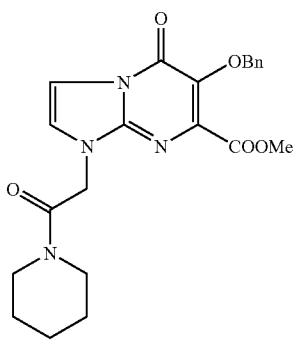 [SMILES: COC(=O)c1nc2n(CC(=O)N3CCCCC3)ccn2c(=O)c1OCc1ccccc1]

The crude product of example 2 was dissolved in DMF (50 ml) and then $K_2CO_3$ (3.3 g, 0.024 mol) was added. After stirring at room temperature for about 0.5 hours, benzyl bromide (4.0 g, 0.0234 mol) was added drop-wise. Then the mixture was heated at 80° C. for another 5 hours. After cooling to room temperature, the solids were filtered off and washed with ethyl acetate. The filtrate was diluted with EA, washed with water and then brine, dried and concentrated. The residue was purified by column chromatography ($CH_2Cl_2$/MeOH=50/1) to give the titled compound (2.0 g, 2-step yield 49.3%).

¹H NMR (300 MHz, DMSO-d⁶) 1.40-1.51 (m, 2H), 1.52-1.70 (m, 4H), 3.37-3.53 (m, 4H), 3.78 (s, 3H), 5.03 (s, 2H), 5.07 (s, 2H), 7.30-7.44 (m, 5H), 7.62 (d, J=2.7 Hz, 1H), 7.77 (d, J=2.7 Hz, 1H).
MS (ESI⁺) m/z 447 (M+23)

Example 4

Preparation of 6-benzyloxy-5-oxo-1-(2-oxo-2-piperidin-1-yl-ethyl)-1,5-dihydro-imidazo[1,2-a]pyrimidine-7-carboxylic acid

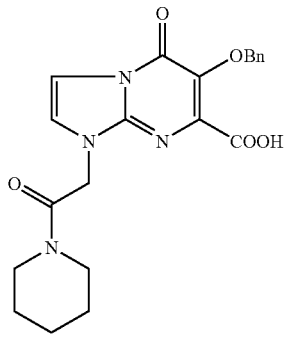 [SMILES: O=C(O)c1nc2n(CC(=O)N3CCCCC3)ccn2c(=O)c1OCc1ccccc1]

A mixture of the product of example 3 (1.0 g, 2.358 mmol) and LiOH (aq., 1N, 14 ml) in THF (10 ml) was stirred at room temperature for about 3 hours. Then diluted HCl (1N) was added dropwise to adjust the pH ~2. The resulting solids were collected by filtration, washed with ethyl acetate and dried to give the titled compound (740 mg, yield 76.3%).
¹H NMR (300 MHz, DMSO-d⁶) 1.40-1.52 (m, 2H), 1.54-1.68 (m, 4H), 3.38-3.54 (m, 4H), 5.02 (s, 2H), 5.08 (s, 2H), 7.28-7.43 (m, 3H), 7.43-7.50 (m, 2H), 7.60 (d, J=2.6 Hz, 1H), 7.74 (d, J=2.6 Hz, 1H), 13.60 (s, 1H)
MS (ESI⁻) m/z 409 (M−1)

Example 5

Preparation of 6-benzyloxy-5-oxo-1-(2-oxo-2-piperidin-1-yl-ethyl)-1,5-dihydro-imidazo[1,2-a]pyrimidine-7-carboxylic acid [3-(4-fluoro-phenyl)-2-oxo-propyl]-amide

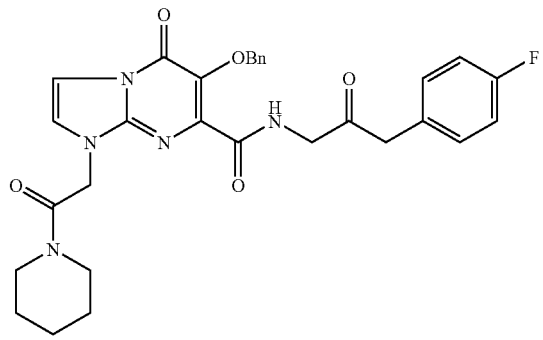 [SMILES: O=C(CNC(=O)c1nc2n(CC(=O)N3CCCCC3)ccn2c(=O)c1OCc1ccccc1)Cc1ccc(F)cc1]

To a solution of the product of example 4 (1.0 g, 2.4 mmol) in THF (10 ml) was added compound 1-amino-3-(4-fluoro-phenyl)-propan-2-one hydrochloride (1.0 g, 4.9 mmol), EDCI.HCl (560 mg, 2.9 mmol), HOBt (400 mg, 2.9 mmol) and TEA (1 g, 9.9 mmol) successively at room temperature. The mixture was stirred overnight, after which saturated sodium bicarbonate was added and then extracted with ethyl acetate. The extracts were combined, washed with brine, and then dried over sodium sulfate. The product was purified by column chromatography (CH₂Cl₂/MeOH=100/1) to give the desired product (540 mg, 40% yield).
¹H NMR (300 MHz, DMSO-d⁶) δ 1.38-1.52 (m, 2H), 1.54-1.65 (m, 4H), 3.36-3.54 (m, 4H), 3.84 (s, 2H), 4.18 (d, J=5.6 Hz, 2H), 5.01 (s, 2H), 5.10 (s, 2H), 7.12 (t, J=8.9 Hz, 2H), 7.17-7.24 (m, 2H), 7.28-7.36 (m, 3H), 7.47 (dd, J=1.9, 7.9 Hz, 2H), 7.61 (d, J=2.8 Hz, 1H), 7.73 (d, J=2.6 Hz, 1H), 8.76 (t, J=5.7 Hz, 1H).
MS (ESI⁻) m/z 558 (M−1)

Example 6

Preparation of 6-benzyloxy-7-[5-(4-fluoro-benzyl)-oxazol-2-yl]-1-(2-oxo-2-piperidin-1-yl-ethyl)-1H-imidazo[1,2-a]pyrimidin-5-one

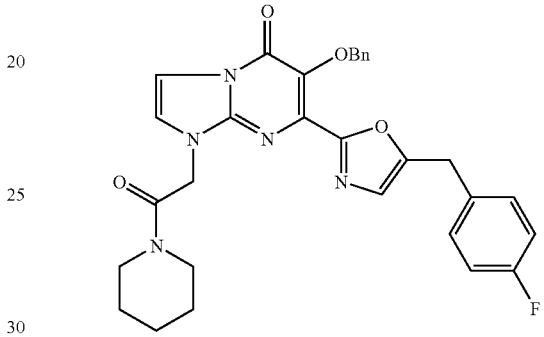

To a solution of the product of example 5 (200 mg, 0.357 mmol) in acetonitrile (3 ml), carbon tetrachloride (330 mg, 2.1 mmol), triethylamine (180 mg, 1.78 mmol) and triphenylphosphine (470 mg, 1.79 mmol) were added successively at room temperature. The mixture was stirred for 3 hours. The product was purified by column chromatography (CH₂Cl₂/MeOH=150/1) to give the titled product (40 mg, 21% yield).
¹H NMR (300 MHz, DMSO-d⁶) δ 1.40-1.50 (m, 2H), 1.52-1.68 (m, 4H), 3.36-3.54 (m, 4H), 4.10 (s, 2H), 5.04 (s, 2H), 5.06 (s, 2H), 7.07-7.16 (m, 3H), 7.26-7.34 (m, 5H), 7.34-7.41 (m, 2H), 7.61 (d, J=2.6 Hz, 1H), 7.73 (d, J=2.6 Hz, 1H).
MS (ESI⁺) m/z 564 (M+23)

Example 7

Preparation of 7-[5-(4-fluoro-benzyl)-oxazol-2-yl]-6-hydroxy-1-(2-oxo-2-piperidin-1-yl-ethyl)-1H-imidazo[1,2-a]pyrimidin-5-one

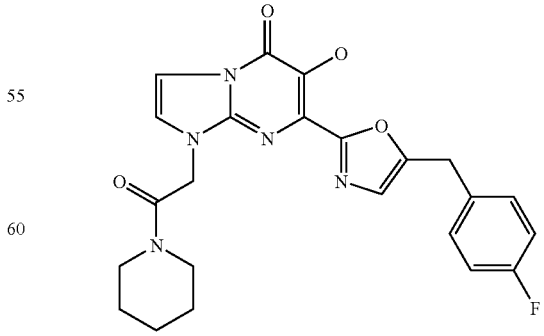

To a solution of the product of example 6 (50 mg, 0.092 mmol) in acetonitrile (2 ml) was added TMSI (150 mg, 0.75 mmol) drop-wise at room temperature. The mixture was stirred for 8 hours, after which methanol (0.1 ml) was added to quench the reaction. Then saturated solution of $Na_2S_2O_3$ was added drop-wise till a yellow solid was precipitated. The resulting solids were collected by filtration, washed with ethyl acetate to give the desired product (10 mg, 24% yield).

$^1$H NMR (300 MHz, CDCl3) δ 1.38-1.50 (m, 2H), 1.52-1.68 (m, 4H), 3.35-3.45 (m, 2H), 3.46-3.55 (m, 2H), 4.21 (s, 2H), 5.01 (s, 2H), 7.18 (t, J=8.9 Hz, 2H), 7.26 (s, 1H), 7.35 (dd, J=5.6, 8.8 Hz, 2H), 7.54 (d, J=2.6 Hz, 1H), 7.64 (d, J=2.7 Hz, 1H), 10.22 (s, 1H).

MS (ESI$^+$) m/z 474 (M+23)

Example 8

Preparation of 6-benzyloxy-1-methyl-5-oxo-1,5-dihydro-imidazo[1,2-a]pyrimidine-7-carboxylic acid methyl ester

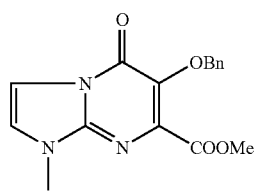 [SMILES: COC(=O)c1nc2n(C)ccn2c(=O)c1OCc1ccccc1]

Adapted from the procedure of example 3 using 6-hydroxy-1-methyl-5-oxo-1,5-dihydro-imidazo[1,2-a]pyrimidine-7-carboxylic acid methyl ester (AU2007001980).

$^1$H NMR (300 MHz, DMSO-d$^6$) 3.66 (s, 3H), 3.79 (s, 3H), 5.02 (s, 2H), 7.30-7.43 (m, 5H), 7.69 (d, J=2.6 Hz, 1H), 7.73 (d, J=2.7 Hz, 1H).

MS (ESI$^+$) m/z 336 (M+23)

Example 9

Preparation of 6-benzyloxy-1-methyl-5-oxo-1,5-dihydro-imidazo[1,2-a]pyrimidine-7-carboxylic acid

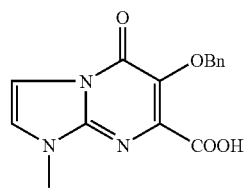 [SMILES: Cn1ccn2c(=O)c(OCc3ccccc3)c(C(=O)O)nc12]

Adapted from the procedure of example 4 using the product of example 8.

$^1$H NMR (300 MHz, DMSO-d$^6$) 3.67 (s, 3H), 5.01 (s, 2H), 7.30-7.50 (m, 5H), 7.68 (d, J=2.6 Hz, 1H), 7.72 (d, J=2.6 Hz, 1H), 13.50-13.59 (brs, 1H).

MS (ESI$^+$) m/z 300 (M+1)

Example 10

Preparation of 6-benzyloxy-1-methyl-5-oxo-1,5-dihydro-imidazo[1,2-a]pyrimidine-7-carboxylic acid [3-(4-chloro-phenyl)-2-oxo-propyl]-amide

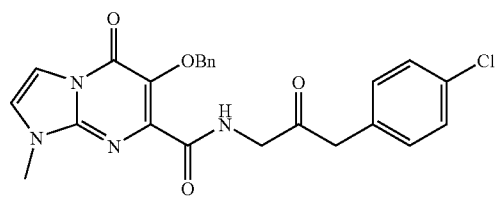 [SMILES: Cn1ccn2c(=O)c(OCc3ccccc3)c(C(=O)NCC(=O)Cc3ccc(Cl)cc3)nc12]

Adapted from the procedure of example 5 using the product of example 9 and 1-amino-3-(4-chloro-phenyl)-propan-2-one hydrochloride.

$^1$H NMR (300 MHz, DMSO-d$^6$) δ 3.69 (s, 3H), 3.87 (s, 2H), 4.20 (d, J=5.5 Hz, 2H), 5.00 (s, 2H), 7.21 (d, J=8.8 Hz, 2H), 7.29-7.40 (m, 5H), 7.45-7.51 (m, 2H), 7.69 (d, J=2.6 Hz, 1H), 7.71 (d, J=2.6 Hz, 1H), 8.71 (t, J=5.6 Hz, 1H)

MS (ESI$^+$) m/z 487 (M+23)

Example 11

Preparation of 6-benzyloxy-7-[5-(4-chloro-benzyl)-thiazol-2-yl]-1-methyl-1H-imidazo[1,2-a]pyrimidin-5-one

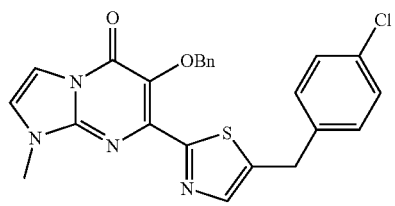 [SMILES: Cn1ccn2c(=O)c(OCc3ccccc3)c(-c3ncc(Cc4ccc(Cl)cc4)s3)nc12]

The product from example 10 (0.23 mmol) and Lawensson's Reagent (57 mg, 0.14 mmol) were mixed with toluene (3 mL) and refluxed for 3 h. The reaction mixture was concentrated in vacuo and flash chromatography afforded the titled product.

$^1$H NMR (300 MHz, DMSO-d$^6$) δ 3.67 (s, 3H), 4.26 (s, 2H), 5.07 (s, 2H), 7.30-7.37 (m, 5H), 7.38-7.52 (m, 4H), 7.66 (d, J=2.6 Hz, 1H), 7.68 (d, J=2.7 Hz, 1H), 7.86 (t, J=0.7 Hz, 1H)

MS (ESI$^+$) m/z 463 (M+1)

Example 12

Preparation of 7-[5-(4-chloro-benzyl)-thiazol-2-yl]-6-hydroxy-1-methyl-1H-imidazo[1,2-a]pyrimidin-5-one

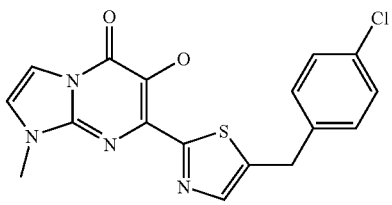 [SMILES: Cn1ccn2c(=O)c(O)c(-c3ncc(Cc4ccc(Cl)cc4)s3)nc12]

To a solution of the product of example 11 (0.135 mmol) in CH$_2$Cl$_2$ (4 ml) was added FeCl$_3$ (66 mg, 0.402 mmol) at room temperature. The mixture was stirred at room temperature for 2 hours, after which CH$_2$Cl$_2$ was evaporated under reduced pressure and ethyl acetate (30 ml) was added. Then the mixture was washed by 1N HCl (10 ml), H$_2$O (10 ml) and brine (10 ml) successively, dried over Na$_2$SO$_4$ and concentrated into about 1 ml. The resulting solids were collected by filtration and washed with cold ethyl acetate (2-3 ml) to give the desired product.

$^1$H NMR (300 MHz, DMSO-d$^6$) δ 3.61 (s, 3H), 4.30 (s, 2H), 7.34-7.45 (m, 4H), 7.59 (dd, J=2.7, 5.0 Hz, 2H), 7.91 (s, 1H), 10.70-10.84 (brs, 1H)

MS (ESI$^+$) m/z 373 (M+1)

HPLC 97.2%

Example 13

Preparation of 6-benzyloxy-1-methyl-5-oxo-1,5-dihydro-imidazo[1,2-a]pyrimidine-7-carboxylic acid [3-(3,4-dichloro-phenyl)-2-oxo-propyl]-amide

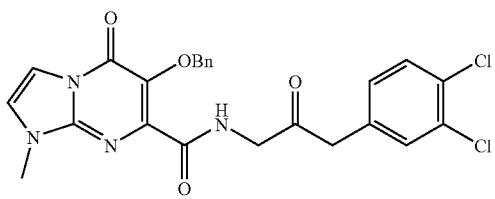 [SMILES: Cn1ccn2c(=O)c(OCc3ccccc3)c(C(=O)NCC(=O)Cc3ccc(Cl)c(Cl)c3)nc12]

Adapted from the procedure of example 5 using the product of example 9 and 1-amino-3-(3,4-dichloro-phenyl)-propan-2-one hydrochloride.

$^1$H NMR (300 MHz, DMSO-d$^6$) δ 3.70 (s, 3H), 3.90 (s, 2H), 4.22 (d, J=5.6 Hz, 2H), 5.00 (s, 2H), 7.17 (dd, J=8.2, 2.1 Hz, 1H), 7.26-7.36 (m, 3H), 7.43-7.51 (m, 3H), 7.57 (d, J=8.1 Hz, 1H), 7.69 (d, J=2.7 Hz, 1H), 7.72 (d, J=2.7 Hz, 1H), 8.74 (t, J=5.7 Hz, 1H).

MS (ESI$^-$) m/z 497 (M−1)

Example 14

Preparation of 6-benzyloxy-7-[5-(3,4-dichloro-benzyl)-thiazol-2-yl]-1-methyl-1H-imidazo[1,2-a]pyrimidin-5-one

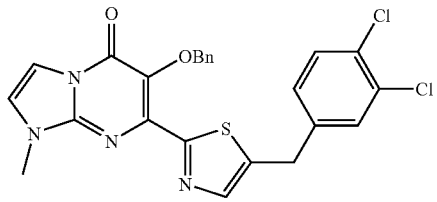 [SMILES: Cn1ccn2c(=O)c(OCc3ccccc3)c(-c3ncc(Cc4ccc(Cl)c(Cl)c4)s3)nc12]

Adapted from the procedure of example 11 using the product of example 13

$^1$H NMR (300 MHz, DMSO-d$^6$) δ 3.68 (s, 3H), 4.28 (s, 2H), 5.07 (s, 2H), 7.29-7.36 (m, 4H), 7.45-7.52 (m, 2H), 7.59-7.70 (m, 4H), 7.89 (s, 1H)

MS (ESI$^+$) m/z 497 (M+1)

Example 15

Preparation of 7-[5-(3,4-Dichloro-benzyl)-thiazol-2-yl]-6-hydroxy-1-methyl-1H-imidazo[1,2-a]pyrimidin-5-one

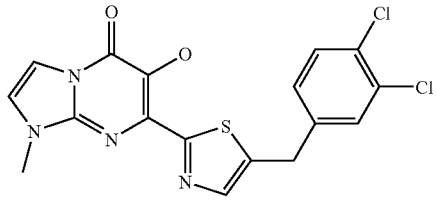 [SMILES: Cn1ccn2c(=O)c(O)c(-c3ncc(Cc4ccc(Cl)c(Cl)c4)s3)nc12]

Adapted from the procedure of example 12 using the product of example 14

$^1$H NMR (300 MHz, DMSO-d$^6$) δ 3.62 (s, 3H), 4.32 (s, 2H), 7.36 (dd, J=1.7, 8.5 Hz, 1H), 7.55-7.74 (m, 4H), 7.93 (s, 1H), 10.75 (s, 1H)

MS (MALDI) m/z 407 (M+1), 429 (M+23), 445 (M+39)

Example 16

Preparation of 6-benzyloxy-1-methyl-5-oxo-1,5-dihydro-imidazo[1,2-a]pyrimidine-7-carboxylic acid [3-(4-chloro-3-fluoro-phenyl)-2-oxo-propyl]-amide

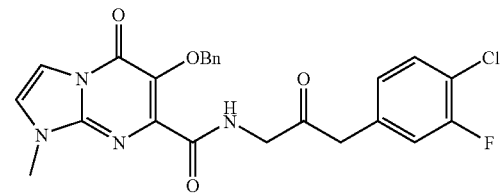 [SMILES: Cn1ccn2c(=O)c(OCc3ccccc3)c(C(=O)NCC(=O)Cc3ccc(Cl)c(F)c3)nc12]

Adapted from the procedure of example 5 using the product of example 9 and example 26.

¹H NMR (300 MHz, DMSO-d⁶) δ 3.70 (s, 3H), 3.90 (s, 2H), 4.21 (d, J=5.7 Hz, 2H), 5.00 (s, 2H), 7.05 (dd, J=8.1, 1.8 Hz, 1H), 7.24 (dd, J=10.5, 1.8 Hz, 1H), 7.28-7.36 (m, 3H), 7.46-7.54 (m, 3H), 7.68-7.72 (m, 2H), 8.73 (t, J=5.4 Hz, 1H).

MS (ESI⁺) m/z 505 (M+23)

Example 17

Preparation of 6-benzyloxy-7-[5-(4-chloro-3-fluoro-benzyl)-thiazol-2-yl]-1-methyl-1H-imidazo[1,2-a]pyrimidin-5-one

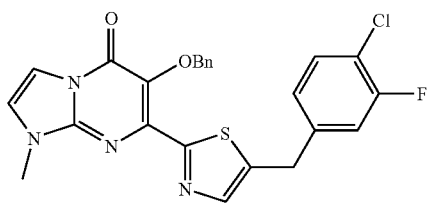 [SMILES: Cn1ccn2c(=O)c(OCc3ccccc3)c(-c3ncc(Cc4ccc(Cl)c(F)c4)s3)nc12]

Adapted from the procedure of example 11 using the product of example 16

¹H NMR (300 MHz, DMSO-d⁶) δ 3.68 (s, 3H), 4.28 (s, 2H), 5.06 (s, 2H), 7.19 (dd, J=8.1, 1.8 Hz, 1H), 7.30-7.35 (m, 3H), 7.40 (dd, J=10.2, 1.8 Hz, 1H), 7.47-7.50 (m, 2H), 7.56 (t, J=7.9 Hz, 1H), 7.65-7.68 (m, 2H), 7.88 (s, 1H)

MS (ESI⁺) m/z 481 (M+1)

Example 18

Preparation of 7-[5-(4-Chloro-3-fluoro-benzyl)-thiazol-2-yl]-6-hydroxy-1-methyl-1H-imidazo[1,2-a]pyrimidin-5-one

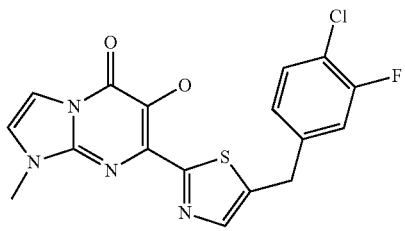 [SMILES: Cn1ccn2c(=O)c(O)c(-c3ncc(Cc4ccc(Cl)c(F)c4)s3)nc12]

Adapted from the procedure of example 12 using the product of example 17

¹H NMR (300 MHz, DMSO-d⁶) δ 3.62 (s, 3H), 4.33 (s, 2H), 7.23 (dd, J=7.8, 1.8 Hz, 1H), 7.45 (dd, J=10.2, 1.8 Hz, 1H), 7.54-7.62 (m, 3H), 7.93 (s, 1H), 10.76 (s, 1H)

MS (ESI⁺) m/z 413 (M+23)

Example 19

Preparation of 6-benzyloxy-1-methyl-5-oxo-1,5-dihydro-imidazo[1,2-a]pyrimidine-7-carboxylic acid [3-(4-fluoro-phenyl)-2-oxo-propyl]-amide

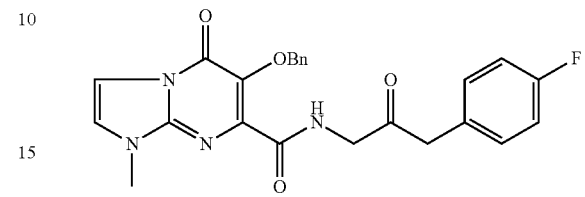

Adapted from the procedure of example 5 using the product of example 9 and 1-amino-3-(4-fluororo-phenyl)-propan-2-one hydrochloride.

¹H NMR (300 MHz, DMSO-d⁶) 3.69 (s, 3H), 3.85 (s, 2H), 4.20 (d, J=5.6 Hz, 2H), 5.00 (s, 2H), 7.13 (t, J=8.9 Hz, 2H), 7.22 (dd, J=8.7, 5.9 Hz, 2H), 7.26-7.40 (m, 3H), 7.48 (dd, J=7.7, 1.8 Hz, 2H), 7.69 (d, J=2.5 Hz, 1H), 7.71 (d, J=2.5 Hz, 1H), 8.69 (t, J=5.3 Hz, 1H).

MS (ESI⁻) m/z 447 (M−1)

Example 20

Preparation of 6-benzyloxy-7-[5-(4-fluoro-benzyl)-thiazol-2-yl]-1-methyl-1H-imidazo[1,2-a]pyrimidin-5-one

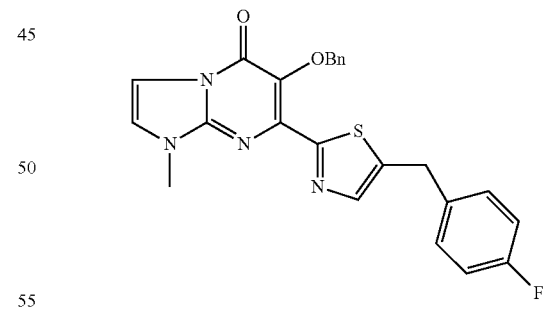

Adapted from the procedure of example 11 using the product of example 19

¹H NMR (300 MHz, CDCl₃) 3.83 (s, 3H), 4.16 (s, 2H), 5.26 (s, 2H), 6.90-7.06 (m, 3H), 7.12-7.22 (m, 2H), 7.27-7.34 (m, 3H), 7.41-7.52 (m, 2H), 7.60 (d, J=2.6 Hz, 1H), 7.78 (s, 1H).

MS (ESI⁺) m/z 447 (M+1)

Example 21

Preparation of 7-[5-(4-fluoro-benzyl)-thiazol-2-yl]-6-hydroxy-1-methyl-1H-imidazo[1,2-a]pyrimidin-5-one

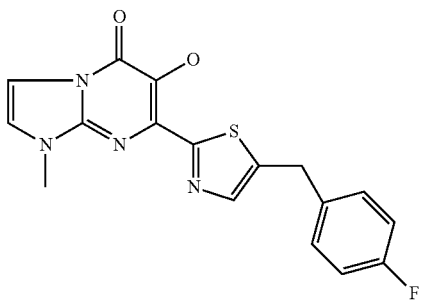 [SMILES: Cn1ccn2c(=O)c(O)c(-c3ncc(Cc4ccc(F)cc4)s3)nc12]

Adapted from the procedure of example 12 using the product of example 20

$^1$H NMR (300 MHz, DMSO-d$^6$) 3.61 (s, 3H), 4.29 (s, 2H), 7.17 (t, J=8.9 Hz, 2H), 7.39 (dd, J=5.7, 8.7 Hz, 2H), 7.56-7.62 (m, 2H), 7.90 (s, 1H), 10.78 (s, 1H)

MS (ESI$^+$) m/z 379 (M+23)

Example 22

Preparation of (4-chloro-3-fluoro-phenyl)-acetonitrile

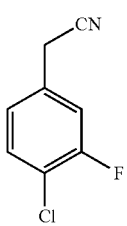

To a boiling solution of 4-chloro-3-fluororobenzyl bromide (10 g, 44.8 mmol) in absolute ethanol (40 ml) was added a solution of potassium cyanide (2.9 g, 44.8 mmol) in water (6 ml). The mixture was refluxed for 1.5 hours, then most of the ethanol was distilled off under reduced pressure and the cooled residue poured into water. The solution was extracted three times with ether. The combined organic layers were washed with brine, dried and concentrated into dryness to give the titled product (7.8 g, 93% yield)

$^1$H NMR (300 MHz, DMSO-d$^6$) 4.09 (s, 2H), 7.25 (ddd, J=0.8, 2.0, 8.2 Hz, 1H), 7.43 (dd, J=2.0, 10.0 Hz, 1H), 7.64 (t, J=8.2 Hz, 1H).

MS (ESI$^-$) m/z 168 (M-1)

Example 23

Preparation of (4-chloro-3-fluoro-phenyl)-acetic acid

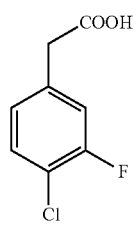 [SMILES: O=C(O)Cc1ccc(Cl)c(F)c1]

A mixture of the product of example 22 (7.8 g, 0.046 mol), water (7.5 ml), concentrated sulfuric acid (7.5 ml) and acetic acid (7.5 ml) was heated at reflux for 2 hours. After being cooled to room temperature, the mixture was poured into ice-water. The resulting solids were collected by filtration and washed by diethyl ether to give the titled product (6.8 g, 79%)

$^1$H NMR (300 MHz, DMSO-d$^6$) 3.64 (s, 2H), 7.14 (ddd, J=0.6, 2.1, 8.2 Hz, 1H), 7.34 (dd, J=2.1, 10.6 Hz, 1H), 7.52 (t, J=8.1 Hz, 1H).

MS (ESI$^-$) m/z 187 (M-1)

Example 24

Preparation of (4-chloro-3-fluoro-phenyl)-acetyl chloride

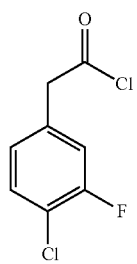 [SMILES: O=C(Cl)Cc1ccc(Cl)c(F)c1]

A mixture of the product of example 23 (4.9 g, 26 mmol) with thionyl chloride (50 ml) was refluxed for 3 hours. Then thionyl chloride was removed under reduced pressure. The residue was redistilled under reduced pressure to give crude titled acyl chloride, which was used directly in the next step reaction. (3.2 g, 60% yield)

Example 25

Preparation of 5-(4-chloro-3-fluoro-benzyl)-oxazole-4-carboxylic acid ethyl ester

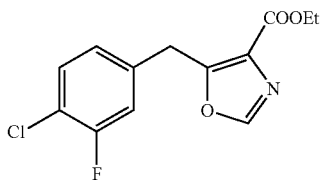 [SMILES: CCOC(=O)c1ncoc1Cc1ccc(Cl)c(F)c1]

To a solution of potassium tert-butoxide (3.5 g, 31.25 mmol) in THF (50 ml) was added ethyl isocyanoacetate (3.5 g, 31.25 mmol) dropwise at 5° C. After stirring for 45 minutes, the product of example 24 (3.2 g, 15.5 mmol) was added dropwise. Then the mixture was stirred overnight at room temperature. The reaction mixture was filtered and the filtrate was concentrated. The residue was purified by column chromatography (PE/EA=5/1) to give the titled compound (2.5 g, 67.7 yield)

$^1$H NMR (300 MHz, DMSO-d$^6$) 1.29 (t, J=7.1 Hz, 3H), 4.30 (q, J=7.1 Hz, 2H), 4.41 (s, 2H), 7.11 (ddd, J=0.6, 2.1, 8.3 Hz, 1H), 7.34 (dd, J=2.0, 10.4 Hz, 1H), 7.54 (t, J=8.1 Hz, 1H), 8.40 (s, 1H).

MS (ESI$^+$) m/z 306 (M+23)

Example 26

Preparation of 1-amino-3-(4-chloro-3-fluoro-phenyl)-propan-2-one hydrochloride

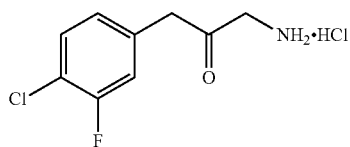

A mixture of the product of example 25 (2.5 g, 10.53 mmol) with hydrochloride acid (6 mol/1, 30 ml) was refluxed for about 3 hours and then cooled to room temperature. The solids were collected by filtration, washed with EA and dried to give the titled product (1.7 g, 81%)

$^1$H NMR (300 MHz, DMSO-d$^6$) 3.96 (s, 2H), 4.03 (s, 2H), 7.10 (dd, J=1.9, 8.2 Hz, 1H), 7.29 (d, J=1.9, 10.4 Hz, 1H), 7.56 (t, J=8.1 Hz, 1H), 8.15-8.42 (brs, 3H).

MS (ESI$^+$) m/z 202 (M+1)

Example 27

Preparation of 5-fluoro-2,N,N-trimethyl-benzenesulfonamide

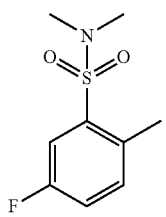

A mixture of 5-fluoro-2-methylbenzene sulfonylchloride (2.1 mL, 14.3 mmol) in THF (18 mL) and 2 M dimethylamine in methanol (18 mL), was stirred at room temperature for 0.5 h. The resulting mixture was concentrated under reduced pressure to give a crude product as a mixture of white solid and colourless oil. The crude product was purified by column (30% EtOAc in Hexane) to give the titled compound as a colourless oil (3.09 g, 99% yield).

Example 28

Preparation of 2-bromomethyl-5-fluoro-N,N-dimethyl-benzenesulfonamide

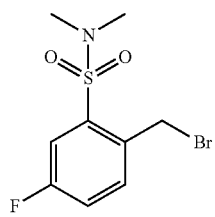

To a solution of the product of example 27 (3 g, 13.8 mmol) in DCE (40 mL), was added n-bromosuccinamide (2.8 g, 15.19 mmol) and stirred at 80° C. for 5 min before AIBN (300 mg, 0.016 mmol) was added and heated at 80° C. for 5 h (95% conversion). The reaction mixture was concentrated under reduced pressure to give a crude product as a yellow solid. The crude product was purified by column (10-20% ethylacetate in hexane) to give the titled product. (50% yield)

MS (ESI$^+$) m/z 296, 298 Br [M+H$^+$]

Example 29

Preparation of 2-cyanomethyl-5-fluoro-N,N-dimethyl-benzenesulfonamide

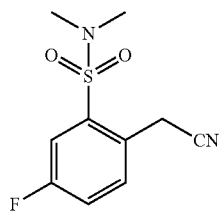 [SMILES: CN(C)S(=O)(=O)c1cc(F)ccc1CC#N]

A mixture of the product of example 28 (~90% pure, 729 mg, 2.46 mmol) in a mixture of DMF:H$_2$O (3 mL:2 mL) and sodium cyanide (362 mg, 7.4 mmol) was stirred at room temperature overnight. The resulting mixture was quenched with saturated NaHCO$_3$ (12 mL) and extracted with ethylacetate (3×30 mL). The extracts were combined and washed with saturated NaCl (2×30 mL) and water (2×30 mL). The organic layer was separated, dried over anhydrous MgSO$_4$ and concentrated under reduced pressure to give the titled product as colourless oil (503 mg, 85% yield).

$^1$H NMR CDCl$_3$, 300 MHz: δ 2.86 (s, 6H, —N(CH$_3$)$_2$), 4.19 (s, 2H, —CH$_2$C≡N), 7.35 (m, 1H, ArH), 7.69 (m, 2H, ArH).

MS (ESI$^+$) m/z 243 [M+H$^+$], 265 [M+Na$^+$]

Example 30

Preparation of 1-chloro-3-(4-fluoro-phenyl)-propan-2-one

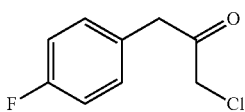 [SMILES: O=C(CCl)Cc1ccc(F)cc1]

1. To a chilled (0° C.) solution of 4-fluoro-phenylacetyl chloride (14.07 mmol, 2.43 g) in diethylether (15 mL), was added a cold solution of freshly distilled diazomethane in diethylether (16 mmol) and stirred at 0° C. for 15 min and then at room temperature for 15 min. The resulting mixture of diazoketone was used in the next step without further purification (confirmed by mass spec).

2. One third of the above diazoketone solution (in diethyl ether) was cooled to −30° C. and 4M HCl in dioxane (3 mL) was added and stirred at −30° C. for 0.5 h and then at room temperature for 0.5 h. The reaction mixture was quenched with water (20 mL) and extracted with ethyl acetate (30 mL). The organic layer was separated and dried over anhydrous MgSO$_4$ and concentrated under reduced pressure to give a crude product as slightly yellow oil. The crude product was purified by column chromatography (15-20% EtOAc in hexane) to give the titled compound with R$_f$=0.016 (200 mg, 19% yield)

$^1$H NMR: CDCl$_3$, 300 MHz: δ 3.88 (s, 2H, —CH$_2$Cl), 4.11 (s, 2H, —CH$_2$(C═O)), 7.04 (t, J=8.7 Hz, 2H, ArH), 7.20 (t, dd=4.8, 8.8 Hz, 2H, ArH).

Example 31

Preparation of 2-[3-(4-fluoro-phenyl)-2-oxo-propyl]-isoindole-1,3-dione

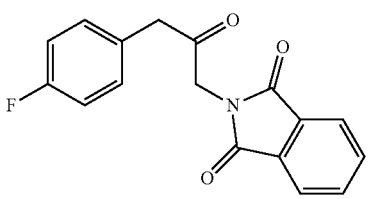 [SMILES: O=C(Cc1ccc(F)cc1)CN1C(=O)c2ccccc2C1=O]

To a solution of the product of example 30 (85 mg, 0.45 mmol) in DMF (1 mL), under a nitrogen atmosphere, was added potassium salt of phthalamide (96 mg, 0.52 mmol). The resulting mixture was stirred at room temperature for 1 h. The reaction mixture was quenched with a mixture of ice-water and filtered. The slightly pink solid was washed with water to give the titled compound as a white product (79 mg, 62% yield).

$^1$H NMR CDCl$_3$, 300 MHz: δ 3.82 (s, 2H, —CH$_2$N—), 4.51 (s, 2H, —CH$_2$(C═O)), 7.04 (m, 2H, ArHF), 7.23 (m, 2H, ArHF), 7.74 (m, 2H, ArH), 7.86 (m, 2H, ArH).

MS (ESI$^+$) m/z 298 [M+H$^+$]

Example 32

Preparation of 2-Chloro-1-(2,6-dimethyl-morpholin-4-yl)-ethanone

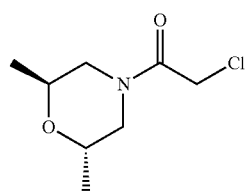

2,6-Dimethylmorpholine (a mixture of trans- and cis-isomers (1.0 g, 8.7 mmol) and TEA (1.34 ml, 9.6 mmol) were dissolved in anhydrous ether (50 ml) and cooled in ice bath. To the above mixture was added dropwise a solution of chloroacetyl chloride (0.69 ml, 8.7 mmol). Then the mixture was warmed to room temperature and stirred for 3 hours. The mixture was washed with water, dried and evaporated under reduced pressure. The residue was purified by column chromatography (EA/PE=1/1) to afford the title compound (0.79 g, yield 47.5%).

$^1$H NMR (300 MHz, DMSO-d$^6$) δ 1.09 (d, J=6.1 Hz, 6H), 2.29 (dd, J=11.2, 13.0 Hz, 1H), 2.72 (dd, J=10.9, 13.3 Hz, 1H), 3.35-3.58 (m, 2H), 3.73 (dt, J=2.0, 13.3 Hz, 1H), 4.19 (dt, J=2.0, 12.9 Hz, 1H), 4.39 (s, 2H)

Example 33

Preparation of 6-Acetoxy-1-[2-(2,6-dimethyl-morpholin-4-yl)-2-oxo-ethyl]-5-oxo-1,5-dihydro-imidazo[1,2-a]pyrimidine-7-carboxylic acid methyl ester

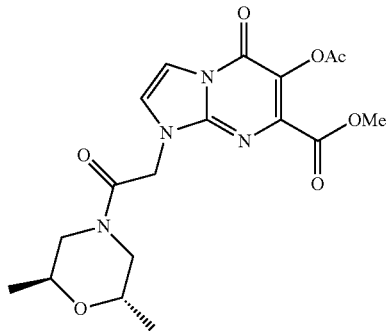 [SMILES: COC(=O)c1nc2n(CC(=O)N3C[C@H](C)O[C@@H](C)C3)ccn2c(=O)c1OC(C)=O]

The title compound was prepared by adapting methods described in example 18.1.1.3 of International patent Application No. PCT/AU2007/001980 in the name of Avexa, using the product of example 32.

$^1$H NMR (300 MHz, DMSO-d$^6$) δ 1.09 (d, J=6.1 Hz, 3H), 1.15 (d, J=6.2 Hz, 3H), 2.26 (s, 3H), 2.35 (t, J=11.9 Hz, 1H), 2.81 (dd, J=10.3, 12.6 Hz, 1H), 3.39-3.54 (m, 1H), 3.55-3.72 (m, 1H), 3.83 (s, 3H), 3.89 (d, J=13.8 Hz, 1H), 4.15 (d, J=12.1 Hz, 1H), 5.05 (d, J=16.7 Hz, 1H), 5.28 (d, J=17.0 Hz, 1H), 7.68 (d, J=2.6 Hz, 1H), 7.81 (d, J=2.6 Hz, 1H).

MS (ESI$^+$) m/z 407 (M+1)

Example 34

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carboxylic acid methyl ester

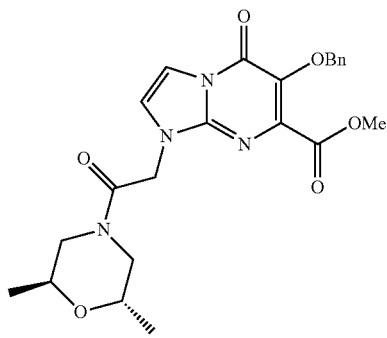

The title compound was prepared by adapting methods described for example 8.1 of International patent Application No. PCT/AU2007/001980 in the name of Avexa, using the product of Example 33.

$^1$H NMR (300 MHz, DMSO-d$^6$) δ 1.09 (d, J=6.2 Hz, 3H), 1.13 (d, J=6.2 Hz, 3H), 2.33 (dd, J=11.0, 13.0 Hz, 1H), 2.78 (dd, J=10.6, 12.7 Hz, 1H), 3.40-3.65 (m, 2H), 3.77 (s, 3H), 3.85 (d, J=12.5 Hz, 1H), 4.14 (d, J=12.5 Hz, 1H), 4.94-5.06 (m, 3H), 5.22 (d, J=16.9 Hz, 1H), 7.26-7.45 (m, 5H), 7.58 (d, J=2.7 Hz, 1H), 7.76 (d, J=2.6 Hz, 1H).

MS (ESI$^-$) m/z 455 (M+1)

Example 35

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carboxylic acid The title compound was prepared by adapting methods described for example 8.2 of International patent Application No. PCT/AU2007/001980 in the name of Avexa, using the product of example 34.

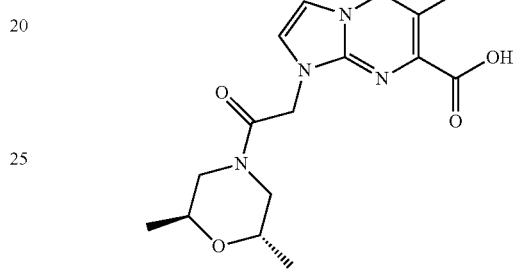

$^1$H NMR (300 MHz, DMSO-d$^6$) δ 1.09 (d, J=6.2 Hz, 3H), 1.14 (d, J=6.2 Hz, 3H), 2.34 (dd, J=10.8, 12.9 Hz, 1H), 2.78 (dd, J=10.8, 13.1 Hz, 1H), 3.41-3.53 (m, 1H), 3.54-3.68 (m, 1H), 3.87 (d, J=12.9 Hz, 1H), 4.14 (d, J=12.6 Hz, 1H), 4.94-5.04 (m, 3H), 5.23 (d, J=16.9 Hz, 1H), 7.29-7.42 (m, 3H), 7.43-7.49 (m, 2H), 7.59 (d, J=2.7 Hz, 1H), 7.75 (d, J=2.6 Hz, 1H), 13.64 (s, 1H).

MS (ESI$^+$) m/z 463 (M+23)

Example 36

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid

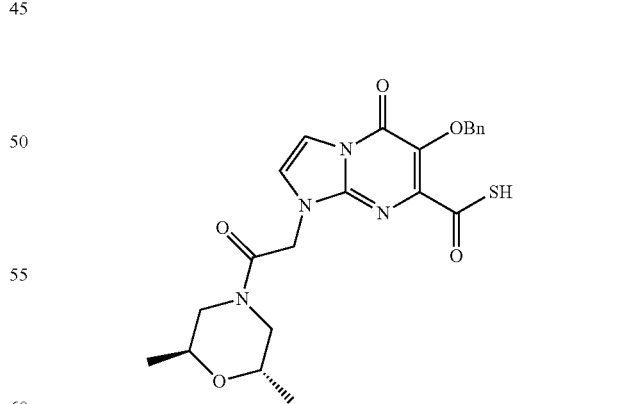

A mixture of the product of example 35 (2.20 g, 5 mmol) and CDI (1.22 g, 7.5 mmol) in dry DMF (10 ml) was stirred at 20° C. for 4 h. Then NaSH (0.85 g 15 mmol) was added in one portion and the resulting mixture was stirred for another 12 h. Hydrochloric acid (1 mol/l, 100 ml) was added to quench the reaction. The resulting solids were collected by filtration, washed with water and dried in vacuo to give the crude carbothioic acid, which was used directly in the next step.

MS (ESI⁻) m/z 455 (M−1)

Example 37

Preparation of 3-(3,4-Dichloro-phenyl)-propionaldehyde

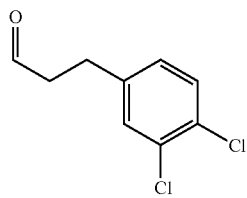 [SMILES: O=CCCc1ccc(Cl)c(Cl)c1]

To a solution of 1,2-dichloro-4-iodobenzene (5.44 g, 20 mmol) in DMF (60 ml) was added Bu$_4$NCl (5.56 g, 20 mmol), propenol (4.64 g, 80 mmol), Pd(OAc)$_2$ (224 mg, 1 mmol) and NaHCO$_3$ (10.0 g, 120 mmol) successively at room temperature. The mixture was heated at 50° C. for 12 hour. After cooling to the room temperature, the mixture was poured into ice-water, extracted with DCM three times. The combined organic layers were washed with brine, dried over Na$_2$SO$_4$ and concentrated under reduced pressure. The residue was purified by column chromatography using PE/EA (20/1) as eluent to afford the title compound (2.01 g, yield 49.8%).

$^1$H NMR (300 MHz, DMSO-d$^6$) δ 2.75-2.90 (m, 4H), 7.24 (dd, J=1.5, 8.4 Hz, 1H), 7.44-7.58 (m, 2H), 9.69 (s, 1H).

Example 38

Preparation of 2-Bromo-3-(3,4-dichloro-phenyl)-propionaldehyde

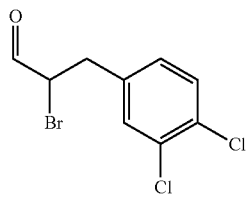 [SMILES: O=CC(Br)Cc1ccc(Cl)c(Cl)c1]

To a solution of the product of example 37 (10 mmol, 2.0 g) in a mixed solvent of DCM (40 ml) with dioxane (4.0 ml) was added TMSBr (15 mmol, 2.3 g) at room temperature. After the mixture was kept at 25° C. for one hour, bromine (1.6 g, 10.0 mmol) was added. Another one hour later, the mixture was poured into water (50 ml) and extracted with DCM three times. The combined organic layers were washed with brine, dried and evaporated into dryness to give the crude title product, which was used directly in the next step reaction.

$^1$H NMR (300 MHz, DMSO-d$^6$) δ 3.12 (dd, J=8.8, 14.7 Hz, 1H), 3.49 (dd, J=5.8, 14.7 Hz, 1H), 5.02 (ddd, J=1.8, 5.9, 8.8 Hz, 1H), 7.31 (dd, J=2.2, 8.4 Hz, 1H), 7.59 (d, 8.4 Hz, 1H), 7.62 (d, J=2.0 Hz, 1H), 9.50 (d, J=1.8 Hz, 1H)

Example 39

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid S-[2-(3,4-dichloro-phenyl)-1-formyl-ethyl]ester

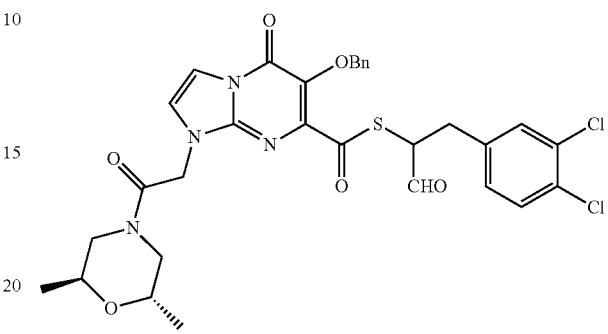

To a solution of the product of example 36 (550 mg, 1.2 mmol) in CH$_2$Cl$_2$ (4 ml) was added the product of example 38 (506 mg, 1.8 mmol) and bis(dimethylamino)naphthalene (385 mg, 1.8 mmol) successively. The mixture was refluxed for 1 h and then evaporated into dryness. The resulting residue was purified by column chromatography using DCM/MeOH (20/1) as eluent to afford the crude title compound (448 mg, crude yield 56%).

MS (ESI⁺) m/z 657 (M$^{[35]}$+1), 659 (M$^{[37]}$+1)

Example 40

Preparation of 6-Benzyloxy-7-[5-(3,4-dichloro-benzyl)-thiazol-2-yl]-1-[2-(2,6-dimethyl-morpholin-4-yl)-2-oxo-ethyl]-1H-imidazo[1,2-a]pyrimidin-5-one

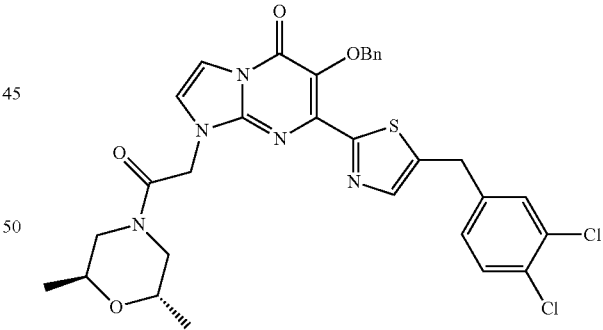

A stirred solution of the product of example 39 (448 mg, 0.68 mmol) and NH$_4$OAc (1.00 g, 13.6 mmol) in AcOH (5 ml) was heated at 80-90° C. for 5 h. Then the mixture was poured into water (20 ml), and then NaOH (10% aq.) was added to adjust pH~10. The mixture was extracted with ethyl acetate. The combined organic extracts were dried and evaporated in vacuo. The residue was purified by column chromatography using EA as eluent to afford the title compound (200 mg, 46.0%).

$^1$H NMR (300 MHz, CDCl$_3$) δ 1.22 (dd, J=6.5, 10.7 Hz, 6H), 2.41 (t, J=11.7 Hz, 1H), 2.86-2.99 (m, 1H), 3.42-3.75 (m, 2H), 3.78-3.90 (m, 1H), 4.14 (s, 2H), 4.35 (d, J=12.9 Hz,

1H), 4.95 (d, J=16.6 Hz, 1H), 5.26-5.36 (m, 3H), 7.04 (dd, J=1.9, 8.5 Hz, 1H), 7.18 (d, J=2.4 Hz, 1H), 7.27-7.35 (m, 4H), 7.40 (d, J=8.2 Hz, 1H), 7.43-7.51 (m, 2H), 7.63 (d, J=2.6 Hz, 1H), 7.78 (s, 1H).

MS (ESI$^+$) m/z 638 (M$^{[35]}$+1), 640 (M$^{[37]}$+1)

Example 41

Preparation of 7-[5-(3,4-Dichloro-benzyl)-thiazol-2-yl]-1-[2-(2,6-dimethyl-morpholin-4-yl)-2-oxo-ethyl]-6-hydroxy-1H-imidazo[1,2-a]pyrimidin-5-one Adapted from the procedure of example 8.5 of PCT/AU2007/001980 using the product of Example 40.

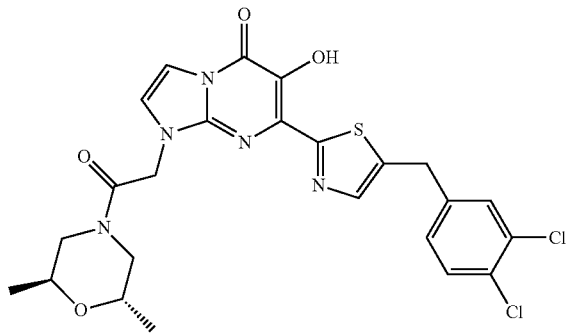 [SMILES: C[C@H]1CN(C(=O)Cn2ccn3c(=O)c(O)c(-c4ncc(Cc5ccc(Cl)c(Cl)c5)s4)nc23)C[C@H](C)O1]

$^1$H NMR (300 MHz, DMSO-d$^6$) δ 1.08 (d, J=6.2 Hz, 3H), 1.15 (d, J=6.1 Hz, 3H), 2.33 (dd, J=10.8, 12.9 Hz, 1H), 2.80 (t, J=11.9 Hz, 1H), 3.37-3.52 (m, 1H), 3.52-3.68 (m, 1H), 3.94 (d, J=13.7 Hz, 1H), 4.13 (d, J=12.9 Hz, 1H), 4.33 (s, 2H), 4.93 (d, J=16.4 Hz, 1H), 5.13 (d, J=17.0 Hz, 1H), 7.33 (dd, J=1.8, 8.6 Hz, 1H), 7.51 (d, J=2.6 Hz, 1H), 7.57-7.67 (m, 3H), 7.94 (s, 1H), 10.80 (s, 1H).

MS (ESI$^+$) m/z 548 (M$^{[35]}$+1), 550 (M$^{[37]}$+1)

HPLC 96.0%

Example 42

Preparation of 6-Benzyloxy-5-oxo-1-(2-oxo-2-piperidin-1-yl-ethyl)-1,5-dihydro-imidazo[1,2-a]pyrimidine-7-carbothioic acid

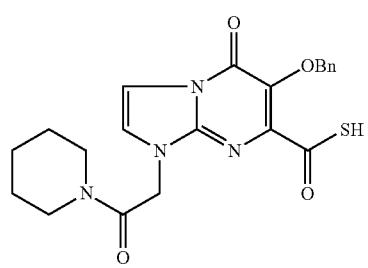 [SMILES: O=C(S)c1nc2n(CC(=O)N3CCCCC3)ccn2c(=O)c1OCc1ccccc1]

Adapted from the procedure used to prepare Example 36.

MS (ESI$^-$) m/z 425 (M−1)

Example 43

Preparation of 2-Bromo-3-phenyl-propionaldehyde

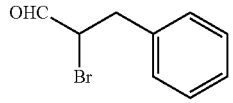 [SMILES: O=CC(Br)Cc1ccccc1]

Adapted from the procedure of example 38 using 3-Phenyl-propionaldehyde, which is commercially available $^1$H NMR (300 MHz, DMSO-d$^6$) δ 3.10 (dd, J=8.8, 14.7 Hz, 1H), 3.49 (dd, J=6.3, 14.5 Hz, 1H), 4.91-4.98 (m, 1 h), 7.10-7.42 (m, 5H), 9.51 (d, J=2.3 Hz, 1H).

Example 44

Preparation of 6-Benzyloxy-5-oxo-1-(2-oxo-2-piperidin-1-yl-ethyl)-1,5-dihydro-imidazo[1,2-a]pyrimidine-7-carbothioic acid S-(1-formyl-2-phenyl-ethyl) ester

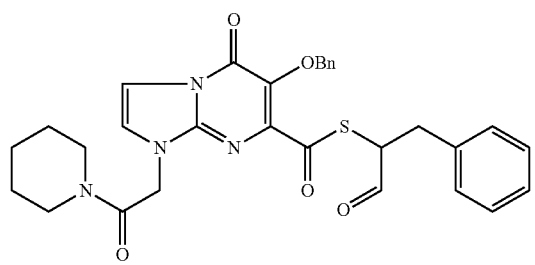 [SMILES: O=CC(Cc1ccccc1)SC(=O)c1nc2n(CC(=O)N3CCCCC3)ccn2c(=O)c1OCc1ccccc1]

Adapted from the procedure of example 39 using the product of example 42 and the product of example of 43.

MS (ESI$^+$) m/z 559 (M+1)

Example 45

Preparation of 6-Benzyloxy-7-(5-benzyl-thiazol-2-yl)-1-(2-oxo-2-piperidin-1-yl-ethyl)-1H-imidazo[1,2-a]pyrimidin-5-one

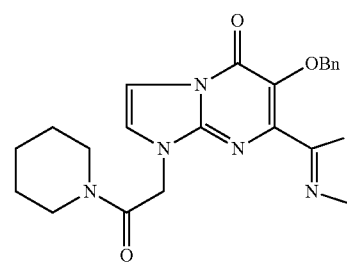

Adapted from the procedure of example 40 using the product of example 44.

$^1$H NMR (300 MHz, DMSO-d$^6$) δ 1.38-1.50 (m, 2H), 1.55-1.66 (m, 4H), 3.37-3.45 (m, 2H), 3.46-3.56 (m, 2H), 4.25 (s, 2), 5.05 (s, 2), 5.08 (s, 2H), 7.24-7.38 (m, 8H), 7.47-7.53 (m, 2H), 7.58 (d, J=2.6 Hz, 1H), 7.69 (d, J=2.7 Hz, 1H), 7.86 (t, J=0.9 Hz, 1H).

MS (ESI$^+$) m/z 562 (M+23)

Example 46

Preparation of 7-(5-Benzyl-thiazol-2-yl)-6-hydroxy-1-(2-oxo-2-piperidin-1-yl-ethyl)-1H-imidazo[1,2-a]pyrimidin-5-one

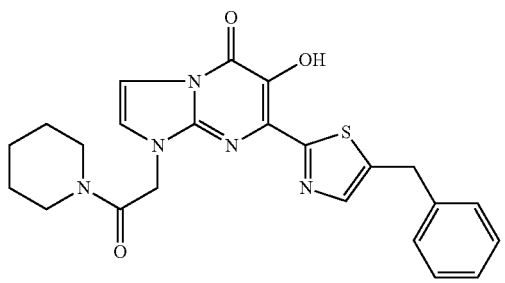 [SMILES: O=C(Cn1ccn2c(=O)c(O)c(-c3ncc(Cc4ccccc4)s3)nc12)N1CCCCC1]

Adapted from the procedure of example 8.5 of PCT/AU2007/001980 using the product of example 45.

$^1$H NMR (300 MHz, DMSO-d$^6$) δ 1.34-1.46 (m, 2H), 1.53-1.65 (m, 4H), 3.35-3.45 (m, 2H?), 3.46-3.55 (m, 2H), 4.29 (s, 2H), 4.98 (s, 2H), 7.18-7.38 (m, 5H), 7.52 (d, J=2.6 Hz, 1H), 7.61 (d, J=2.6 Hz, 1H), 7.91 (s, 1H).

MS (ESI$^+$) m/z 472 (M+23)

Example 47

Preparation of methyl 2-(3-oxopropyl)benzoate

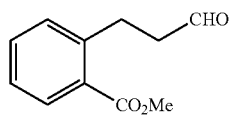

Adapted from the procedure of example 37 using 2-iodobenzoic acid methyl ester $^1$H NMR (300 MHz, DMSO-d$^6$) δ 2.69-2.75 (m, 2H), 3.11 (t, J=7.8 Hz, 2H), 3.80 (s, 3H), 7.28-7.36 (m, 2H), 7.48 (dd, J=1.5, 7.5 Hz, 1H), 7.79 (dd, J=1.5, 7.8 Hz, 1H), 9.69 (t, J=1.5 Hz, 1H).

MS (ESI$^+$) m/z 233 (M+23), 265 (M+55)

Example 48

Preparation of methyl 2-(2-bromo-3-oxopropyl)benzoate

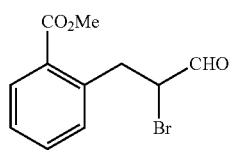 [SMILES: COC(=O)c1ccccc1CC(Br)C=O]

Adapted from the procedure of example 38 using the product of example 47.

$^1$H NMR (300 MHz, CDCl$_3$) δ 3.35 (dd, J=7.8, 14.1 Hz, 1H), 3.89 (s, 3H), 3.90 (dd, J=6.3, 14.1 Hz, 1H), 4.68-4.74 (m, 1H), 7.31-7.38 (m, 2H), 7.45-7.51 (m, 1H), 7.98-8.01 (m, 1H), 9.51 (d, J=2.4 Hz, 1H).

Example 49

Preparation of 2-{2-[6-Benzyloxy-5-oxo-1-(2-oxo-2-piperidin-1-yl-ethyl)-1,5-dihydro-imidazo[1,2-a]pyrimidine-7-carbonylsulfanyl]-3-oxo-propyl}-benzoic acid methyl ester

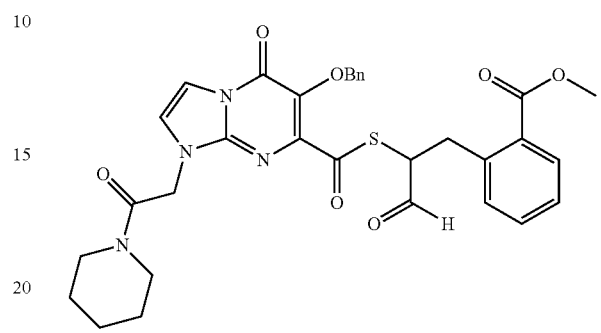

Adapted from the procedure of example 39 using the product of example 48 and the product of example 42.

MS (ESI$^+$) m/z 639 (M+23)

Example 50

Preparation of 2-{2-[6-Benzyloxy-5-oxo-1-(2-oxo-2-piperidin-1-yl-ethyl)-1,5-dihydro-imidazo[1,2-a]pyrimidin-7-yl]-thiazol-5-ylmethyl}-benzoic acid methyl ester

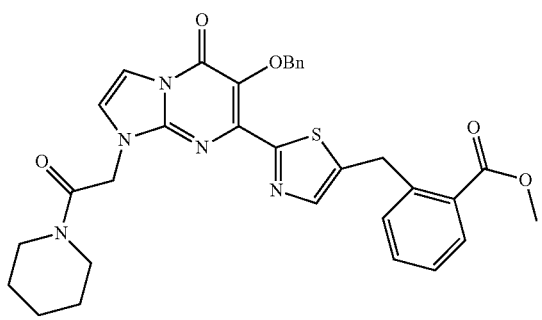 [SMILES: COC(=O)c1ccccc1Cc1cnc(-c2nc3n(CC(=O)N4CCCCC4)ccn3c(=O)c2OCc2ccccc2)s1]

Adapted from the procedure of example 40 using the product of example 49.

$^1$H NMR (300 MHz, CDCl$_3$) δ 1.23-1.24 (m, 2H), 1.59-1.63 (m, 4H), 3.48-3.56 (m, 4H), 3.83 (s, 3H), 4.60 (s, 2H), 5.02 (s, 2H), 5.23 (s, 2H), 7.14 (d, J=2.7 Hz, 1H), 7.25-7.35 (m, 5H), 7.43-7.50 (m, 3H), 7.60 (d, J=2.4 Hz, 1H), 7.73 (s, 1H), 7.96 (d, J=7.8, 1H).

MS (ESI$^+$) m/z 598 (M+1)

Example 51

Preparation of 2-{2-[6-Hydroxy-5-oxo-1-(2-oxo-2-piperidin-1-yl-ethyl)-1,5-dihydro-imidazo[1,2-a]pyrimidin-7-yl]-thiazol-5-ylmethyl}-benzoic acid methyl ester

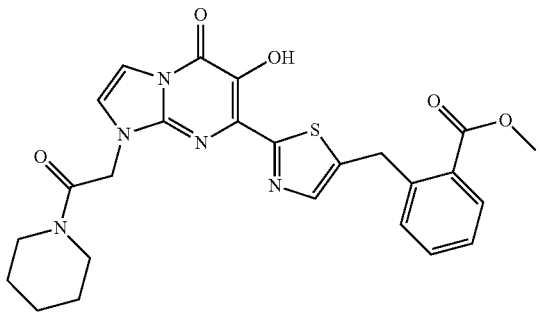 [SMILES: COC(=O)c1ccccc1Cc1cnc(-c2nc3n(CC(=O)N4CCCCC4)ccn3c(=O)c2O)s1]

Adapted from the procedure of example 8.5 of PCT/AU2007/001980 using the product of example 50.

$^1$H NMR (300 MHz, CDCl$_3$) δ 1.39-1.40 (m, 2H), 1.59-1.60 (m, 4H), 3.39-3.50 (m, 4H), 3.84 (s, 3H), 4.58 (s, 2H), 4.96 (s, 2H), 7.50-7.59 (m, 5H), 7.86-7.89 (m, 2H), 10.80 (s, 1H)

MS (ESI$^+$) m/z 508 (M+1)

HPLC 91.7%

Example 52

Preparation of 5-Fluoro-2-iodo-benzoic acid

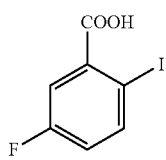

To a solution of 2-Amino-5-fluoro-benzoic acid (15.5 g, 99.94 mmol) in 6N HCl (300 ml) was added dropwise a solution of NaNO$_2$ (8.28 g, 119.93 mmol) in H$_2$O (50 mL) at −5° C. The mixture was stirred for 40 minutes, and then added to the mixture of KI (24.88 g, 149.91 mmol) and ice (200 g). After stirring for 1 hour at 5° C., the mixture was extracted with H$_2$O and dichloromethane, dried and concentrated to give the titled compound as a pale yellow solid (11 g, yield 41%).

$^1$H NMR (300 MHz, CDCl$_3$) δ 7.17 (dt, J=3.3, 8.7 Hz, 1H), 7.54 (dd, J=3.0, 9.3 Hz, 1H), 7.99 (dd, J=5.4, 8.7 Hz, 1H), 13.56 (s, 1H).

MS (ESI$^-$) m/z 265 (M−1)

Example 53

Preparation of 5-Fluoro-2-iodo-benzoic acid methyl ester

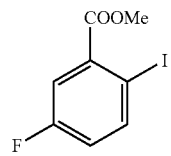 [SMILES: COC(=O)c1cc(F)ccc1I]

A mixture of 5-fluoro-2-iodo-benzoic acid (10.05 g, 39.47 mmol) and conc. H$_2$SO$_4$ (10 mL) in MeOH (100 ml) was reflux for 6 hours. After cooling to room temperature, NaOH (2N) was added dropwise to adjust the pH~8. After most of organic solvent was removed under reduced pressure, the mixture was extracted with dichloromethane three times. The combined organic layers were washed with water, dried and concentrated to give the titled compound (10.80 g, yield 98%)

$^1$H NMR (300 MHz, DMSO-d$^6$) δ 3.83 (s, 3H), 7.19 (dt, J=2.7, 8.4 Hz, 1H), 7.56 (dd, J=3, 9 Hz, 1H), 8.00 (dd, J=5.1, 9 Hz, 1H).

MS (ESI$^+$) m/z 303 (M+23), 335 (M+55)

Example 54

Preparation of 5-Fluoro-2-(3-oxo-propyl)-benzoic acid methyl ester

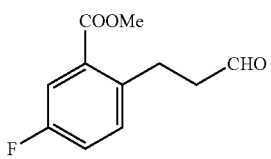

Adapted from the procedure of example 37 using the product of example 53.

$^1$H NMR (300 MHz, DMSO-d$^6$) δ 2.74 (t, J=7.2 Hz, 2H), 3.10 (t, J=7.2 Hz, 2H), 3.83 (s, 3H), 7.37-7.43 (m, 2H), 7.56 (dd, J=2.7, 9.6 Hz, 1H), 9.69 (s, 1H).

MS (ESI$^+$) m/z 233 (M+23), 265 (M+55)

Example 55

Preparation of 2-(2-Bromo-3-oxo-propyl)-5-fluoro-benzoic acid methyl ester

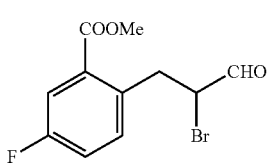

Adapted from the procedure of example 38 using the product of example 54.

$^1$H NMR (300 MHz, DMSO-d$^6$) δ 3.37-3.45 (dd, J=8.4, 14.1 Hz, 1H), 3.77-3.82 (m, 1H), 3.84 (s, 3H), 4.85-4.91 (m,

1H), 7.44-7.50 (m, 2H), 7.64 (dd, J=2.7, 9.6 Hz, 1H), 9.49 (d, J=2.4 Hz, 1H)
MS (ESI⁺) m/z 311 (M[35]+23), 313 (M[37]+23)

Example 56

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidine-7-carbonylsulfanyl}-3-oxo-propyl)-5-fluoro-benzoic acid methyl ester Adapted from the procedure of example 39 using the product of example 55 and the product of example 36.

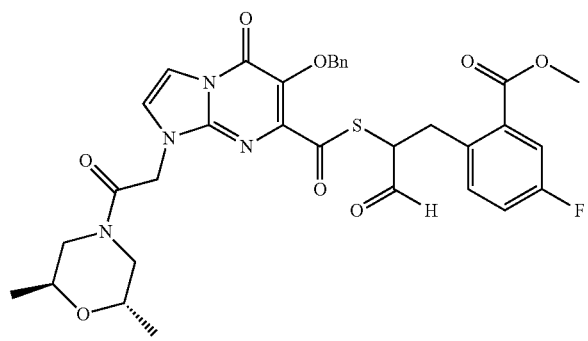 [SMILES: COC(=O)c1cc(F)ccc1CC(C=O)SC(=O)c1nc2n(CC(=O)N3C[C@H](C)O[C@@H](C)C3)ccn2c(=O)c1OCc1ccccc1]

MS (ESI⁺) m/z 687 (M+23)

Example 57

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidin-7-yl}-thiazol-5-ylmethyl)-5-fluoro-benzoic acid methyl ester

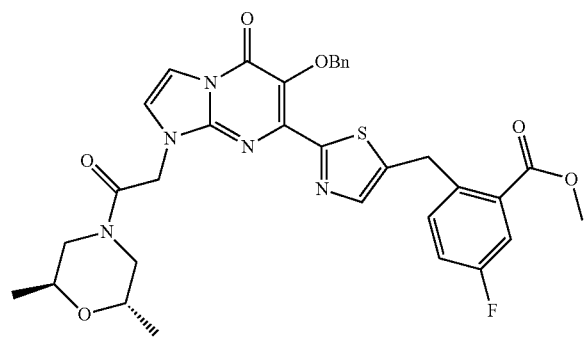

Adapted from the procedure of example 40 using the product of example 56.

¹H NMR (300 MHz, DMSO-d⁶) δ 1.07 (d, J=6.3 Hz, 3H), 1.13 (d, J=6.0 Hz, 3H), 2.30 (t, J=11.4 Hz, 1H), 2.77 (t, J=11.1 Hz, 1H), 3.38-3.44 (m, 1H), 3.54-3.58 (m, 1H), 3.80 (s, 3H), 3.94 (d, J=12.5 Hz, 1H), 4.14 (d, J=12.9 Hz, 1H), 4.52 (s, 2H), 4.96 (d, J=17.1 Hz, 1H), 5.04 (s, 2H), 5.17 (d, J=16.8 Hz, 1H), 7.28-7.34 (m, 3H), 7.42-7.48 (m, 3H), 7.51-7.56 (m, 2H), 7.62 (dd, J=2.7, 9.6 Hz, 1H), 7.67-7.68 (m, 1H), 7.79 (s, 1H).
MS (ESI⁺) m/z 646 (M+1)

Example 58

Preparation of 2-(2-{1-[2-(2,6-Dimethyl-morpholin-4-yl)-2-oxo-ethyl]-6-hydroxy-5-oxo-1,5-dihydro-imidazo[1,2-a]pyrimidin-7-yl}-thiazol-5-ylmethyl)-5-fluoro-benzoic acid methyl ester

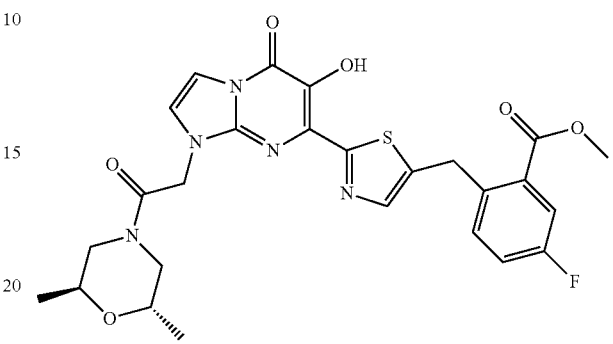

Adapted from the procedure of example 8.5 of PCT/AU2007/001980 using the product of example 57.
¹H NMR (300 MHz, DMSO-d⁶) δ 1.08 (d, J=6.3 Hz, 3H), 1.15 (d, J=6.0 Hz, 3H), 2.31 (t, J=12.3 Hz, 1H), 2.79 (t, J=12.3 Hz, 1H), 3.38-3.43 (m, 1H), 3.54-3.60 (m, 1H), 3.95 (d, J=13.2 Hz, 1H), 4.13 (d, J=12.6 Hz, 1H), 4.57 (s, 2H), 4.91 (d, J=16.8 Hz, 1H), 5.12 (d, J=17.1 Hz, 1H), 7.43-7.50 (m, 2H), 7.56-7.66 (m, 3H), 7.86 (s, 1H), 10.8 (s, 1H).
MS (ESI⁺) m/z 556 (M+1)
HPLC 98.2%

Example 59

Preparation of 3-(3-Chloro-4-fluoro-phenyl)-propionaldehyde

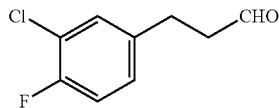 [SMILES: O=CCCc1ccc(F)c(Cl)c1]

Adapted from the procedure of example 37 using 2-Chloro-1-fluoro-4-iodo-benzene.
¹H NMR (300 MHz, DMSO-d⁶) δ 2.75-2.87 (m, 4H), 7.21-7.34 (m, 2H), 7.46 (dd, J=2.1, 7.2 Hz, 1H), 9.69 (s, 1H).

Example 60

Preparation of 2-Bromo-3-(3-chloro-4-fluoro-phenyl)-propionaldehyde

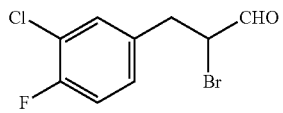 [SMILES: O=CC(Br)Cc1ccc(F)c(Cl)c1]

Adapted from the procedure of example 38 using the product of example 59.

$^1$H NMR (300 MHz, DMSO-d$^6$) δ 3.11 (dd, J=8.7, 14.7 Hz, 1H), 3.51 (dd, J=6.0, 14.7 Hz, 1H), 4.97-5.03 (m, 1H), 7.31-7.40 (m, 2H), 7.54 (dd, J=1.8, 7.2 Hz, 1H), 9.50 (d, J=1.8 Hz, 1H)

Example 61

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid 5-[2-(3-chloro-4-fluoro-phenyl)-1-formyl-ethyl]ester

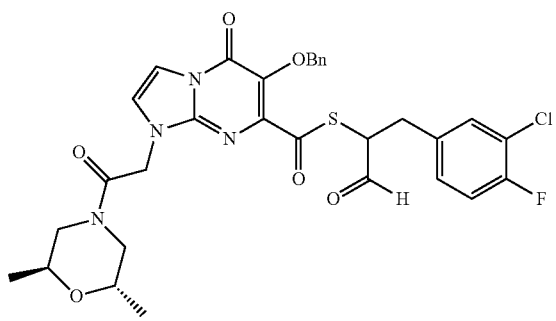 [SMILES: C[C@H]1CN(C(=O)Cn2ccn3c(=O)c(OCc4ccccc4)c(C(=O)SC(C=O)Cc4ccc(F)c(Cl)c4)nc23)C[C@H](C)O1]

Adapted from the procedure of example 39 using the product of example 60.

The titled compound was used directly in the next step.

Example 62

Preparation of 6-Benzyloxy-7-[5-(3-chloro-4-fluoro-benzyl)-thiazol-2-yl]-1-[2-(2,6-dimethyl-morpholin-4-yl)-2-oxo-ethyl]-1H-imidazo[1,2-a]pyrimidin-5-one

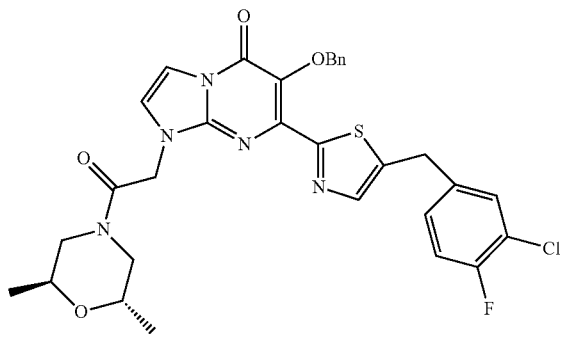 [SMILES: C[C@H]1CN(C(=O)Cn2ccn3c(=O)c(O)c(-c4ncc(Cc5ccc(F)c(Cl)c5)s4)nc23)C[C@H](C)O1]

Adapted from the procedure of example 40 using the product of example 61.

$^1$H NMR (300 MHz, DMSO-d$^6$) δ 1.08 (d, J=6.3 Hz, 3H), 1.14 (d, J=6.3 Hz, 3H), 2.28-2.36 (m, 1H), 2.76-2.85 (m, 1H), 3.41-3.47 (m, 1H), 3.57-3.63 (m, 1H), 3.93 (d, J=12 Hz, 1H), 4.14 (d, J=13.2 Hz, 1H), 4.26 (s, 2H), 4.98 (d, J=16.8 Hz, 1H), 5.08 (s, 2H), 5.19 (d, J=16.8 Hz, 1H), 7.30-7.41 (m, 5H), 7.47-7.58 (m, 4H), 7.70 (d, J=2.7 Hz, 1H), 7.87 (s, 1H).

MS (ESI$^-$) m/z 620 (M−1)

Example 63

Preparation of 7-[5-(3-Chloro-4-fluoro-benzyl)-thiazol-2-yl]-1-[2-(2,6-dimethyl-morpholin-4-yl)-2-oxo-ethyl]-6-hydroxy-1H-imidazo[1,2-a]pyrimidin-5-one

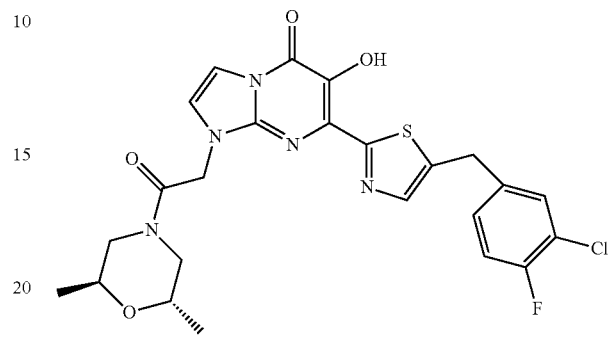

Adapted from the procedure of example 8.5 of PCT/AU2007/001980 using the product of example 62.

$^1$H NMR (300 MHz, DMSO-d$^6$) δ 1.08 (d, J=6.3 Hz, 3H), 1.14 (d, J=5.9 Hz, 3H), 2.27-2.36 m, 1H), 2.76-2.84 (m, 1H), 3.39-3.43 (m, 1H), 3.56-3.60 (m, 1H), 3.94 (d, J=12.6 Hz, 1H), 4.13 (d, J=13.2 Hz, 1H), 4.31 (s, 2H), 4.93 (d, J=16.8 Hz, 1H), 5.13 (d, J=17.1 Hz, 1H), 7.34-7.42 (m, 2H), 7.51 (d, J=2.4 Hz, 1H), 7.58 (dd, J=2.1, 7.8 Hz, 1H), 7.62 (d, J=2.7 Hz, 1H), 7.93 (s, 1H).

MS (ESI$^+$) m/z 532 (M+1)

HPLC 95.9%

Example 64

Preparation of 6-Acetoxy-3-bromo-5-oxo-1,5-dihydro-imidazo[1,2-a]pyrimidine-7-carboxylic acid methyl ester

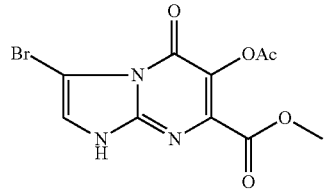 [SMILES: COC(=O)c1nc2[nH]cc(Br)n2c(=O)c1OC(C)=O]

To a stirred of 6-Methyl-5-oxo-1,5-dihydro-imidazo[1,2-a]pyrimidine-7-carboxylic acid methyl ester (1 g, 3.98 mmol) in DMF (6 ml) was added NBS (0.78 g, 4.38 mol) at room temperature. After stirring at room temperature overnight, the mixture was poured into water (30 ml) and the solids were collected by filtration, washed with water and cold methanol successively, and dried in vacuo to afford the desired product (0.67 g, yield 51.1%).

$^1$H NMR (300 MHz, DMSO-d$^6$) δ 2.24 (s, 3H), 3.82 (s, 3H), 7.86 (s, 1H), 13.34-13.60 (brs, 1H)

MS (ESI$^+$) m/z 330 (M$^{[79]}$+1), 332 (M$^{[81]}$+1)

Example 65

Preparation of 1-(2,6-Dimethyl-morpholin-4-yl)-2-iodo-ethanone

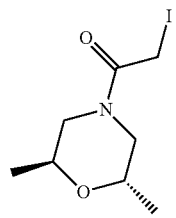

A mixture of the product of example 32 (800 mg, 4.2 mmol) and KI (1.4 g, 8.4 mmol) in acetone (50 ml) was stirred at room temperature for 6 hours. Then the solids were removed by filtration and the filtrate was concentrated under reduced pressure. The residue was suspended in EA and the solids were removed by filtration. The filtrate was concentrated in vacuo to give the iodide (955 mg, yield 80.6%), which was used directly in the next step.

Example 66

Preparation of 6-Acetoxy-3-bromo-1-[2-(2,6-dimethyl-morpholin-4-yl)-2-oxo-ethyl]-5-oxo-1,5-dihydro-imidazo[1,2-a]pyrimidine-7-carboxylic acid methyl ester

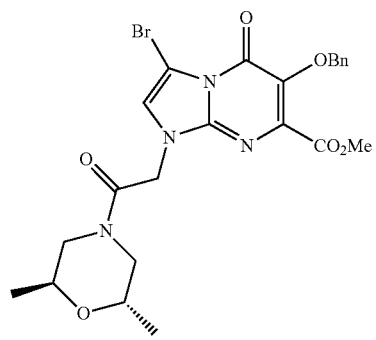 [SMILES: COC(=O)c1nc2n(CC(=O)N3C[C@H](C)O[C@@H](C)C3)cc(Br)n2c(=O)c1OCc1ccccc1]

Adapted from the procedure of example 33 using the product of example 64 and the product of example 65.

$^1$H NMR (300 MHz, CDCl$_3$) δ 1.23 (dd, J=6.2, 13.2 Hz, 6H), 2.34 (s, 3H), 2.42 (t, 12.2 Hz, 1H), 2.95 (t, J=10.6 Hz, 1H), 3.46-3.76 (m, 3H), 3.91 (s, 3H), 4.35 (d, J=12.7 Hz, 1H), 4.84 (d, J=14.2 Hz, 1H), 5.02 (d, J=14.0 Hz, 1H), 7.15 (s, 1H).

MS (ESI$^+$) m/z 485 (M$^{[79]}$+1), 487 (M$^{[81]}$+1)

Example 67

Preparation of 6-Benzyloxy-3-bromo-1-[2-(2,6-dimethyl-morpholin-4-yl)-2-oxo-ethyl]-5-oxo-1,5-dihydro-imidazo[1,2-a]pyrimidine-7-carboxylic acid methyl ester

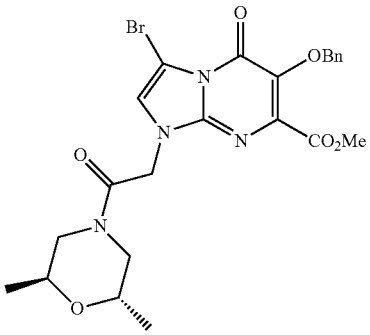 [SMILES: COC(=O)c1nc2n(CC(=O)N3C[C@H](C)O[C@@H](C)C3)cc(Br)n2c(=O)c1OCc1ccccc1]

Adapted from the procedure of example 34 using the product of example 66.

$^1$H NMR (300 MHz, CDCl$_3$) δ 1.15-1.29 (m, 6H), 2.40 (dd, J=11.5, 12.9 Hz, 1H), 2.91 (dd, J=11.0, 12.8 Hz, 1H), 3.45-3.72 (m, 3H), 3.85 (s, 3H), 4.34 (d, J=13.1 Hz, 1H), 4.77 (d, J=16 Hz, 1H), 4.98 (d, J=16.1 Hz, 1H), 5.14 (s, 2H), 7.11 (s, 1H), 7.28-7.42 (m, 3H), 7.44-7.55 (m, 2H).

MS (ESI$^+$) m/z 533 (M$^{[79]}$+1), 535 (M$^{[81]}$+1)

Example 68

Preparation of 6-Benzyloxy-1-[2-(2,6-dimethyl-morpholin-4-yl)-2-oxo-ethyl]-3-(1,1-dioxo-1l6-isothiazolidin-2-yl)-5-oxo-1,5-dihydro-imidazo[1,2-a]pyrimidine-7-carboxylic acid methyl ester

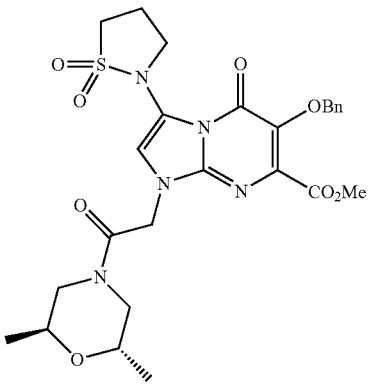 [SMILES: COC(=O)c1nc2n(CC(=O)N3C[C@H](C)O[C@@H](C)C3)cc(N3CCCS3(=O)=O)n2c(=O)c1OCc1ccccc1]

The product of example 67 (460 mg, 8.6 mmol), sulfonamide (210 mg, 1.73 mmol), K$_2$CO$_3$ (240 mg, 1.73 mmol), CuI (30 mg, 0.17 mmol) and DMEDA (30 mg, 0.34 mmol) were mixed in toluene (10 ml) and heated at 90° C. for 3 hours. After being cooled to room temperature, the mixture was filtered, washed with DCM. The filtrate was concentrated into dryness, and the residue was purified by column chromatography using DCM/EA (5/2) as eluent to give the title compound (129 mg, 26.0% yield).

$^1$H NMR (300 MHz, DMSO-d$^6$) δ 1.12 (q, J=6.2 Hz, 6H), 2.34 (dd, J=10.5, 12.4 Hz, 1H), 2.41-2.50 (m, 2H?), 2.78 (dd,

J=10.6, 13.0 Hz, 1H), 3.41-3.53 (m, 3H), 3.55-3.67 (m, 1H), 3.77 (s, 3H), 3.78-3.91 (m, 3H), 4.14 (d, J=12.9 Hz, 1H), 4.95 (d, J=17.2 Hz, 1H), 5.02 (s, 2H), 5.19 (d, J=16.8 Hz, 1H), 7.29-7.44 (m, 5H), 7.70 (s, 1H).
MS (ESI$^+$) m/z 574 (M+1)

Example 69

Preparation of 6-Benzyloxy-1-[2-(2,6-dimethyl-morpholin-4-yl)-2-oxo-ethyl]-3-(1,1-dioxo-1l6-isothiazolidin-2-yl)-5-oxo-1,5-dihydro-imidazo[1,2-a]pyrimidine-7-carboxylic acid

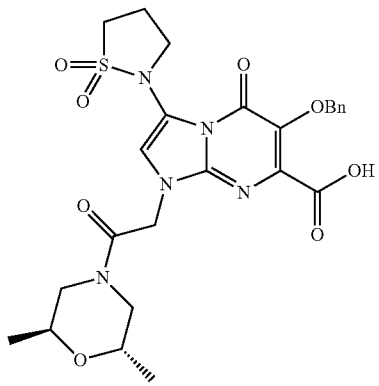 [SMILES: C[C@H]1CN(C(=O)Cn2cc(N3CCCS3(=O)=O)n3c(=O)c(OCc4ccccc4)c(C(=O)O)nc23)C[C@H](C)O1]

Adapted from the procedure of example 35 using the product of example 68.
$^1$H NMR (300 MHz, DMSO-d$^6$) δ 1.09 (d, J=6.2 Hz, 3H), 1.14 (d, J=5.8 Hz, 3H), 2.28-2.39 (m, 1H), 2.42-2.50 (m, 2H), 2.74-2.86 (m, 1H), 3.42-3.54 (m, 3H), 3.56-3.64 (m, 1H), 3.77-3.92 (m, 3H), 4.10-4.20 (m, 1H), 4.92-5.04 (m, 3H), 5.20 (d, J=16.8 Hz, 1H), 7.31-7.42 (m, 3H), 7.43-7.48 (m, 2H), 7.69 (s, 1H), 13.54-13.75 (brs, 1H)
MS (ESI$^+$) m/z 560 (M+1)

Example 70

Preparation of 6-Benzyloxy-1-[2-(2,6-dimethyl-morpholin-4-yl)-2-oxo-ethyl]-3-(1,1-dioxo-1l6-isothiazolidin-2-yl)-5-oxo-1,5-dihydro-imidazo[1,2-a]pyrimidine-7-carbothioic acid

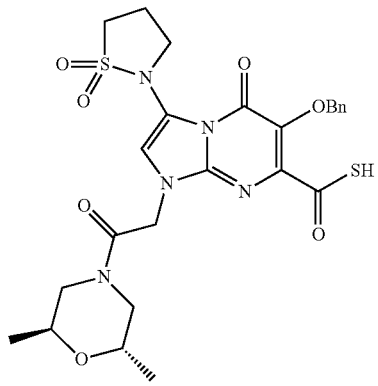

Adapted from the procedure of example 36 using the product of example 69.
MS (ESI$^-$) m/z 574 (M−1)

Example 71

Preparation of 3-(4-Fluoro-phenyl)-propionaldehyde

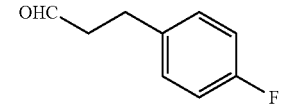 [SMILES: O=CCCc1ccc(F)cc1]

Adapted from the procedure of example 37 using 1-fluoro-4-iodo-benzene.
$^1$H NMR (300 MHz, DMSO-d$^6$) δ 2.71-2.89 (m, 4H), 7.09 (t, J=9.0 Hz, 2H), 7.26 (dd, J=5.6, 8.8 Hz, 2H), 9.70 (t, J=1.3 Hz, 1H)

Example 72

Preparation of 3-Bromo-3-(4-fluoro-phenyl)-propionaldehyde

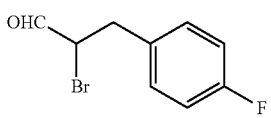 [SMILES: O=CC(Br)Cc1ccc(F)cc1]

Adapted from the procedure of example 38 using the product of example 71.
$^1$H NMR (300 MHz, DMSO-d$^6$) δ 3.10 (dd, J=8.5, 14.7 Hz, 1H), 3.47 (dd, J=6.2, 14.6 Hz, 1H), 4.90-4.98 (m, 1H), 7.15 (t, J=8.9 Hz, 2H), 7.33 (dd, J=5.6, 8.5 Hz, 2H), 9.50 (d, J=2.0 Hz, 1H)

Example 73

Preparation of 6-Benzyloxy-1-[2-(2,6-dimethyl-morpholin-4-yl)-2-oxo-ethyl]-3-(1,1-dioxo-1l6-isothiazolidin-2-yl)-5-oxo-1,5-dihydro-imidazo[1,2-a]pyrimidine-7-carbothioic acid S-[1-(4-fluoro-benzyl)-2-oxo-ethyl]ester

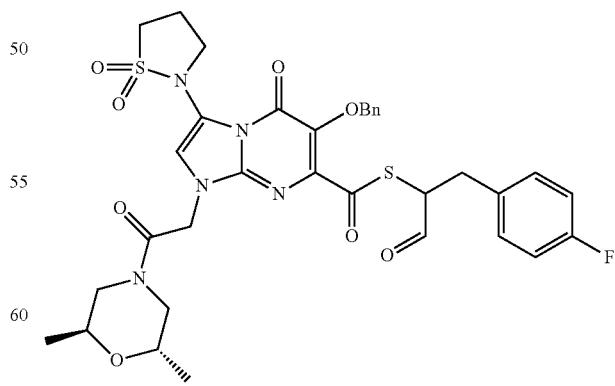

Adapted from the procedure of example 39 using the product of example 70 and the product of example 72.
MS (ESI$^+$) m/z 748 (M+23)

Example 74

Preparation of 6-Benzyloxy-1-[2-(2,6-dimethyl-morpholin-4-yl)-2-oxo-ethyl]-3-(1,1-dioxo-1l6-isothiazolidin-2-yl)-7-[5-(4-fluoro-benzyl)-thiazol-2-yl]-1H-imidazo[1,2-a]pyrimidin-5-one

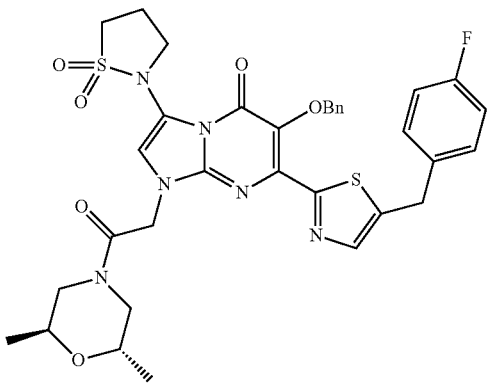 [SMILES: C[C@H]1CN(C(=O)Cn2cc(N3CCCS3(=O)=O)n3c(=O)c(OCc4ccccc4)c(-c4ncc(Cc5ccc(F)cc5)s4)nc23)C[C@H](C)O1]

Adapted from the procedure of example 40 using the product of 73.

$^1$H NMR (300 MHz, CDCl$_3$) δ 1.22 (dd, J=6.2, 14.3 Hz, 6H), 2.31-2.48 (m, 1H), 2.51-2.69 (m, 2H), 2.86-2.99 (m, 1H), 3.38-3.60 (m, 3H), 3.60-3.90 (m, 2H), 3.90-4.06 (m, 2H), 4.15 (s, 2H), 4.34 (d, J=13.5 Hz, 1H), 4.88 (d, J=15.6 Hz, 1H), 5.12-5.33 (m, 3H), 7.02 (t, J=8.5 Hz, 2H), 7.11-7.21 (m, 2H), 7.20-7.30 (m, 4H?), 7.36-7.45 (m, 2H), 7.74 (s, 1H).

MS (ESI$^-$) m/z 705 (M–1)

Example 75

Preparation of 1-[2-(2,6-Dimethyl-morpholin-4-yl)-2-oxo-ethyl]-3-(1,1-dioxo-1l6-isothiazolidin-2-yl)-7-[5-(4-fluoro-benzyl)-thiazol-2-yl]-6-hydroxy-1H-imidazo[1,2-a]pyrimidin-5-one

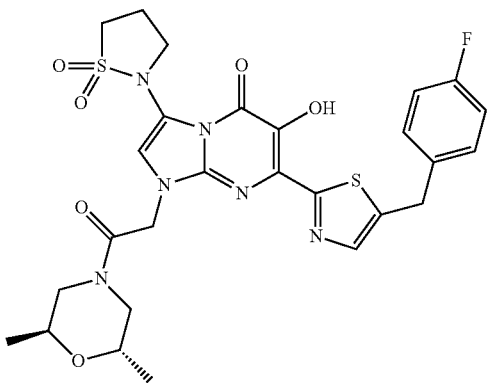

Adapted from the procedure of example 8.5 of PCT/AU2007/001980 using the product of example 74.

$^1$H NMR (300 MHz, DMSO-d$^6$) δ 1.08 (d, J=6.3 Hz, 3H), 1.15 (d, J=6.2 Hz, 3H), 2.24-2.38 (m, 1H), 2.39-2.50 (m, 2H), 2.82 (dd, J=10.4, 13.2 Hz, 1H), 3.35-3.50 (m, 3H), 3.51-3.65 (m, 1H), 3.80 (t, J=6.4 Hz, 2H), 3.94 (d, J=12.9 Hz, 1H), 4.14 (d, J=12.5 Hz, 1H), 4.29 (s, 2H), 4.88 (d, J=17.1 Hz, 1H), 5.08 (d, J=16.9 Hz, 1H), 7.16 (t, J=8.8 Hz, 2H), 7.36 (dd, J=5.4, 8.3 Hz, 2H), 7.62 (s, 1H), 7.90 (s, 1H), 10.76 (s, 1H)

MS (ESI$^+$) m/z 639 (M+23)

HPLC 97.6%

Example 76

Preparation of 2-(2-{5-Benzyloxy-1-[2-(2,6-dimethyl-morpholin-4-yl)-2-oxo-ethyl]-4-oxo-3a,4-dihydro-1H-indol-6-yl}-thiazol-5-ylmethyl)-5-fluoro-benzoic acid The product of example 58 (1.1 g, 1.70 mmol) was dissolved in DMF (10 ml) and then LiOH.H$_2$O (143 mg, 3.41 mmol) was added. The mixture was stirred for 3 hours at room temperature. The reaction mixture was directly poured into 1N HCl (20 ml), The resulting solids were collected by filtration and recrystallized from MeOH to give titled compound (740 mg, yield 69%)

$^1$H NMR (300 MHz, DMSO-d$^6$) δ 1.07 (d, J=6.3 Hz, 3H), 1.13 (d, J=6.0 Hz, 3H), 2.30 (t, J=11.4 Hz, 1H), 2.77 (t, J=10.8 Hz, 1H), 3.38-3.44 (m, 1H), 3.54-3.59 (m, 1H), 3.91 (d, J=12.3 Hz, 1H), 4.11 (d, J=12.6 Hz, 1H), 4.57 (s, 2H), 4.95 (d, J=16.8 Hz, 1H), 5.04 (s, 2H), 5.16 (d, J=17.1 Hz, 1H), 7.29-7.33 (m, 3H), 7.40-7.51 (m, 4H), 7.55 (d, J=2.7 Hz, 1H), 7.62 (dd, J=2.4, 9.6 Hz, 1H), 7.67 (d, J=2.7 Hz, 1H), 7.75 (s, 1H), 13.3 (s, 1H).

MS (ESI$^+$) m/z 632 (M+1), 654 (M+23)

Example 77

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidin-7-yl}-thiazol-5-ylmethyl)-5-fluoro-N,N-dimethyl-benzamide

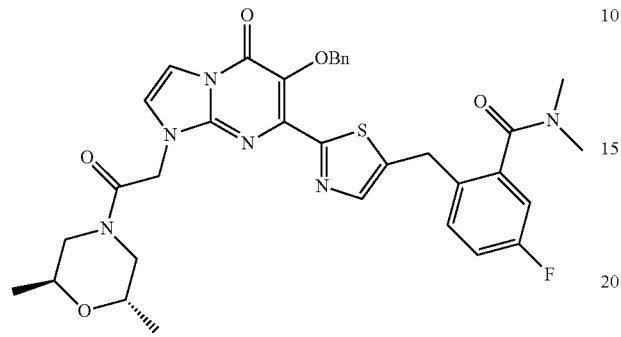

To a solution of the product of 76 (120 mg, 0.19 mmol) in dichloromethane (15 ml), EDCI.HCl (44 mg, 0.23 mmol), HOBt (31 mg, 0.23 mmol), NMe$_2$NH.HCl (31 mg, 0.38 mmol) and TEA (58 mg, 0.57 mmol) was added successively. The mixture was stirred at room temperature overnight, after which it was poured into water and extracted with DCM. The combined organic layers were washed with water, dried and concentrated. The residue was purified by column chromatography to give the titled product (62 mg, yield 50%).

$^1$H NMR (300 MHz, DMSO-d$^6$) δ 1.08 (d, J=6.3 Hz, 3H), 1.15 (d, J=6.3 Hz, 3H), 2.28-2.37 (m, 1H), 2.52 (s, 3H), 2.77-2.85 (m, 1H), 2.91 (s, 3H), 3.43-3.45 (m, 1H), 3.60-3.62 (m, 1H), 3.94 (d, J=12.3 Hz, 1H), 4.10-4.14 (m, 1H), 4.17 (s, 2H), 5.0 (d, J=16.5 Hz, 1H), 5.06 (s, 2H), 5.17 (d, J=16.8 Hz, 1H), 7.14 (dd, J=3, 8.7 Hz, 1H), 7.23-7.28 (m, 1H), 7.31-7.37 (m, 3H), 7.41-7.46 (m, 1H), 7.47-7.50 (m, 2H), 7.57 (d, J=2.9 Hz, 1H), 7.70 (d, J=2.7 Hz, 1H), 7.74 (s, 1H).

MS (ESI$^+$) m/z 681 (M+23)

Example 78

Preparation of 2-(2-{1-[2-(2,6-Dimethyl-morpholin-4-yl)-2-oxo-ethyl]-6-hydroxy-5-oxo-1,5-dihydro-imidazo[1,2-a]pyrimidin-7-yl}-thiazol-5-ylmethyl)-5-fluoro-N,N-dimethyl-benzamide

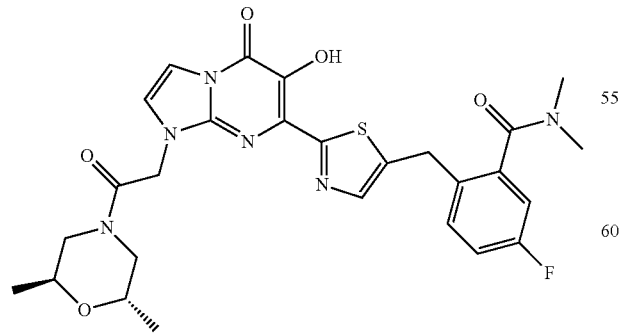

Adapted from the procedure of example 8.5 of PCT/AU2007/001980 using the product of example 77.

$^1$H NMR (300 MHz, DMSO-d$^6$) δ 1.05 (d, J=6.3 Hz, 3H), 1.12 (d, J=6.0 Hz, 3H), 2.25-2.34 (m, 1H), 2.58 (s, 3H), 2.74-2.85 (m, 1H), 2.93 (s, 3H), 3.39-3.42 (m, 1H), 3.56-3.59 (m, 1H), 3.92 (d, J=12.6 Hz, 1H), 4.10 (d, J=12.6 Hz, 1H), 4.17 (s, 2H), 4.90 (d, J=16.5 Hz, 1H), 5.13 (d, J=16.8 Hz, 1H), 7.15 (dd, J=2.7, 9.0 Hz, 1H), 7.19-7.26 (m, 1H), 7.42-7.47 (m, 1H), 7.49 (d, J=2.7 Hz, 1H), 7.60 (d, J=2.7 Hz 1H), 7.79 (s, 1H), 10.8 (s, 1H).

MS (ESI$^+$) m/z 569 (M+1), 591 (M+23)

Example 79

Preparation of 6-Benzyloxy-1-[2-(2,6-dimethyl-morpholin-4-yl)-2-oxo-ethyl]-3-(1,1-dioxo-1l6-isothiazolidin-2-yl)-5-oxo-1,5-dihydro-imidazo[1,2-a]pyrimidine-7-carbothioic acid S-[1-(3,4-dichloro-benzyl)-2-oxo-ethyl]ester

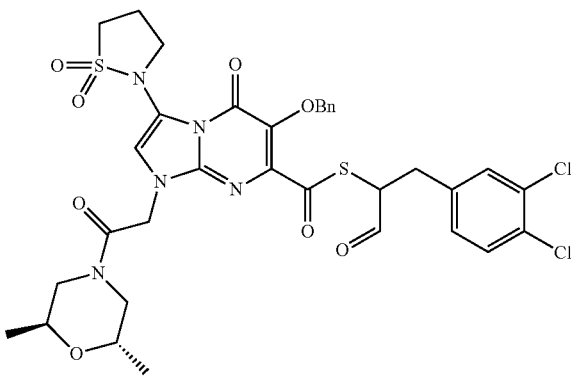 [SMILES: C[C@H]1CN(C(=O)Cn2cc(N3CCCS3(=O)=O)n3c(=O)c(OCc4ccccc4)c(C(=O)SC(C=O)Cc4ccc(Cl)c(Cl)c4)nc23)C[C@H](C)O1]

Adapted from the procedure of example 39 using the product of example 70 and the product of example 38.

MS (ESI$^+$) m/z 776 (M$^{[35]}$+1), 778 M$^{[37]}$+1)

Example 80

Preparation of 6-Benzyloxy-7-[5-(3,4-dichloro-benzyl)-thiazol-2-yl]-1-[2-(2,6-dimethyl-morpholin-4-yl)-2-oxo-ethyl]-3-(1,1-dioxo-1l6-isothiazolidin-2-yl)-1H-imidazo[1,2-a]pyrimidin-5-one

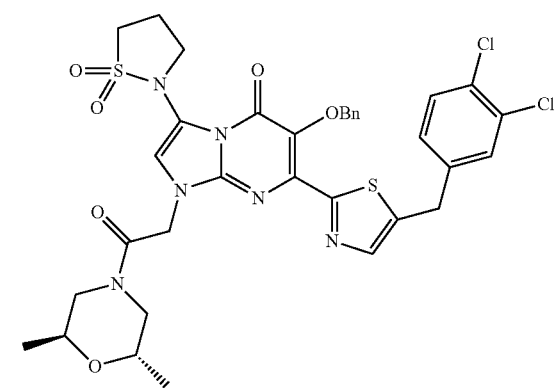 [SMILES: C[C@H]1CN(C(=O)Cn2cc(N3CCCS3(=O)=O)n3c(=O)c(OCc4ccccc4)c(-c4ncc(Cc5ccc(Cl)c(Cl)c5)s4)nc23)C[C@H](C)O1]

Adapted from the procedure of example 40 using the product of example 79.

¹H NMR (300 MHz, CDCl₃) δ 1.18-1.34 (m, 6H), 2.43 (t, J=11.5 Hz, 1H), 2.62 (t, =7.0 Hz, 2H), 2.85-3.05 (m, 1H), 3.41-3.88 (m, 5H), 3.92-4.06 (m, 2H), 4.15 (s, 2H), 4.36 (d, J=12.3 Hz, 1H), 4.80-5.00 (m, 1H), 5.01-5.40 (m, 3H), 7.05 (d, J=7.6 Hz, 1H), 7.20-7.35 (m, 5H), 7.38-7.50 (m, 3H), 7.76 (s, 1H)

MS (ESI⁻) m/z 755 (M[35]−1), 757 (M[37]−1)

Example 81

Preparation of 7-[5-(3,4-Dichloro-benzyl)-thiazol-2-yl]-1-[2-(2,6-dimethyl-morpholin-4-yl)-2-oxo-ethyl]-3-(1,1-dioxo-1l6-isothiazolidin-2-yl)-6-hydroxy-1H-imidazo[1,2-a]pyrimidin-5-one

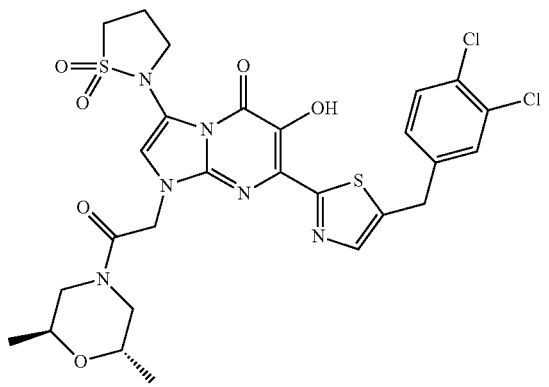 [SMILES: C[C@H]1CN(C(=O)Cn2cc(N3CCCS3(=O)=O)n3c(=O)c(O)c(-c4ncc(Cc5ccc(Cl)c(Cl)c5)s4)nc23)C[C@H](C)O1]

Adapted from the procedure of example 8.5 of PCT/AU2007/001980 using the product of example 80.

¹H NMR (300 MHz, DMSO-d⁶) δ 1.08 (d, J=6.3 Hz, 3H), 1.15 (d, J=6.2 Hz, 3H), 2.32 (dd, J=11.4, 13.6 Hz, 1H), 2.38-2.50 (m, 2H), 2.70-2.85 (m, 1H), 3.38-3.50 (m, 3H), 3.51-3.68 (m, 1H), 3.80 (t, J=6.8 Hz, 2H), 3.94 (d, J=12.3 Hz, 1H), 4.13 (d, J=12.1 Hz, 1H), 4.32 (s, 2H), 4.89 (d, J=16.9 Hz, 1H), 5.10 (d, J=16.5 Hz, 1H), 7.33 (dd, J=2.3, 8.4 Hz, 1H), 7.58-7.66 (m, 3H), 7.93 (s, 1H), 10.75 (s, 1H)

MS (ESI⁺) m/z 689 (M[35]+23), 691 (M[37]+23)
HPLC 98.7%

Example 82

Preparation of 5-Fluoro-2-methoxy-benzenesulfonyl chloride

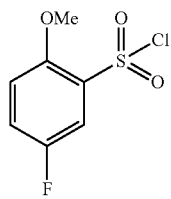 [SMILES: COc1ccc(F)cc1S(=O)(=O)Cl]

1-fluoro-4-methoxybenzene (10.0 g, 0.079 mol) was added dropwise to sulfurochloridic acid (31.4 ml, 0.474 mol) at 0° C., The mixture was stirred at room temperature for about 6 h, after which it was added dropwise into ice water. The mixture was extracted with CH₂Cl₂ three times. The combined extracts were washed with brine, dried over sodium sulfate and concentrated in vacuo to give the title product (15.0 g, 84.6% yield).

¹H NMR (300 MHz, DMSO-d⁶) δ 3.74 (s, 3H), 6.97 (dd, J=4.3, 8.9 Hz, 1H), 7.13 (dt, J=3.4, 8.6 Hz, 1H), 7.41 (dd, J=3.3, 8.8 Hz, 1H)

Example 83

Preparation of 4-(5-Fluoro-2-methoxy-benzenesulfonyl)-morpholine

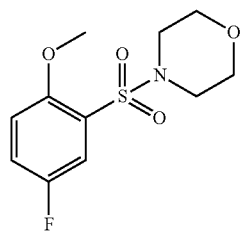 [SMILES: COc1ccc(F)cc1S(=O)(=O)N1CCOCC1]

To a mixture of morpholine (5.8 g, 66.9 mmol) and TEA (9.3 ml, 66.9 mol) in CH₂Cl₂ (20 ml) was added dropwise a solution of the product of example 82 (5.0 g, 22 mmol) in CH₂Cl₂ (10 ml) at 0° C. After stirring at room temperature for one hour, the mixture was diluted with CH₂Cl₂, washed with water, dried and concentrated under reduced pressure. The resulting residue was purified by column chromatography (PE/EA=10/1) to give the titled compound (5.53 g, yield 90.3%).

¹H NMR (300 MHz, DMSO-d⁶) δ 3.10 (t, J=4.6 Hz, 4H), 3.59 (t, J=4.6 Hz, 4H), 3.89 (s, 3H), 7.31 (dd, J=4.4, 9.1 Hz, 1H), 7.46-7.59 (m, 2H).

MS (ESI⁺) m/z 298 (M+23)

Example 84

Preparation of 4-Fluoro-2-(morpholine-4-sulfonyl)-phenol

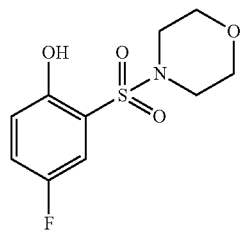 [SMILES: O=S(=O)(c1cc(F)ccc1O)N1CCOCC1]

To a solution of 4-(5-fluoro-2-methoxyphenylsulfonyl) morpholine (0.5 g 1.8 mmol) in CH₂Cl₂ (10 ml) was added dropwise a solution of tribromoborane (0.593 mg 2.36 mmol) in CH₂Cl₂ (20 ml) at 0° C. The mixture was stirred at room temperature for 1 h, after which methanol (10 ml) was added to quench the reaction. The solvent was evaporated under reduced pressure and ethyl acetate (30 ml) was added, washed with water and then brine, dried and concentrated into dryness to give the product (427 mg, 90% yield).

¹H NMR (300 MHz, DMSO-d⁶) δ 3.11 (t, J=4.7 Hz, 4H), 3.59 (t, J=4.7 Hz, 4H), 7.01-7.09 (m, 1H), 7.33-7.42 (m, 2H), 10.72 (s, 1H)

Example 85

Preparation of Trifluoro-methanesulfonic acid 4-fluoro-2-(morpholine-4-sulfonyl)-phenyl ester

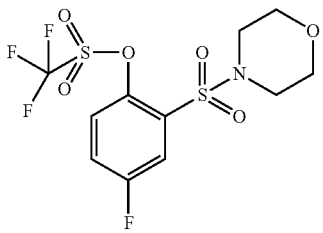 [SMILES: O=S(=O)(c1cc(F)ccc1OS(=O)(=O)C(F)(F)F)N1CCOCC1]

To a solution of 4-fluoro-2-(morpholinosulfonyl)phenol (0.4 g, 1.5 mmol) and DMAP (0.28 g 2.29 mmol) in $CH_2Cl_2$ (10 ml), $Tf_2O$ (0.93 ml 5.5 mmol) was added dropwise at 0° C. The mixture was stirred at room temperature for 4 h, after which the mixture was washed with hydrochloric acid (1N, 20 ml) and then extracted with EA. The extracts were combined, washed with brine, dried over sodium sulfate and evaporated into dryness. The resulting residue was purified by column chromatography using PE/EA (10/1) as eluent to give the desired product (469 mg, yield 78%).

$^1$H NMR (300 MHz, DMSO-d$^6$) δ 3.09 (t, J=4.7 Hz, 4H), 3.64 (t, J=4.7 Hz, 4H), 7.70-7.86 (m, 3H)

Example 86

Preparation of 3-[4-Fluoro-2-(morpholine-4-sulfonyl)-phenyl]-acrylic acid methyl ester

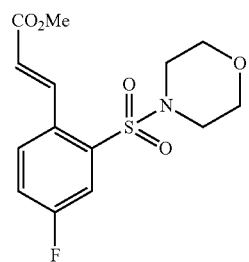 [SMILES: COC(=O)/C=C/c1ccc(F)cc1S(=O)(=O)N1CCOCC1]

To a solution of the product of example 85 (100 mg 0.254 mmol) in dry DMF (3 ml) was added methyl acrylate (0.09 ml, 1.02 mmol), Pd(PPh$_3$)$_2$Cl$_2$(17.83 mg, 0.0254 mmol), DPPP (10.5 mg, 0.0254 mmol) and DIPEA (0.2 ml, 1.02 mmol) successively at room temperature in sealed tube. The mixture was heated at 120° C. for about 24 h. After cooling to room temperature, the mixture was poured into ice water and extracted with EA three times. The combined extracts were washed with brine, dried over sodium sulfate and concentrated under reduced pressure. The residue was purified by column chromatography (PE/EA=5/1) to give the desire product (36 mg, yield 43%).

$^1$H NMR (300 MHz, DMSO-d$^6$) δ 3.03 (t, J=4.7 Hz, 4H), 3.59 (t, J=4.7 Hz, 4H), 3.75 (s, 3H), 6.65 (d, J=16.1 Hz, 1H), 7.60-7.75 (m, 2H), 8.12 (dd, J=5.1, 8.4 Hz, 1H), 8.33 (d, J=15.7 Hz, 1H).

MS (ESI$^+$) m/z 352 (M+23)

Example 87

Preparation of 3-[4-Fluoro-2-(morpholine-4-sulfonyl)-phenyl]-propionic acid methyl ester

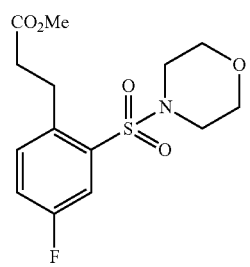 [SMILES: COC(=O)CCc1ccc(F)cc1S(=O)(=O)N1CCOCC1]

To a solution of the product of example 86 (200 mg, 0.608 mmol) in MeOH (10 ml) was added Pd/C (20 mg, 10% Pd on carbon). The mixture was stirred at room temperature under H2 atmosphere overnight. The mixture was filtered and the filtrate was concentrated in vacuo. The resulting residue was purified by column chromatography (PE/EA=3/1) to give the desire product (150 mg, yield 74.5%).

$^1$H NMR (300 MHz, DMSO-d$^6$) δ 2.65 (t, J=8.0 Hz, 2H), 3.05 (t, J=4.7 Hz, 4H), 3.18 (t, J=8.0 Hz, 2H), 3.56-3.66 (m, 7H), 7.48-7.64 (m, 3H).

Example 88

Preparation of 3-[4-Fluoro-2-(morpholine-4-sulfonyl)-phenyl]-propionaldehyde

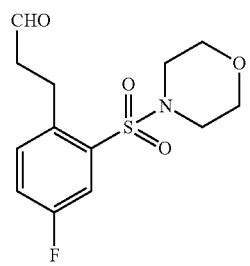 [SMILES: O=CCCc1ccc(F)cc1S(=O)(=O)N1CCOCC1]

The solution of the product of example 87 (830 mg, 2.5 mmol) in toluene (5 ml) was cooled down to −70° C. DIBAL-H (1 mol/l in toluene, 3.12 ml) was added dropwise. After completion of addition, the mixture was stirred at −70° C. for one hour. Then the reaction was quenched by adding MeOH (2 ml), after which it was warmed to room temperature. The mixture was dissolved in EA, washed with brine, dried and evaporated under reduced pressure. The residue was purified by column chromatography (PE:EA=3:2) to afford the title compound (355 mg, 47% yield).

$^1$H NMR (300 MHz, DMSO-d$^6$) δ 2.81 (dt, J=0.9, 7.6 Hz, 2H), 3.06 (t, J=4.7 Hz, 4H), 3.17 (t, J=7.7 Hz, 2H), 3.63 (t, J=4.7 Hz, 4H), 7.46-7.64 (m, 3H), 9.71 (t, J=1.0 Hz, 1H)

Example 89

Preparation of 3-Bromo-3-[4-fluoro-2-(morpholine-4-sulfonyl)-phenyl]-propionaldehyde

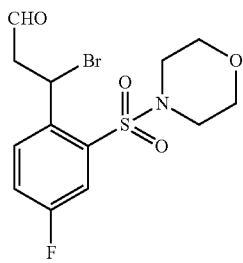 [SMILES: O=CCC(Br)c1ccc(F)cc1S(=O)(=O)N1CCOCC1]

Adapted from the procedure of example 38 using the product of example 88

$^1$H NMR (300 MHz, DMSO-d$^6$) δ 3.06 (t, J=4.7 Hz, 4H), 3.47 (dd, J=8.9, 15.0 Hz, 1H), 3.65 (t, J=4.7 Hz, 4H), 3.80 (dd, J=6.2, 15.2 Hz, 1H), 4.92-5.03 (m, 1H), 7.54-7.75 (m, 3H), 9.52 (d, J=1.8 Hz, 1H)

Example 90

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid S-{1-[4-fluoro-2-(morpholine-4-sulfonyl)-benzyl]-2-oxo-ethyl}ester

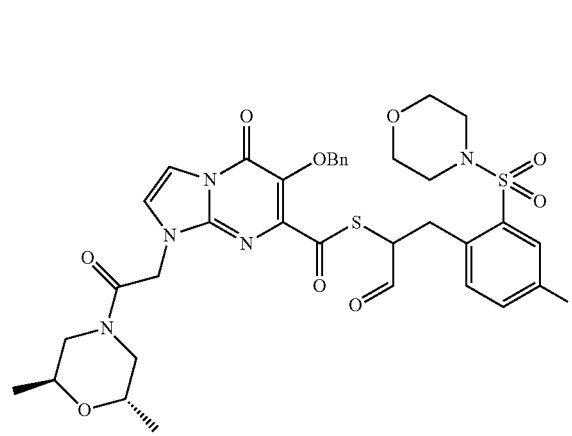

Adapted from the procedure of example 39 using the product of example 89.

MS (ESI$^+$) m/z 778 (M+23)

Example 91

Preparation of 6-Benzyloxy-1-[2-(2,6-dimethyl-morpholin-4-yl)-2-oxo-ethyl]-7-{5-[4-fluoro-2-(morpholine-4-sulfonyl)-benzyl]-thiazol-2-yl}-1H-imidazo[1,2-a]pyrimidin-5-one

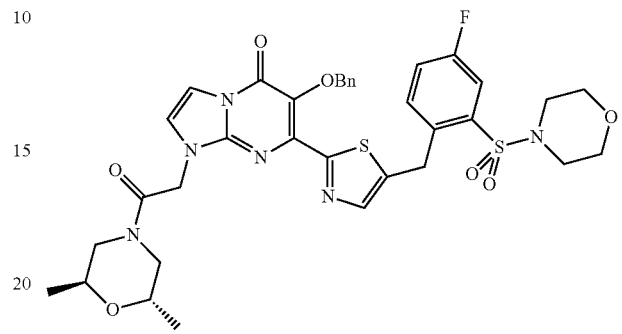

Adapted from the procedure of example 40 using the product of example 90.

$^1$H NMR (300 MHz, DMSO-d$^6$) δ 1.07 (d, J=5.8 Hz, 3H), 1.14 (d, J=6.0 Hz, 3H), 2.31 (t, J=11.6 Hz, 1H), 2.80 (t, J=11.8 Hz, 1H), 2.99-3.09 (m, 4H), 3.37-3.49 (m, 1H), 3.51-3.68 (m, 5H), 3.94 (d, J=12.8 Hz, 1H), 4.14 (d, J=12.8 Hz, 1H), 4.61 (s, 2H), 4.92-5.09 (m, 3H), 5.20 (d, J=16.6 Hz, 1H), 7.27-7.36 (m, 3H), 7.44-7.53 (m, 2H), 7.54-7.69 (m, 4H), 7.71 (d, J=2.4 Hz, 1H), 7.86 (s, 1H)

MS (ESI$^+$) m/z 759 (M+23)

Example 92

Preparation of 1-[2-(2,6-Dimethyl-morpholin-4-yl)-2-oxo-ethyl]-7-{5-[4-fluoro-2-(morpholine-4-sulfonyl)-benzyl]-thiazol-2-yl}-6-hydroxy-1H-imidazo[1,2-a]pyrimidin-5-one

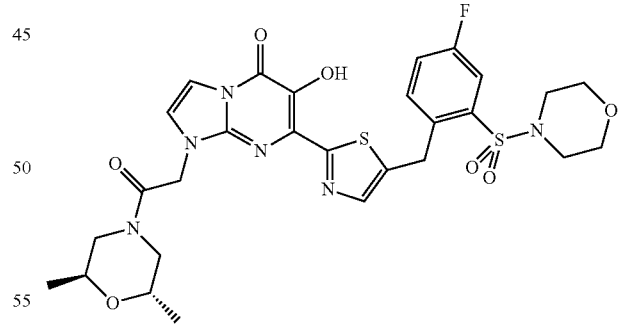

Adapted from the procedure of example 8.5 of PCT/AU2007/001980 using the product of example 91.

$^1$H NMR (300 MHz, DMSO-d$^6$) δ 1.07 (d, J=6.2 Hz, 3H), 1.14 (d, J=5.9 Hz, 3H), 2.31 (dd, J=10.8, 12.7 Hz, 1H), 2.80 (t, J=11.8 Hz, 1H), 3.08 (t, J=4.5 Hz, 4H), 3.35-3.48 (m, 1H), 3.50-3.68 (m, 5H), 3.95 (d, J=11.9 Hz, 1H), 4.13 (d, J=11.3 Hz, 1H), 4.63 (s, 2H), 4.92 (d, J=16.1 Hz, 1H), 5.12 (d, J=15.4 Hz, 1H), 7.46-7.75 (m, 5H), 7.91 (s, 1H), 10.81 (s, 1H)

MS (ESI$^+$) m/z 669 (M+23)

HPLC 98.2%

Example 93

Preparation of 6-Benzyloxy-1-[2-(2,6-dimethyl-morpholin-4-yl)-2-oxo-ethyl]-7-{5-[4-fluoro-2-(morpholine-4-carbonyl)-benzyl]-thiazol-2-yl}-1H-imidazo[1,2-a]pyrimidin-5-one

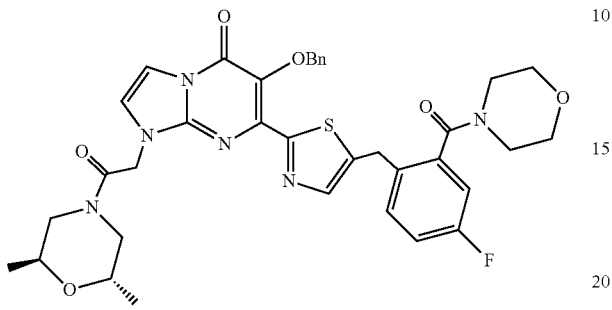

Adapted from the procedure of example 77 using morpholine.

$^1$H NMR (300 MHz, DMSO-d$^6$) δ 1.07 (J=6.3 Hz, 3H), 1.13 (J=6.0 Hz, 3H), 2.30 (t, J=12.6 Hz, 1H), 2.6-2.83 (m, 2H), 2.96-3.05 (m, 2H), 3.38-3.60 (m, 7H), 3.91 (d, J=12.3 Hz, 1H), 4.09-4.13 (m, 2H), 4.29-4.33 (m, 1H), 4.96 (d, J=16.8 Hz, 1H), 5.04 (s, 2H), 5.17 (d, J=16.8 Hz, 1H), 7.16-7.33 (m, 5H), 7.43-7.48 (m, 3H), 7.56 (d, J=2.7 Hz, 1H), 7.69 (d, J=2.7 Hz, 1H), 7.74 (s, 1H).

MS (ESI$^-$) m/z 699 (M−1)

Example 94

Preparation of 1-[2-(2,6-Dimethyl-morpholin-4-yl)-2-oxo-ethyl]-7-{5-[4-fluoro-2-(morpholine-4-carbonyl)-benzyl]-thiazol-2-yl}-6-hydroxy-1H-imidazo[1,2-a]pyrimidin-5-one

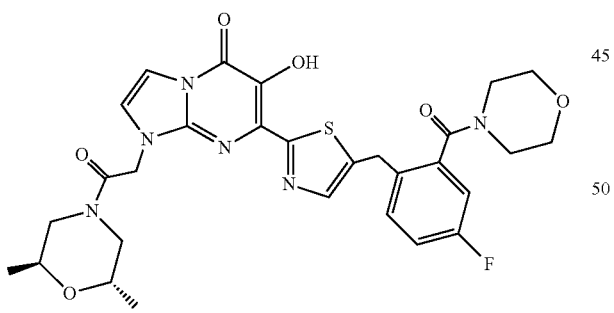

Adapted from the procedure of example 8.5 of PCT/AU2007/001980 using the product of example 93.

$^1$H NMR (300 MHz, DMSO-d$^6$) δ 1.06 (J=6.0 Hz, 3H), 1.13 (J=6.0 Hz, 3H), 2.30 (t, J=12.9 Hz, 1H), 2.74-2.84 (m, 2H), 3.09-3.16 (m, 2H), 3.38-3.63 (m, 7H), 3.91 (d, J=13.2 Hz, 1H), 4.06-4.15 (m, 2H), 4.27-4.35 (m, 1H), 4.90 (d, J=16.5 Hz, 1H), 5.10 (d, J=16.8 Hz, 1H), 7.18-7.27 (m, 2H), 7.45-7.50 (m, 2H), 7.60 (d, J=2.7 Hz, 1H), 7.80 (s, 1H), 10.78 (s, 1H).

MS (ESI$^-$) m/z 609 (M−1)
HPLC 99.8%

Example 95

Preparation of 5-Fluoro-2-methoxy-N,N-dimethyl-benzenesulfonamide

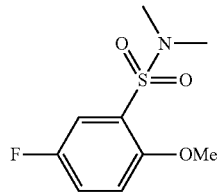

Adapted from the procedure of example 83 using hydrochlorate of dimethylamine.

$^1$H NMR (300 MHz, DMSO-d$^6$) δ 2.74 (s, 6H), 3.88 (s, 3H), 7.25-7.34 (m, 1H), 7.47-7.56 (m, 2H)

Example 96

Preparation of 5-Fluoro-2-hydroxy-N,N-dimethyl-benzene sulfonamide

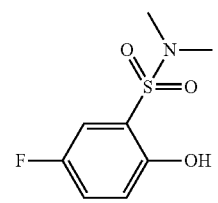

Adapted from the procedure of example 84 using the product of example 95.

$^1$H NMR (300 MHz, CDCl$_3$) δ 2.80 (s, 6H), 7.0-7.10 (m, 1H), 7.18-7.30 (m, 2H), 8.66 (s, 1H).

MS (ESI$^-$) m/z 218 (M−1)

Example 97

Preparation of Trifluoro-methanesulfonic acid 2-dimethylsulfamoyl-4-fluoro-phenyl ester

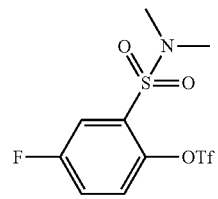 [SMILES: CN(C)S(=O)(=O)c1cc(F)ccc1OS(=O)(=O)C(F)(F)F]

Adapted from the procedure of example 85 using the product of example 96.

$^1$H NMR (300 MHz, DMSO-d$^6$) δ 2.77 (s, 6H), 7.68-7.85 (m, 3H)

MS (ESI$^+$) m/z 374 (M+23)

Example 98

Preparation of 3-(2-Dimethylsulfamoyl-4-fluoro-phenyl)-acrylic acid methyl ester

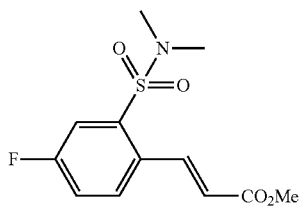 [SMILES: COC(=O)/C=C/c1ccc(F)cc1S(=O)(=O)N(C)C]

Adapted from the procedure of example 86 using the product of example 97.

¹H NMR (300 MHz, CDCl₃) δ 2.81 (s, 6H), 3.83 (s, 3H), 6.30 (d, J=16.1 Hz, 1H), 7.30-7.45 (m, 1H), 7.65-7.79 (m, 2H), 8.48 (d, J=15.7 Hz, 1H).
MS (ESI⁺) m/z 288 (M+1)

Example 99

Preparation of 3-(2-Dimethylsulfamoyl-4-fluoro-phenyl)-propionic acid methyl ester

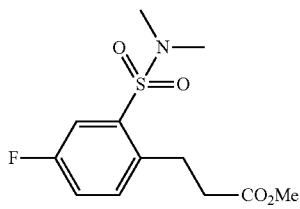

Adapted from the procedure of example 87 using the product of example 97.

¹H NMR (300 MHz, CDCl₃) δ 2.68 (t, J=7.9 Hz, 2H), 2.83 (s, 6H), 3.26 (t, J=7.7 Hz, 2H), 3.67 (s, 3H), 7.21 (dt, J=2.6, 8.1 Hz, 1H), 7.37 (dd, J=5.5, 8.4 Hz, 1H), 7.58 (dd, J=2.6, 8.4 Hz, 1H)
MS (ESI⁺) m/z 312 (M+23)

Example 100

Preparation of 5-Fluoro-N,N-dimethyl-2-(3-oxo-propyl)-benzenesulfonamide

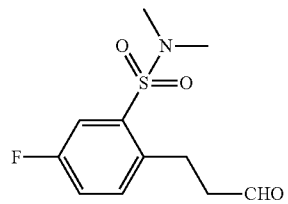 [SMILES: CN(C)S(=O)(=O)c1cc(F)ccc1CCC=O]

Adapted from the procedure of example 88 using the product of example 99.

¹H NMR (300 MHz, CDCl₃) δ 2.79-2.91 (m, 8H), 3.25 (t, J=7.5 Hz, 2H), 7.14-7.26 (m, 1H), 7.36 (dd, J=5.5, 8.5 Hz, 1H), 7.57 (dd, J=2.8, 8.7 Hz, 1H), 9.81 (s, 1H)
MS (ESI⁻) m/z 258 (M−1)

Example 101

Preparation of 2-(2-Bromo-3-oxo-propyl)-5-fluoro-N,N-dimethyl-benzenesulfonamide

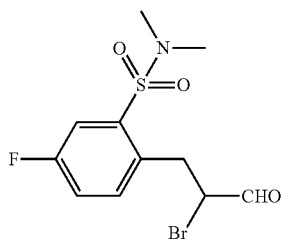 [SMILES: CN(C)S(=O)(=O)c1cc(F)ccc1CC(Br)C=O]

Adapted from the procedure of example 89 using the product of example 100.

¹H NMR (300 MHz, DMSO-d⁶) δ 2.77 (s, 6H), 3.46 (dd, J=8.4, 14.9 Hz, 1H), 3.81 (dd, J=6.3, 15.0 Hz, 1H), 4.88-4.99 (m, 1H), 7.49-7.74 (m, 3H), 9.51 (d, J=2.2 Hz, 1H)

Example 102

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid S-[2-(2-dimethylsulfamoyl-4-fluoro-phenyl)-1-formyl-ethyl] ester

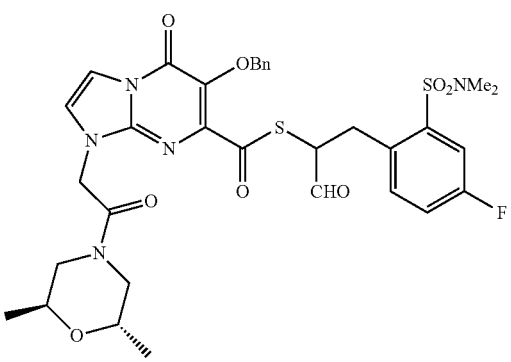

Adapted from the procedure of example 39 using the product of example 101.

MS (ESI⁺) m/z 736 (M+23)

Example 103

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidin-7-yl}-thiazol-5-ylmethyl)-5-fluoro-N,N-dimethyl-benzenesulfonamide

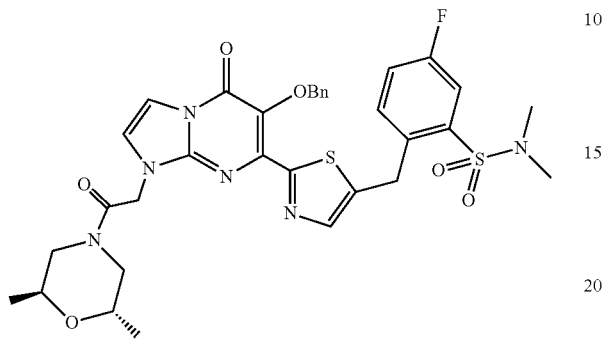

Adapted from the procedure of example 40 using the product of example 102.

$^1$H NMR (300 MHz, DMSO-d$^6$) δ 1.08 (d, J=6.1 Hz, 3H), 1.15 (d, J=5.9 Hz, 3H), 2.32 (dd, J=10.9, 12.9 Hz, 1H), 2.73 (s, 6H), 2.74-2.86 (m, 1H), 3.38-3.49 (m, 1H), 3.51-3.67 (m, 1H), 3.94 (d, J=12 Hz, 1H), 4.13 (d, J=13.0 Hz, 1H), 4.59 (s, 2H), 4.98 (d, J=16.9 Hz, 1H), 5.06 (s, 2H), 5.18 (d, J=17.1 Hz, 1H), 7.26-7.39 (m, 3H), 7.44-7.65 (m, 6H), 7.70 (d, J=2.7 Hz, 1H), 7.86 (s, 1H)

MS (ESI$^+$) m/z 717 (M+23)

Example 104

Preparation of 2-(2-{1-[2-(2,6-Dimethyl-morpholin-4-yl)-2-oxo-ethyl]-6-hydroxy-5-oxo-1,5-dihydro-imidazo[1,2-a]pyrimidin-7-yl}-thiazol-5-ylmethyl)-5-fluoro-N,N-dimethyl-benzenesulfonamide

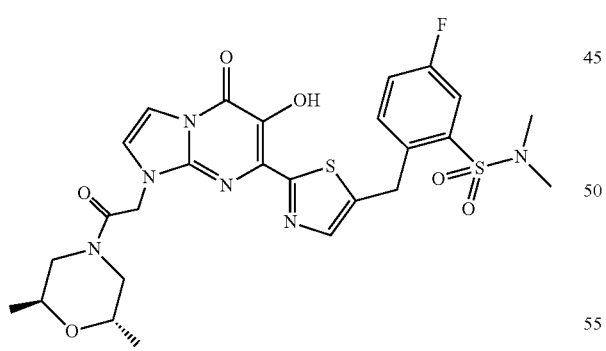

Adapted from the procedure of example 8.5 of PCT/AU2007/001980 using the product of example 103.

$^1$H NMR (300 MHz, DMSO-d$^6$) δ 1.07 (d, J=6.1 Hz, 3H), 1.14 (d, J=6.2 Hz, 3H), 2.31 (t, J=11.8 Hz, 1H), 2.71-2.85 (m, 7H), 3.30-3.48 (m, 1H), 3.49-3.67 (m, 1H), 3.95 (d, J=12.8 Hz, 1H), 4.13 (d, J=13.0 Hz, 1H), 4.62 (s, 2H), 4.92 (d, J=16.7 Hz, 1H), 5.13 (d, J=16.6 Hz, 1H), 7.50 (d, J=2.6 Hz, 1H), 7.52-7.68 (m, 4H), 7.90 (s, 1H)

MS (ESI$^-$) m/z 603 (M−1)

HPLC 94.5%

Example 105

Preparation of 4-(2-Chloro-acetyl)-piperazine-1-carboxylic acid tert-butyl ester

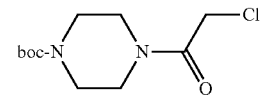

Piperazine-1-carboxylic acid tert-butyl ester (3.0 g, 16.1 mmol) and DIPEA (3.1 ml, 18.0 mmol) were dissolved in DCM (32 ml) and cooled in ice bath. To the above stirred mixture was added a solution of chloroacetyl chloride (1.33 ml, 16.7 mmol) at 0° C. Three hours later, the mixture was washed with water, dried and evaporated under reduced pressure. The residue was purified by column chromatography using EA/PE (4/1) as eluent to afford the title compound (3.3 g, yield 78.0%).

$^1$H NMR (300 MHz, CDCl$_3$) δ 1.47 (s, 9H), 3.40-3.53 (m, 6H), 3.54-3.64 (m, 2H), 4.07 (s, 2H)

MS (ESI$^+$) m/z 263 (M+1)

Example 106

Methyl 6-acetoxy-1-(2-(4-(tert-butoxycarbonyl)piperazin-1-yl)-2-oxoethyl)-5-oxo-1,5-dihydroimidazo[1,2-a]pyrimidine-7-carboxylate

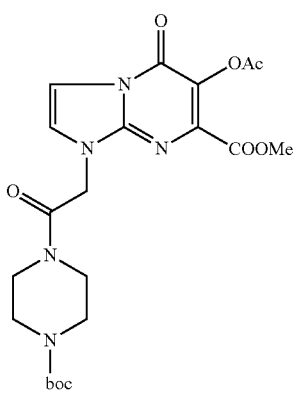

Adapted from the procedure of example 33 using the product of example 105.

$^1$H NMR (300 MHz, DMSO-d$^6$) δ 1.42 (s, 9H), 2.26 (s, 3H), 3.32-3.36 (m, 2H), 3.42-3.48 (m, 4H), 3.52-3.59 (m, 2H), 3.83 (s, 3H), 5.16 (s, 2H), 7.68 (d, J=2.4 Hz, 1H), 7.80 (d, J=2.4 Hz, 1H)

MS (ESI$^+$) m/z 478 (M+1)

Example 107

Methyl 6-(benzyloxy)-1-(2-(4-(tert-butoxycarbonyl)piperazin-1-yl)-2-oxoethyl)-5-oxo-1,5-dihydroimidazo[1,2-a]pyrimidine-7-carboxylate

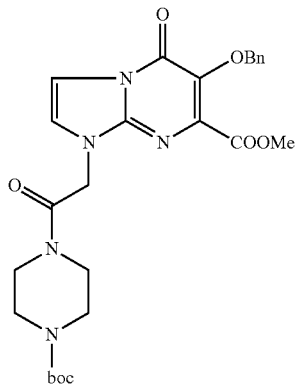

Adapted from the procedure of example 34 using the product of example 106.

$^1$H NMR (300 MHz, DMSO-d$^6$) δ 1.42 (s, 9H), 3.32-3.37 (m, 2H), 3.40-3.47 (m, 4H), 3.50-3.56 (m, 2H), 3.77 (s, 3H), 5.03 (s, 2H), 5.12 (s, 2H), 7.30-7.44 (m, 5H), 7.60 (d, J=2.7 Hz, 1H), 7.77 (d, J=2.7 Hz, 1H)

MS (ESI$^+$) m/z 526 (M+1)

Example 108

6-(Benzyloxy)-1-(2-(4-(tert-butoxycarbonyl)piperazin-1-yl)-2-oxoethyl)-5-oxo-1,5-dihydroimidazo[1,2-a]pyrimidine-7-carboxylic acid

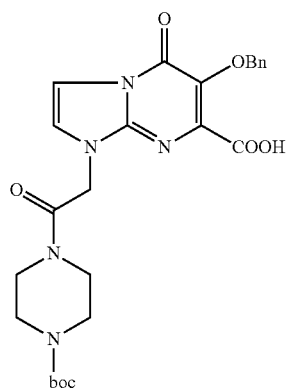

Adapted from the procedure of example 35 using the product of example 107.

$^1$H NMR (300 MHz, DMSO-d$^6$) δ 1.43 (s, 9H), 3.25-3.60 (m, 8H), 5.02 (s, 2H), 5.12 (s, 2H), 7.29-7.42 (m, 3H), 7.43-7.50 (m, 2H), 7.57 (d, J=2.7 Hz, 1H), 7.73 (d, J=2.7 Hz, 1H)

MS (ESI$^+$) m/z 512 (M+1)

Example 109

6-(Benzyloxy)-1-(2-(4-(tert-butoxycarbonyl)piperazin-1-yl)-2-oxoethyl)-5-oxo-1,5-dihydroimidazo[1,2-a]pyrimidine-7-carbothioic S-acid

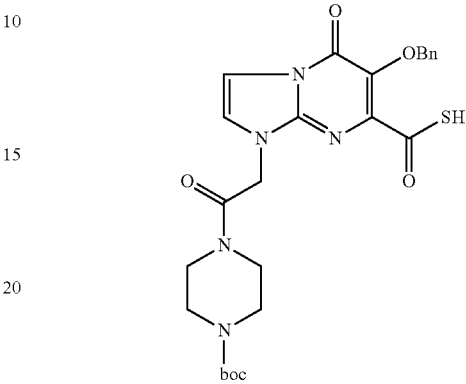

Adapted from the procedure of example 36 using the product of example 108.

MS (ESI$^-$) m/z 526 (M-1)

Example 110 tert-Butyl-4-(2-(6-(benzyloxy)-7-((1-(4-fluorophenyl)-3-oxopropan-2-ylthio)carbonyl)-5-oxoimidazo[1,2-a]pyrimidin-1(5H)-yl)acetyl)piperazine-1-carboxylate

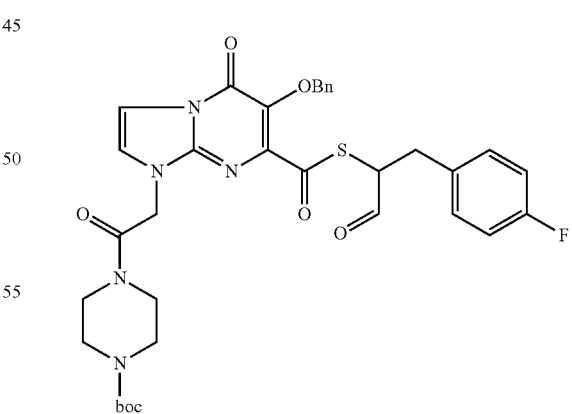

Adapted from the procedure of example 39 using the product of example 109 and the product of example 84

MS (ESI$^+$) m/z 678 (M+1), 700 (M+23), 732 (M+55)

Example 111 tert-Butyl 4-(2-(6-(benzyloxy)-7-(5-(4-fluorobenzyl)thiazol-2-yl)-5-oxoimidazo[1,2-a]pyrimidin-1(5H)-yl)acetyl)piperazine-1-carboxylate

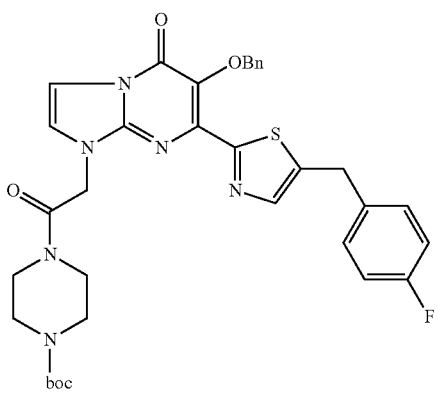

Adapted from the procedure of example 39 using the product of example 110.

$^1$H NMR (300 MHz, DMSO-d$^6$) δ 1.43 (s, 9H), 3.32-3.37 (m, 2H), 3.40-3.50 (m, 4H), 3.55-3.60 (m, 2H), 4.24 (s, 2H), 5.08 (s, 2H), 5.10 (s, 2H), 7.15 (t, J=8.7 Hz, 2H), 7.30-7.37 (m, 5H), 7.46-7.51 (m, 2H), 7.57 (d, J=2.7 Hz, 1H), 7.70 (d, J=2.7 Hz, 1H), 7.83 (s, 1H)

MS (ESI$^+$) m/z 659 (M+1), 681 (M+23)

Example 112

6-(Benzyloxy)-7-(5-(4-fluorobenzyl)thiazol-2-yl)-1-(2-oxo-2-(piperazin-1-yl)ethyl)imidazo[1,2-a]pyrimidin-5(1H)-one

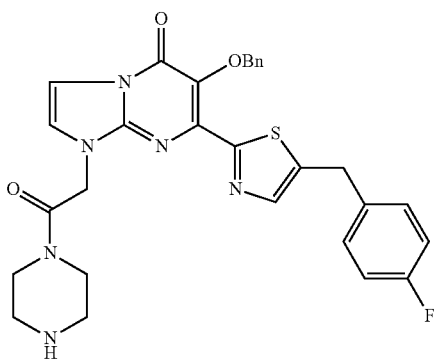 [SMILES: O=C(Cn1ccn2c(=O)c(OCc3ccccc3)c(-c3ncc(Cc4ccc(F)cc4)s3)nc12)N1CCNCC1]

To a solution of the product of example 111 (4.32 g, 8.23 mmol) in MeOH (50 ml), 6N HCl (25 ml) was added dropwise at room temperature. The mixture was stirred for 2 hours, after which saturated sodium bicarbonate was added to adjust the pH 9~10, and then extracted with CH$_2$Cl$_2$. The extracts were combined, washed with brine, and then dried over sodium sulfate. The solvent was removed under pressure to give the titled product as yellow slide (3.0 g, 82% yield).

$^1$H NMR (300 MHz, DMSO-d$^6$) δ 3.02-3.10 (m, 2H), 3.14-3.23 (m, 2H), 3.60-3.68 (m, 2H), 3.78-3.83 (m, 2H), 4.25 (s, 2H), 5.09 (s, 2H), 5.13 (s, 2H), 7.17 (t, J=8.7 Hz, 2H), 7.30-7.38 (m, 5H), 7.44-7.50 (m, 2H), 7.54 (d, J=2.7 Hz, 1H), 7.72 (d, J=2.7 Hz, 1H), 7.86 (s, 1H), 8.50-9.18 (brs, 1H)

MS (ESI$^+$) m/z 559 (M+1), 581 (M+23)

Example 113

6-(benzyloxy)-7-(5-(4-fluorobenzyl)thiazol-2-yl)-1-(2-oxo-2-(4-pivaloylpiperazin-1-yl)ethyl)imidazo[1,2-a]pyrimidin-5(1H)-one

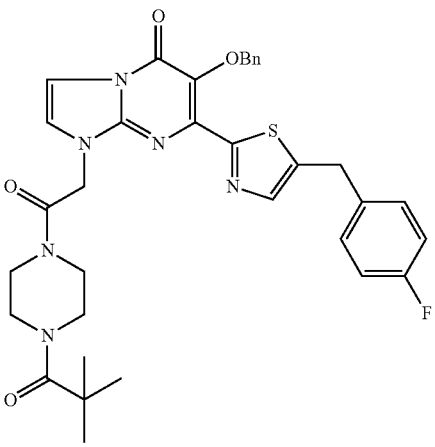 [SMILES: CC(C)(C)C(=O)N1CCN(C(=O)Cn2ccn3c(=O)c(OCc4ccccc4)c(-c4ncc(Cc5ccc(F)cc5)s4)nc23)CC1]

A mixture of the product of example 112 (200 mg, 0.36 mmol) and DIPEA (50.94 mg, 0.39 mmol) in CH$_2$Cl$_2$ (10 ml) was stirred at 0° C. Then pivaloyl chloride (47.48 mg, 0.39 mmol) was added dropwise. The mixture was stirred at room temperature for 2 hours, after which saturated sodium bicarbonate was added and then extracted with ethyl acetate. The extracts were combined, washed with brine, and then dried over sodium sulfate. The product was purified by column chromatography (CH$_2$Cl$_2$/MeOH=10/1) to give the desired product (207 mg, 90% yield).

$^1$H NMR (300 MHz, DMSO-d$^6$) δ 1.22 (s, 9H), 3.43-3.50 (m, 2H), 3.52-3.71 (m, 6H), 4.24 (s, 2H), 5.08 (s, 2H), 5.11 (s, 2H), 7.16 (t, J=8.7 Hz, 2H), 7.28-7.38 (m, 5H), 7.45-7.52 (m, 2H), 7.57 (d, J=2.7 Hz, 1H), 7.71 (d, J=2.7 Hz, 1H), 7.83 (s, 1H)

MS (ESI$^+$) m/z 643 (M+1)

Example 114

Preparation of 1-{2-[4-(2,2-Dimethyl-propionyl)-piperazin-1-yl]-2-oxo-ethyl}-7-[5-(4-fluoro-benzyl)-thiazol-2-yl]-6-hydroxy-1H-imidazo[1,2-a]pyrimidin-5-one

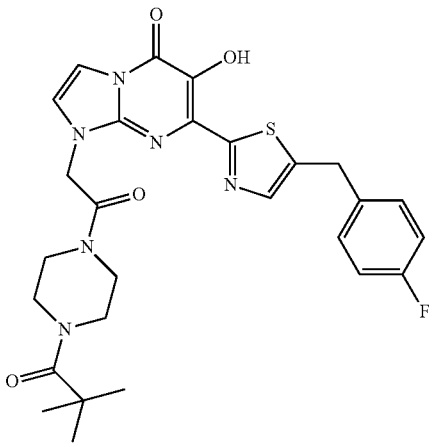 [SMILES: CC(C)(C)C(=O)N1CCN(C(=O)Cn2ccn3c(=O)c(O)c(-c4ncc(Cc5ccc(F)cc5)s4)nc23)CC1]

Adapted from the procedure of example 8.5 of PCT/AU2007/001980 using the product of example 113.

$^1$H NMR (300 MHz, DMSO-d$^6$) δ 1.22 (s, 9H), 3.40-3.50 (m, 2H), 3.50-3.74 (m, 6H), 4.28 (s, 2H), 5.04 (s, 2H), 7.15 (t, J=9.0 Hz, 2H), 7.34 (dd, J=6.1, 8.9 Hz, 2H), 7.50 (d, J=2.8 Hz, 1H), 7.62 (d, J=2.5 Hz, 1H), 7.91 (s, 1H), 10.83 (s, 1H)

MS(ESI$^+$) m/z 575 (M+23)

HPLC 97.7%

Example 115

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidin-7-yl}-thiazol-5-ylmethyl)-5-fluoro-N-isopropyl-benzamide

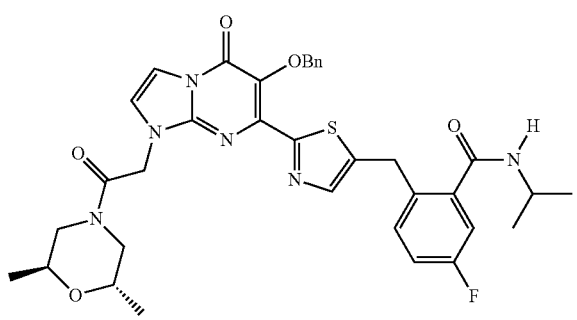 [SMILES: CC(C)NC(=O)c1cc(F)ccc1Cc1cnc(-c2nc3n(CC(=O)N4C[C@H](C)O[C@@H](C)C4)ccn3c(=O)c2O)s1]

Adapted from the procedure of example 77 using isopropylamine.

$^1$H NMR (300 MHz, DMSO-d$^6$) δ 1.07-1.18 (m, 12H), 2.31 (t, J=12.6 Hz, 1H), 2.80 (t, J=13.2 Hz, 1H), 3.42-3.44 (m, 1H), 3.58-3.60 (m, 1H), 3.89-3.94 (m, 1H), 3.97-4.05 (m, 1H), 4.10 (d, J=12.3 Hz, 1H), 4.36 (s, 2H), 4.96 (d, J=17.1 Hz, 1H), 5.04 (s, 2H), 5.16 (d, J=16.8 Hz, 1H), 7.14-7.19 (m, 1H), 7.21-7.27 (m, 1H), 7.31-7.34 (m, 3H), 7.38-7.43 (m, 1H), 7.49-7.54 (m, 2H), 7.55 (d, J=2.7 Hz, 1H), 7.67 (d, J=2.7 Hz, 1H), 7.73 (s, 1H), 8.28 (d, J=7.5 Hz, 1H)

MS (ESI$^+$) m/z 673 (M+1)

Example 116

Preparation of 2-(2-{1-[2-(2,6-Dimethyl-morpholin-4-yl)-2-oxo-ethyl]-6-hydroxy-5-oxo-1,5-dihydro-imidazo[1,2-a]pyrimidin-7-yl}-thiazol-5-ylmethyl)-5-fluoro-N-isopropyl-benzamide

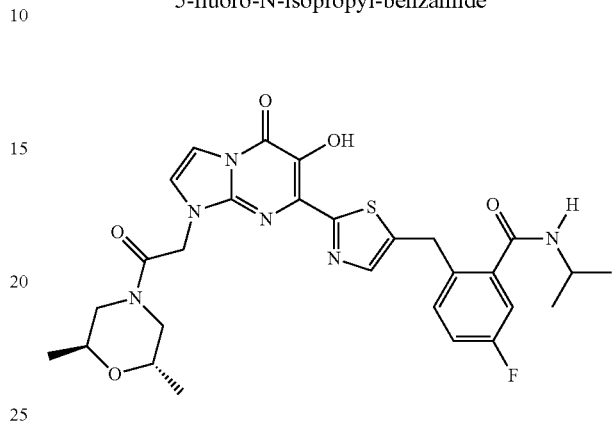

Adapted from the procedure of example 8.5 of PCT/AU2007/001980 using the product of example 115.

$^1$H NMR (300 MHz, DMSO-d$^6$) δ 1.03-1.28 (m, 12H), 2.30 (t, J=12.6 Hz, 1H), 2.79 (t, J=12.1 Hz, 1H), 3.39-3.42 (m, 1H), 3.57-3.62 (m, 1H), 3.91 (d, J=13.8 Hz, 1H), 3.99-4.06 (m, 1H), 4.11 (d, J=12.6 Hz, 1H), 4.37 (s, 2H), 4.90 (d, J=16.5 Hz, 1H), 5.16 (d, J=17.1 Hz, 1H), 7.15-7.28 (m, 2H), 7.42-7.47 (m, 1H), 7.48 (d, J=2.7 Hz, 1H), 7.59 (d, J=2.7 Hz, 1H), 7.80 (s, 1H), 8.32 (d, J=7.5 Hz, 1H), 10.88 (s, 1H).

MS (ESI$^-$) m/z 581 (M−1)

Example 117

2-((2-(6-(benzyloxy)-1-(2-((2S,6R)-2,6-dimethyl-morpholino)-2-oxoethyl)-5-oxo-1,5-dihydroimidazo[1,2-a]pyrimidin-7-yl)thiazol-5-yl)methyl)-5-fluorobenzamide

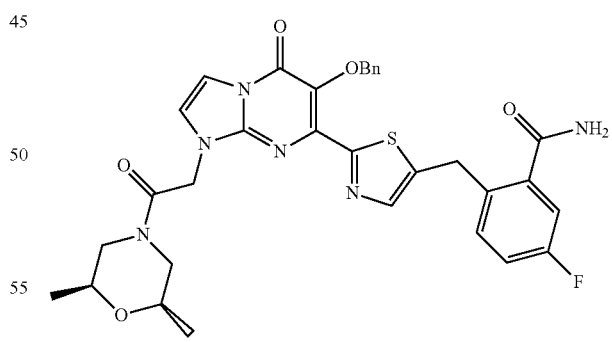

A mixture of the product of example 76 (63 mg, 0.1 mmol), BOP (66.3 mg, 0.15 mmol), HOBt (20.2 mg, 0.15 mmol), NH$_4$Cl (11 mg, 0.2 mmol) and DIPEA (46 mg, 0.4 mmol) in DMF (1 ml) was stirred at rt for 10 h, after which water was added and then extracted with CH$_2$Cl$_2$. The extracts were combined, washed with brine, and then dried over sodium sulfate. The product was purified by column chromatography (CH$_2$Cl$_2$/EA/MeOH=8/2/1) to give the desired product (38 mg, 60% yield).

¹H NMR (300 MHz, DMSO-d⁶) δ 1.09 (d, J=6.1 Hz, 3H), 1.15 (d, J=6.1 Hz, 3H), 2.26-2.39 (m, 1H), 2.75-2.87 (m, 1H), 3.39-3.52 (m, 1H), 3.54-3.67 (m, 1H), 3.89-3.99 (m, 1H), 4.08-4.19 (m, 1H), 4.43 (s, 2H), 4.98 (d, J=17.4 Hz, 1H), 5.07 (s, 2H), 5.19 (d, J=16.5 Hz, 1H), 7.23-7.45 (m, 6H), 7.48-7.60 (m, 4H), 7.70 (d, J=3.0 Hz, 1H), 7.76 (s, 1H), 7.94 (s, 1H)

MS (ESI⁺) m/z 631 (M+1), 653 (M+23)

Example 118

2-((2-(1-(2-((2S,6R)-2,6-dimethylmorpholino)-2-oxoethyl)-6-hydroxy-5-oxo-1,5-dihydroimidazo[1,2-a]pyrimidin-7-yl)thiazol-5-yl)methyl)-5-fluorobenzamide

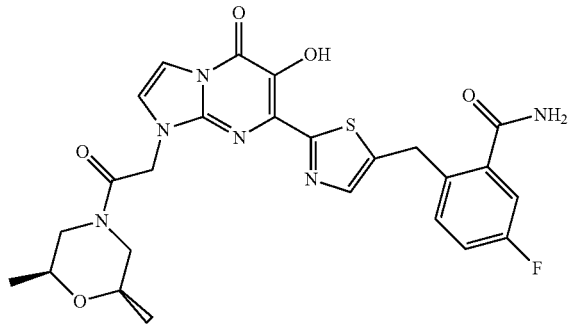 [SMILES: C[C@@H]1CN(C(=O)Cn2ccn3c(=O)c(O)c(-c4ncc(Cc5ccc(F)cc5C(N)=O)s4)nc23)C[C@H](C)O1]

Adapted from the procedure of example 8.5 of PCT/AU2007/001980 using the product of example 117.

¹H NMR (300 MHz, DMSO-d⁶) δ 1.08 (d, J=6.1 Hz, 3H), 1.15 (d, J=6.1 Hz, 3H), 2.26-2.38 (m, 1H), 2.75-2.87 (m, 1H), 3.39-3.52 (m, 1H), 3.54-3.66 (m, 1H), 3.94 (d, J=13.8 Hz, 1H), 4.13 (d, J=12.9 Hz, 1H), 4.44 (s, 2H), 4.92 (d, J=16.8 Hz, 1H), 5.11 (d, J=16.8 Hz, 1H), 7.23-7.34 (m, 2H), 7.41-7.47 (m, 1H), 7.49 (d, J=3.0 Hz, 1H), 7.56 (s, 1H), 7.61 (d, J=3.0 Hz, 1H), 7.83 (s, 1H), 7.96 (s, 1H), 10.91 (s, 1H)

MS (ESI⁺) m/z 541 (M+1)

Example 119

Preparation of 2-Chloro-1-(2-methyl-piperidin-1-yl)-ethanone

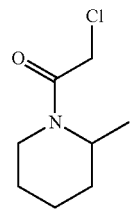

Adapted from the procedure of example 105 using 2-methyl-piperidine.

The crude product was used directly in the next step.

MS (ESI⁺) m/z 176 (M[35]+1), 178 (M[37]+1)

Example 120

Methyl-6-acetoxy-1-(2-(2-methylpiperidin-1-yl)-2-oxoethyl)-5-oxo-1,5-dihydroimidazo[1,2-a]pyrimidine-7-carboxylate

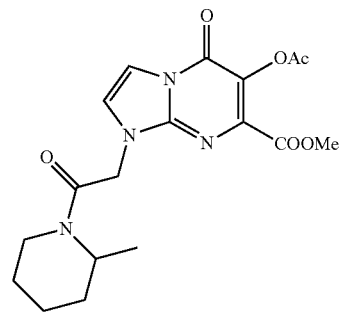 [SMILES: COC(=O)c1nc2n(CC(=O)N3CCCCC3C)ccn2c(=O)c1OC(C)=O]

Adapted from the procedure of example 33 using the product of example 119.

¹H NMR (300 MHz, DMSO-d⁶) δ 1.12-1.88 (m, 9H), 2.36 (s, 3H), 2.68-2.85 (m, 0.5H), 3.19-3.36 (m, 0.5H), 3.57-3.72 (m, 0.5H), 3.93 (s, 3H), 4.13-4.27 (m, 0.5H), 4.34-4.48 (m, 0.5H), 4.75-5.14 (m, 2.5H), 7.24 (d, J=2.7 Hz, 1H), 7.62 (d, J=2.7 Hz, 1H)

MS (ESI⁺) m/z 391 (M+1)

Example 121

Preparation of methyl6-(benzyloxy)-1-(2-(2-methylpiperidin-1-yl)-2-oxoethyl)-5-oxo-1,5-dihydroimidazo[1,2-a]pyrimidine-7-carboxylate

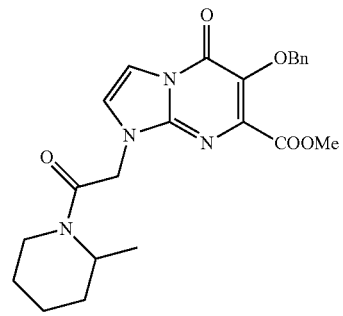

Adapted from the procedure of example 34 using the product of example 120.

¹H NMR (300 MHz, DMSO-d⁶) δ 1.00-1.74 (m, 9H), 2.60-2.75 (m, 0.5H), 3.08-3.24 (m, 0.5H), 3.47-3.62 (m, 0.5H), 3.70 (s, 3H), 3.99-4.12 (m, 0.5H), 4.24-4.38 (m, 0.5H), 4.65-5.00 (m, 2.5H), 5.09 (s, 2H), 7.15 (d, J=2.7 Hz, 1H), 7.18-7.34 (m, 3H), 7.36-7.47 (m, 2H), 7.55 (d, J=2.5 Hz, 1H)

MS (ESI⁺) m/z 439 (M+1), 461 (M+23)

Example 122

Preparation of 6-(benzyloxy)-1-(2-(2-methylpiperidin-1-yl)-2-oxoethyl)-5-oxo-1,5-dihydroimidazo[1,2-a]pyrimidine-7-carboxylic acid

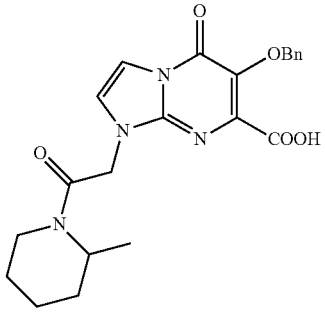 [SMILES: CC1CCCCN1C(=O)Cn1ccn2c(=O)c(OCc3ccccc3)c(C(=O)O)nc12]

Adapted from the procedure of example 35 using the product of example 121.

$^1$H NMR (300 MHz, DMSO-d$^6$) δ 1.07-1.86 (m, 9H), 2.67-2.85 (m, 0.5H), 3.20-3.37 (m, 0.5H), 3.54-3.69 (m, 0.5H), 4.09-4.23 (m, 0.5H), 4.32-4.46 (m, 0.5H), 4.74-5.15 (m, 2.5H), 5.39 (s, 2H), 7.23 (d, J=2.7 Hz, 1H), 7.30-7.42 (m, 3H), 7.46-7.56 (m, 2H), 7.65 (d, J=2.5 Hz, 1H)

MS (ESI$^+$) m/z 425 (M+1), 447 (M+23)

Example 123

Preparation of 6-(benzyloxy)-1-(2-(2-methylpiperidin-1-yl)-2-oxoethyl)-5-oxo-1,5-dihydroimidazo[1,2-a]pyrimidine-7-carbothioic S-acid

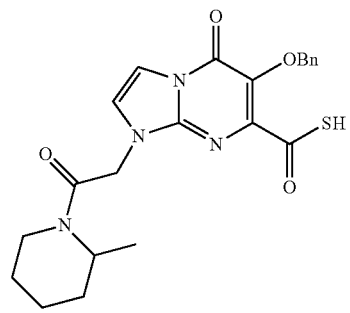 [SMILES: CC1CCCCN1C(=O)Cn1ccn2c(=O)c(OCc3ccccc3)c(C(=O)S)nc12]

Adapted from the procedure of example 36 using the product of example 122.

MS (ESI$^+$) m/z 463 (M+23)

Example 124

Preparation of S-1-(4-fluorophenyl)-3-oxopropan-2-yl 6-(benzyloxy)-1-(2-(2-methylpiperidin-1-yl)-2-oxoethyl)-5-oxo-1,5-dihydroimidazo[1,2-a]pyrimidine-7-carbothioate

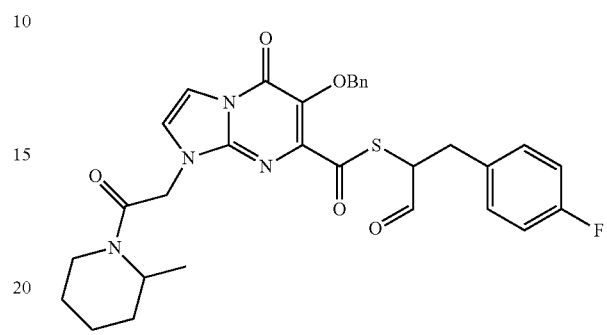

Adapted from the procedure of example 39 using the product of example 123 and the product of example 72.

MS (ESI$^+$) m/z 645 (M+55)

Example 125

Preparation of 6-(benzyloxy)-7-(5-(4-fluorobenzyl)thiazol-2-yl)-1-(2-(2-methylpiperidin-1-yl)-2-oxoethyl)imidazo[1,2-a]pyrimidin-5(1H)-one

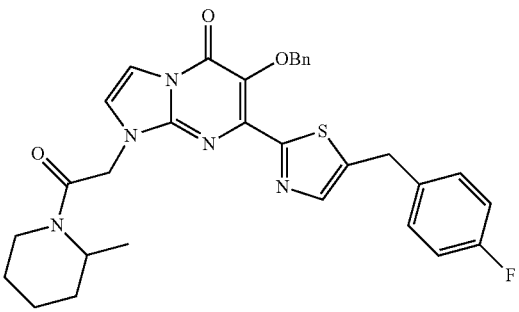 [SMILES: CC1CCCCN1C(=O)Cn1ccn2c(=O)c(OCc3ccccc3)c(-c3ncc(Cc4ccc(F)cc4)s3)nc12]

Adapted from the procedure of example 40 using the product of example 124.

$^1$H NMR (300 MHz, DMSO-d$^6$) δ 1.09-1.82 (m, 9H), 2.66-2.83 (m, 0.5H), 3.18-3.34 (m, 0.5H), 3.60-3.78 (m, 0.5H), 4.16 (s, 2H), 4.19-4.31 (m, 0.5H), 4.34-4.47 (m, 0.5H), 4.76-5.01 (m, 2.5H), 5.27 (s, 2H), 7.02 (t, J=8.7 Hz, 2H), 7.11-7.36 (m, 6H), 7.48 (m, 2H), 7.62 (d, J=2.7 Hz, 1H), 7.75 (s, 1H)

MS (ESI$^+$) m/z 572 (M+1), 594 (M+23)

Example 126

7-(5-(4-fluorobenzyl)thiazol-2-yl)-6-hydroxy-1-(2-(2-methylpiperidin-1-yl)-2-oxoethyl)imidazo[1,2-a]pyrimidin-5(1H)-one

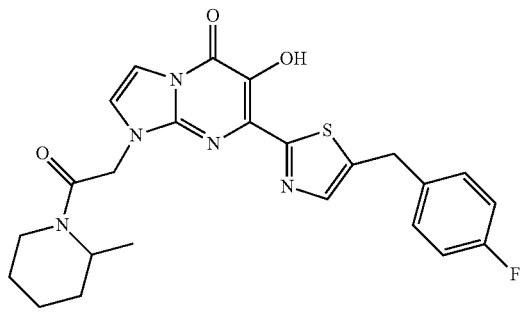 [SMILES: CC1CCCCN1C(=O)Cn1ccn2c(=O)c(O)c(-c3ncc(Cc4ccc(F)cc4)s3)nc12]

Adapted from the procedure of example 8.5 of PCT/AU2007/001980 using the product of example 125.

$^1$H NMR (300 MHz, DMSO-d$^6$) δ 1.00-1.77 (m, 9H), 2.58-2.77 (m, 0.5H), 3.07-3.27 (m, 0.5H), 3.65-3.83 (m, 0.5H), 4.05-4.20 (m, 0.5H), 4.28 (s, 2H), 4.46-4.67 (m, 0.5H), 4.80-5.12 (m, 2.5H), 7.17 (t, J=8.7 Hz, 2H), 7.31-7.41 (m, 2H), 7.53 (s, 1H), 7.61 (d, J=2.4 Hz, 1H), 7.90 (s, 1H)

MS (ESI$^+$) m/z 482 (M+1), 504 (M+23)

HPLC 92.7%

Example 127

Preparation of 4-fluoro-2-methylsulfanyl-1-nitro-benzene

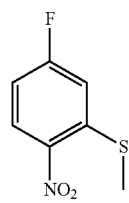

To a mixture of compound 2,4-difluoro-1-nitro-benzene (10 g, 62.9 mmol), pyridine (10 ml, 124 mmol) in MeOH (30 ml) was added the solution of sodium thiomethoxide(20%, 300 mmol) in methanol drop-wise at 0° C. The mixture was stirred for 2 hour and then diluted with dichloromethane. The mixture was washed with brine, dried over MgSO4 and evaporated under reduced pressure. The resulting residue was recrystallized from ethyl acetate to give titled compound (10 g, yield 85%)

$^1$H NMR (300 MHz, CDCl$_3$) δ 2.50 (s, 3H), 6.93-6.98 (m, 1H), 7.05 (dd, J=2.7, 9.6 Hz, 1H), 8.35 (m, 1H).

Example 128

Preparation of 4-fluoro-2-methylsulfanyl-1phenylamine

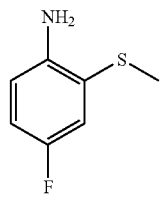

A mixture of 4-fluoro-2-methylsulfanyl-1-nitro-benzene (3.4 g, 18.2 mmol) and 300 mg Pd/C in EtOH (100 ml) was stirred under H$_2$ (5 MP) at room temperature for about 3 hours. Then the reaction mixture was filtered and the filtrate was concentrated. The residue was purified by column chromatography (PE/EA=20/1) to give the titled compound (2.8 g, 96% yield)

$^1$H NMR (300 MHz, CDCl$_3$) δ 2.38 (s, 3H), 3.87 (brs, 2H), 6.62-6.66 (m, 1H), 6.75-6.82 (m, 1H), 7.01-7.05 (dd, J=3, 9 Hz, 1H)

Example 129

Preparation of 4-fluoro-1-iodo-2-methylsulfanyl-benzene

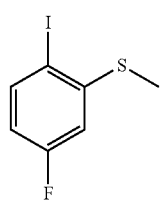

To a suspension of 4-fluoro-2-methylsulfanyl-1phenylamine (1.9 g, 11 mol) in HCl (4N, 40 ml) was added drop-wise the solution of NaNO$_2$ (869 mg, 12.6 mol) in 6 ml water at 0° C. The mixture was stirred at 0° C. for 1.5 h. Then KI (3.5 g 21.1 mol) in 6 ml water was added. The mixture was warmed to room temperature and stirred overnight, after which it was extracted with ethyl acetate. The combined organic layers were washed with brine, dried and concentrated. The residue was purified by flash column chromatography (PE) to give the titled compound (1.7 g, 40% yield).

$^1$H NMR (300 MHz, CDCl$_3$) δ 2.46 (s, 3H), 6.57-6.64 (m, 1H), 6.79-6.84 (dd, J=3.0, 9.9 Hz, 1H), 7.68-7.74 (m, 1H)

MS (EI$^+$) m/z 268 (M$^+$)

Example 130

Preparation of Preparation of 3-(4-fluoro-2-methylsulfanyl-phenyl)-acrylic acid methyl ester

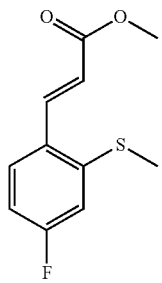

4-fluoro-1-iodo-2-methylsulfanyl-benzene (6.8 g 25.3 mmol), $K_2CO_3$ (9.9 g, 63.4 mmol), methyl acrylate (5.7 ml, 63.4 mmol), Tetra-n-butylammonium chloride (7.0 g, 25.3 mmol) and Pd(OAc)$_2$ (1.1 g, 5.07 mmol) were mixed in DMF (150 ml). The mixture was heated at 50° C. under the atmosphere of $N_2$ overnight, after which water was added and then extracted with ethyl acetate. The extracts were combined, washed with brine, dried over sodium sulfate and evaporated under reduced pressure. The residue was purified by column chromatography to give the desired product (4.8 g, yield 89%).

$^1$H NMR (300 MHz, CDCl$_3$) δ 2.50 (s, 3H), 3.83 (s, 3H), 6.31-6.37 (d, J=15.9 Hz, 1H), 6.84-6.91 (m, 1H), 6.96-7.00 (dd, J=2.4, 9.6 Hz, 1H), 7.49-7.54 (m, 1H), 8.06 (d, J=16.2 Hz, 1H)

MS (ESI+) m/z 227 (M+1)

Example 131

Preparation of 3-(4-fluoro-2-methylsulfanyl-phenyl)-propionic acid methyl ester

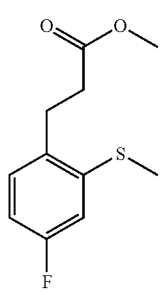

A mixture of 3-(4-fluoro-2-methylsulfanyl-phenyl)-acrylic acid methyl ester (11 g, 48.6 mmol) and 1 g Pd/C in EtOH (100 ml) was stirred under $H_2$ (5 MP) at room temperature for about 6 hours. The reaction mixture was filtered and the filtrate was concentrated.

The residue was purified by flash column chromatography to give the titled compound (11 g, yield 100%)

$^1$H NMR (300 MHz, CDCl$_3$) δ 2.47 (s, 3H), 2.64 (t, J=7.8 Hz, 2H), 3.00 (t, J=7.8 Hz, 2H), 3.68 (s, 3H), 6.74-6.80 (m, 1H), 6.86-6.90 (dd, J=2.4, 9.6 Hz, 1H), 7.09-7.14 (m, 1H)

MS (ESI+) m/z 251 (M+23)

Example 132

Preparation of 3-(4-Fluoro-2-methanesulfonyl-phenyl)-propionic acid methyl ester

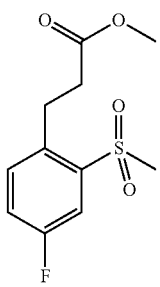 [SMILES: COC(=O)CCc1ccc(F)cc1S(C)(=O)=O]

To a solution of 3-(4-fluoro-2-methylsulfanyl-phenyl)-propionic acid methyl ester (1 g, 4.3 mmol) in acetic acid (10 ml) was added dropwise the solution of KMnO$_4$ (1.3 g, 8.2 mmol) in 10 ml H$_2$O. The mixture was stirred at room temperature for 3 hours, and then poured into saturated Na$_2$S$_2$O$_3$ solution and extracted with ethyl acetate. The organic layer was washed with brine, and then dried over Na$_2$SO$_4$. The product was purified by column chromatography to give the titled compound (1.2 g, yield 98%)

$^1$H NMR (300 MHz, CDCl$_3$) δ 2.75 (t, J=7.8 Hz, 2H) 3.14 (s, 3H), 3.30 (t, J=7.8 Hz, 2H), 3.68 (s, 3H), 7.24-7.31 (m, 1H), 7.38-7.43 (m, 1H), 7.76 (dd, J=3, 8.7 Hz, 1H),

MS (ESI$^+$) m/z 283 (M+23)

Example 133

Preparation of 3-(4-Fluoro-2-methanesulfonyl-phenyl)-propan-1-ol

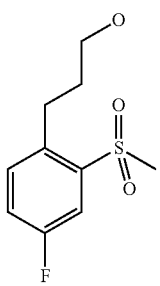

To a solution of the product of example 132 (1.2 g, 4.6 mmol) in dried THF (20 ml), was added LiAlH$_4$ (344 mg 9.3 mmol) at 0° C. The mixture was stirred at room temperature for 3 hours, after which H$_2$O (10 ml) was added dropwise to quench the reaction. The result mixture was extracted with ethyl acetate. The extracts were washed with H$_2$O, and then dried over Na$_2$SO$_4$ and evaporated under reduced pressure. The residue was purified by column chromatography to give the titled compound (860 mg, 80% yield)

$^1$H NMR (300 MHz, CDCl$_3$) δ 1.91-2.00 (m, 2H), 3.08-3.11 (m, 2H), 3.10 (s, 3H), 3.66 (t, J=12 Hz, 2H), 7.29 (dd, J=2.7, 7.5 Hz, 1H), 7.38-7.43 (m, 1H), 7.76 (dd, J=2.7, 8.7 Hz, 1H).

MS (ESI+) m/z 233 (M+1)

Example 134

Preparation of 3-(4-Fluoro-2-methanesulfonyl-phenyl)-propionaldehyde

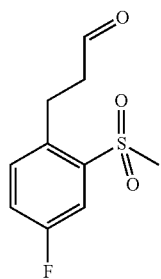

To the solution of the product of example 133 (1.0 g, 4.3 mmol) in dichloromethane (100 ml), was added Pyridinium Chlorochromate (1.65 g 6.4 mmol) at 0° C. The mixture was stirred at room temperature for 5 hours. The result mixture was washed with water, and the organic layer was dried over $Na_2SO_4$. The product was purified by column chromatography to give the titled compound (555 mg, yield 58%)

$^1$H NMR (300 MHz, $CDCl_3$) δ 2.46 (s, 3H), 2.97 (t, J=7.5 Hz, 2H), 3.66 (t, J=7.5 Hz, 2H), 6.73-6.79 (m, 1H), 6.86 (dd, J=2.7, 9.6 Hz, 1H), 7.07-7.12 (m, 1H), 9.81 (s, 1H).

MS (ESI+) m/z 285 (M+55)

Example 135

Preparation of 2-Bromo-3-(4-fluoro-2-methanesulfonyl-phenyl)-propionaldehyde

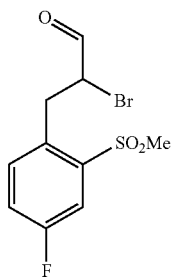 [SMILES: CS(=O)(=O)c1cc(F)ccc1CC(Br)C=O]

Adapted from the procedure of example 38 using the product of 134.

The titled product was used directly in next step.

Example 136

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid S-[1-(4-fluoro-2-methanesulfonyl-benzyl)-2-oxo-ethyl]ester

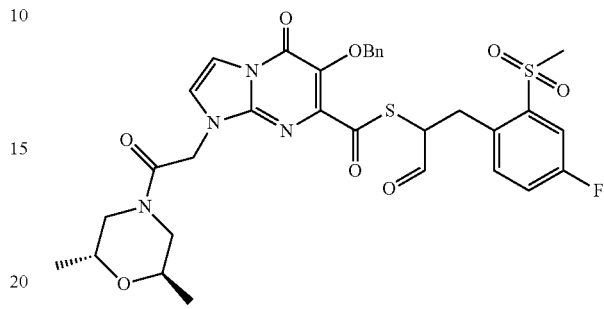

Adapted from the procedure of example 39 using the products of 36 and 135.

MS (ESI$^+$) m/z 685 (M+1)

Example 137

Preparation of 6-Benzyloxy-1-[2-(2,6-dimethyl-morpholin-4-yl)-2-oxo-ethyl]-7-[5-(4-fluoro-2-methanesulfonyl-benzyl)-thiazol-2-yl]-1H-imidazo[1,2-a]pyrimidin-5-one

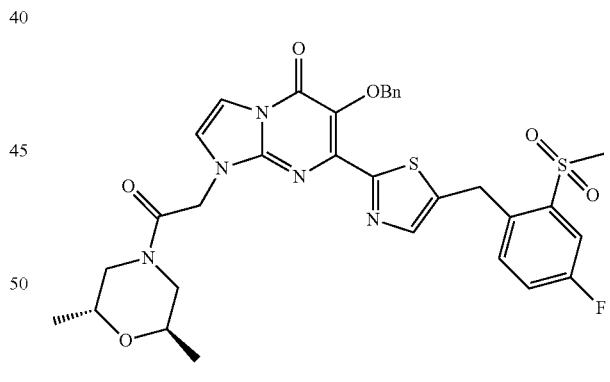

Adapted from the procedure of example 40 using the product of example 136

$^1$H NMR (300 MHz, $CDCl_3$) δ 1.22 (d, J=6.4 Hz, 3H), 1.26 (d, J=6.0 Hz, 3H) □2.42 (t, J=12.9 Hz, 1H), 2.92 (s, 3H), 2.95 (t, J=12.6 Hz, 1H), 3.57-3.59 (m, 1H), 3.65-3.69 (m, 1H), 3.83 (d, J=12.1 Hz, 1H), 4.36 (d, J=13.5 Hz, 1H), 4.70 (s, 2H), 4.96 (d, J=16.5 Hz, 1H), 5.27 (d, J=16.5 Hz, 1H) 5.32 (s, 2H), 7.20 (d, J=2.4 Hz, 1H), 7.31-7.39 (m, 5H), 7.48-7.51 (m, 2H), 7.65 (d, J=2.4 Hz, 1H), 7.80-7.84 (m, 2H).

MS (ESI$^+$) m/z 688 (M+23)

Example 138

Preparation of 1-[2-(2,6-Dimethyl-morpholin-4-yl)-2-oxo-ethyl]-7-[5-(4-fluoro-2-methanesulfonyl-benzyl)-thiazol-2-yl]-6-hydroxy-1H-imidazo[1,2-a]pyrimidin-5-one

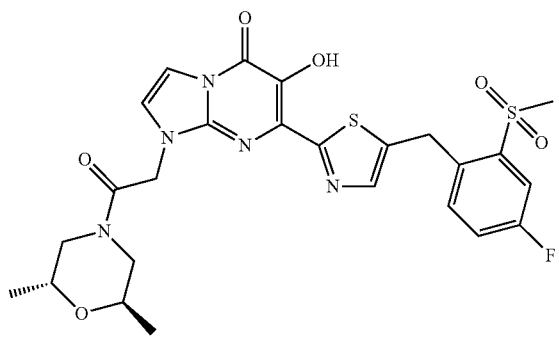

Adapted from the procedure of example 8.5 of PCT/AU2007/001980 using the product of example 137.

$^1$H NMR (300 MHz, CDCl$_3$) δ 1.08 (d, J=6.0 Hz, 3H), 1.15 (d, J=6.4 Hz, 3H), 2.32 (t, J=10.1 Hz, 1H), 2.79 (t, J=12.3 Hz, 1H), 3.34 (s, 3H), 3.38-3.40 (m, 1H), 3.57-3.61 (m, 1H), 3.91-3.97 (m, 1H), 4.09-4.15 (m, 1H), 4.70 (s, 2H), 4.93 (d, J=16.5 Hz, 1H), 5.13 (d, J=16.2 Hz, 1H), 7.51 (d, J=2.7 Hz, 1H), 7.59-7.63 (m, 3H), 7.74-7.77 (m, 1H), 7.93 (m, 1H), 10.83 (s, 1H).

MS (ESI$^+$) m/z 576 (M+1)

HPLC 97.8%

Example 139

Preparation of 2-(2-{6-Benzyloxy-1-[2-(2,6-dimethyl-morpholin-4-yl)-2-oxo-ethyl]-5-oxo-1,5-dihydro-imidazo[1,2-a]pyrimidin-7-yl}-thiazol-5-ylmethyl)-N-cyclopropyl-5-fluoro-benzamide

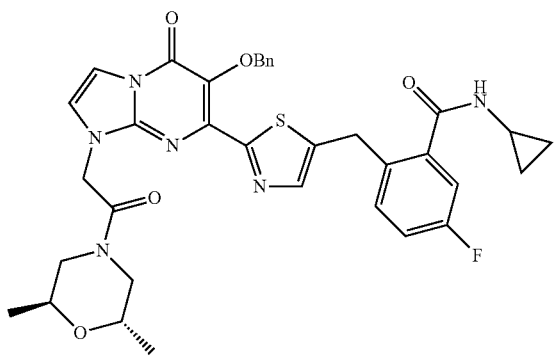 [SMILES: C[C@H]1CN(C(=O)Cn2ccn3c(=O)c(OCc4ccccc4)c(-c4ncc(Cc5ccc(F)cc5C(=O)NC5CC5)s4)nc23)C[C@H](C)O1]

Adapted from the procedure of example 77 using the product of example 76 and cyclopropylamine.

An impure intermediate was used for the subsequent step.

MS (ESI$^+$) m/z 671 (M+1)

Example 140

Preparation of N-Cyclopropyl-2-(2-{1-[2-(2,6-dimethyl-morpholin-4-yl)-2-oxo-ethyl]-6-hydroxy-5-oxo-1,5-dihydro-imidazo[1,2-a]pyrimidin-7-yl}-thiazol-5-ylmethyl)-5-fluoro-benzamide

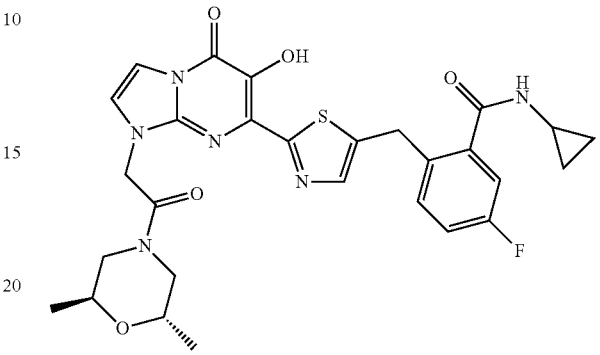

Adapted from the procedure of example 8.5 of PCT/AU2007/001980 using the product of example 139.

$^1$H NMR (300 MHz, DMSO-d$^6$) δ 0.47-0.55 (m, 2H), 0.64-0.72 (m, 2H), 1.08 (d, J=6.2 Hz, 3H), 1.16 (d, J=5.9 Hz, 3H), 2.32 (t, J=11.8 Hz, 1H), 2.74-2.87 (m, 2H), 3.35-3.51 (m, 1H), 3.52-3.69 (m, 1H), 3.94 (d, J=13.3 Hz, 1H), 4.13 (d, J=12.6 Hz, 1H), 4.39 (s, 2H), 4.92 (d, J=17.0 Hz, 1H), 5.13 (d, J=16.8 Hz, 1H), 7.18-7.34 (m, 2H), 7.46 (dd, J=5.6, 8.6 Hz, 1H), 7.50 (d, J=2.7 Hz, 1H), 7.62 (d, J=2.9 Hz, 1H), 7.84 (s, 1H), 8.52 (d, J=4.1 Hz, 1H).

MS (ESI$^+$) m/z 581 (M+1)

HPLC 90.1%

Example 141

6-(benzyloxy)-7-(5-(4-fluorobenzyl)thiazol-2-yl)-1-(2-(4-methyl piperazin-1-yl)-2-oxoethyl)imidazo[1,2-a]pyrimidin-5(1H)-one

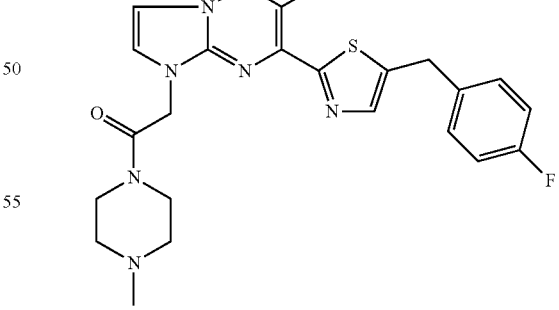

A solution of the paraformaldehyde (300 mg) in MeOH (3 ml) was stirred at 70° C. for about 1 h. After cooling down to 0° C., this solution was added dropwise to a mixture of the product of example 124 (341 mg, 0.61 mmol), NaBH$_3$CN (115 mg, 1.83 mmol) and MeCOONa (105 mg, 1.22 mmol) in MeOH (10 ml) at 0° C. Then the mixture was warmed to room temperature and stirred for 2 hours, after which saturated sodium bicarbonate was added and then the mixture was extracted with ethyl acetate. The extracts were combined, washed with brine, and then dried over sodium sulfate. The product was purified by column chromatography (CH$_2$Cl$_2$/MeOH=10/1) to give the desired product (279 mg, 80% yield).

$^1$H NMR (300 MHz, DMSO-d$^6$) δ 2.20 (s, 3H), 2.24-2.30 (m, 2H), 2.36-2.43 (m, 2H), 3.41-3.47 (m, 2H), 3.52-3.60 (m, 2H), 4.25 (s, 2H), 5.08 (s, 4H), 7.16 (t, J=8.7 Hz, 2H), 7.30-7.38 (m, 5H), 7.46-7.52 (m, 2H), 7.58 (d, J=2.7 Hz, 1H), 7.70 (d, J=2.7 Hz, 1H), 7.85 (s, 1H)

MS (ESI$^+$) m/z 573 (M+1), 595 (M+23)

Example 142

7-(5-(4-fluorobenzyl)thiazol-2-yl)-6-hydroxy-1-(2-(4-methyl piperazin-1-yl)-2-oxoethyl)imidazo[1,2-a]pyrimidin-5(1H)-one

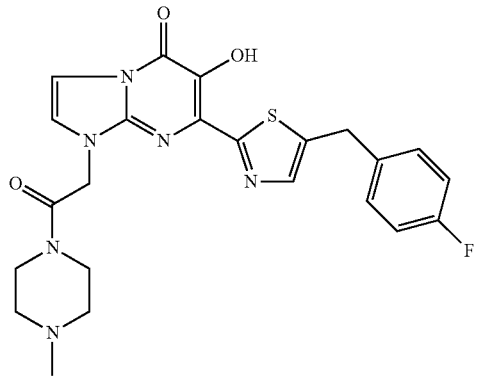 [SMILES: CN1CCN(C(=O)Cn2ccn3c(=O)c(O)c(-c4ncc(Cc5ccc(F)cc5)s4)nc23)CC1]

Adapted from the procedure of example 8.5 of PCT/AU2007/001980 using the product of example 141.

$^1$H NMR (300 MHz, CDCl$_3$) δ 2.36 (s, 3H), 2.43-2.60 (m, 4H), 3.62-3.79 (m, 4H), 4.19 (s, 2H), 4.86 (s, 2H), 6.99-7.10 (m, 3H), 7.18-7.25 (m, 2H), 7.53-7.63 (m, 2H)

MS (ESI$^+$) m/z 483 (M+1), 505 (M+23)

Example 143

7-(5-(4-fluorobenzyl)thiazol-2-yl)-6-hydroxy-1-(2-oxo-2-(piperazin-1-yl)ethyl)imidazo[1,2-a]pyrimidin-5(1H)-one

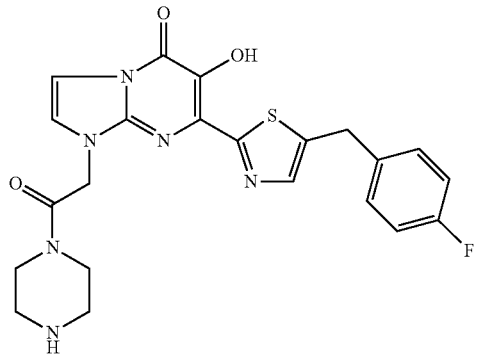 [SMILES: O=C(Cn1ccn2c(=O)c(O)c(-c3ncc(Cc4ccc(F)cc4)s3)nc12)N1CCNCC1]

Adapted from the procedure of example 8.5 of PCT/AU2007/001980 using the product of example 112.

$^1$H NMR (300 MHz, CDCl$_3$) δ 2.83-2.96 (m, 4H), 3.57-3.67 (m, 4H), 4.19 (s, 2H), 4.86 (s, 2H), 7.00-7.10 (m, 3H), 7.20-7.26 (m, 2H), 7.57-7.64 (m, 2H)

MS (ESI$^+$) m/z 491 (M+23)

Example 144

Preparation of 2-(bromomethyl)thiazole

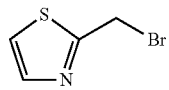

The titled compound was made by bromination of 2-methylthiazole in CCl$_4$ with NBS/AIBN in 35% yield.

$^1$H NMR (300 MHz, CDCl$_3$) δ 4.76 (s, 2H), 7.39 (d, J=3.2 Hz, 1H), 7.76 (d, J=3.2 Hz, 1H)

Example 145

Methyl 6-acetoxy-5-oxo-1-(thiazol-2-ylmethyl)-1,5-dihydroimidazo[1,2-a]pyrimidine-7-carboxylate

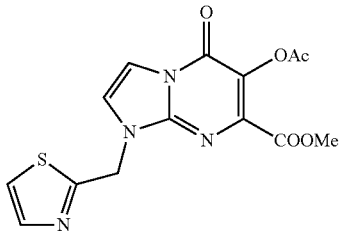 [SMILES: COC(=O)c1nc2n(Cc3nccs3)ccn2c(=O)c1OC(C)=O]

Adapted from the procedure of example 33 using the product of example 144.

$^1$H NMR (300 MHz, DMSO-d$^6$) δ 2.27 (s, 3H), 3.84 (s, 3H), 5.73 (s, 2H), 7.75-7.80 (m, 2H), 7.87 (d, J=2.6 Hz, 1H), 7.92 (d, J=2.6 Hz, 1H)

MS (ESI$^+$) m/z 349 (M+1)
MS (ESI$^+$) m/z 307 (M+1)

Example 146

Preparation of methyl 6-(benzyloxy)-5-oxo-1-(thiazol-2-ylmethyl)-1,5-dihydroimidazo[1,2-a]pyrimidine-7-carboxylate

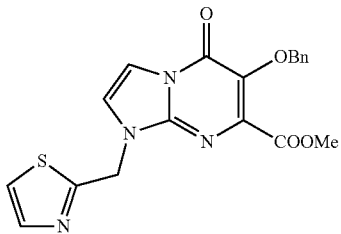 [SMILES: COC(=O)c1nc2n(Cc3nccs3)ccn2c(=O)c1OCc1ccccc1]

Adapted from the procedure of example 34 using the product of example 145.

$^1$H NMR (300 MHz, DMSO-d$^6$) δ 3.78 (s, 3H), 5.03 (s, 2H), 5.67 (s, 2H), 7.30-7.46 (m, 5H), 7.72-7.87 (m, 4H)

MS (ESI$^+$) m/z 397 (M+1)

Example 147

Preparation of 6-(benzyloxy)-5-oxo-1-(thiazol-2-ylmethyl)-1,5-dihydroimidazo[1,2-a]pyrimidine-7-carboxylic acid

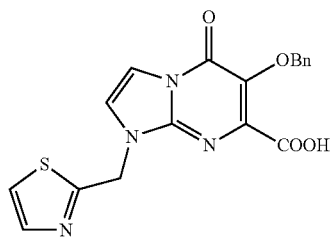 [SMILES: O=C(O)c1nc2n(Cc3nccs3)ccn2c(=O)c1OCc1ccccc1]

Adapted from the procedure of example 35 using the product of example 146.

$^1$H NMR (300 MHz, DMSO-d$^6$) δ 5.02 (s, 2H), 5.68 (s, 2H), 7.30-7.50 (m, 5H), 7.74-7.84 (m, 4H)

MS (ESI$^-$) m/z 381 (M−1)

Example 148

Preparation of 6-(benzyloxy)-7-(5-(4-fluorobenzyl)thiazol-2-yl)-1-(thiazol-2-ylmethyl)imidazo[1,2-a]pyrimidin-5(1H)-one

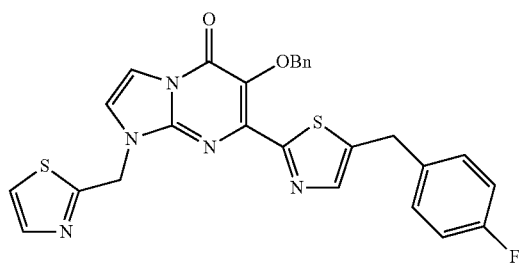 [SMILES: O=c1c(OCc2ccccc2)c(-c2ncc(Cc3ccc(F)cc3)s2)nc2n(Cc3nccs3)ccn12]

Adapted from the procedure of example 36, 39, 40 using the product of example 147.

$^1$H NMR (300 MHz, DMSO-d$^6$) δ 4.25 (s, 2H), 5.08 (s, 2H), 5.67 (s, 2H), 7.11-7.21 (m, 2H), 7.27-7.40 (m, 5H), 7.46-7.53 (m, 2H), 7.72-7.86 (m, 5H)

MS (ESI$^+$) m/z 530 (M+1), 552 (M+23)

Example 149

Preparation of 7-(5-(4-fluorobenzyl)thiazol-2-yl)-6-hydroxy-1-(thiazol-2-ylmethyl)imidazo[1,2-a]pyrimidin-5(1H)-one

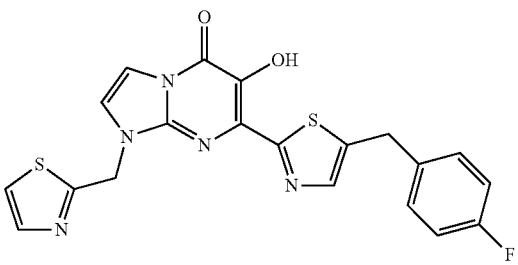 [SMILES: O=c1c(O)c(-c2ncc(Cc3ccc(F)cc3)s2)nc2n(Cc3nccs3)ccn12]

Adapted from the procedure of example 8.5 of PCT/AU2007/001980 using the product of example 148.

$^1$H NMR (300 MHz, DMSO-d$^6$) δ 4.29 (s, 2H), 5.60 (s, 2H), 7.12-7.23 (m, 2H), 7.32-7.42 (m, 2H), 7.66-7.80 (m, 4H), 7.91 (s, 1H)

MS (ESI$^+$) m/z 440 (M+1), 462 (M+23), 494 (M+55)

HPLC 85.2%

Example 150

Preparation of 2-Chloro-1-(4-methyl-piperidin-1-yl)-ethanone

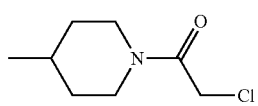

To a mixture of 4-Methyl-piperidine (5.00 g, 50.42 mmol) and triethylamine (7.65 g, 75.63 mmol) in ethyl ether (25 ml) was added dropwise a solution of chloroacetyl chloride (6.83 g, 60.50 mmol) in ethyl ether (30 mL). The mixture was warmed to room temperature and stirred overnight. Then the mixture was diluted with dichloromethane, washed with water, dried and concentrated in vacuo to afford the crude titled compound (crude yield 100%), which was used directly in the subsequent step reaction.

Example 151

Preparation of 6-Acetoxy-1-[2-(4-methyl-piperidin-1-yl)-2-oxo-ethyl]-5-oxo-1,5-dihydro-imidazo[1,2-a]pyrimidine-7-carboxylic acid methyl ester

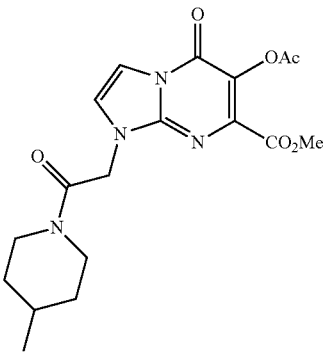

Adapted from the procedure of example 33 using the product of example 150.

$^1$H NMR (300 MHz, DMSO-d$^6$) δ 0.93 (d, J=6.0 Hz, 3H), 1.16-1.20 (m, 1H), 1.62-1.74 (m, 4H), 2.27 (s, 3H), 2.63 (t, J=12.6 Hz, 1H), 3.10 (t, J=11.4 Hz, 1H), 3.84 (s, 3H), 3.90 (d, J=13.5 Hz, 1H), 4.25 (d, J=13.2 Hz, 1H), 5.10 (d, J=16.8 Hz, 1H), 5.17 (d, J=16.8 Hz, 1H), 7.70 (d, J=2.4 Hz, 1H), 7.81 (d, J=2.4 Hz, 1H).

MS (ESI$^-$) m/z 389 (M−1)

Example 152

Preparation of 6-Benzyloxy-1-[2-(4-methyl-piperidin-1-yl)-2-oxo-ethyl]-5-oxo-1,5-dihydro-imidazo[1,2-a]pyrimidine-7-carboxylic acid methyl ester

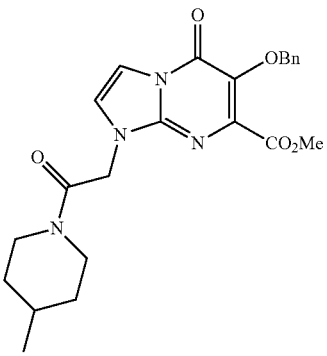 [SMILES: COC(=O)c1nc2n(CC(=O)N3CCC(C)CC3)ccn2c(=O)c1OC(C)=O]

Adapted from the procedure of example 34 using the product of example 151.

$^1$H NMR (300 MHz, DMSO-d$^6$) δ 0.92 (d, J=6 Hz, 3H), 0.98-0.99 (m, 1H), 1.15-1.23 (m, 1H), 1.62-1.74 (m, 3H), 2.61 (t, J=12.6 Hz, 1H), 3.07 (t, J=11.7 Hz, 1H), 3.78 (s, 3H), 3.90 (d, J=13.8 Hz, 1H), 4.25 (d, J=13.2 Hz, 1H), 5.01-5.14 (m, 2H), 5.03 (s, 2H), 7.33-7.44 (m, 5H), 7.62 (d, J=2.7 Hz, 1H), 7.81 (d, J=2.7 Hz, 1H).

MS (ESI$^+$) m/z 439 (M+1), 461 (M+23)

Example 153

Preparation of 6-Benzyloxy-1-[2-(4-methyl-piperidin-1-yl)-2-oxo-ethyl]-5-oxo-1,5-dihydro-imidazo[1,2-a]pyrimidine-7-carboxylic acid

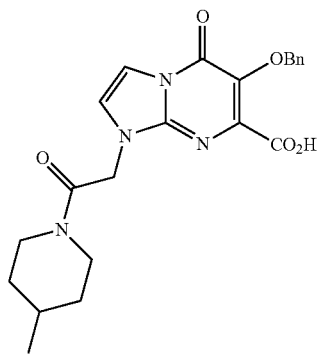 [SMILES: CC1CCN(C(=O)Cn2ccn3c(=O)c(OCc4ccccc4)c(C(=O)O)nc23)CC1]

Adapted from the procedure of example 35 using the product of example 152.

$^1$H NMR (300 MHz, DMSO-d$^6$) δ 0.93 (d, J=6 Hz, 3H), 0.99-1.00 (m, 1H), 1.17-1.24 (m, 1H), 1.61-1.73 (m, 3H), 2.62 (t, J=12.0 Hz, 1H), 3.08 (t, J=12.9 Hz, 1H), 3.90 (d, J=13.5 Hz, 1H), 4.26 (d, J=13.2 Hz, 1H), 5.02 (s, 2H), 5.07-5.15 (m, 2H), 7.33-7.42 (m, 3H), 7.45-7.49 (m, 2H), 7.60 (d, J=2.8 Hz, 1H), 7.73 (d, J=2.6 Hz, 1H), 13.47 (s, 1H).

MS (ESI$^+$) m/z 425 (M+1), 447 (M+23)

Example 154

Preparation of 6-Benzyloxy-1-[2-(4-methyl-piperidin-1-yl)-2-oxo-ethyl]-5-oxo-1,5-dihydro-imidazo[1,2-a]pyrimidine-7-carbothioic acid

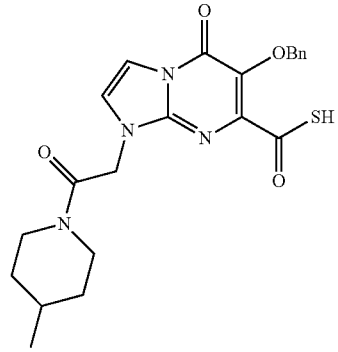 [SMILES: CC1CCN(C(=O)Cn2ccn3c(=O)c(OCc4ccccc4)c(C(=O)S)nc23)CC1]

Adapted from the procedure of example 36 using the product of example 153.

MS (ESI$^-$) m/z 439 (M−1)

Example 155

Preparation of 6-Benzyloxy-1-[2-(4-methyl-piperidin-1-yl)-2-oxo-ethyl]-5-oxo-1,5-dihydro-imidazo[1,2-a]pyrimidine-7-carbothioic acid S-[2-(4-fluorophenyl)-1-formyl-ethyl]ester

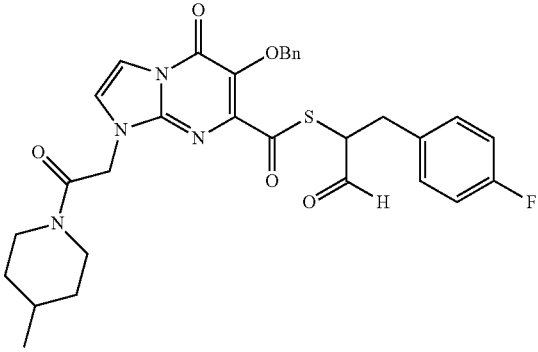 [SMILES: CC1CCN(C(=O)Cn2ccn3c(=O)c(OCc4ccccc4)c(C(=O)SC(C=O)Cc4ccc(F)cc4)nc23)CC1]

Adapted from the procedure of example 39 using the product of example 154 and the product of example 72.

MS (ESI⁺) m/z 591 (M+1)

Example 156

Preparation of 6-Benzyloxy-7-[5-(4-fluoro-benzyl)-thiazol-2-yl]-1-[2-(4-methyl-piperidin-1-yl)-2-oxo-ethyl]-1H-imidazo[1,2-a]pyrimidin-5-one

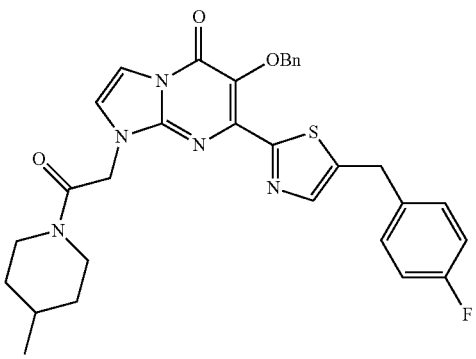 [SMILES: CC1CCN(C(=O)Cn2ccn3c(=O)c(OCc4ccccc4)c(-c4ncc(Cc5ccc(F)cc5)s4)nc23)CC1]

Adapted from the procedure of example 38 using the product of 155.

$^1$H NMR (300 MHz, DMSO-d$^6$) δ 0.92 (d, J=4.8 Hz, 3H), 0.98-1.00 (m, 1H), 1.14-1.23 (m, 1H), 1.60-1.73 (m, 3H), 2.61 (t, J=12.6 Hz, 1H), 3.04-3.13 (m, 1H), 3.90-3.94 (m, 1H), 4.17-4.23 (m, 1H), 4.24 (s, 2H), 5.04-5.06 (m, 2H), 5.07 (s, 2H), 7.09-7.20 (m, 2H), 7.30-7.36 (m, 5H), 7.49-7.52 (m, 2H), 7.59 (d, J=2.7 Hz, 1H), 7.70 (d, J=2.4 Hz, 1H), 7.85 (s, 1H).

MS (ESI⁻) m/z 570 (M−1)

Example 157

Preparation of 7-[5-(4-Fluoro-benzyl)-thiazol-2-yl]-6-hydroxy-1-[2-(4-methyl-piperidin-1-yl)-2-oxo-ethyl]-1H-imidazo[1,2-a]pyrimidin-5-one

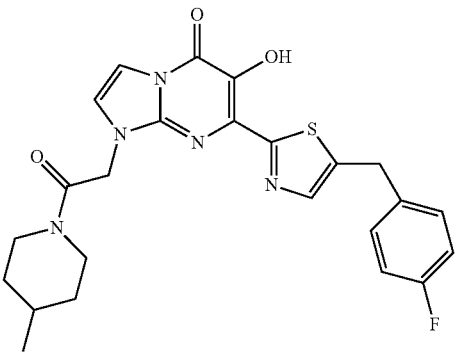 [SMILES: CC1CCN(C(=O)Cn2ccn3c(=O)c(O)c(-c4ncc(Cc5ccc(F)cc5)s4)nc23)CC1]

Adapted from the procedure of example 8.5 of PCT/AU2007/001980 using the product of example 156.

$^1$H NMR (300 MHz, DMSO-d$^6$) δ 1.10-1.24 (m, 4H), 1.40-1.71 (m, 4H), 2.60-2.64 (m, 1H), 3.02-3.11 (m, 1H), 3.87-3.94 (m, 1H), 4.16-4.23 (m, 1H), 4.26 (s, 2H), 4.94-5.06 (m, 2H), 7.11-7.17 (m, 2H), 7.30-7.36 (m, 2H), 7.50 (d, J=2.4 Hz, 1H), 7.60 (d, J=2.7 Hz, 1H), 7.90 (s, 1H), 10.8 (s, 1H).

MS (ESI⁺) m/z 482 (M+1) □504 (M+23)

HPLC 91.6%

Example 158

Preparation of 3-(4-fluorophenyl)butanal

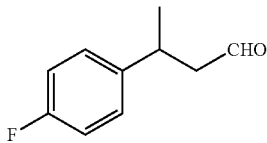

Adapted from the procedure of example 37 using crotonyl alcohol.

$^1$H NMR (300 MHz, DMSO-d$^6$) δ 1.20 (d, J=7.2 Hz, 3H), 2.68-2.74 (m, 2H), 3.26-3.40 (m, 1H), 7.11 (t, J=9.3 Hz, 2H), 7.27-7.34 (m, 2H), 9.61 (t, J=1.8 Hz, 1H)

Example 159

Preparation of 2-bromo-3-(4-fluorophenyl)butanal

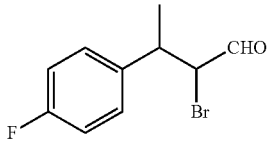

Adapted from the procedure of example 38 using the product of example 158.

¹H NMR (300 MHz, DMSO-d⁶) δ 1.30 (d, J=6.6 Hz, 3H), 3.43-3.55 (m, 1H), 4.83-4.91 (m, 1H), 7.16 (t, J=9 Hz, 2H), 7.33-7.43 (m, 2H), 9.36 (d, J=3.6 Hz, 1H)

Example 160

Preparation of S-3-(4-fluorophenyl)-1-oxobutan-2-yl-6-(benzyloxy)-1-(2-((2S,6R)-2,6-dimethylmorpholino)-2-oxoethyl)-5-oxo-1,5-dihydroimidazo[1,2-a]pyrimidine-7-carbothioate

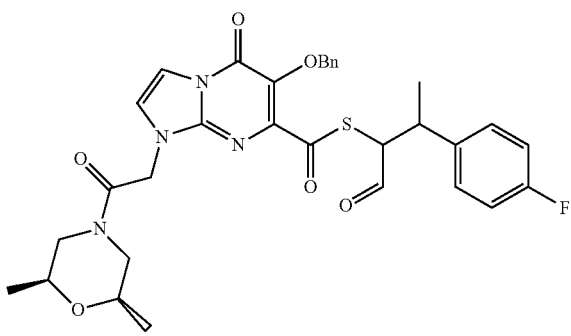 [SMILES: CC(c1ccc(F)cc1)C(C=O)SC(=O)c1nc2n(CC(=O)N3C[C@@H](C)O[C@@H](C)C3)ccn2c(=O)c1OCc1ccccc1]

Adapted from the procedure of example 39 using the product of example 159.

Example 161

Preparation of 6-(benzyloxy)-1-(2-((2S,6R)-2,6-dimethyl morpholino)-2-oxoethyl)-7-(5-(1-(4-fluorophenyl)ethyl)thiazol-2-yl)imidazo[1,2-a]pyrimidin-5(1H)-one

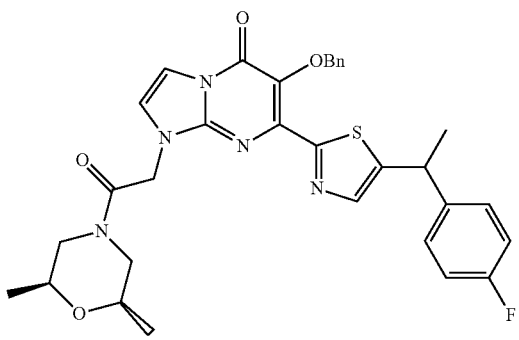 [SMILES: CC(c1ccc(F)cc1)c1cnc(-c2nc3n(CC(=O)N4C[C@@H](C)O[C@@H](C)C4)ccn3c(=O)c2OCc2ccccc2)s1]

Adapted from the procedure of example 40 using the product of example 160.

¹H NMR (300 MHz, DMSO-d⁶) δ 1.09 (d, J=6.0 Hz, 3H), 1.15 (d, J=6.0 Hz, 3H), 1.66 (d, J=6.9 Hz, 3H), 2.25-2.39 (m, 1H), 2.73-2.87 (m, 1H), 3.37-3.51 (m, 1H), 3.53-3.67 (m, 1H), 3.94 (d, J=12.3 Hz, 1H), 4.14 (d, J=12.6 Hz, 1H), 4.48-4.60 (m, 1H), 4.99 (d, J=17.7 Hz, 1H), 5.07 (s, 2H), 5.21 (d, J=16.8 Hz, 1H), 7.17 (t, J=8.7 Hz, 2H), 7.27-7.41 (m, 5H), 7.43-7.53 (m, 2H), 7.54-7.61 (m, 1H), 7.66-7.74 (m, 1H), 7.81-7.89 (m, 1H)

MS (ESI⁺) m/z 602 (M+1)

Example 162

Preparation of 1-(2-((2S,6R)-2,6-dimethylmorpholino)-2-oxoethyl)-7-(5-(1-(4-fluorophenyl)ethyl)thiazol-2-yl)-6-hydroxyimidazo[1,2-a]pyrimidin-5(1H)-one

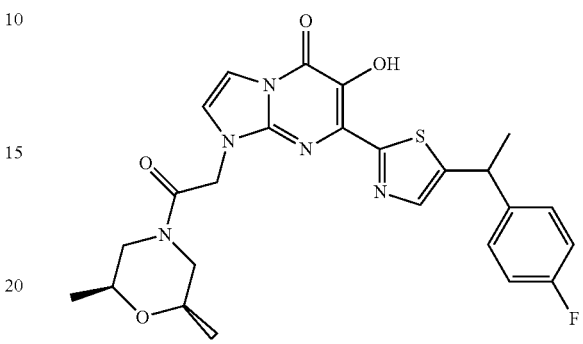

Adapted from the procedure of example 8.5 of PCT/AU2007/001980 using the product of example 161.

¹H NMR (300 MHz, DMSO-d⁶) δ 1.09 (d, J=6.0 Hz, 3H), 1.15 (d, J=6.1 Hz, 3H), 1.69 (d, J=7.2 Hz, 3H), 2.26-2.38 (m, 1H), 2.75-2.86 (m, 1H), 3.37-3.49 (m, 1H), 3.53-3.66 (m, 1H), 3.94 (d, J=12.9 Hz, 1H), 4.14 (d, J=12.6 Hz, 1H), 4.55-4.65 (m, 1H), 4.91 (d, J=17.1 Hz, 1H), 5.12 (d, J=16.8 Hz, 1H), 7.17 (t, J=8.7 Hz, 2H), 7.35-7.43 (m, 2H), 7.51 (d, J=2.7 Hz, 1H), 7.63 (d, J=2.7 Hz, 1H), 7.92 (m, 1H), 10.85 (s, 1H)

MS (ESI⁺) m/z 534 (M+23)

HPLC 99.6%

Example 163

Preparation of 2-((2-(6-(benzyloxy)-1-(2-((2S,6R)-2,6-dimethyl morpholino)-2-oxoethyl)-5-oxo-1,5-dihydroimidazo[1,2-a]pyrimidin-7-yl)thiazol-5-yl)methyl)-5-fluorobenzonitrile

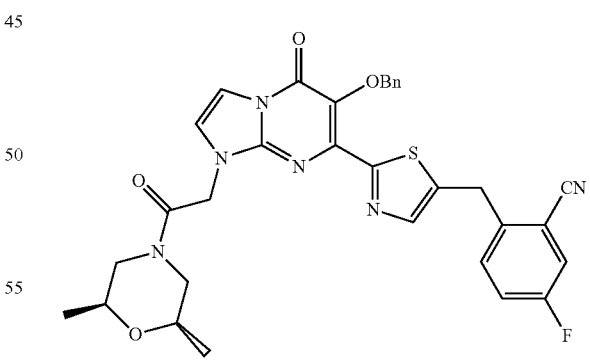

To a solution of the product of example 117 (15 mg, 0.024 mmol) in DMF (0.5 ml), POCl₃ (0.1 ml) was added dropwise. The mixture was stirred at room temperature for 20 hours, after which water was added, and then extracted with CH₂Cl₂. The extracts were combined, washed with brine, and then dried over sodium sulfate. The product was purified by column chromatography (CH₂Cl₂/EA/MeOH=8/2/1) to give the desired product (6 mg, 40% yield).

$^1$H NMR (300 MHz, DMSO-d$^6$) δ 1.08 (d, J=6.0 Hz, 3H), 1.15 (d, J=6.3 Hz, 3H), 2.25-2.39 (m, 1H), 2.70-2.91 (m, 1H), 3.37-3.50 (m, 1H), 3.52-3.65 (m, 1H), 3.89-3.99 (m, 1H), 4.08-4.19 (m, 1H), 4.46 (s, 2H), 4.99 (d, J=16.2 Hz, 1H), 5.08 (s, 2H), 5.21 (d, J=16.5 Hz, 1H), 7.26-7.39 (m, 3H), 7.43-7.53 (m, 2H), 7.55-7.74 (m, 4H), 7.83-7.92 (m, 2H)

MS (ESI$^+$) m/z 613 (M+1), 635 (M+23)

Example 164

Preparation of 2-((2-(1-(2-(((2S,6R)-2,6-dimethyl-morpholino)-2-oxoethyl)-6-hydroxy-5-oxo-1,5-dihydroimidazo[1,2-a]pyrimidin-7-yl)thiazol-5-yl)methyl)-5-fluorobenzonitrile

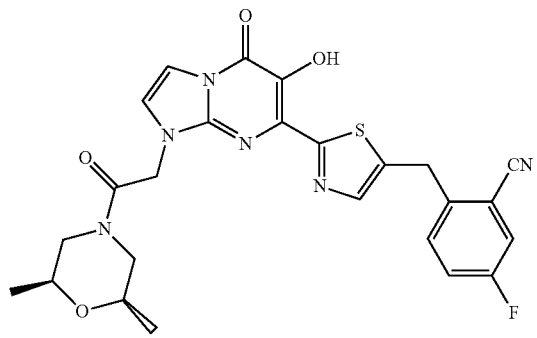 [SMILES: C[C@@H]1CN(C(=O)Cn2ccn3c(=O)c(O)c(-c4ncc(Cc5ccc(F)cc5C#N)s4)nc23)C[C@H](C)O1]

Adapted from the procedure of example 8.5 of PCT/AU2007/001980 using the product of example 163.

$^1$H NMR (300 MHz, DMSO-d$^6$) δ 1.08 (d, J=6.4 Hz, 3H), 1.15 (d, J=6.3 Hz, 3H), 2.25-2.39 (m, 1H), 2.74-2.86 (m, 1H), 3.37-3.47 (m, 1H), 3.53-3.65 (m, 1H), 3.95 (d, J=13.2 Hz, 1H), 4.14 (d, J=12.5 Hz, 1H), 4.50 (s, 2H), 4.87-5.00 (d, J=17.1 Hz, 1H), 5.07-5.19 (d, J=16.8 Hz, 1H), 7.52 (d, J=2.7 Hz, 1H), 7.56-7.70 (m, 3H), 7.85-7.95 (m, 2H), 10.73 (s, 1H)

MS (ESI$^−$) m/z 521 (M−1)

HPLC 94.3%

Example 165

Preparation of 3-(4-fluoro-2-methylsulfanyl-phenyl)-propionaldehyde

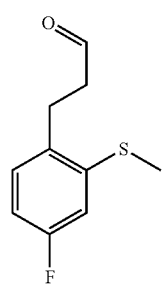

To a solution of 3-(4-fluoro-2-methylsulfanyl-phenyl)-propionic acid methyl ester (1 g, 4.3 mmol) in dry toluene was added DIBAL-H (5.2 ml in toluene, 1N) drop-wise at −78° C. After stirring at this temperature for 1 h, methanol (5 ml) was added dropwise to quench the reaction. The mixture was warmed to room temperature and diluted with EA. The mixture was washed with brine, dried and concentrated. The residue was purified by column chromatography to give the titled compound (804 mg, yield 92%)

$^1$H NMR (300 MHz, CDCl$_3$) δ 2.45 (s, 3H), 2.77 (t, J=7.5 Hz, 2H), 2.97 (t, J=7.5 Hz, 2H), 6.72-6.79 (m, 1H), 6.84-6.88 (m, 1H), 7.06-7.12 (m, 1H), 9.81 (d, J=0.9 Hz, 1H)

Example 166

Preparation of 2-bromo-3-(4-fluoro-2-methylsulfanyl-phenyl)-propionaldhyde

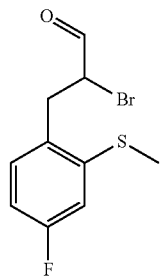

Adapted from the procedure of example 38 using the product of example 165.

Example 167

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid S-[1-(4-fluoro-2-methylsulfanyl-benzyl)-2-oxo-ethyl]ester Adapted from the procedure of example 39 using the product of example 166.

MS (ESI$^+$) m/z 653 (M+1)

Example 168

Preparation of 6-Benzyloxy-1-[2-(2,6-dimethyl-morpholin-4-yl)-2-oxo-ethyl]-7-[5-(4-fluoro-2-methyl-sulfanyl-benzyl)-thiazol-2-yl]-1H-imidazo[1,2-a]pyrimidin-5-one

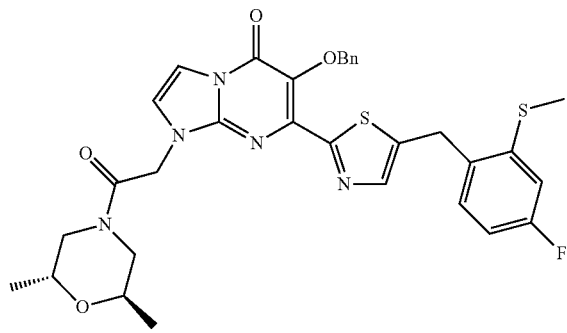

Adapted from the procedure of example 40 using the product of example 167.

$^1$H NMR (300 MHz, DMSO-d$^6$) δ 1.08 (d, J=6.3 Hz, 3H), 1.16 (d, J=6.0 Hz, 3H), 2.33 (t, J=11.4, 1H), 2.50 (s, 3H), 2.80 (t, J=11.1 Hz, 1H), 3.41-3.47 (m, 1H), 3.57-3.63 (m, 1H), 3.94 (d, J=12.6 Hz, 1H), 4.14 (d, J=12.9 Hz, 1H), 4.25 (s, 2H), 4.96 (d, J=16.8 Hz, 1H), 5.06 (s, 2H), 5.20 (d, J=17.1 Hz, 1H), 6.95-7.02 (m, 1H), 7.11-7.15 (m, 1H), 7.31-7.37 (m, 4H), 7.48-7.52 (m, 2H), 7.58 (d, J=2.7 Hz, 1H), 7.70 (d, J=2.7 Hz, 1H), 7.82 (s, 1H).

MS (ESI+) m/z 634 (M+1)

Example 169

Preparation of 6-Benzyloxy-1-[2-(2,6-dimethyl-morpholin-4-yl)-2-oxo-ethyl]-7-[5-(4-fluoro-2-methane-sulfinyl-benzyl)-thiazol-2-yl]-1H-imidazo[1,2-a]pyrimidin-5-one

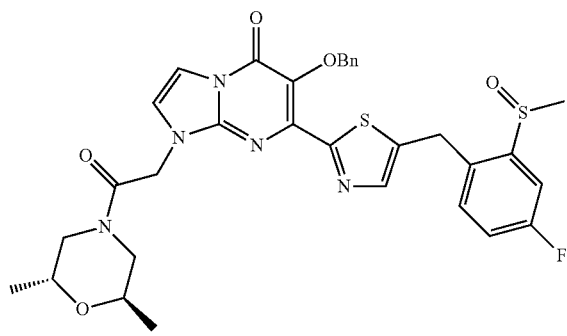

The mixture of the product of example 168 (160 mg, 0.25 mmol), H$_2$O$_2$ (30%, 1 ml) and HOAc (5 ml) was stirred at room temperature for 3 h. H$_2$O (6 ml) was added and then extracted with ethyl acetate. The organic layer was washed with H$_2$O, dried and concentrated. The residue was purified by column chromatography (ethyl acetate) to give the titled compound (170 mg, 100% yield)

$^1$H NMR (300 MHz, DMSO-d$^6$) δ 1.07 (d, J=6.3 Hz, 3H), 1.13 (d, J=6.0 Hz, 3H), 2.26-2.35 (m, 1H), 2.62 (s, 3H), 2.70-2.87 (m, 1H), 3.39-3.44 (m, 1H), 3.55-3.57 (m, 1H), 3.89-3.95 (m, 1H), 4.08-4.13 (m, 1H), 4.34 (s, 2H), 4.96 (d, J=17.5 Hz, 1H), 5.06 (s, 2H), 5.15 (d, J=16.5 Hz, 1H), 7.23-7.32 (m, 3H), 7.35-7.41 (m, 1H), 7.44-7.47 (m, 3H), 7.55-7.57 (d, J=2.7 Hz, 1H), 7.61-7.65 (m, 1H), 7.68-7.70 (d, J=2.7 Hz, 1H), 7.82 (s, 1H).

MS (ESI+) m/z 672 (M+23)

Example 170

Preparation of 1-[2-(2,6-Dimethyl-morpholin-4-yl)-2-oxo-ethyl]-7-[5-4-fluoro-2-methanesulfinyl-benzyl)-thiazol-2-yl]-6-hydroxy-1H-imidazo[1,2-a]pyrimidin-5-one

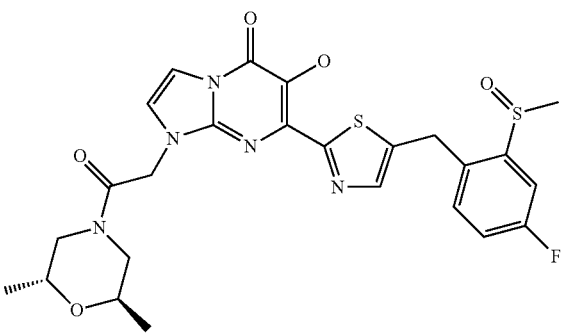

Adapted from the procedure of example 8.5 of PCT/AU2007/001980 using the product of example 169.

$^1$H NMR (300 MHz, DMSO-d$^6$) δ 1.06 (d, J=6.3 Hz, 3H), 1.12 (d, J=5.9 Hz, 3H), 2.27-2.35 (m, 1H), 2.68 (s, 3H), 2.75-2.82 (m, 1H), 3.38-3.43 (m, 1H), 3.55-3.57 (m, 1H), 3.91-3.96 (m, 1H), 4.08-4.13 (m, 1H), 4.41 (s, 2H), 4.93 (d, J=16.8 Hz, 1H), 5.12 (d, J=16.2 Hz, 1H), 7.39-7.51 (m, 3H), 7.62-7.67 (m, 2H), 7.89 (s, 1H), 10.76 (s, 1H).

MS (ESI+) m/z 582 (M+23)

Example 171

Preparation of Acetic acid 1-[2-(2,6-dimethyl-morpholin-4-yl)-2-oxo-ethyl]-7-[5-(4-fluoro-2-methane-sulfinyl-benzyl)-thiazol-2-yl]-5-oxo-1,5-dihydro-imidazo[1,2-a]pyrimidin-6-yl ester

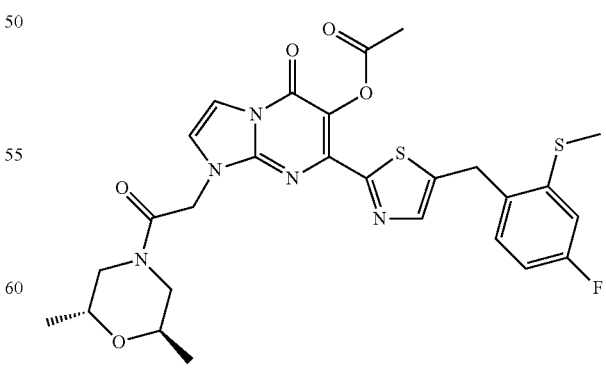

The product of example 168 was subjected to deprotection as per example 8.5 of PCT/AU2007/001980. The crude product (70 mg, contains MeOH) was mixed with Et$_3$N (0.1 ml)

and 4-dimethylaminopyridine (30 mg) in 5 ml dichloromethane. To this solution was added acetyl chloride (0.1 ml). The mixture was stirred at room temperature for 2 hours, and then poured into H₂O and dichloromethane. The organic layer was washed with H₂O, dried and concentrated. The residue was purified by column chromatography to give the titled compound (37 mg, 50% yield)

¹H NMR (300 MHz, CDCl₃) δ 1.20 (d, J=5.7 Hz, 3H), 1.21 (d, J=5.7 Hz, 3H), 2.41-2.46 (m, 1H), 2.46 (s, 3H), 2.50 (s, 3H), 2.93-3.02 (t, J=11.7 Hz, 1H), 3.52-3.65 (m, 2H), 3.81-3.88 (m, 1H), 4.22 (s, 2H), 4.44 (d, J=12.6 Hz, 1H), 4.88-5.11 (m, 2H), 6.78-6.85 (m, 1H), 6.90-6.95 (m, 1H), 7.10-7.17 (m, 2H), 7.60 (d, J=2.7 Hz, 1H), 7.70 (s, 1H).

Example 172

Preparation of 1-[2-(2,6-Dimethyl-morpholin-4-yl)-2-oxo-ethyl]-7-[5-(4-fluoro-2-methylsulfanyl-benzyl)-thiazol-2-yl]-6-hydroxy-1H-imidazo[1,2-a]pyrimidin-5-one

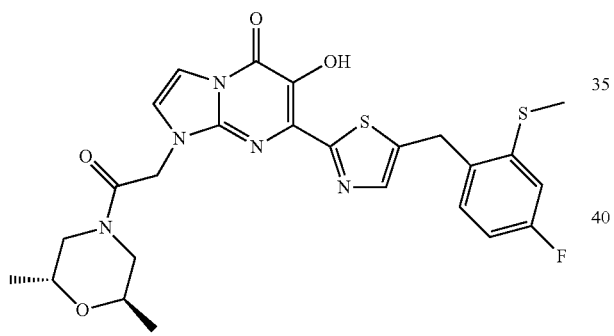

To a solution of the product of example 171 (38 mg, 0.06 mmol) in MeOH (5 ml) was added K₂CO₃ (20 mg, 0.14 mmol) and then the mixture was stirred at room temperature for 2 hours. The mixture was poured into water and extracted with dichloromethane. The organic layers were dried and concentrated. The resulting solids were collected and washed with cold MeOH (2-3 ml) to give the title compound (15 mg, yield 42%).

¹H NMR (300 MHz, CDCl₃) δ 1.19 (d, J=6.3 Hz, 3H), 1.21 (d, J=5.7 Hz, 3H), 2.37-2.45 (m, 1H), 2.47 (s, 3H), 2.90-2.99 (m, 1H), 3.52-3.60 (m, 2H), 3.80-3.84 (d, J=12.6 Hz, 1H), 4.24 (s, 2H), 4.36 (d, J=13.8 Hz, 1H), 4.78 (d, J=15.9 Hz, 1H), 4.93 (d, J=15.9 Hz, 1H), 6.79-6.85 (m, 1H), 6.86-6.95 (m, 1H), 7.07 (d, J=2.4 Hz, 1H), 7.14-7.19 (m, 1H), 7.57 (d, J=2.4 Hz, 1H), 7.63 (s, 1H), 11.25 (s, 1H).

MS (ESI−) m/z 542 (M−1)

HPLC 92.0%

Example 173

Preparation of 6-Acetoxy-1-[2-(3,5-dimethyl-piperidin-1-yl)-2-oxo-ethyl]-5-oxo-1,5-dihydro-imidazo[1,2-a]pyrimidine-7-carboxylic acid methyl ester

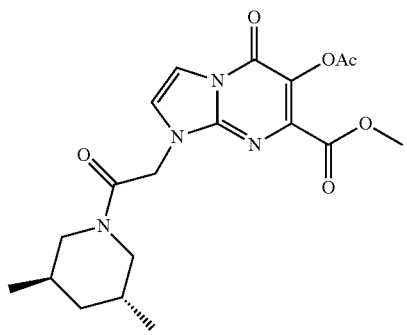

Adapted from the procedure of example 33.

¹H NMR (300 MHz, CDCl₃) δ 0.92 (J=6.6 Hz, 3H), 0.97 (J=6.6 Hz, 3H), 1.27 (t, J=6.9 Hz, 1H), 1.60-1.67 (m, 2H), 1.86-1.91 (m, 1H), 2.11 (t, J=11.7 Hz, 1H), 2.38 (s, 3H), 2.66 (t, J=12 Hz, 1H), 3.76-3.82 (m, 1H), 3.94 (s, 3H), 4.49-4.55 (m, 1H), 5.02 (s, 2H), 7.25 (d, J=3.0 Hz, 1H), 7.66 (d, J=2.7 Hz, 1H).

Example 174

Preparation of 1-[2-(3,5-Dimethyl-piperidin-1-yl)-2-oxo-ethyl]-6-hydroxy-5-oxo-1,5-dihydro-imidazo[1,2-a]pyrimidine-7-carboxylic acid methyl ester

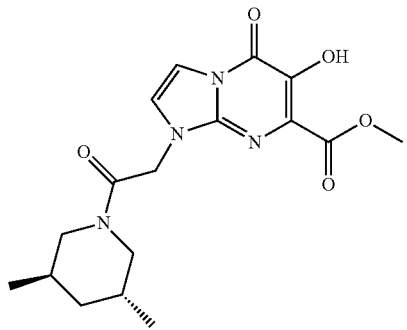

Adapted from the procedure of example 172 using the product of example 173.

The titled product was used directly in next step.

Example 175

Preparation of 6-Benzyloxy-1-[2-(3,5-dimethyl-piperidin-1-yl)-2-oxo-ethyl]-5-oxo-1,5-dihydro-imidazo[1,2-a]pyrimidine-7-carboxylic acid methyl ester

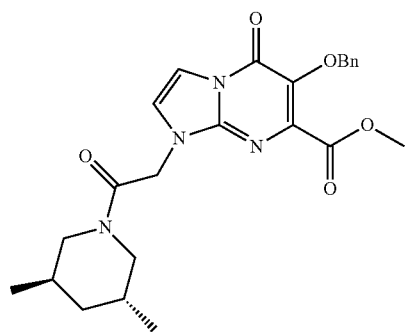

Adapted from the procedure of example 34 using the product of example 174.

The titled product was used directly in next step.

Example 176

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carboxylic acid

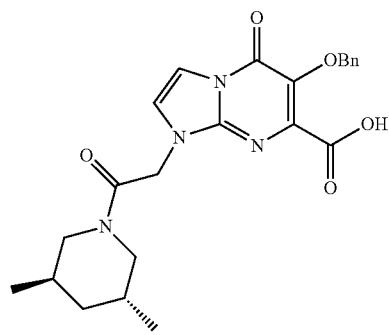 [SMILES: C[C@@H]1C[C@@H](C)CN(C(=O)Cn2ccn3c(=O)c(OCc4ccccc4)c(C(=O)O)nc23)C1]

Adapted from the procedure of example 35 using the product of example 175.

$^1$H NMR (300 MHz, CDCl$_3$) δ 0.75-0.87 (m, 1H), 0.84 (J=6.9 Hz, 3H), 0.91 (J=6.3 Hz, 3H), 1.43-1.49 (m, 1H), 1.66-1.76 (m, 1H), 1.75-1.80 (m, 1H), 2.10 (t, J=12 Hz, 1H), 2.59 (t, J=12 Hz, 1H), 3.85 (d, J=12 Hz, 1H), 4.26 (d, J=10.5 Hz, 1H), 5.02 (s, 2H), 5.06 (d, J=16.5 Hz, 1H), 5.15 (d, J=16.5 Hz, 1H), 7.33-7.42 (m, 3H), 7.45-7.48 (m, 2H), 7.60 (d, J=2.7 Hz, 1H), 7.75 (d, J=2.4 Hz, 1H), 13.64 (s, 1H).

MS (ESI$^-$) m/z 437 (M−1)

Example 177

Preparation of 6-Benzyloxy-1-[2-(2,6-dimethyl-morpholin-4-yl)-2-oxo-ethyl]-5-oxo-1,5-dihydro-imidazo[1,2-a]pyrimidine-7-carbothioic acid

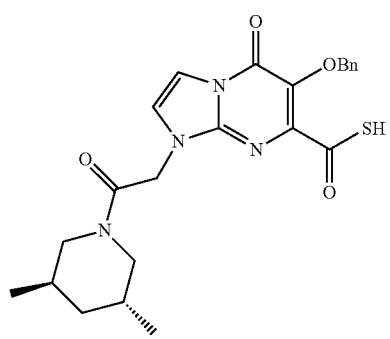 [SMILES: C[C@@H]1C[C@@H](C)CN(C(=O)Cn2ccn3c(=O)c(OCc4ccccc4)c(C(=O)S)nc23)C1]

Adapted from the procedure of example 36 using the product of example 176.

The titled product was used directly in next step.

Example 178

Preparation of 6-Benzyloxy-1-[2-(3,5-dimethyl-piperidin-1-yl)-2-oxo-ethyl]-5-oxo-1,5-dihydro-imidazo[1,2-a]pyrimidine-7-carbothioic acid S-[2-(4-fluorophenyl)-1-formyl-ethyl]ester

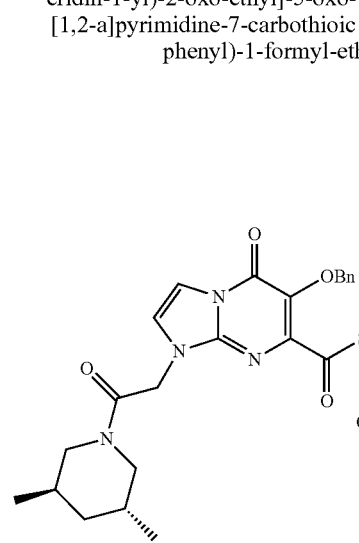

Adapted from the procedure of example 39 using the product of example 177 and the product of example 72.

The titled product was used directly in next step.

Example 179

Preparation of 6-Benzyloxy-1-[2-(3,5-dimethyl-piperidin-1-yl)-2-oxo-ethyl]-7-[5-(4-fluoro-benzyl)-thiazol-2-yl]-1H-imidazo[1,2-a]pyrimidin-5-one

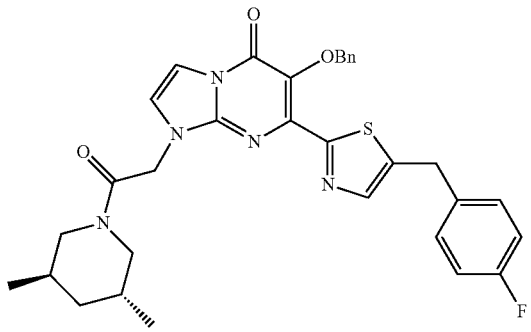 [SMILES: C[C@@H]1C[C@@H](C)CN(C(=O)Cn2ccn3c(=O)c(OCc4ccccc4)c(-c4ncc(Cc5ccc(F)cc5)s4)nc23)C1]

Adapted from the procedure of example 40 using the product of example 178.

$^1$H NMR (300 MHz, CDCl$_3$) δ 0.75-0.92 (m, 7H), 1.56-1.63 (m, 2H), 1.83-1.80 (d, J=13.8 Hz, 1H), 2.05 (t, J=12.3 Hz, 1H), 2.60 (t, J=13.5 Hz, 1H), 3.76-3.81 (m, 1H), 4.15 (s, 2H), 4.48 (d, J=11.7 Hz, 1H), 5.05 (s, 2H), 5.25 (s, 2H), 6.96-7.03 (m, 2H), 7.15-7.20 (m, 3H), 7.27-7.30 (m, 3H), 7.46-7.48 (m, 2H), 7.61 (d, J=2.7 Hz, 1H), 7.73 (s, 1H)

MS (ESI$^+$) m/z 586 (M+1)

Example 180

Preparation of 1-[2-(3,5-Dimethyl-piperidin-1-yl)-2-oxo-ethyl]-7-[5-(4-fluoro-benzyl)-thiazol-2-yl]-6-hydroxy-1H-imidazo[1,2-a]pyrimidin-5-one

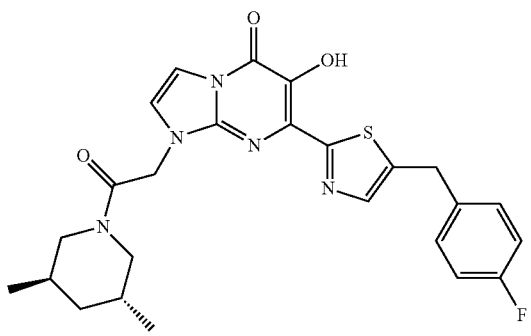 [SMILES: C[C@@H]1C[C@@H](C)CN(C(=O)Cn2ccn3c(=O)c(O)c(-c4ncc(Cc5ccc(F)cc5)s4)nc23)C1]

Adapted from the procedure of example 8.5 of PCT/AU2007/001980 using the product of example 179.

$^1$H NMR (300 MHz, CDCl$_3$) δ 0.90-0.932 (m, 7H), 1.55-1.88 (m, 3H), 2.10 (t, J=13.2 Hz, 1H), 2.65 (t, J=12.6 Hz, 1H), 3.84-3.90 (m, 1H), 4.22 (s, 2H), 4.49-4.54 (m, 1H), 5.05 (s, 2H), 4.87-4.92 (m, 2H), 7.03-7.11 (m, 3H), 7.23-7.26 (m, 2H), 7.62 (s, 1H□), 7.67 (m, 1H).

MS (ESI$^-$) m/z 494 (M−1)

The following compounds were also prepared by the methods set out in this application:

Example 181

6-Hydroxy-3-morpholin-4-ylmethyl-5-oxo-1-(2-oxo-2-piperidin-1-yl-ethyl)-1,5-dihydro-imidazo[1,2-a]pyrimidine-7-carboxylic acid 3,4-dichloro-benzylamide

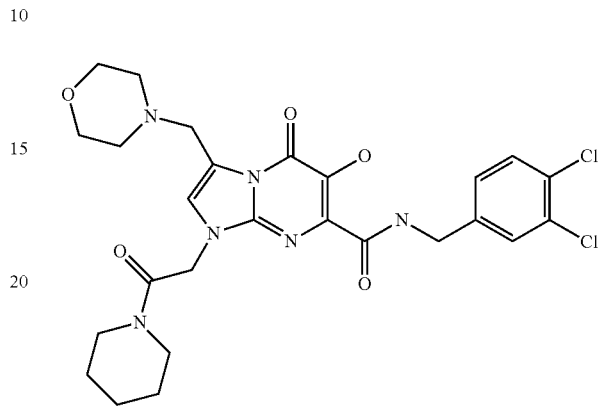

$^1$H NMR (300 MHz, DMSO-d$_6$): δ 11.3 (1H, s), 9.426 (1H, m), 7.58 (2H, m), 7.31 (2H, m), 5.056 (2H, s), 4.52 (2H, d, J=6.6 Hz), 4.025 (2H,$), 3.57 (4H, m), 3.43 (4H, m), 1.58 (4H, m), 1.44 (2H, m).

Example 182

1-[2-((2S,6S)-2,6-Dimethyl-morpholin-4-yl)-2-oxo-ethyl]-7-[5-(4-fluoro-benzyl)-thiazol-2-yl]-6-hydroxy-1H-imidazo[1,2-a]pyrimidin-5-one

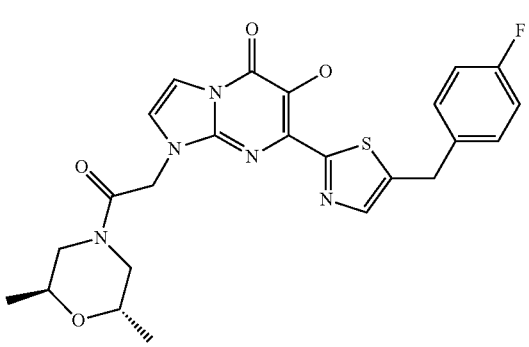 [SMILES: C[C@H]1CN(C(=O)Cn2ccn3c(=O)c(O)c(-c4ncc(Cc5ccc(F)cc5)s4)nc23)C[C@H](C)O1]

$^1$H NMR (300 MHz, DMSO-d$_6$): δ: 10.81 (1H, m), 7.91 (1H, s), 7.62 (1H, d, J=3 Hz), 7.5 (1H, d, 2.7 Hz), 7.37 (2H, m), 7.16 (2H, m), 5.13 (1H, d, J=16.5 Hz), 4.92 (1H, d, J=17.1 Hz), 4.288 (2H, s), 4.13 (1H, m), 3.94 (1H, m), 3.43 (1H, m), 3.27 (1H, m), 2.8 (1H, m), 2.28 (1H, m), 1.10 (6H, m).

Example 183

7-[5-(4-Fluoro-benzyl)-thiazol-2-yl]-6-hydroxy-1-(1-methyl-2-oxo-pyrrolidin-3-yl)-1H-imidazo[1,2-a]pyrimidin-5-one

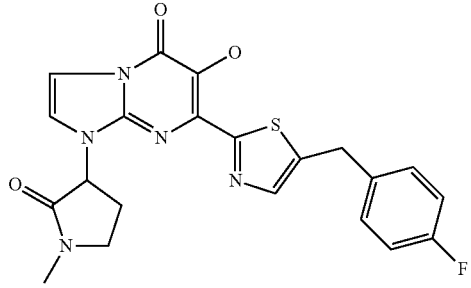 [SMILES: CN1CCC(n2ccn3c(=O)c(O)c(-c4ncc(Cc5ccc(F)cc5)s4)nc23)C1=O]

$^1$H NMR (300 MHz, DMSO-$d_6$): δ: 10.78 (1H, s), 7.9 91H, s), 7.64 (2H, s), 7.38 (2H, m), 7.17 (2H, m), 5.24 (1H, t, J=9.3 Hz), 4.278 (2H, s), 3.5 (2H, m), 2.81 (3H, s), 2.54 (1H, m), 2.32 (1H, m).

Example 184

1-[2-(2,6-Dimethyl-morpholin-4-yl)-1-methyl-2-oxo-ethyl]-7-[5-(4-fluoro-benzyl)-thiazol-2-yl]-6-hydroxy-1H-imidazo[1,2-a]pyrimidin-5-one

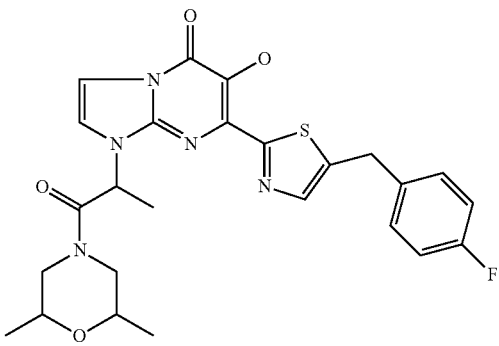 [SMILES: CC1CN(C(=O)C(C)n2ccn3c(=O)c(O)c(-c4ncc(Cc5ccc(F)cc5)s4)nc23)CC(C)O1]

$^1$H NMR (300 MHz, DMSO-$d_6$): δ: 10.78 (1H, s) 7.92 91H, m), 7.72 (1H, m), 7.63 (1H, m), 7.36 (2H, m), 7.16 (2H, m), 5.68 (2H, m), 4.289 (2H, s), 4.11 (1H, d, J=13.5 Hz), 3.42 (1H, m), 3.2 (1H, m), 2.8 (1H, m), 2.3 (1H, m), 1.59 (3H, m), 1.05 (H, m).

Example 185

1-[2-(2-Aza-bicyclo[2.2.1]hept-2-yl)-2-oxo-ethyl]-7-[5-(4-fluoro-benzyl)-thiazol-2-yl]-6-hydroxy-1H-imidazo[1,2-a]pyrimidin-5-one

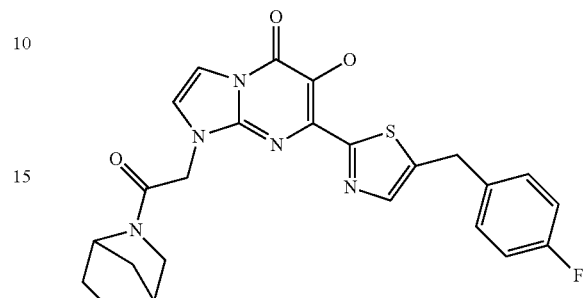

$^1$H NMR (300 MHz, DMSO-$d_6$): δ: 10.8 (1 h, s, br), 7.9 (1H, br), 7.6 (2H, m), 7.36 (2H, m), 7.17 (2H, m), 4.75 (2H, m), 4.27 (3H, m), 3.34 (1H, m), 2.99 (1H, m), 1.8 (6H, m).

Example 186

1-[2-((2R,6R)-2,6-Dimethyl-morpholin-4-yl)-2-oxo-ethyl]-3-(1,1-dioxo-1lambda*6*-isothiazolidin-2-yl)-6-hydroxy-5-oxo-1,5-dihydro-imidazo[1,2-a]pyrimidine-7-carboxylic acid 2-dimethylsulfamoyl-4-fluoro-benzylamide

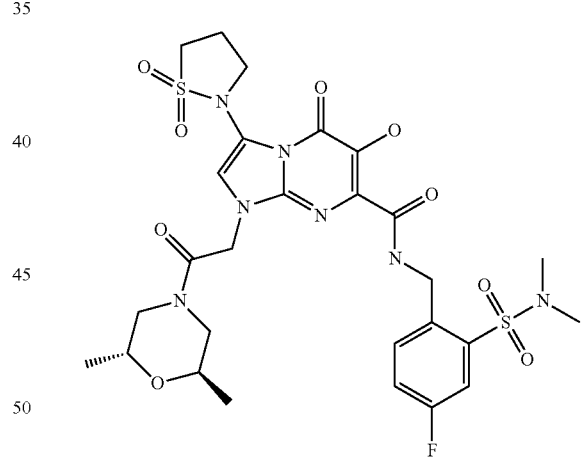

1-[2-((2R,6R)-2,6-Dimethyl-morpholin-4-yl)-2-oxo-ethyl]-3-(1,1-dioxo-1lambda*6*-isothiazolidin-2-yl)-6-hydroxy-5-oxo-1,5-dihydro-imidazo[1,2-a]pyrimidine-7-carboxylic acid methyl ester (30 mg, 0.062 mmol) was dissolved in MeOH (1 mL) and 2-aminomethyl-5-fluoro-N,N-dimethyl-benzenesulfonamide (22 mg, 0.093 mmol) was added. The reaction was heated at reflux for 24 hours then filtered hot and the filtrate concentrated. The product was recrystalised from methanol and ether and isolated (17 mg, 43% yield) as a pale yellow solid.

$^1$H NMR (300 MHz, $CDCl_3$): δ 9.29 (1H, t, J=6.6 Hz, $NHCH_2$), 7.66 (1H, s, Ar—CH), 7.61 (1H, dd, J=8.7, 2.4 Hz, Ar—CH), 7.53 (2H, m, Ar—CH), 5.13 (1H, d, J=17.1 Hz, $OCHCH_3$), 5.03 (1H, d, J=16.2 Hz, $OCHCH_3$), 4.82 (2H, m,

NHCH₂), 4.15 (1H, d, J=12.3 Hz, NCH₂CO), 3.86-3.75 (3H, m, 1×NCH₂C=O, NCH₂), 3.60 (1H, m, NCH₂), 3.48 (1H, m, NCH₂), 3.43 (2H, t, J=7.2 Hz, NCH₂), 2.82 (6H, s, N[CH₃]₂), 2.44 (2H, t, J=7.2 Hz, SO₂CH₂), 2.33 (2H, dd, J=11.4, 12.0 Hz, CH₂), 1.12 (3H, d, J=7.2 Hz, OCHCH₃), 1.08 (3H, s, J=6.0 Hz, OCHCH₃).

Example 187

1-[2-(3,5-Dimethyl-piperidin-1-yl)-2-oxo-ethyl]-3-(1,1-dioxo-1lambda*6*-isothiazolidin-2-yl)-6-hydroxy-5-oxo-1,5-dihydro-imidazo[1,2-a]pyrimidine-7-carboxylic acid 2-dimethylsulfamoyl-4-fluoro-benzylamide

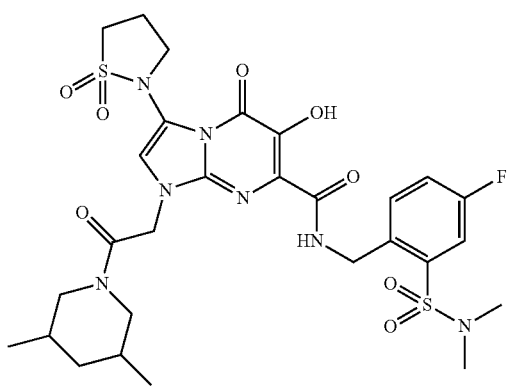

synthetic scheme

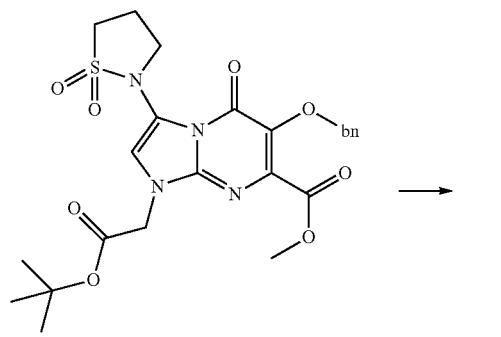

Mw = 532

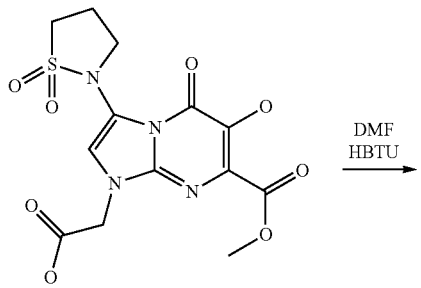

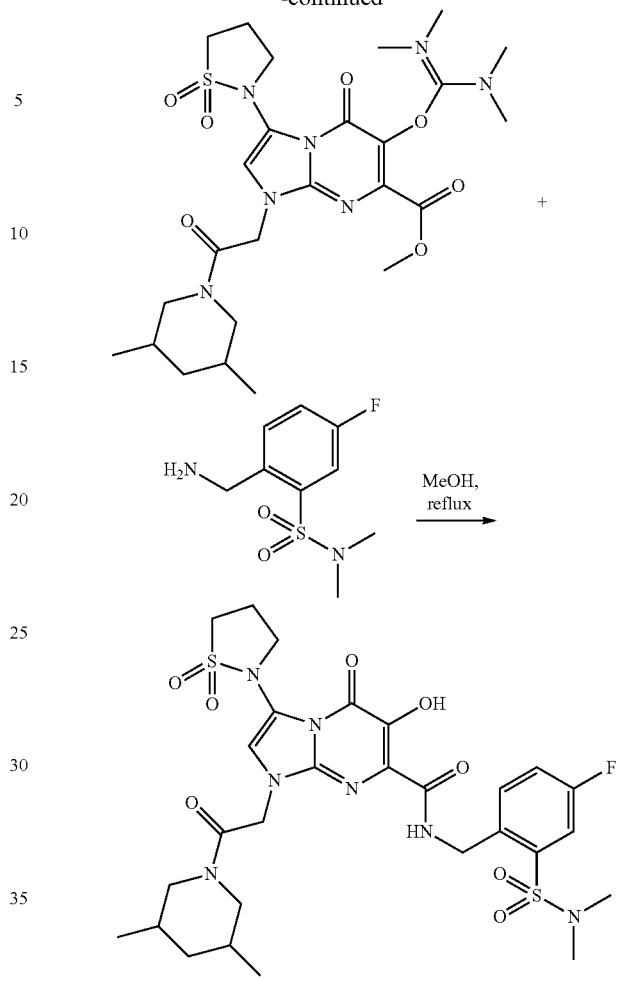

6-Benzyloxy-1-tert-butoxycarbonylmethyl-3-(1,1-dioxo-1lambda*6*-isothiazolidin-2-1)-5-oxo-1,5-dihydro-imidazo[1,2-a]pyrimidine-7-carboxylic acid methyl ester (266 mg, 0.5 mmol) was stirred with dichloromethane (1 ml) and trifluoroacetice acid (2 ml) for 4 hours at room temperature. The reaction mixture was evaporated to dryness and the residue was dissolved in dimethylformamide (2.5 ml). HBTU (474 mg, 1.25 mmol) and 3,5-dimethylpiperidine (226 mg, 2 mmol) were added. The resulting mixture was stirred overnight and room temperature, and then evaporated to dryness. The residue was dissolved in methanol (20 ml), and 2-aminomethyl-5-fluoro-N,N-dimethyl-benzenesulfonamide (580 mg, 2.5 mmol) was added. The reaction was heated at reflux for 6 days, then evaporated to dryness. The residue was taken up in dichloromethane (50 ml) and 1M HCl solution (150 ml). The aqueous phase was extracted with dichloromethane (3×50 ml). The combined organic phase was dried over MgSO₄ and evaporated to dryness. The residue was purified on preparative HPLC to afford the title product as colorless amorphous solid (185 mg, 54.2% overall yield.)

¹H NMR (300 MHz, DMSO-d₆): δ 11.3 (1H, broad; —OH), 9.26 (1H, t, J=6.32 Hz, NHCH₂), 7.65 (1H, s, Ar—CH), 7.6 (1H, dd, J=9.15, 1.92 Hz, Ar—CH), 7.53 (2H, m, Ar—CH), 5.09 (1H, d, J=16.9 Hz, NCH₂CO), 5.06 (1H, d, J=16.9 Hz, NCH₂CO), 4.82 (2H, t, J=6.53 Hz, NHCH₂), 4.25 (1H, m), 3.43 (2H, dd, J=7.31, 6.85 Hz), 2.81 (6H, s), 2.58 (1H, m); 2.44 (2H, m), 2.07 (1H, dd, J=12.33, 11.88 Hz), 1.72 (2H, m), 1.44 (1H, br), 0.85 (6H, m).

Example 188

3-(1,1-Dioxo-1lambda*6*-isothiazolidin-2-yl)-6-hydroxy-5-oxo-1-(2-oxo-2-piperidin-1-yl-ethyl)-1,5-dihydro-imidazo[1,2-a]pyrimidine-7-carboxylic acid 2-dimethylsulfamoyl-4-fluoro-benzylamide

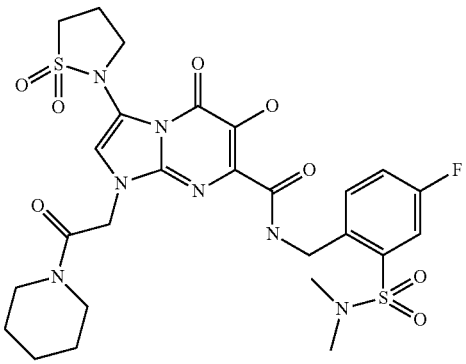 [SMILES: CN(C)S(=O)(=O)c1cc(F)ccc1CNC(=O)c1nc2n(CC(=O)N3CCCCC3)cc(N3CCCS3(=O)=O)n2c(=O)c1O]

Following the same procedure for Example 187 but using piperidine, the title product was obtained in 35.8% yield as a yellowish amorphous solid.

$^1$H NMR (300 MHz, DMSO-d$_6$): δ 11.3 (1H, br), 9.3 (1H, dd, J=6.8, 6.3 Hz), 7.658 (1H, s), 7.58 (3H, m), 5.06 (2H, br), 4.82 (2H, m), 4.52 (2H, m), 3.77 (2H, m), 3.43 (4H, m), 2.82 (3H, s), 2.76 (3H, s), 2.44 (2H, m), 1.59 (2H, br), 1.45 (2H, br).

Example 189

3-(1,1-Dioxo-1lambda*6*-isothiazolidin-2-yl)-6-hydroxy-1-[2-(2-methyl-piperidin-1-yl)-2-oxo-ethyl]-5-oxo-1,5-dihydro-imidazo[1,2-a]pyrimidine-7-carboxylic acid 2-dimethylsulfamoyl-4-fluoro-benzylamide

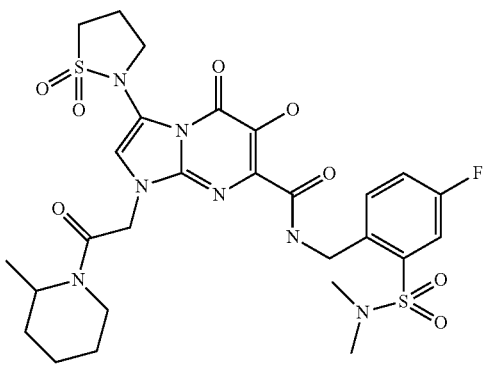 [SMILES: CC1CCCCN1C(=O)Cn1cc(N2CCCS2(=O)=O)n2c(=O)c(O)c(C(=O)NCc3ccc(F)cc3S(=O)(=O)N(C)C)nc12]

Following the same procedure for Example 188 but using 2-methylpiperidine, the title product was obtained in 22.5% yield as a yellowish amorphous solid.

$^1$H NMR (300 MHz, DMSO-d$_3$): δ: 11.316 (1H, s). 9.24 (1H, s), 7.6 (6H, m), 4.82 (2H, m), 4.52 (2H, m), 3.77 (2H, m), 3.42 (2H, m), 2.81 (3H, s), 2.76 (3H, s), 2.73 (1H, s), 1.60 (5H, m), 1.30 (3H, m), 1.10 (2H, m).

Example 190

1-[2-(3,5-Dimethyl-piperidin-1-yl)-2-oxo-ethyl]-3-(1,1-dioxo-1lambda*6*-isothiazolidin-2-yl)-6-hydroxy-5-oxo-1,5-dihydro-imidazo[1,2-a]pyrimidine-7-carboxylic acid 3,4-dichloro-benzylamide

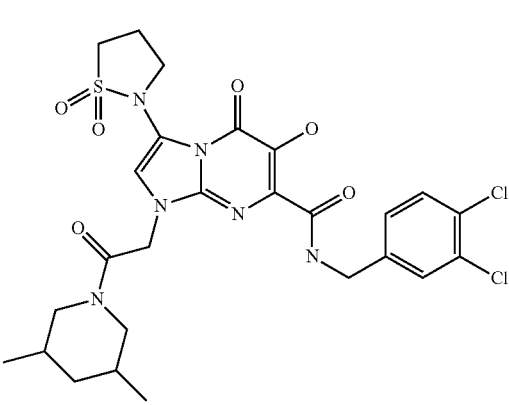 [SMILES: CC1CC(C)CN(C(=O)Cn2cc(N3CCCS3(=O)=O)n3c(=O)c(O)c(C(=O)NCc4ccc(Cl)c(Cl)c4)nc23)C1]

Following the same procedure for Example 187 but using 3,4-dichlorobenzylamine, the title product was obtained in 55% yield as a yellowish amorphous solid.

$^1$H NMR (300 MHz, DMSO-d$_6$): δ 11.4 (1H, broad; —OH), 9.396 (1H, t, J=6.39 Hz, NHCH$_2$), 7.63 (1H, s, Ar—CH), 7.56 (2H, m), 7.5 (1H, m, Ar—CH),), 7.3 (1H, m, Ar—CH), 5.09 (2H, s), 4.5 (2H, m), 4.3 (1H, m), 3.76 (2H, m), 3.55 (br), 3.42 (2H, m), 2.43 (2H, m); 2.05 (1H, dd, J=12.33, 11.88 Hz), 1.72 (2H, m), 1.4 (1H, br), 0.85 (6H, m).

Example 191

1-[2-(3,5-Dimethyl-piperidin-1-yl)-2-oxo-ethyl]-6-hydroxy-3-methylsulfanylmethyl-5-oxo-1,5-dihydro-imidazo[1,2-a]pyrimidine-7-carboxylic acid 3,4-dichloro-benzylamide

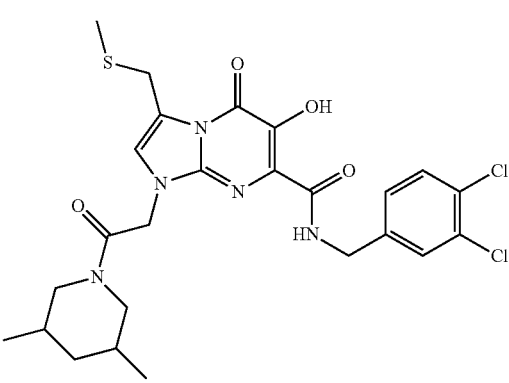 [SMILES: CSCc1cn(CC(=O)N2CC(C)CC(C)C2)c2nc(C(=O)NCc3ccc(Cl)c(Cl)c3)c(O)c(=O)n12]

Step 1:

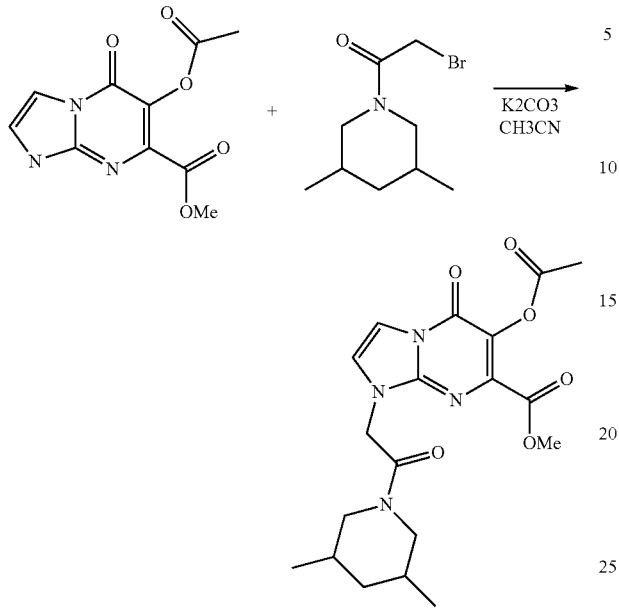

6-Acetoxy-5-oxo-1,5-dihydro-imidazo[1,2-a]pyrimidine-7-carboxylic acid methyl ester (3 g, 11.95 mmol) was mixed with $K_2CO_3$ (3.3 g, 23.9 mmol), 18-crown-6 ether (0.3 g) and 2-Bromo-1-(3,5-dimethyl-piperidin-1-yl)-ethanone (4.2 g, 17.93 mmol) in acetonitrile (60 ml). The resulting mixture was stirred overnight at room temperature. The solvents were removed, and the residue taken up in ethylacetate; washed with water and 1N HCl. After drying over $MgSO_4$, the organic phase was evaporated to dryness and the residue was purified on silica gel to give 6-acetoxy-1-[2-(3,5-dimethyl-piperidin-1-yl)-2-oxo-ethyl]-5-oxo-1,5-dihydro-imidazo[1,2-a]pyrimidine-7-carboxylic acid methyl ester (2.92 g, 60.5% yield).

$^1$H NMR (300 MHz, DMSO-$d_6$): 7.77 (1H, d, J=2.74 Hz, Ar—CH), 7.67 (1H, d, J=2.74 Hz, Ar—CH), 5.15 81H, d, J=16.9 Hz), 5.13 (1H, d, J=16.9 Hz), 4.25 (1H, m), 3.85 (1H, m), 3.82 (3H, s), 2.59 (1H, dd, J=13.25, 11.88 Hz), 2.25 (3H, s), 2.09 (1H, dd, J=13.35, 11.88 Hz), 1.78 (1H, m), 1.69 (1H, m), 1.48 91H, m), 0.88 (6H, m).

Step 2

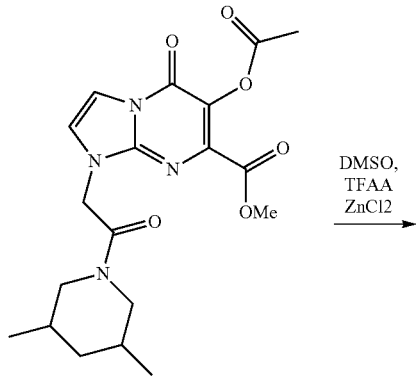

DMSO (5.96 ml, 84.1 mmol, 10 equivalents) was dissolved in 1,2-dichloroethane (35 ml) and the solution was cooled to 0° C. under nitrogen atmosphere. Trifluoroacetic acid anhydride (11.69 ml, 84.1 mmol, 10 equivalents) was added dropwise. The resulting solution was stirred at 0° C. for 1 hour then 6-ccetoxy-1-[2-(3,5-dimethyl-piperidin-1-yl)-2-oxo-ethyl]-5-oxo-1,5-dihydro-imidazo[1,2-a]pyrimidine-7-carboxylic acid methyl ester (from step 1; 3.4 g, 8.41 mmol) $ZnCl_2$ (2.29 g, 16.8 mmol, 2 equivalent) were added, and the reaction mixture was stirred at 80° C. for four hours. The mixture was poured into brine (200 ml) and water (200 ml) and extracted with dichloromethane. After drying over $MgSO_4$, the solvent was removed, and the residue was purified on silica gel to afford the product (1.7 g, 47.9% yield).

$^1$H NMR (300 MHz, CDCl$_3$): 9.75 (1H, br), 6.98 (1H, s), 4.86 (2H, s), 4.50 (1H, m), 4.28 (2H, s), 4.00 (3H, s), 3.82 (1H, m), 2.63 (1H, dd, J=12.79, 11.88 Hz), 2.15 (3H, s), 2.09 (1H, dd, J=12.79, 11.88 Hz), 1.88 (1H, m), 1.7 (4H, m), 0.95 (6H, m).

Step 3

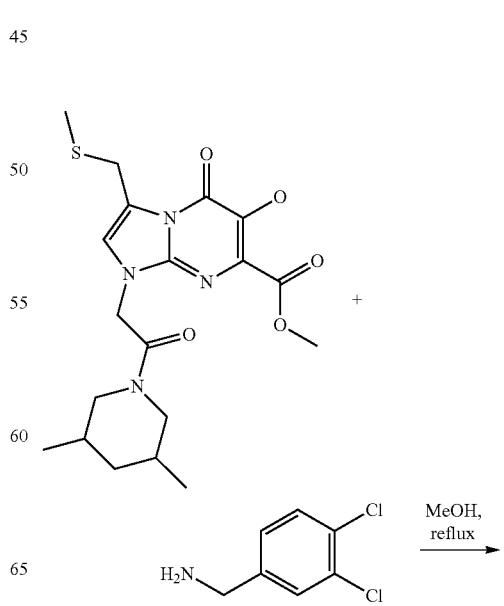

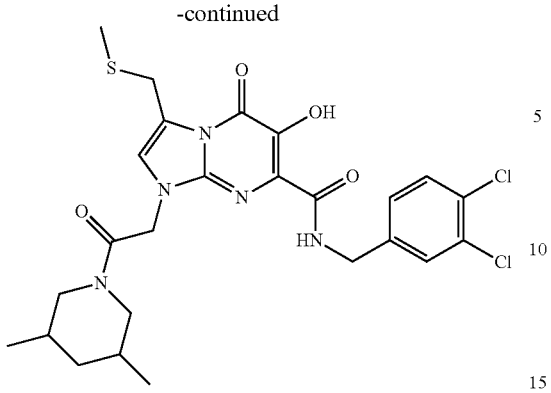

Following the same procedure for Example 49 but using 1-[2-(3,5-dimethyl-piperidin-1-yl)-2-oxo-ethyl]-6-hydroxy-3-methylsulfanylmethyl-5-oxo-1,5-dihydro-imidazo[1,2-a]pyrimidine-7-carboxylic acid methyl ester from step 2 and 3,4-dichlorobenzylamine, the title product was obtained in 76.4% yield as a yellowish amorphous solid.

$^1$H NMR (300 MHz, CDCl$_3$): δ 11.22 (1H, s; —OH), 7.87 (1H, dd, J=6.39, 5.94 Hz, NHCH$_2$), 7.43 (2H, m, Ar—CH), 7.18 (1H, m), 6.86 (1H, m, Ar—CH),), 4.76 (2H, s), 4.59 (2H, m), 4.48 (1H, m), 4.28 (2H, s), 3.66 (1H, m), 2.58 (1H, dd, J=13.25, 11.88 Hz), 2.15 (3H, s), 2.06 (1H, t, J=12.33 Hz), 1.82 (1H, m), 1.57, (3H, s), 1.52 (3H, m), 0.90 (6H, d, J=6.39 Hz).

Example 192

1-[2-(3,5-Dimethyl-piperidin-1-yl)-2-oxo-ethyl]-6-hydroxy-3-methylsulfanylmethyl-5-oxo-1,5-dihydro-imidazo[1,2-a]pyrimidine-7-carboxylic acid 2-dimethylsulfamoyl-4-fluoro-benzylamide

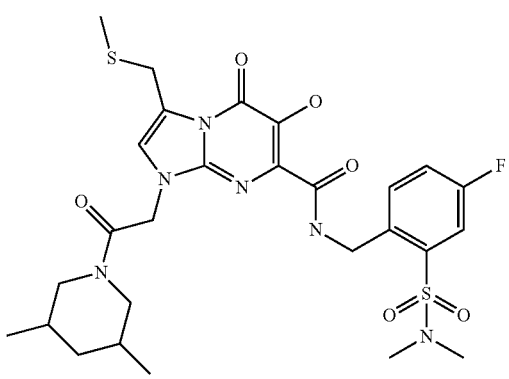 [SMILES: CSCc1cn(CC(=O)N2CC(C)CC(C)C2)c2nc(C(=O)NCc3ccc(F)cc3S(=O)(=O)N(C)C)c(O)c(=O)n12]

Following the same procedure for Example 187 but using 1-[2-(3,5-dimethyl-piperidin-1-yl)-2-oxo-ethyl]-6-hydroxy-3-methylsulfanylmethyl-5-oxo-1,5-dihydro-imidazo[1,2-a]pyrimidine-7-carboxylic acid methyl ester Example 191 and 2-aminomethyl-5-fluoro-N,N-dimethyl-benzenesulfonamide, the title product was obtained in 84.7% yield as a yellowish amorphous solid.

$^1$H NMR (300 MHz, CDCl$_3$): δ 11.18 (1H, s; —OH), 8.73 (1H, j, J=6.85 Hz, NHCH$_2$), 7.71 (1H, dd, J=8.68, 5.02 Hz, Ar—CH), 7.57 (1H, dd, J=8.22, 2.74 Hz), 7.28 (2H, m, Ar—CH),), 6.92 (1H, s), 4.81 (4H, m), 4.48 (1H, m), 4.26 (2H, s), 3.78 (1H, m), 2.87 (6H, s), 2.68 (1H, dd, J=13.70, 11.88 Hz), 2.13 (3H, s), 2.10 (1H, t, J=12.33 Hz), 1.88 (1H, m), 1.59, (7H, br), 0.92 (6H, m).

Example 193

1-[2-(3,5-Dimethyl-piperidin-1-yl)-2-oxo-ethyl]-6-hydroxy-3-methanesulfonylmethyl-5-oxo-1,5-dihydro-imidazo[1,2-a]pyrimidine-7-carboxylic acid 3,4-dichloro-benzylamide

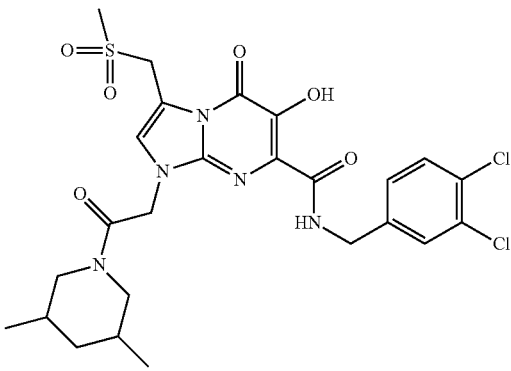 [SMILES: CC1CC(C)CN(C(=O)Cn2cc(CS(C)(=O)=O)n3c(=O)c(O)c(C(=O)NCc4ccc(Cl)c(Cl)c4)nc23)C1]

Step 1

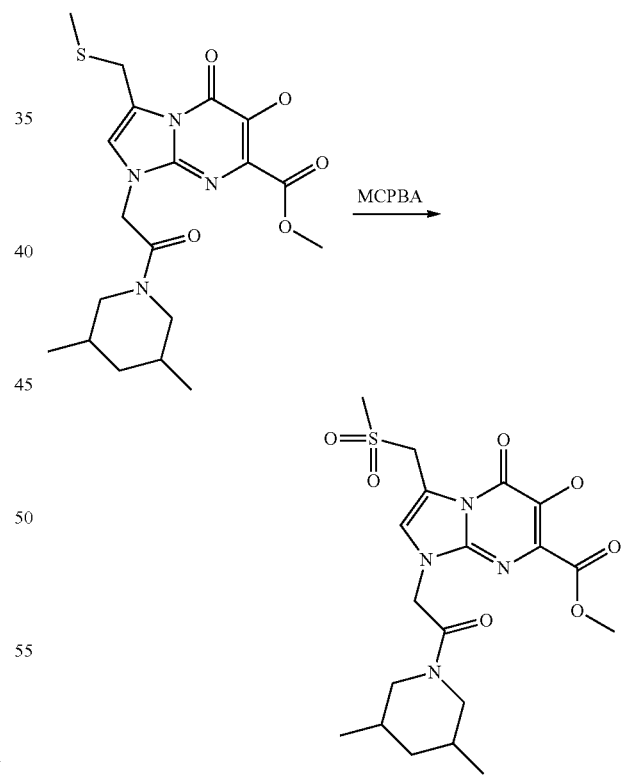

1-[2-(3,5-dimethyl-piperidin-1-yl)-2-oxo-ethyl]-6-hydroxy-3-methylsulfanylmethyl-5-oxo-1,5-dihydro-imidazo[1,2-a]pyrimidine-7-carboxylic acid methyl ester from example 54 (0.35 g, 0.83 mmol) was dissolved in dichloromethane (10 ml) and cooled to 0° C. M-Chloroperoxybenzoic acid (0.286 g, 2 equivalents) were added. The reaction mixture was stirred for 2 hours, then more MCPBA (150 mg) was added, and the stirring was continued for one hour. The reaction was quenched with a solution of Na$_2$S$_2$O$_3$, the aqueous phase was extracted with dichloromethane, dried over MgSO$_4$ and evaporated to dryness to give the product as mixture with m-chlorobenzoic acid (0.7 g, treated as 100% yield, contains ~50% m-Cl-benzoic acid by NMR).

$^1$H NMR (300 MHz, CDCl$_3$): δ 10 (1H, br; —OH), 7.31 (1H, s), 5.12 (1H, d, J=15.07 Hz), 5.10 (1H, d, H=15.07 Hz), 4.93 (2H, s), 4.52 (2H, s), 4.01 (3H, s), 3.78 (2H, m), 3.01 (3H, s), 2.67 (1H, dd, J=13.7, 11.42 Hz), 2.15 (3H, s), 2.10 (1H, dd, J=12.33, 11.88 Hz), 1.92 (1H, m), 1.7 (2H, m), 0.98 (3H, d, J=6.39 Hz), 0.91 (3H, d, J=6.85 Hz).

Step 2

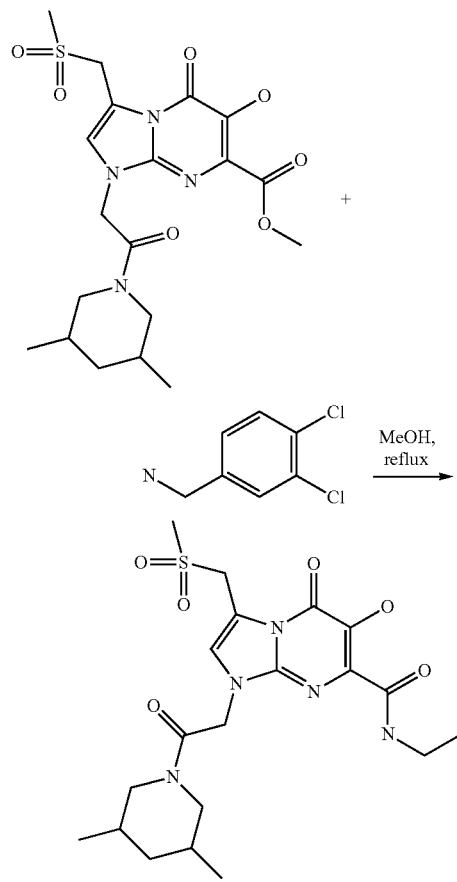

Following the same procedure for Example 187 but using the methyl ester from step 2 and 3,4-dichlorobenzylamine, the title product was obtained in 41.5% yield as a yellowish amorphous solid.

$^1$H NMR (300 MHz, CDCl$_3$): δ 11.45 (1H, br; —OH), 7.87 (1H, br), 7.44 (2H, m), 7.19 (2H, m, Ar—CH),), 5.16 (1H, d, J=15.07 Hz), 5.09 (1H, d, J=15.07), 4.81 (2H, m), 4.60 (2H, m), 4.44 (2H, s), 3.64 (1H, m), 3.01 (3H, s), 2.6 (1H, t, J=12.33 Hz), 2.0 (6H, m, br), 1.52 (2H, m), 0.92 (6H, m).

Example 194

1-[2-(3,5-Dimethyl-piperidin-1-yl)-2-oxo-ethyl]-6-hydroxy-3-methanesulfonylmethyl-5-oxo-1,5-dihydro-imidazo[1,2-a]pyrimidine-7-carboxylic acid 2-dimethylsulfamoyl-4-fluoro-benzylamide

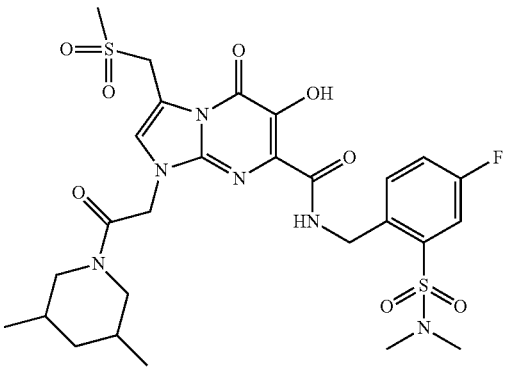 [SMILES: CC1CC(C)CN(C(=O)Cn2cc(CS(C)(=O)=O)n3c(=O)c(O)c(C(=O)NCc4ccc(F)cc4S(=O)(=O)N(C)C)nc23)C1]

Following the same procedure for Example 187 but using the methyl ester from Example 55 and 2-aminomethyl-5-fluoro-N,N-dimethyl-benzenesulfonamide, the title product was obtained in 42.5% yield as a colorless amorphous solid.

$^1$H NMR (300 MHz, CDCl$_3$): δ 11.38 (1H, br; —OH), 8.76 (1H, t, J=6.39 Hz), 7.70 (1H, dd, J=8.68, 5.02 Hz), 7.59 (1H, m, Ar—CH), 7.3 (1H, m), 7.24 (1H, s), 5.09 (1H, d, J=15.07 Hz), 5.08 (1H, d, J=15.07 Hz), 4.90 (1H, d, J=16.45 Hz), 4.87 (1H, d, J=16.45 Hz), 4.79 (2H, m), 4.45 (1H, m), 3.7 (1H, m), 2.97 (3H, s), 2.87 (6H, s), 2.72 (1H, dd, J=12.79, 12.33 Hz), 2.13 (1H, t, J=12.33 Hz), 1.9 (7H, m, br), 1.6 (1H, m, br), 0.99 (3H, d, J=6.396 Hz), 0.91 (3H, d, J=6.396 Hz).

Example 195

1-[2-((2S,6S)-2,6-Dimethyl-morpholin-4-yl)-2-oxo-ethyl]-7-[5-(4-fluoro-benzyl)-thiazol-2-yl]-6-hydroxy-1HS-imidazo[1,2-a]pyrimidin-5-one

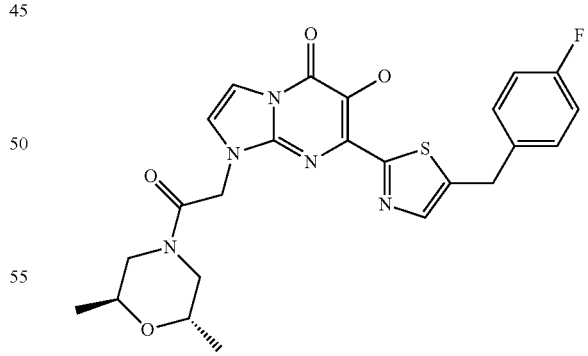

Adapted the procedures of examples 39-41 using the product of example 36 and 72.

$^1$H NMR (300 MHz, DMSO-d$_6$): δ: 10.81 (1H, m), 7.91 (1H, s), 7.62 (1H, d, J=3 Hz), 7.5 (1H, d, 2.7 Hz), 7.37 (2H, m), 7.16 (2H, m), 5.13 (1H, d, J=16.5 Hz), 4.92 (1H, d, J=17.1 Hz), 4.288 (2H, s), 4.13 (1H, m), 3.94 (1H, m), 3.43 (1H, m), 3.27 (1H, m), 2.8 (1H, m), 2.28 (1H, m), 1.10 (6H, m).

MS (ESI$^-$) m/z 498 [M+H]$^+$

3. BIOLOGICAL EXAMPLES

Example 3.1

Activity of Selected Examples Against Wild Type and Mutant Integrases and HIV Strains PhenoScreen Assay Monogram Bioscience' PhenoScreen assay allows the evaluation of integrase inhibitors for activity against a variety of HIV variants. The assay uses virus generated from 2 DNA constructs; one containing the HIV LTR, gag and pol regions, as well as a luciferase reporter gene in place of the viral envelope genes, and a second DNA construct containing the amphotrophic murine leukemia virus (A-MLV) envelope gene required to pseudotype virions and render them capable of entry into a target cell. Viruses generated using these constructs by transfection into a producer cell line such as 293T are capable of one-round of infection only. Successful integration events are directly proportional to the levels of luciferase expression 48-72 h after infection.

The viral variants chosen by Avexa Ltd. to screen their in-house integration inhibitors against consist of mutations within the viral integrase enzyme known to confer resistance to a number of known integration inhibitors published in the literature. In particular, the viral variants containing the Q148H/G140S double mutation in integrase, and the N155H/E92Q double mutation in integrase, represent two of the more common viruses identified to arise in patients that are failing treatment with Isentress (Raltegravir, MK-0518).

Mutant Enzymes:

HIV integrase was mutated within a shuttle vector (pG-EMNLHE) containing the majority of the HIV-1 gag and pol sequence using site directed mutagenesis to generate integrase sequences that have been published as conferring resistance to published integrase inhibitors. These include, but are not limited to, mutations such as Q148K, Q148H/G140S and N155H/E92Q. The integrase coding region was then subject to PCR and cloned into a bacterial expression vector. The specific introduction of desired mutation(s) was confirmed by sequence analysis. Proteins were expressed, purified and used in strand transfer assays.

Strand Transfer Assay (Enzyme Assay):

A strand transfer assay procedure similar to that published (Ovenden et al. Phytochemistry. 2004 December; 65(24): 3255-9.) is used. Briefly, 400 ng of the enzyme, wild type or drug resistant mutant, is mixed with the compound to be tested and incubated with 30 nM substrate DNA. The substrate DNA is designed to mimic HIV DNA termini that has undergone 3' end processing, and consists of the annealed U5 LTR sequence oligonucleotides tagged with Digoxigenin (DIG; 5'-ACTGCTAGAGATTTTCCACACTGAC-TAAAAGGGTC-DIG-3') or biotin (5'-Bio-GACCCTTT-TAGTCAGTGTGGAAAATCTCTAGCA-3') so that each substrate has either a DIG or Bio tag on opposite strands. Reactions are carried out for 1 hr at 37° C. Products generated as a result of strand transfer activity are bound to streptavidin plates and detected using anti-DIG-alkaline phosphatase conjugate and p-nitro phenyl phosphate substrate.

Both the Phenosense assay and the Enzyme assay give substantially the same activity values for any particular compound and enzyme pair. The activity of one compound in one assay can therefore be directly compared to the activity of a second compound in the other assay.

TABLE 1

Activity of selected examples against wild type and mutant integrases and HIV-s

| | Phenosense assay | | | | | | Enzyme | | |
|---|---|---|---|---|---|---|---|---|---|
| Compound | WT | Y143R | E92Q N155H | G140S Q148H | T125K F121Y | T661 S153Y | WT | E92Q/ N155H | G140S/ Q148H |
| 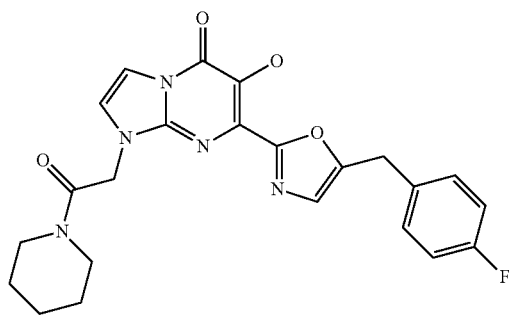 | ++++ | +++ | +++ | ++ | +++ | ++++ | ++++ | | |

Example 7

TABLE 1-continued

Activity of selected examples against wild type and mutant integrases and HIV-s

| Compound | WT | Y143R | Phenosense assay E92Q N155H | G140S Q148H | T125K F121Y | T661 S153Y | WT | Enzyme E92Q/ N155H | G140S/ Q148H |
|---|---|---|---|---|---|---|---|---|---|
| example 21 | | | | | | | ++++ | +++ | ++++ |
| example 12 | | | | | | | ++++ | +++ | +++ |
| example 15 | | | | | | | ++++ | +++ | +++ |
| example 18 | | | | | | | ++++ | +++ | +++ |

TABLE 1-continued

Activity of selected examples against wild type and mutant integrases and HIV-s

| Compound | Phenosense assay | | | | | | Enzyme | | |
|---|---|---|---|---|---|---|---|---|---|
| | WT | Y143R | E92Q N155H | G140S Q148H | T125K F121Y | T661 S153Y | WT | E92Q/ N155H | G140S/ Q148H |
| 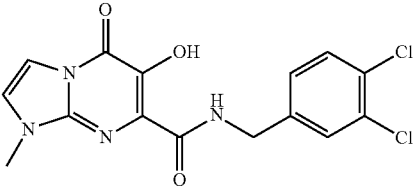 Comparative example 1[a] | ++++ | ++++ | + | + | ++ | +++ | +++ | NA | NA |
| 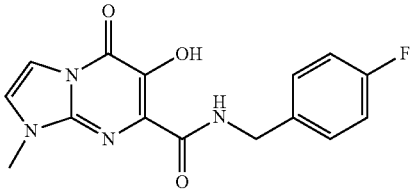 Comparative example 2[b] | +++ | +++ | + | + | + | ++ | +++ | NA | NA |

++++ indicates value between 0.001 μM and 0.1 μM
+++ indicates value between 1 μM and 0.1 μM
++ indicates value between 1 μM and 10 μM
+ indicates value greater than 10 μM
[a]Example 18.3 in International Patent Application No. PCT/AU2007/001980.
[b]Example 18.2 in International Patent Application No. PCT/AU2007/001980.

On the basis of the results set out in Table 1 above, the compounds of the present invention have superior activity profiles against mutant HIV integrases than their closest analogues in International Patent Application No. PCT/AU2007/001980 in the name of Avexa.Ltd which are not of the present invention.

Example 3.2

Reporter Viruses

Infectivity assays using reporter viruses derived from lentiviral vectors capable of a single round of infection were used to determine the activity ($EC_{50}$) of compounds. The DNA used to generate viruses for infection was the full-length HIV-1 genome which had been envelope-deleted. In addition, a reporter gene (the firefly luciferase gene from *Photinus pyralis*) was cloned into the nef region of the HIV backbone for ease of assay readout. Viruses were generated via liposomal transfection of the lentiviral-derived DNA backbone together with a vesicular stomatitis virus glycoprotein (VSV-G) expression plasmid into 293T cells. Culture supernatants containing VSV-G pseudotyped virions were harvested 64 h post transfection, clarified by centrifugation to remove cell debris, and frozen at −70° C. until use.

Mutant Integrase Viruses:

HIV integrase was mutated within a shuttle vector (pGEM) containing the majority of the HIV-1 gag and pol sequence using site-directed mutagenesis to generate sequences that are known to confer resistance to published integrase inhibitors. These include but are not limited to mutations such as Q148H/G140S (in table # QHGS). The mutated integrase coding region within the shuttle vector was sequence verified, and then exchanged for the wild-type (WT) coding sequence in the reporter virus DNA backbone.

Assay Method:

293T cells were plated out at 12000 cells per well in Cell-View 96-well cell culture plates (Invitrogen) 16 h prior to compound addition. Compounds were preincubated with cells for 4 h at 37° C. prior to the addition of virus sufficient to generate approximately 10000 Luciferase light units (as measured by the Victor Wallace luminometer) upon assaying using the Bright-Glo™ reagent (Promega) according to the manufacturer's instructions at 48 h post infection.

Example 3.2

Reporter Viruses

Infectivity assays using reporter viruses derived from lentiviral vectors capable of a single round of infection were used to determine the activity ($EC_{50}$) of compounds. The DNA used to generate viruses for infection was the full-length HIV-1 genome which had been envelope-deleted. In addition, a reporter gene (the firefly luciferase gene from *Photinus pyralis*) was cloned into the nef region of the HIV backbone for ease of assay readout. Viruses were generated via liposomal transfection of the lentiviral-derived DNA backbone together with a vesicular stomatitis virus glycoprotein (VSV-G) expression plasmid into 293T cells. Culture supernatants containing VSV-G pseudotyped virions were harvested 64 h post transfection, clarified by centrifugation to remove cell debris, and frozen at −70° C. until use.

Mutant Integrase Viruses:

HIV integrase was mutated within a shuttle vector (pGEM) containing the majority of the HIV-1 gag and pol sequence using site-directed mutagenesis to generate sequences that are known to confer resistance to published integrase inhibitors. These include but are not limited to mutations such as Q148H/G140S (in tables 2 and 3 # QHGS), N155H/E92Q (in table 2 # NHEQ), F121Y/T124K (in table 2 FYTK), Y143R (in table 2 # Y143R) and the triple mutant Q148K/G140A/E138A. (in table 2 # QKGAEA). The mutated integrase coding region within the shuttle vector was sequence verified, and then exchanged for the wild-type (WT) coding sequence in the reporter virus DNA backbone.

Assay Method:

293T cells were plated out at 12000 cells per well in CellView 96-well cell culture plates (Invitrogen) 16 h prior to compound addition. Compounds were preincubated with cells for 4 h at 37° C. prior to the addition of virus sufficient to generate approximately 10000 Luciferase light units (as measured by the Victor Wallace luminometer) upon assaying using the Bright-Glo™ reagent (Promega) according to the manufacturer's instructions at 48 h post infection.

TABLE 2

Assay results for Example 3.2

| Compound | Luciferase assay results | | | | | |
|---|---|---|---|---|---|---|
| | WT | QHGS | NHEQ | FYTK | Y143R | QKGAEA |
| Example 41 | +++ | ++ | ND | ND | ND | ND |
| Example 46 | +++ | + | ND | ND | ND | ND |
| Example 63 | ++ | ++ | ++ | ND | ND | ND |

TABLE 2-continued

Assay results for Example 3.2

| Compound | Luciferase assay results | | | | | |
|---|---|---|---|---|---|---|
| | WT | QHGS | NHEQ | FYTK | Y143R | QKGAEA |
| 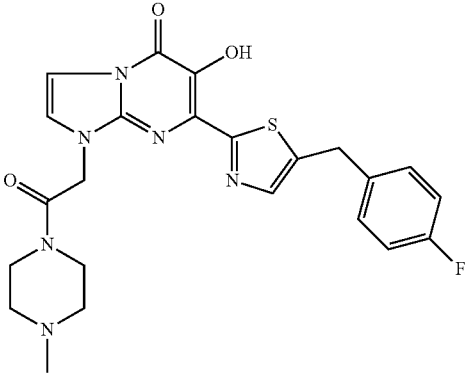 Example 142 | ++ | + | ++ | ND | ND | ND |
| 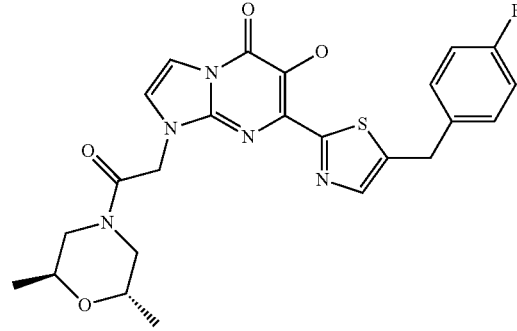 [SMILES: C[C@H]1CN(C(=O)Cn2ccn3c(=O)c(O)c(-c4ncc(Cc5ccc(F)cc5)s4)nc23)C[C@H](C)O1] Example 195 | +++ | ++ | ++ | ND | ND | ND |

The compounds of the present invention show activity against the triple mutant QKGAEA which is resistant to many published integrase inhibitors.

$EC_{50}$ 1 nM–100 nM=+++

$EC_{50}$ 100 nM to 1 uM=++

$EC_{50}$>1 uM=+

ND: Not determined

TABLE 3

Assay results for Example 3.2 against the QHGS mutant

| Example | Molecular structure | $EC_{50}$ |
|---|---|---|
| Example 58 | 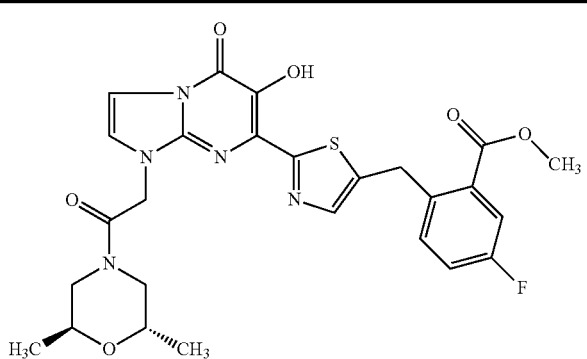 | ++ |

TABLE 3-continued
Assay results for Example 3.2 against the QHGS mutant
| Example | Molecular structure | EC$_{50}$ |
|---|---|---|
| Example 182 | 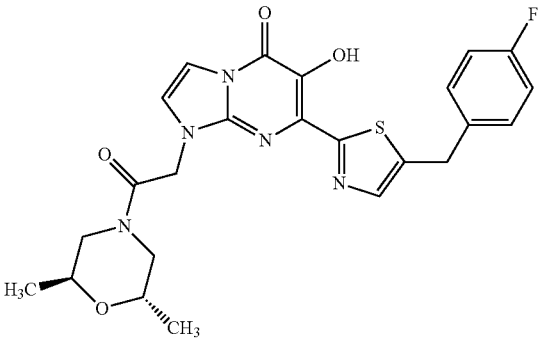 [SMILES: C[C@H]1CN(C(=O)Cn2ccn3c(=O)c(O)c(-c4ncc(Cc5ccc(F)cc5)s4)nc23)C[C@H](C)O1] | +++ |
| Example 75 | 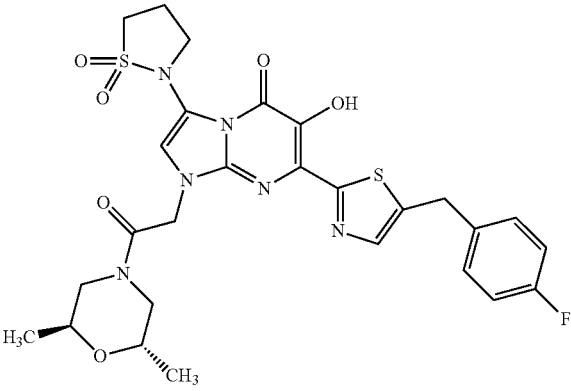 [SMILES: C[C@H]1CN(C(=O)Cn2cc(N3CCCS3(=O)=O)n3c(=O)c(O)c(-c4ncc(Cc5ccc(F)cc5)s4)nc23)C[C@H](C)O1] | ++ |
| Example 104 | 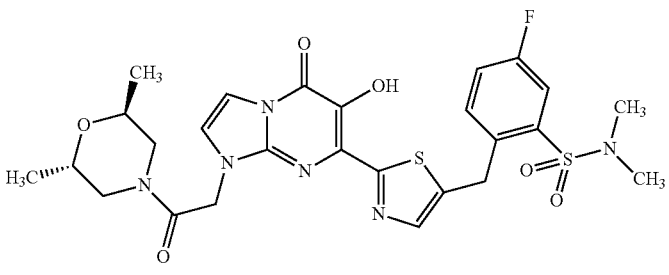 | +++ |
| Example 126 | 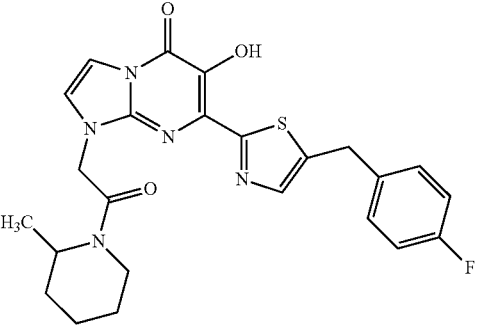 [SMILES: CC1CCCCN1C(=O)Cn1ccn2c(=O)c(O)c(-c3ncc(Cc4ccc(F)cc4)s3)nc12] | ++ |

TABLE 3-continued

Assay results for Example 3.2 against the QHGS mutant

| Example | Molecular structure | EC$_{50}$ |
|---|---|---|
| Example 138 | 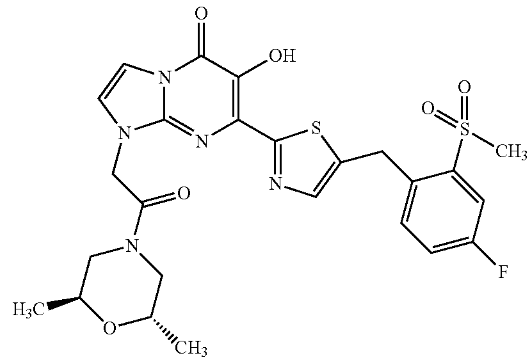 [SMILES: C[C@H]1CN(C(=O)Cn2ccn3c(=O)c(O)c(-c4ncc(Cc5ccc(F)cc5S(C)(=O)=O)s4)nc23)C[C@H](C)O1] | ++ |
| Example 157 | 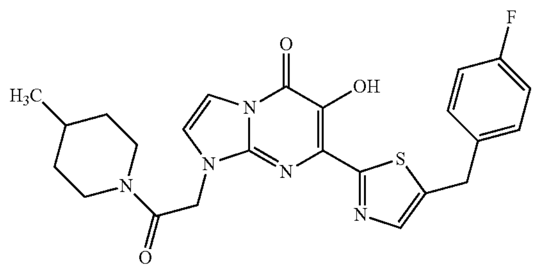 [SMILES: CC1CCN(C(=O)Cn2ccn3c(=O)c(O)c(-c4ncc(Cc5ccc(F)cc5)s4)nc23)CC1] | ++ |
| Example 168 | 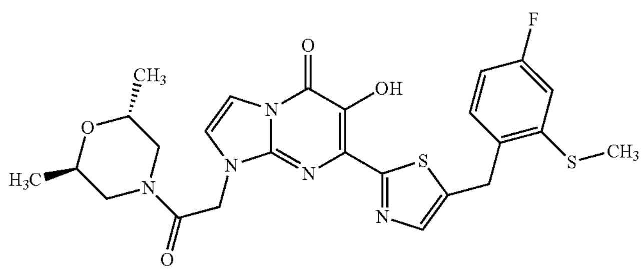 | ++ |
| Example 180 | 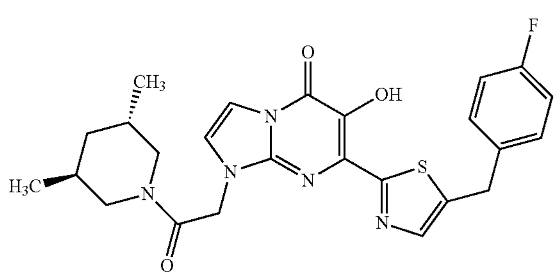 [SMILES: C[C@H]1C[C@H](C)CN(C(=O)Cn2ccn3c(=O)c(O)c(-c4ncc(Cc5ccc(F)cc5)s4)nc23)C1] | ++ |
| Example 183 | 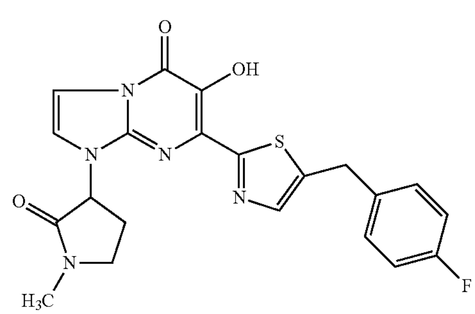 [SMILES: CN1CCC(n2ccn3c(=O)c(O)c(-c4ncc(Cc5ccc(F)cc5)s4)nc23)C1=O] | ++ |

TABLE 3-continued

Assay results for Example 3.2 against the QHGS mutant

| Example | Molecular structure | EC$_{50}$ |
|---|---|---|
| Example 184 | 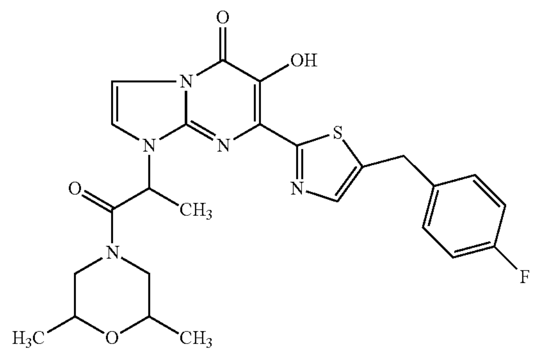 [SMILES: CC1CN(C(=O)C(C)n2ccn3c(=O)c(O)c(-c4ncc(Cc5ccc(F)cc5)s4)nc23)CC(C)O1] | + |
| Example 185 | 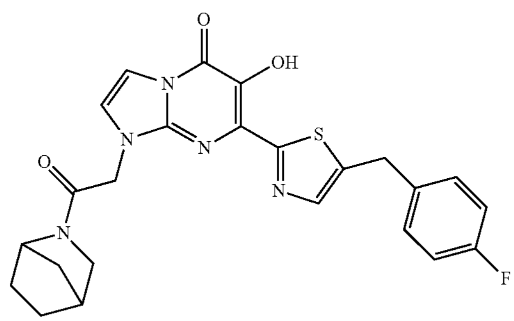 [SMILES: O=C(Cn1ccn2c(=O)c(O)c(-c3ncc(Cc4ccc(F)cc4)s3)nc12)N1CC2CCC1C2] | + |
| Example 181 | 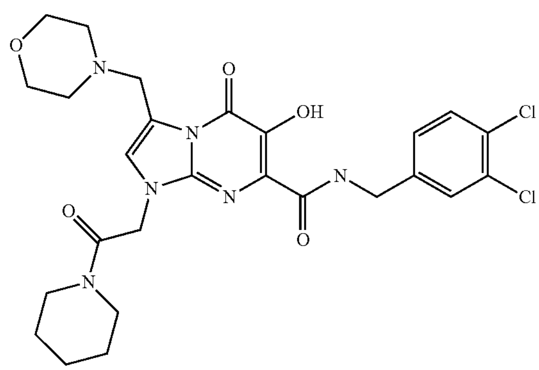 [SMILES: O=C(NCc1ccc(Cl)c(Cl)c1)c1nc2n(CC(=O)N3CCCCC3)cc(CN3CCOCC3)n2c(=O)c1O] | ++ |
| Example 187 | 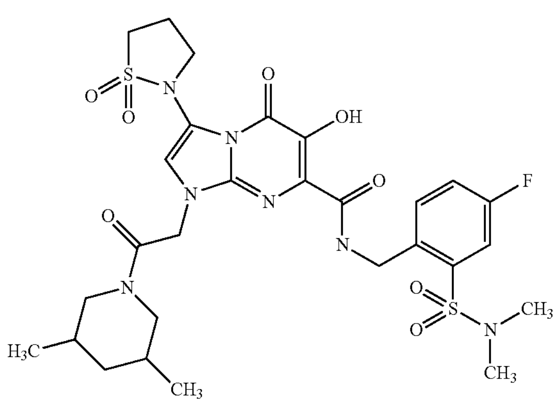 | +++ |

TABLE 3-continued

Assay results for Example 3.2 against the QHGS mutant

| Example | Molecular structure | EC$_{50}$ |
|---|---|---|
| Example 186 | 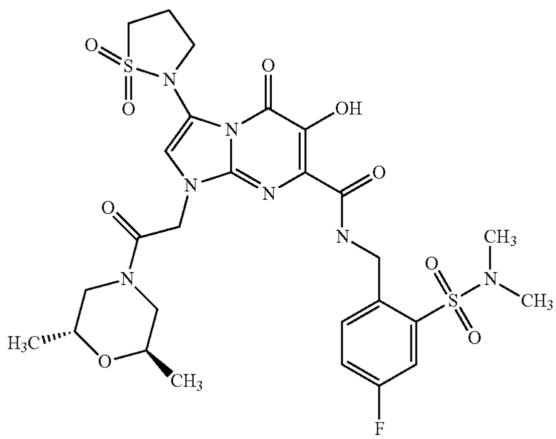 | +++ |
| Example 188 | 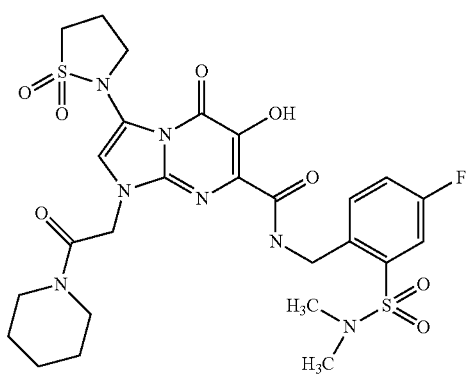 [SMILES: CN(C)S(=O)(=O)c1cc(F)ccc1CNC(=O)c1nc2n(CC(=O)N3CCCCC3)cc(N3CCCS3(=O)=O)n2c(=O)c1O] | +++ |
| Example 189 | 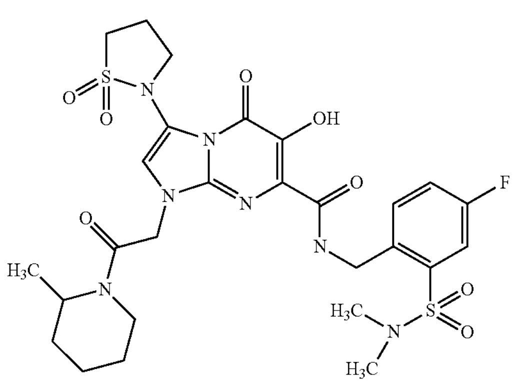 [SMILES: CC1CCCCN1C(=O)Cn1cc(N2CCCS2(=O)=O)n2c(=O)c(O)c(C(=O)NCc3ccc(F)cc3S(=O)(=O)N(C)C)nc12] | ++ |

TABLE 3-continued
Assay results for Example 3.2 against the QHGS mutant
| Example | Molecular structure | $EC_{50}$ |
|---|---|---|
| Example 190 | 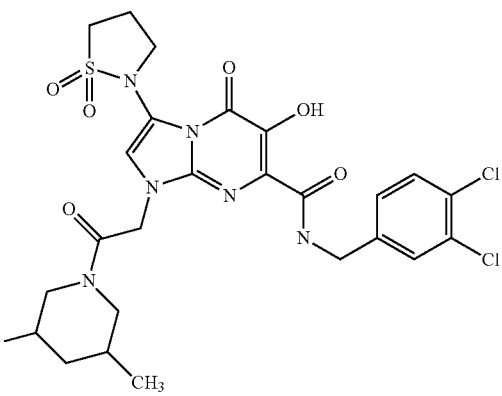 | ++ |
| Example 191 | 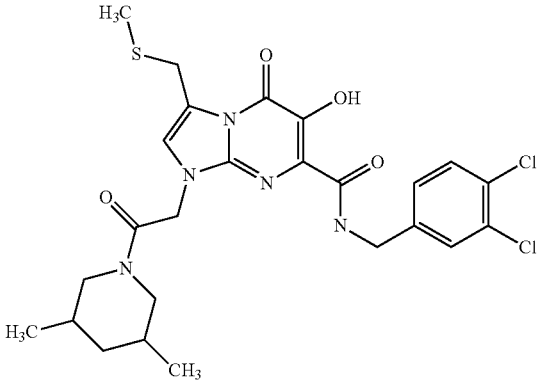 [SMILES: CSCc1cn(CC(=O)N2CC(C)CC(C)C2)c2nc(C(=O)NCc3ccc(Cl)c(Cl)c3)c(O)c(=O)n12] | + |
| Example 192 | 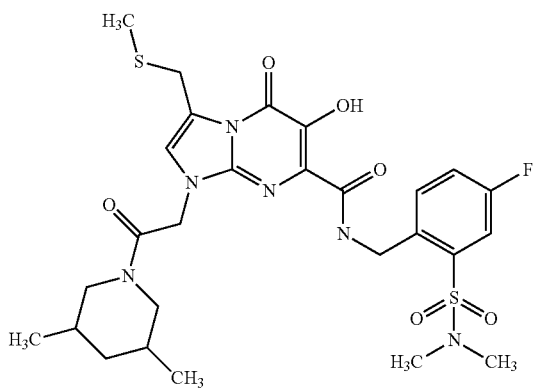 [SMILES: CSCc1cn(CC(=O)N2CC(C)CC(C)C2)c2nc(C(=O)NCc3ccc(F)cc3S(=O)(=O)N(C)C)c(O)c(=O)n12] | +++ |
| Example 193 | 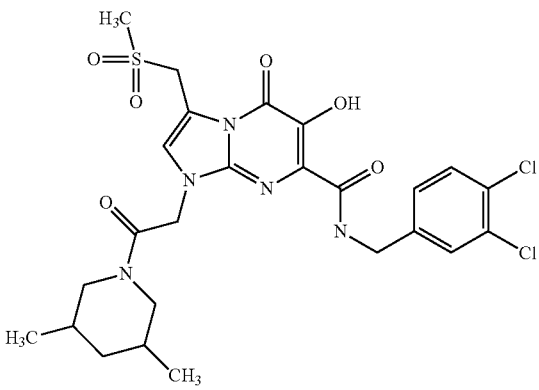 [SMILES: CC1CC(C)CN(C(=O)Cn2cc(CS(C)(=O)=O)n3c(=O)c(O)c(C(=O)NCc4ccc(Cl)c(Cl)c4)nc23)C1] | +++ |

TABLE 3-continued

Assay results for Example 3.2 against the QHGS mutant

| Example | Molecular structure | $EC_{50}$ |
|---|---|---|
| Example 194 | 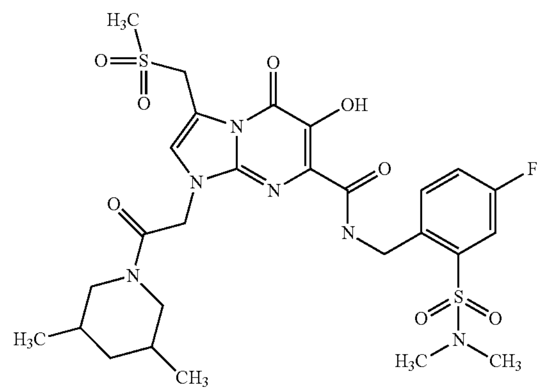 [SMILES: CC1CC(C)CN(C(=O)Cn2cc(CS(C)(=O)=O)n3c(=O)c(O)c(C(=O)NCc4ccc(F)cc4S(=O)(=O)N(C)C)nc23)C1] | +++ |

$EC_{50} < 500$ nM = +++
$EC_{50}$ 500-1000 nM = ++
$EC_{50}$ 1,000-10,000 nM = +

The compounds of the present invention show activity against the mutant QHGS which is resistant to many published integrase inhibitors.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of Formula I or a pharmaceutically acceptable salt thereof wherein:

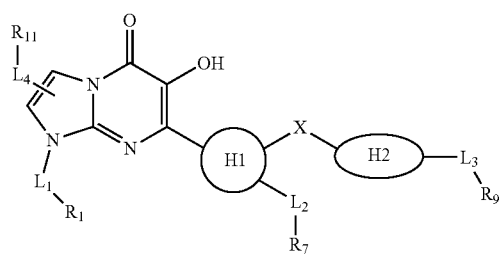

I $L_1$-$R_1$ is hydrogen or is a substituent wherein
$L_1$ is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
each $R_1$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, alkylheteroaryl, a 4-7 membered lactam, $S(O)NR_3R_4$, $SO_2NR_3R_4$, $SO_2C_{1-10}$alkyl, $C_{5-10}$cycloalkyl wherein one or more of the carbon atoms of the cycloalkyl ring are replaced with one or more oxygen atoms;
$R_3$ and $R_4$ are each independently selected from the group consisting of hydrogen, $C_{3-6}$cycloalkyl, $C_{1-10}NR_5R_6$, —(CO)(CO)$NR_5R_6$; or $R_3$ and $R_4$ taken together with the attached nitrogen form a 5-7 membered heterocyclic ring which contains zero to two additional heteroatoms selected from N, O or S where S can be at the S, S(O) or $S(O)_2$ oxidation state and wherein said heterocyclic ring is optionally substituted at the carbon or nitrogen atoms with one or more substituents selected from halo, $C_{1-4}$-alkyl, $CO_2C_{1-4}$alkyl, $NR_5R_6$; $C_{1-4}$-alkyl$NR_5R_6$ and further wherein two carbons of said 5-7 membered heterocyclic ring may optionally be bridged by a $C_{1-3}$ alkylene bridging group;
$R_5$ and $R_6$ are each independently selected from the group consisting of H and $C_{1-4}$-alkyl or $R_5$ and $R_6$ together with the attached nitrogen form a 5-7 membered heterocyclic ring which contains zero to two additional heteroatoms selected from N, O or S where S can be at the S, S(O) or $S(O)_2$ oxidation state and wherein said heterocyclic ring is optionally substituted at the carbon or nitrogen atoms with one or more substituents selected from halo and $C_{1-4}$-alkyl and further wherein two carbons of said 5-7 membered heterocyclic ring may optionally be bridged by a $C_{1-3}$ alkylene bridging group;

$L_4$-$R_{11}$ is 0-2 substituents wherein:
  each $L_4$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
each $R_{11}$ is independently selected from the group consisting of hydrogen, $C_{1-10}$alkyl wherein one or more of the carbon atoms of the alkyl chain may optionally be replaced with oxygen atoms, $C_{1-10}$alkyl where one of the carbon atoms is replaced by S in the S, S(O), or S(O)$_2$ oxidation state, $C_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;
  when $R_{11}$ is alkylaryl, the aryl group of said alkylaryl substituent is optionally substituted with a substituent selected from $C_{1-10}$alkyl, —O—$C_{1-10}$alkyl, $C_{1-10}$alkylNR$_3$R$_4$, —O—$C_{1-10}$alkylNR$_3$R$_4$, halo, NR$_3$R$_4$, alkylaryl, —O-alkylaryl, SO$_2$NR$_3$R$_4$
  $H_1$ is a 5-membered aromatic ring containing between 1 and 3 heteroatoms wherein each heteroatom is independently selected from the group consisting of N, O and S;
$L_2$-$R_7$ is 0-2 substituents wherein:
  each $L_2$ is independently absent or is group consisting of Z, $C_{1-3}$alkylene, >C=Z, —$CZ_2$-, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
each $R_7$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;
  X is CR$_8$R$_{8'}$,
  each of R$_8$ and R$_{8'}$ is independently selected from the group consisting of H and CH$_3$, preferably H;
  $H_2$ is a 5- or 6-membered saturated, partially saturated or aromatic ring containing between 0 and 4 heteroatoms independently selected from the group consisting of N, O and S;
  $L_3$-$R_9$ is 0-3 substituents wherein:
    each $L_3$ is independently absent or is selected from the group consisting of Z, $C_{1-3}$alkylene, >C=Z, —$CZ_2$—, —C(=Z)$C_{1-3}$alkylene, —$CZ_2$—$C_{1-3}$alkylene, —$C_{1-3}$alkylene-C(=Z)—, —$C_{1-3}$alkylene-$CZ_2$— wherein each Z is independently selected from O, S, and NH;
    each $R_9$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, heterocyclyl, heteroaryl, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms.

2. A compound according to claim 1 wherein $L_1$ is CH$_2$(C=O)— and $R_1$ is selected from the group consisting of N-piperidine, N-piperazine, N, N'-methyl-piperazine, and morpholino wherein each $R_1$ is optionally substituted at the carbon or nitrogen atoms with one or two methyl groups.

3. A compound according to claim 1 wherein $H_1$ is a five membered aromatic heterocycle selected from the group consisting of thiazole, oxazole, oxadiazole, thiadiazole, imidazole, triazole, and tetrazole.

4. A compound according to claim 3 wherein $H_1$ is thiazole.

5. A compound according claim 1 wherein $H_2$ is phenyl.

6. A compound according to claim 1 wherein $L_4$-$R_{11}$ is one substituent wherein $L_4$ is absent or is —CH$_2$— and $R_{11}$ is NR$_3$R$_4$.

7. A compound according to claim 1 wherein $L_3$-$R_9$ is at least 2 substituents wherein the first $L_3$-$R_9$ is halo and in the second $L_3$-$R_9$, $L_3$ is absent or is selected from >C=O and $R_9$ is selected from the group consisting of halo, NR$_3$R$_4$ and SO$_2$NR$_3$R$_4$.

8. A compound according to claim 1 wherein $L_3$-$R_9$ is one substituent and is halo.

9. A compound according to claim 1 wherein at least one NR$_3$R$_4$ is independently selected from the group consisting of morpholino, a five-membered cyclic sulphonamide (such as isothiazolidine) and a six membered cyclic sulphonamide.

10. A compound according to claim 1 wherein the group "$C_{1-10}$alkyl where one of the carbon atoms is replaced by S in the S, S(O), or S(O)$_2$ oxidation state" is methylsulfanylmethyl or methylsulfonylmethyl.

11. A compound according to claim 1 wherein the compound is selected from the group consisting of:

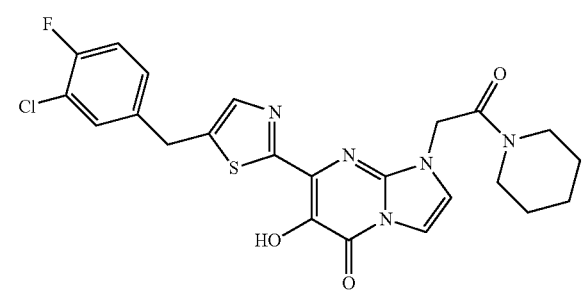

7-[5-(3-Chloro-4-fluoro-benzyl)-thiazol-2-yl]-6-hydroxy-1-(2-oxo-2-piperidin-1-yl-ethyl)-1H-imidazo[1,2-a]pyrimidin-5-one;

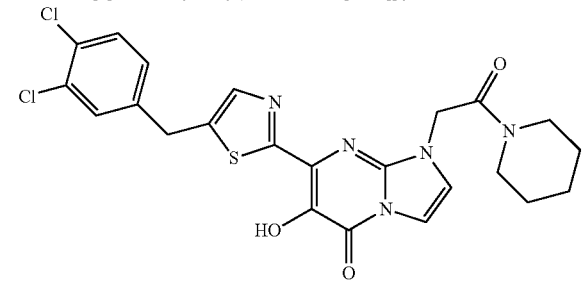

7-[5-(3,4-Dichloro-benzyl)-thiazol-2-yl]-6-hydroxy-1-(2-oxo-2-piperidin-1-yl-ethyl)-1H-imidazo[1,2-a]pyrimidin-5-one;

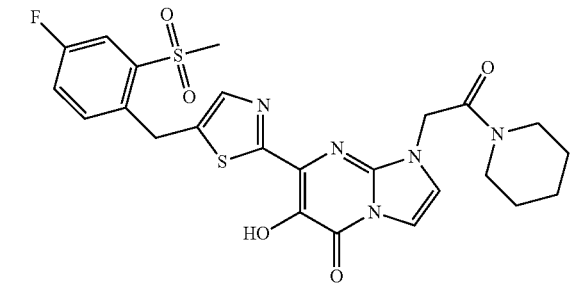

7-[5-(4-Fluoro-2-methanesulfonyl-benzyl)-thiazol-2-yl]-6-hydroxy-1-(2-oxo-2-piperidin-1-yl-ethyl)-1H-imidazo[1,2-a]pyrimidin-5-one;

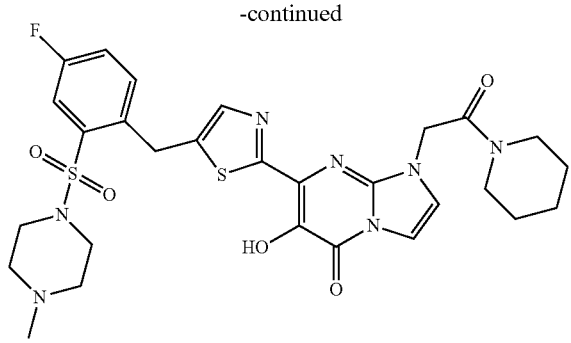

7-{5-[4-Fluoro-2-(4-methyl-piperazine-1-sulfonyl)-benzyl]-
thiazol-2-yl}-6-hydroxy-1-(2-oxo-2-piperidin-1-yl-ethyl)-
1H-imidazo[1,2-a]pyrimidin-5-one;

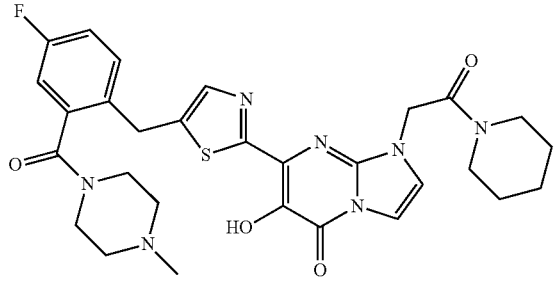

7-{5-[4-Fluoro-2-(4-methyl-piperazine-1-carbonyl)-benzyl]-thiazol-
2-yl}-6-hydroxy-1-(2-oxo-2-piperidin-1-yl-ethyl)-1H-
imidazo[1,2-a]pyrimidin-5-one;

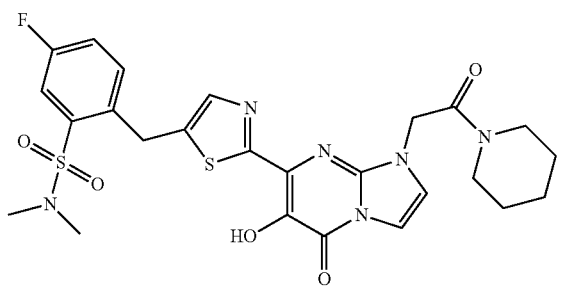

5-Fluoro-2-{2-[6-hydroxy-5-oxo-1-(2-oxo-2-piperidin-1-yl-ethyl)-
1,5-dihydro-imidazo[1,2-a]pyrimidin-7-yl]-thiazol-5-ylmethyl}-
N,N-dimethyl-benzenesulfonamide;

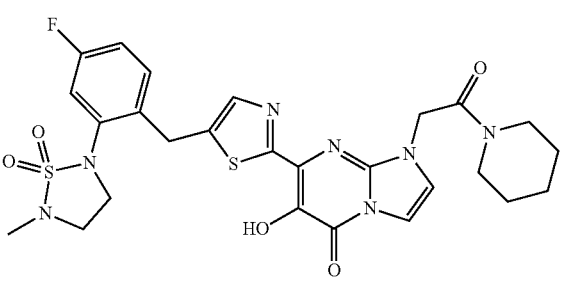

7-{5-[4-Fluoro-2-(5-methyl-1,1-dioxo-[1,2,5]-
thiadiazolidin-2-yl)-benzyl]-thiazol-2-yl}-6-hydroxy-1-(2-oxo-
2-piperidin-1-yl-ethyl)-1H-imidazo[1,2-a]pyrimidin-5-one;

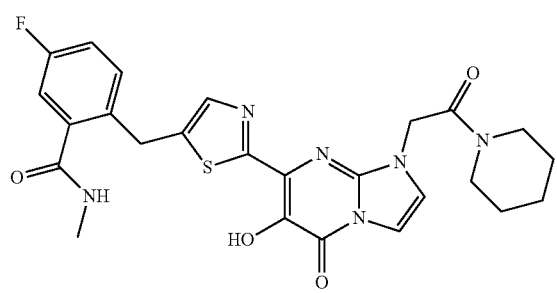

5-Fluoro-2-{2-[6-hydroxy-5-oxo-1-(2-oxo-2-piperidin-1-yl-ethyl)-
1,5-dihydro-imidazo[1,2-a]pyrimidin-7-yl]-thiazol-5-ylmethyl}-
N-methyl-benzamide;

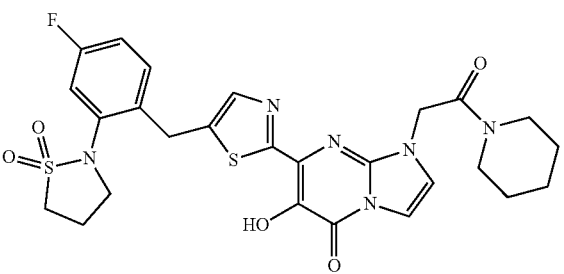

7-{5-[2-(1,1-Dioxo-isothiadiazolidin-2-yl)-4-fluoro-
benzyl]-thiazol-2-yl}-6-hydroxy-1-(2-oxo-2-piperidin-1-yl-
ethyl)-1H-imidazo[1,2-a]pyrimidin-5-one;

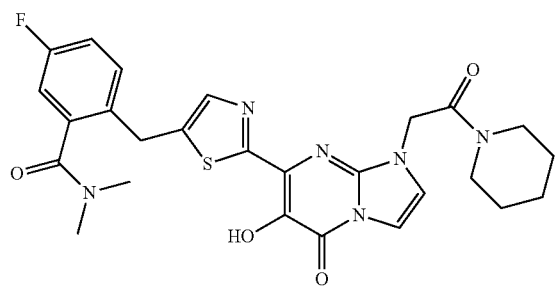

5-Fluoro-2-{2-[6-hydroxy-5-oxo-1-(2-oxo-2-piperidin-1-yl-ethyl)-
1,5-dihydro-imidazo[1,2-a]pyrimidin-7-yl]-thiazol-5-ylmethyl}-
N,N-dimethyl-benzamide;

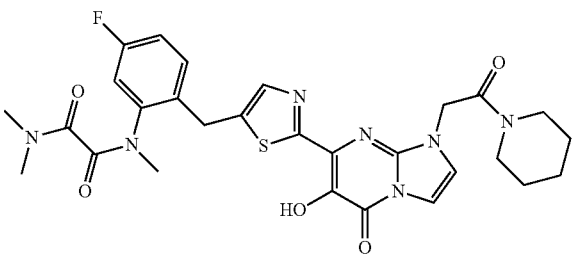

N-(5-Fluoro-2-{2-[6-hydroxy-5-oxo-1-(2-oxo-2-piperidin-1-yl-
ethyl)-1,5-dihydro-imidazo[1,2-a]pyrimidin-7-yl]-thiazol-5-
ylmethyl}-phenyl)-N,N',N'-trimethyl-oxalamide;

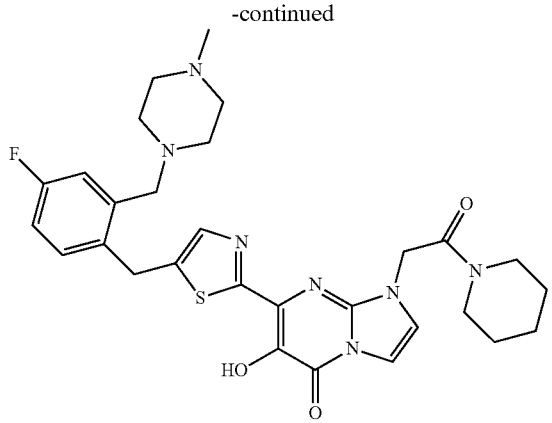

7-{5-[4-Fluoro-2-(4-methyl-piperazin-1-ylmethyl)-benzyl]-thiazol-2-yl}-6-hydroxy-1-(2-oxo-2-piperidin-1-yl-ethyl)-1H-imidazo[1,2-a]pyrimidin-5-one;

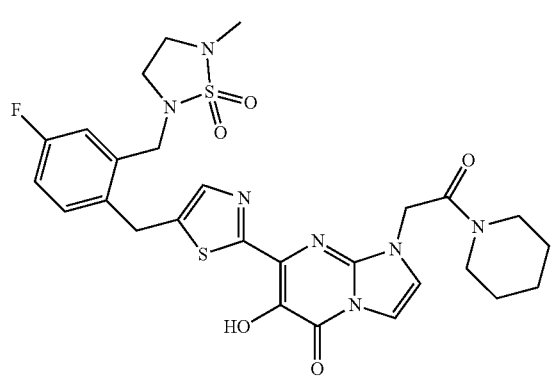

7-(5-(4-fluoro-2-((5-methyl-1,1-dioxido-1,2,5-thiadiazolidin-2-yl)methyl)-benzyl)thiazol-2-yl)-6-hydroxy-1-(2-oxo-2-piperidin-1-yl)ethyl)imidazo[1,2-a]pyrimidin-5(1H)-one;

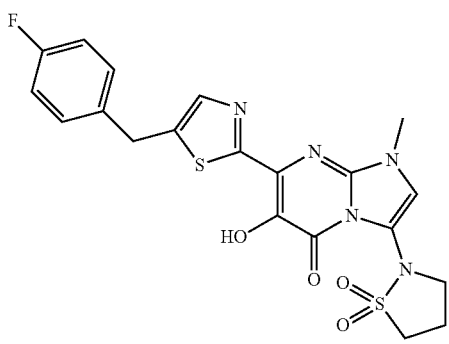

3-(1,1-Dioxo-isothiazolidin-2-yl)-7-[5-(4-fluoro-benzyl)-thiazol-2-yl]-6-hydroxy-1-methyl-1H-imidazo-[1,2-a]pyrimidin-5-one;

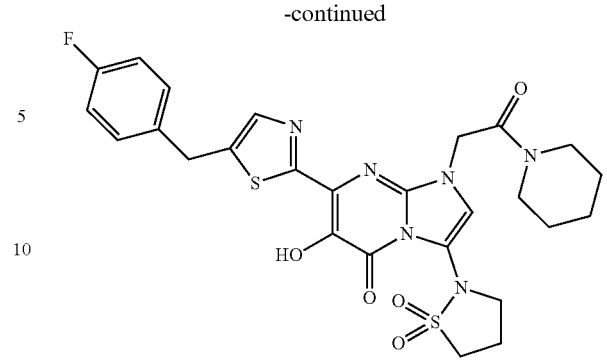

3-(1,1-Dioxo-isothiazolidin-2-yl)-7-[5-(4-fluoro-benzyl)-thiazol-2-yl]-6-hydroxy-1-(2-oxo-2-piperidin-1-yl-ethyl)-1H-imidazo[1,2-a]pyrimidin-5-one;

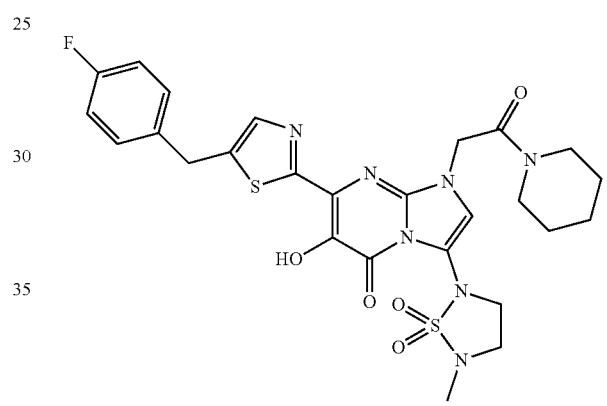

7-[5-(4-Fluoro-benzyl)-thiazol-2-yl]-6-hydroxy-3-(5-methyl-1,1-dioxo-[1,2,5]thiadiazolidin-2-yl)-1-(2-oxo-2-piperidin-1-yl-ethyl)-1H-imidazo[1,2-a]pyrimidin-5-one;

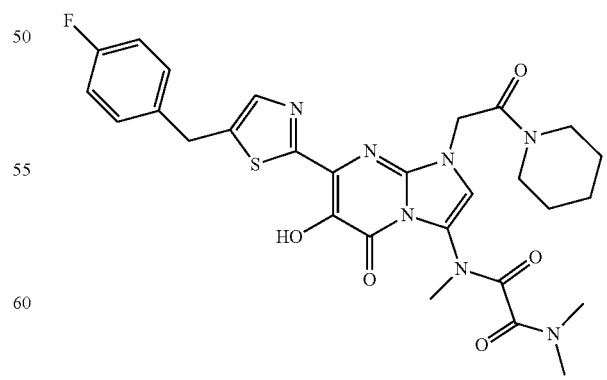

N-[7-[5-(4-Fluoro-benzyl)-thiazol-2-yl]-6-hydroxy-5-oxo-1-(2-oxo-2-piperidin-1-yl-ethyl)-1,5-dihydro-imidazo[1,2-a]-pyrimidin-3-yl]-N,N',N'-trimethyl-oxalamide;

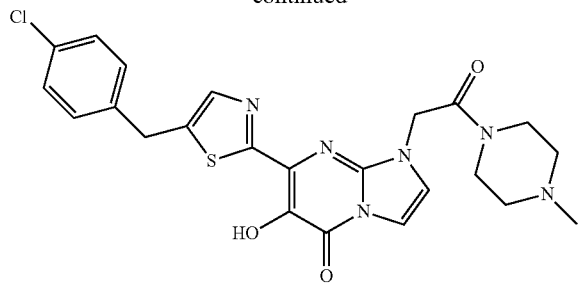

7-[5-(4-Chloro-benzyl)-thiazol-2-yl]-6-hydroxy-1-[2-(4-methyl-piperazin-1-yl)-2-oxo-ethyl]-1H-imidazo[1,2-a]-pyrimidin-5-one;

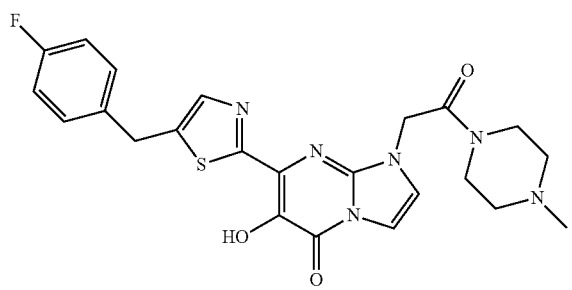

7-[5-(4-Fluoro-benzyl)-thiazol-2-yl]-6-hydroxy-1-[2-(4-methyl-piperazin-1-yl)-2-oxo-ethyl]-1H-imidazo[1,2-a]-pyrimidin-5-one;

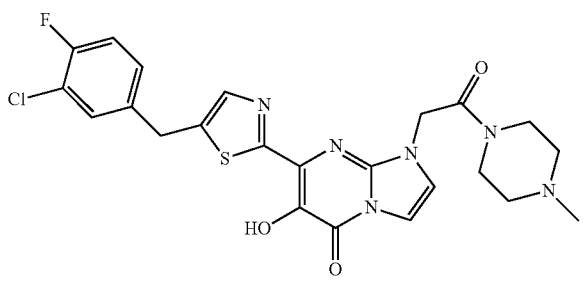

7-[5-(3-Chloro-4-fluoro-benzyl)-thiazol-2-yl]-6-hydroxy-1-[2-(4-methyl-piperazin-1-yl)-2-oxo-ethyl]-1H-imidazo[1,2-a]-pyrimidin-5-one;

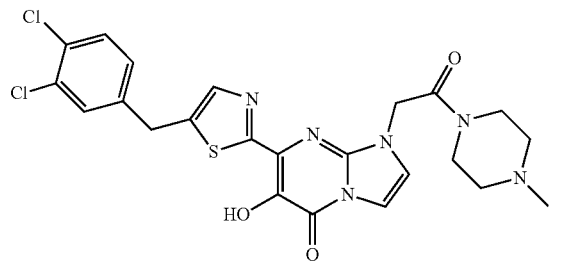

7-[5-(3,4-Dichloro-benzyl)-thiazol-2-yl]-6-hydroxy-1-[2-(4-methyl-piperazin-1-yl)-2-oxo-ethyl]-1H-imidazo[1,2-a]-pyrimidin-5-one;

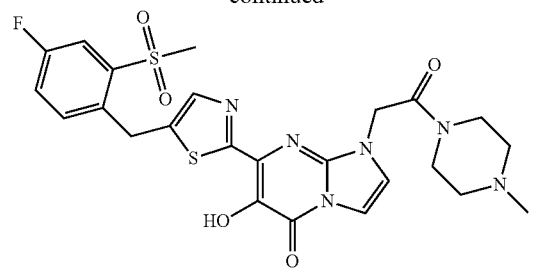

7-[5-(4-Fluoro-2-methanesulfonyl-benzyl)-thiazol-2-yl]-6-hydroxy-1-[2-(4-methyl-piperazin-1-yl)-2-oxo-ethyl]-1H-imidazo[1,2-a]pyrimidin-5-one;

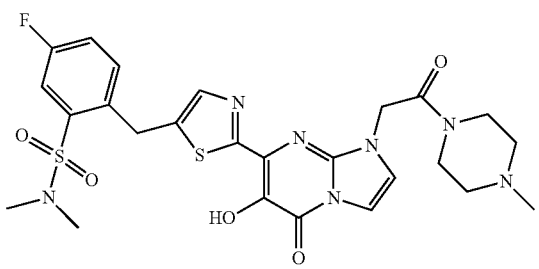

7-{5-[4-Fluoro-2-(4-methyl-piperazine-1-sulfonyl)-benzyl]-thiazol-2-yl}-6-hydroxy-1-[2-(4-methyl-piperazin-1-yl)-2-oxo-ethyl]-1H-imidazo[1,2-a]pyrimidin-5-one;

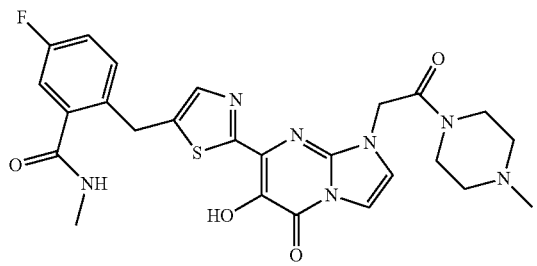

5-Fluoro-2-(2-{6-hydroxy-1-[2-(4-methyl-piperazin-1-yl)-2-oxo-ethyl]-5-oxo-1,5-dihydro-imidazo[1,2-a]pyrimidin-7-yl}-thiazol-5-ylmethyl)-N,N-dimethyl-benzenesulfonamide;

5-Fluoro-2-(2-{6-hydroxy-1-[2-(4-methyl-piperazin-1-yl)-2-oxo-ethyl]-5-oxo-1,5-dihydro-imidazo[1,2-a]pyrimidin-7-yl}-thiazol-5-ylmethyl)-N-methyl-benzamide;

-continued

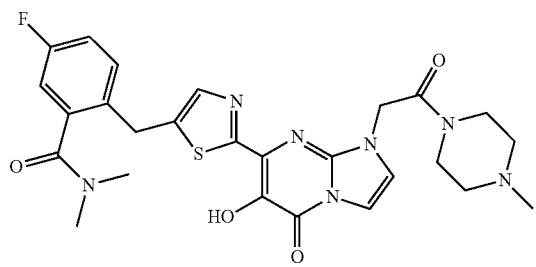

5-Fluoro-2-(2-{6-hydroxy-1-[2-(4-methyl-piperazin-1-yl)-2-oxo-ethyl]-5-oxo-1,5-dihydro-imidazo[1,2-a]pyrimidin-7-yl}-thiazol-5-ylmethyl)-N,N-dimethyl-benzamide;

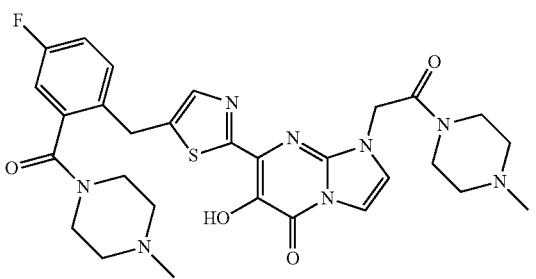

7-{5-[4-Fluoro-2-(4-methyl-piperazin-1-carbonyl)-benzyl]-thiazol-2-yl}-6-hydroxy-1-[2-(4-methyl-piperazin-1-yl)-2-oxo-ethyl]-1H-imidazo[1,2-a]pyrimidin-5-one;

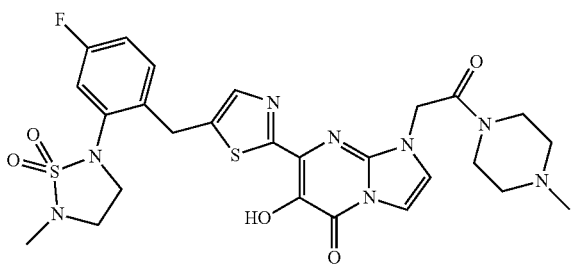

7-{5-[4-Fluoro-2-(5-methyl-1,1-dioxo-[1,2,5]thiadiazolidin-2-yl)-benzyl]-thiazol-2-yl}-6-hydroxy-1-[2-(4-methyl-piperazin-1-yl)-2-oxo-ethyl]-1H-imidazo-[1,2-a]pyrimidin-5-one;

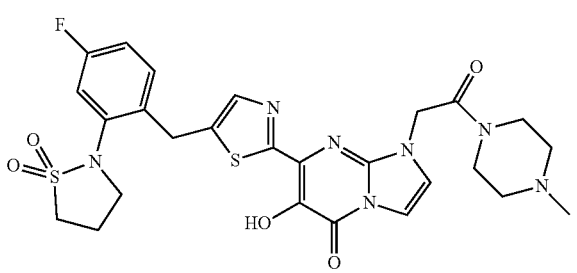

7-{5-[2-(1,1-Dioxo-isothiadiazolidin-2-yl)-4-fluoro-benzyl]-thiazol-2-yl}-6-hydroxy-1-[2-(4-methyl-piperazin-1-yl)-2-oxo-ethyl]-1H-imidazo[1,2-a]pyrimidin-5-one;

-continued

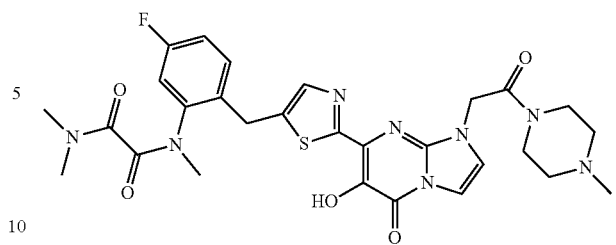

N-[5-Fluoro-2-(2-{6-hydroxy-1-[2-(4-methyl-piperazin-1-yl)-2-oxo-ethyl]-5-oxo-1,5-dihydro-imidazo[1,2-a]pyrimidin-7-yl}-thiazol-5-ylmethyl)-phenyl]-N,N',N'-trimethyl-oxalamide;

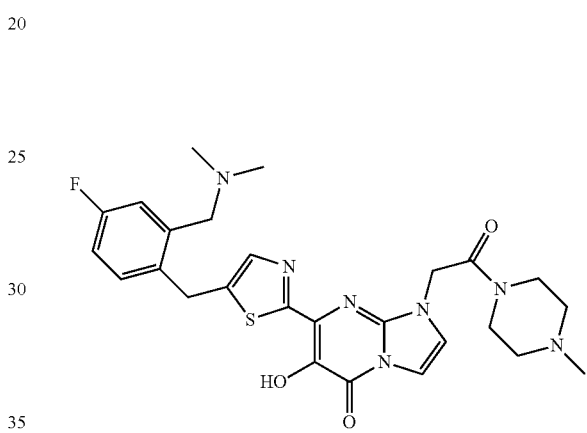

7-[5-(2-Dimethylaminomethyl-4-fluoro-benzyl)-thiazol-2-yl]-6-hydroxy-1-[2-(4-methyl-piperazin-1-yl)-2-oxo-ethyl]-1H-imidazo[1,2-a]pyrimidin-5-one;

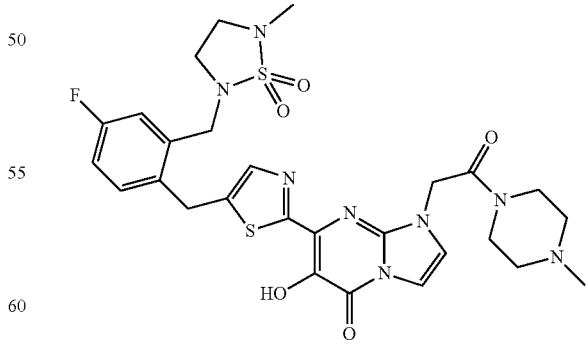

7-(5-[4-fluoro-2-((5-methyl-1,1-dioxido-1,2,5-thiadiazolidin-2-yl)methyl)benzyl]thiazol-2-yl)-6-hydroxy-1-(2-oxo-2-(piperidin-1-yl)ethyl)-imidazo[1,2-a]pyrimidin-5(1H)-one;

-continued

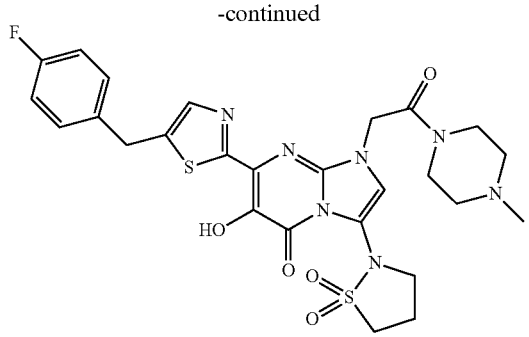

3-(1,1-Dioxo-isothiazolidin-2-yl)-7-
[5-(4-fluoro-benzyl)-thiazol-2-yl]-6-hydroxy-1-
[2-(4-methyl-piperazin-1-yl)-2-oxo-ethyl]-
1H-imidazo[1,2-a]pyrimidin-5-one;

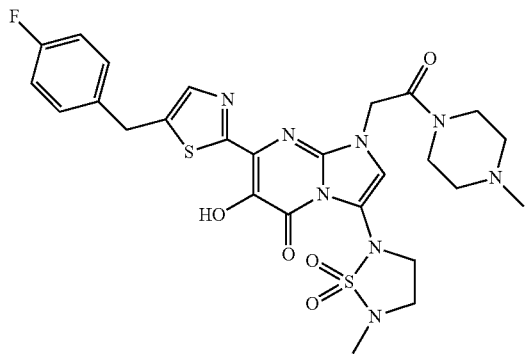

7-(5-(4-Fluoro-benzyl)-thiazol-2-yl]-6-hydroxy-3-(5-
methyl-1,1-dioxo-[1,2,5]thiadiazolidin-2-yl)-
1-[2-(4-methyl-piperazin-1-yl)-2-oxo-ethyl]-1H-
imidazo[1,2-a]pyrimidin-5-one; and -continued

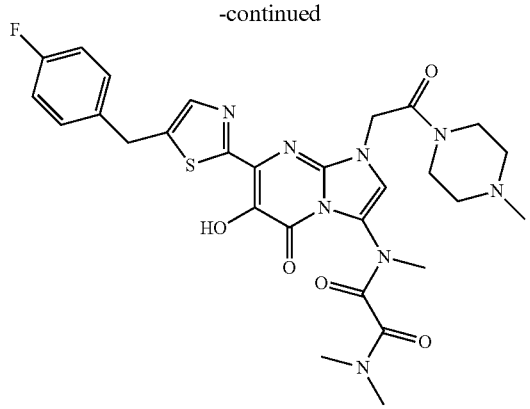

N-{7-(5-(4-Fluoro-benzyl)-thiazol-2-yl]-6-hydroxy-1-
[2-(4-methyl-piperazin-1-yl)-2-oxo-ethyl]-5-oxo-
1,5-dihydro-imidazo[1,2-a]pyrimidin-3-yl}-
N,N',N'-trimethyl-oxalamide.

12. A pharmaceutical composition comprising a compound according to claim 1 and a pharmaceutically acceptable carrier, diluent or excipient.

13. A method of treatment of a viral infection in a subject comprising administering to said subject an effective amount of a compound according to claim 1 or a pharmaceutically acceptable salt thereof.

14. The method according to claim 13 wherein the viral infection is a HIV or SIV infection.

15. The method according to claim 14 wherein the HIV or SIV infection comprises a viral strain resistant to other integrase inhibitors such as Isentrass (raltregavir, MK-0158) or elvitegravir.

16. The method according to claim 14 wherein the viral strain comprises HIV integrase enzyme containing the Q148H/G140S double mutation, N155H/E92Q double mutation, the F121Y/T124K double mutation or the Q148K/G140A/E138A triple mutation.

* * * * *